United States Patent
Feng et al.

(10) Patent No.: US 9,206,191 B2
(45) Date of Patent: Dec. 8, 2015

(54) INDAZOLES FOR THE TREATMENT AND PROPHYLAXIS OF RESPIRATORY SYNCYTIAL VIRUS INFECTION

(71) Applicant: Hoffmann-La Roche Inc., Little Falls, NJ (US)

(72) Inventors: Song Feng, Shanghai (CN); Lu Gao, Shanghai (CN); Di Hong, Shanghai (CN); Lisha Wang, Shanghai (CN); Hongying Yun, Shanghai (CN); Shu-Hai Zhao, Cupertino, CA (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/593,240

(22) Filed: Jan. 9, 2015

(65) Prior Publication Data
US 2015/0158879 A1 Jun. 11, 2015

Related U.S. Application Data

(63) Continuation of application No. PCT/EP2013/064349, filed on Jul. 8, 2013, and a continuation of application No. PCT/CN2013/077232, filed on Jun. 14, 2013, and a continuation of application No. PCT/CN2012/078440, filed on Jul. 10, 2012.

(51) Int. Cl.
| | |
|---|---|
| *A61K 31/00* | (2006.01) |
| *C07D 471/02* | (2006.01) |
| *C07D 491/107* | (2006.01) |
| *C07D 403/06* | (2006.01) |
| *C07D 471/04* | (2006.01) |
| *C07D 401/14* | (2006.01) |
| *C07D 405/14* | (2006.01) |
| *C07D 409/14* | (2006.01) |

(52) U.S. Cl.
CPC .......... *C07D 491/107* (2013.01); *C07D 401/14* (2013.01); *C07D 403/06* (2013.01); *C07D 405/14* (2013.01); *C07D 409/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 6,774,134 B2 * | 8/2004 | Yu et al. ............ | 514/312 |
| 2002/0099208 A1 | 7/2002 | Yu et al. | |

FOREIGN PATENT DOCUMENTS

WO 02/26228 A1 4/2002

OTHER PUBLICATIONS

PCT Written Opinion for PCT/EP2013/064349.

* cited by examiner

*Primary Examiner* — Heidi Reese
(74) *Attorney, Agent, or Firm* — Tony W. Peng

(57) ABSTRACT

The invention provides novel compounds having the general formula:

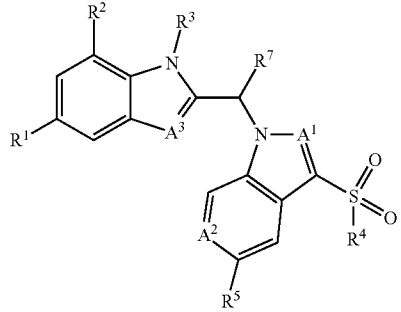

wherein $R^1$, $R^2$, $R^3$, $R^4$, $R^5$, $R^7$, $A^1$, $A^2$ and $A^3$ are as described herein, compositions including the compounds and methods of using the compounds.

25 Claims, No Drawings

INDAZOLES FOR THE TREATMENT AND PROPHYLAXIS OF RESPIRATORY SYNCYTIAL VIRUS INFECTION

This application is a continuation of International Application No. PCT/EP2013/064349, filed Jul. 8, 2013, and claims priority to International Application No. PCT/CN2013/077232, filed Jun. 14, 2013, and to International Application No. PCT/CN2012/078440, filed Jul. 10, 2012, each of which is incorporated herein by reference in its entirety.

The present invention relates to organic compounds useful for therapy and/or prophylaxis in a mammal, and in particular to respiratory syncytial virus (RSV) inhibitors useful for treating RSV infection.

FIELD OF THE INVENTION

Respiratory Syncytial Virus (RSV) belongs to the family of Paramyxoviridae, subfamily of Pneumovirinae. The human RSV is a major cause of acute upper and lower respiratory tract infection in infants and children. Almost all children are infected by RSV at least once by age of three. Natural human immunity against RSV is incomplete. In normal adults and elder children, RSV infection is mainly associated with upper respiratory track symptoms. Severe case of RSV infection often leads to bronchiolitis and pneumonia, which requires hospitalization. High-risk factors for lower respiratory tract infections include premature birth, congenital heart disease, chronic pulmonary disease, and immunocompromised conditions. A severe infection at young age may lead to recurrent wheezing and asthma. For the elderly, RSV-related mortality rate becomes higher with advancing age.

RSV Fusion (F) protein is a surface glycoprotein on the viral envelope which, together with the G surface glycoprotein, mediates viral entry into host cell. The F protein initiates viral penetration by fusing viral and host cellular membranes and subsequently promotes viral spread after infection by melding infected cells to adjacent uninfected cells, resulting in characteristic syncytial formation. By inhibiting viral entry and spread, it is expected that treatment with chemicals described here will decrease the duration and severity of respiratory symptoms and subsequent risk of prolonged hospitalization and complications. It is also expected to limit the ability of individuals to transmit RSV within households, nursing homes and the hospital setting to other hosts potentially at high risk of complications.

There is no RSV vaccine available for human use, despite of many attempts in subunit vaccine and live-attenuated vaccine approaches. Virazole®, the aerosol form of ribavirin, is the only approved antiviral drug for treatment of RSV infection. However, it is rarely used clinically, due to limited efficacy and potential side effects. Two marketed prophylaxis antibodies were developed by MedImmune (CA, USA).

RSV-IGIV (brand name RespiGam) is polyclonal-concentrated RSV neutralizing antibody administered through monthly infusion of 750 mg/kg in hospital (Wandstrat T L, Ann Pharmacother. 1997 January; 31(1):83-8). Subsequently, the usage of RSV-IGIV was largely replaced by palivizumab (brand name Synagis®), a humanized monoclonal antibody against RSV fusion (F) protein approved for prophylaxis in high-risk infants in 1998. When administered intramuscularly at 15 mg/kg once a month for the duration of RSV season, palivizumab demonstrated 45-55% reduction of hospitalization rate caused by RSV infection in selected infants (Pediatrics. 1998 September; 102(3):531-7; Feltes T F et al, J Pediatr. 2003 October; 143(4):532-40). Unfortunately, palivizumab is not effective in the treatment of established RSV infection. A newer version monoclonal antibody, motavizumab, was designed as potential replacement of palivizumab but failed to show additional benefit over palivizumab in recent Phase III clinical trials (Feltes T F et al, Pediatr Res. 2011 August; 70(2):186-91).

A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor, RSV-604, in stem cell transplantation patients by February 2010 (www.clinicaltrials.gov), but has not released the final results. Most of other small molecules were put on hold for various reasons.

RNAi therapeutics against RSV has also been thoroughly studied. ALN-RSV01 (Alnylam Pharmaceuticals, MA, USA) is a siRNA targeting on RSV gene. A nasal spray administered for two days before and for three days after RSV inoculation decreased infection rate among adult volunteers (DeVincenzo J. et al, Proc Natl Acad Sci USA. 2010 May 11; 107(19):8800-5). In another Phase II trial using naturally infected lung transplantation patients, results were not sufficient for conclusion of antiviral efficacy, though certain health benefits have been observed (Zamora M R et al, Am J Respir Crit Care Med. 2011 Feb. 15; 183(4):531-8). Additional Phase IIb clinical trials in similar patient population for ALN-RSV01 are on-going (www.clinicaltrials.gov).

Nevertheless, safe and effective treatment for RSV disease is needed urgently.

SUMMARY OF THE INVENTION

Objects of the present invention are novel compounds of formula I, their manufacture, medicaments based on a compound in accordance with the invention and their production as well as the use of compounds of formula I for the treatment or prophylaxis of RSV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl, and tert-butyl.

The term "$C_{1-3}$alkyl" alone or in combination signifies a saturated, linear- or branched chain alkyl group containing 1 to 3 carbon atoms, for example methyl, ethyl, propyl, isopropyl and the like.

The term "$C_xH_{2x}$" alone or in combination signifies a saturated, linear- or branched chain alkyl group containing 1 to 6, particularly 1 to 4 carbon atoms. Particular "$C_xH_{2x}$" groups are saturated, linear alkyl chain containing 1 to 6, particularly 1 to 4 carbon atoms.

The term "$C_yH_{2y}$" alone or in combination signifies a saturated, linear- or branched chain alkyl group containing from 2 to 6, particularly from 2 to 4 carbon atoms.

The term "$C_zH_{2z}$" alone or in combination signifies a chemical link or a saturated, linear- or branched chain alkyl group containing from 1 to 6. Particular "$C_zH_{2z}$" signifies a chemical link or a saturated, linear or branched chain alkyl group containing from 1 to 4 carbon atoms.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "cycloalkyl" groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "amino", alone or in combination, refers to primary (—$NH_2$), secondary (—NH—) or tertiary amino

The term "halogen" means fluorine, chlorine, bromine or iodine. Halogen is particularly fluorine or chlorine.

The term "halopyridinyl" means pyridinyl substituted by halogen.

The term "hydroxy" alone or in combination refers to the group —OH.

The term "carbonyl" alone or in combination refers to the group —C(O)—.

The term "carboxy" alone or in combination refers to the group —COOH.

The term "sulfonyl" alone or in combination refers to the group —$S(O)_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of RSV

The present invention provides (i) novel compounds having the general formula I:

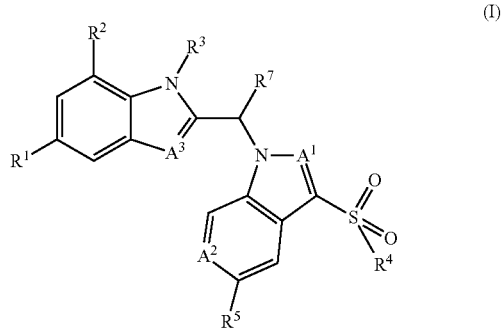

wherein
$R^1$ is hydrogen or halogen;
$R^2$ is hydrogen or halogen;
$R^3$ is azetidinyl; $C_{1-6}$alkoxypyridinyl; $C_{1-6}$alkylsulfonyl-$C_xH_{2x}$—; carboxycycloalkyl; difluorocycloalkyl; 1,1-dioxo-tetrahydrothienyl; halopyridinyl; hydroxy-$C_yH_{2y}$—; hydroxy-$C_xH_{2x}$-cycloalkyl; hydroxy-$C_yH_{2y}$—O—$C_yH_{2y}$—; hydroxycycloalkyl-$C_zH_{2z}$—, unsubstituted or substituted by $C_{1-3}$alkyl, hydroxy or hydroxy-$C_xH_{2x}$—; 4-hydroxypiperidin-1-yl-$C_yH_{2y}$—; 3-hydroxy-pyrrolidin-1-yl-$C_yH_{2y}$—; morpholinyl-$C_yH_{2y}$—; oxetanyl; oxetanyl-$C_xH_{2x}$—, unsubstituted or substituted by $C_{1-3}$alkyl; piperidinyl; oxo-piperidinyl; oxo-pyrrolidinyl; pyrrolidinyl, unsubstituted or substituted by $C_{1-6}$alkylcarbonyl, $C_{1-6}$alkylsulfonyl, hydroxy-$C_yH_{2y}$—, hydroxy-$C_xH_{2x}$-carbonyl, amino-$C_xH_{2x}$-carbonyl or trifluoromethyl-$C_xH_{2x}$—; tetrahydrofuran-3-yl-$C_zH_{2z}$—; tetrahydropyranyl; trifluoromethyl-$C_xH_{2x}$—;

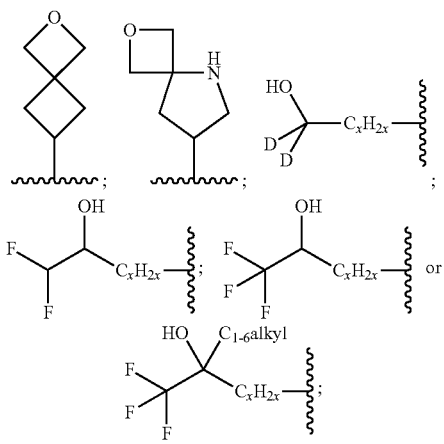

$R^4$ is $C_{1-6}$alkyl or cycloalkyl;
$R^5$ is hydrogen or halogen;
$R^7$ is hydrogen or $C_{1-6}$alkyl;
$A^1$ is —N— or —CH;
$A^2$ is —N—, —NO or —CH;
$A^3$ is —N— or —CH;
x is 1-6;
y is 2-6;
z is 0-6;
or pharmaceutically acceptable salts thereof.

Further embodiment of present invention is (ii) a compound of formula I, wherein
R¹ is hydrogen or chloro;
R² is hydrogen or fluoro;
R³ is azetidin-3-yl; methoxypyridinyl; methylsulfonylethyl; methylsulfonylpropyl; carboxycyclobutyl; difluorocyclopentyl; 1,1-dioxo-tetrahydrothienyl; chloropyridinyl; fluoropyridinyl; hydroxypropyl; hydroxybutyl; hydroxyisopropylethyl; hydroxyisopropylpropyl; hydroxymethylcyclobutyl; hydroxyisopropylcyclobutyl; hydroxyethoxyethyl; hydroxycyclobutyl; hydroxycyclohexyl; hydroxycyclopentyl; hydroxycyclopropylethyl; 4-hydroxypiperidin-1-ylethyl; 3-hydroxy-pyrrolidin-1-ylethyl; morpholinylethyl; oxetan-3-yl; oxetan-3-ylmethyl; oxetan-3-ylethyl; piperidin-4-yl; 2-oxo-piperidin-4-yl; 2-oxo-pyrrolidin-4-yl; pyrrolidin-3-yl, unsubstituted or once substituted by methylcarbonyl, ethylcarbonyl, isopropylcarbonyl, methylsulfonyl, hydroxyethyl, hydroxymethylcarbonyl, hydroxyisopropylcarbonyl, aminomethylcarbonyl or trifluoromethylmethyl; tetrahydrofuran-3-yl; tetrahydrofuran-3-ylmethyl; tetrahydropyran-4-yl; trifluoromethylethyl; trifluoromethylpropyl;

R⁴ is methyl, ethyl, isopropyl or cyclopropyl;
R⁵ is hydrogen or fluoro;
R⁷ is hydrogen or methyl;
A¹ is —N— or —CH;
A² is —N—, —NO or —CH;
A³ is —N— or —CH;
or pharmaceutically acceptable salts thereof.

Another embodiment of present invention is (iii) a compound of formula I or a pharmaceutically acceptable salt thereof, wherein
R¹ is halogen;
R² is hydrogen or halogen;
R³ is azetidinyl; $C_{1-6}$alkoxypyridinyl; $C_{1-6}$alkylsulfonyl-$C_xH_{2x}$—; carboxycycloalkyl; difluorocycloalkyl; 1,1-dioxo-tetrahydrothienyl; halopyridinyl; hydroxy-$C_yH_{2y}$—; hydroxy-$C_xH_{2x}$-cycloalkyl; hydroxy-$C_yH_{2y}$—O—$C_yH_{2y}$—; hydroxycycloalkyl-$C_zH_{2z}$—, unsubstituted or substituted by $C_{1-3}$alkyl, hydroxy or hydroxy-$C_xH_{2x}$—; 4-hydroxypiperidin-1-yl-$C_yH_{2y}$—; 3-hydroxy-pyrrolidin-1-yl-$C_yH_{2y}$—; morpholinyl-$C_yH_{2y}$—; oxetanyl; oxetanyl-$C_xH_{2x}$—, unsubstituted or substituted by $C_{1-3}$alkyl; piperidinyl; oxo-piperidinyl; oxo-pyrrolidinyl; pyrrolidinyl, unsubstituted or substituted by $C_{1-6}$alkylcarbonyl, $C_{1-6}$alkylsulfonyl, hydroxy-$C_yH_{2y}$—, hydroxy-$C_xH_{2x}$-carbonyl, amino-$C_xH_{2x}$-carbonyl or trifluoromethyl-$C_xH_{2x}$—; tetrahydrofuran-3-yl-$C_zH_{2z}$—; tetrahydropyranyl; trifluoromethyl-$C_xH_{2x}$—;

R⁴ is $C_{1-6}$alkyl;
R⁵ is hydrogen;
R⁷ is hydrogen or $C_{1-6}$alkyl;
A¹ is —N—;
A² is —N—, —NO or —CH;
A³ is —N— or —CH;
x is 1-6;
y is 2-6;
z is 0-6.

Further embodiment of present invention is (iv) a compound of formula I or a pharmaceutically acceptable salt thereof, wherein
R¹ is chloro;
R² is hydrogen or fluoro;
R³ is azetidin-3-yl; methoxypyridinyl; methylsulfonylethyl; methylsulfonylpropyl; carboxycyclobutyl; difluorocyclopentyl; 1,1-dioxo-tetrahydrothienyl; chloropyridinyl; fluoropyridinyl; hydroxypropyl; hydroxybutyl; hydroxyisopropylethyl; hydroxyisopropylpropyl; hydroxymethylcyclobutyl; hydroxyisopropylcyclobutyl; hydroxyethoxyethyl; hydroxycyclobutyl; hydroxycyclohexyl; hydroxycyclopentyl; hydroxycyclopropylethyl; 4-hydroxypiperidin-1-ylethyl; 3-hydroxy-pyrrolidin-1-ylethyl; morpholinylethyl; oxetan-3-yl; oxetan-3-ylmethyl; oxetan-3-ylethyl; piperidin-4-yl; 2-oxo-piperidin-4-yl; 2-oxo-pyrrolidin-4-yl; pyrrolidin-3-yl, unsubstituted or once substituted by methylcarbonyl, ethylcarbonyl, isopropylcarbonyl, methylsulfonyl, hydroxyethyl, hydroxymethylcarbonyl, hydroxyisopropylcarbonyl, aminomethylcarbonyl or trifluoromethylmethyl; tetrahydrofuran-3-yl; tetrahydrofuran-3-ylmethyl; tetrahydropyran-4-yl; trifluoromethylethyl; trifluoromethylpropyl;

$R^4$ is methyl, ethyl or isopropyl;

$R^5$ is hydrogen;

$R^7$ is hydrogen or methyl;

$A^1$ is —N—;

$A^2$ is —N—, —NO or —CH;

$A^3$ is —N— or —CH.

Another embodiment of present invention is (v) a compound of formula I or a pharmaceutically acceptable salt thereof, wherein $R^1$ is halogen;

$R^2$ is hydrogen or halogen;

$R^3$ is azetidinyl; $C_{1-6}$alkylsulfonyl-$C_xH_{2x}$—; carboxycycloalkyl; difluorocycloalkyl; 1,1-dioxo-tetrahydrothienyl; halopyridinyl; hydroxy-$C_yH_{2y}$—; hydroxy-$C_xH_{2x}$-cycloalkyl; hydroxy-$C_yH_{2y}$—O—$C_yH_{2y}$—; hydroxycycloalkyl-$C_zH_{2z}$—, unsubstituted or substituted by $C_{1-3}$alkyl, hydroxy or hydroxy-$C_xH_{2x}$—; 4-hydroxypiperidin-1-yl-$C_yH_{2y}$—; 3-hydroxy-pyrrolidin-1-yl-$C_yH_{2y}$—; morpholinyl-$C_yH_{2y}$—; oxetanyl; oxetanyl-$C_xH_{2x}$—; oxo-piperidinyl; oxo-pyrrolidinyl; pyrrolidinyl, unsubstituted or substituted by $C_{1-6}$alkylcarbonyl, $C_{1-6}$alkylsulfonyl, hydroxy-$C_yH_{2y}$—, hydroxy-$C_xH_{2x}$-carbonyl, amino-$C_xH_{2x}$-carbonyl or trifluoromethyl-$C_xH_{2x}$—; tetrahydrofuran-3-yl-$C_zH_{2z}$—; tetrahydropyranyl; trifluoromethyl-$C_xH_{2x}$—;

$R^4$ is $C_{1-6}$alkyl;

$R^5$ is hydrogen;

$R^7$ is hydrogen or $C_{1-6}$alkyl;

$A^1$ is —N—;

$A^2$ is —N—;

$A^3$ is —N— or —CH;

x is 1-6;

y is 2-6;

z is 0-6.

Further embodiment of present invention is (vi) a compound of formula I or a pharmaceutically acceptable salt thereof, wherein $R^1$ is chloro;

$R^2$ is hydrogen or fluoro;

$R^3$ is azetidin-3-yl; methylsulfonylethyl; methylsulfonylpropyl; carboxycyclobutyl; difluorocyclopentyl; 1,1-dioxotetrahydrothienyl; fluoropyridinyl; hydroxypropyl; hydroxybutyl; hydroxyisopropylethyl; hydroxyisopropylpropyl; hydroxymethylcyclobutyl; hydroxyisopropylcyclobutyl; hydroxyethoxyethyl; hydroxycyclobutyl; hydroxycyclohexyl; hydroxycyclopentyl; hydroxycyclopropylethyl; 4-hydroxypiperidin-1-ylethyl; 3-hydroxy-pyrrolidin-1-ylethyl; morpholinylethyl; oxetan-3-yl; oxetan-3-ylmethyl; oxetan-3-ylethyl; 2-oxo-piperidin-4-yl; 2-oxo-pyrrolidin-4-yl; pyrrolidin-3-yl, unsubstituted or once substituted by methylcarbonyl, isopropylcarbonyl, methylsulfonyl, hydroxyethyl, hydroxymethylcarbonyl, hydroxyisopropylcarbonyl, aminomethylcarbonyl or trifluoromethylmethyl; tetrahydrofuran-3-yl; tetrahydrofuran-3-ylmethyl; tetrahydropyran-4-yl; trifluoromethylethyl; trifluoromethylpropyl;

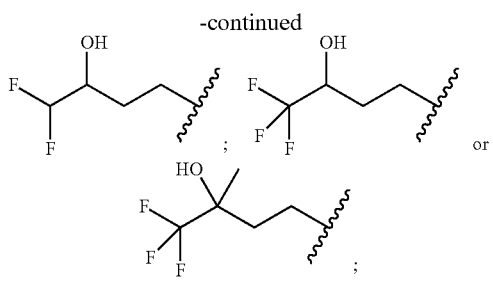

R⁴ is methyl;
R⁵ is hydrogen;
R⁷ is hydrogen or methyl;
A¹ is —N—;
A² is —N—;
A³ is —N— or —CH.

Another embodiment of present invention is (vii) a compound of formula I or a pharmaceutically acceptable salt thereof, wherein
R¹ is halogen;
R² is hydrogen;
R³ is $C_{1-6}$alkoxypyridinyl; $C_{1-6}$alkylsulfonyl-$C_xH_{2x}$—; difluorocycloalkyl; 1,1-dioxo-tetrahydrothienyl; halopyridinyl; oxetanyl; piperidinyl; $C_{1-6}$alkylcarbonylpyrrolidinyl; tetrahydrofuran-3-yl; tetrahydropyranyl or trifluoromethyl-$C_xH_{2x}$—;
R⁴ is $C_{1-6}$alkyl;
R⁵ is hydrogen;
R⁷ is hydrogen;
A¹ is —N—;
A² is —CH;
A³ is —N—;
x is 1-6.

Further embodiment of present invention is (viii) a compound of formula I or a pharmaceutically acceptable salt thereof, wherein
R¹ is chloro;
R² is hydrogen;
R³ is methoxypyridinyl; methylsulfonylethyl; methylsulfonylpropyl; difluorocyclopentyl; 1,1-dioxo-tetrahydrothienyl; chloropyridinyl; fluoropyridinyl; oxetan-3-yl; piperidin-4-yl; 1-methylcarbonylpyrrolidin-3-yl; 1-ethylcarbonylpyrrolidin-3-yl; tetrahydrofuran-3-yl; tetrahydropyran-4-yl or trifluoromethylpropyl;
R⁴ is methyl, ethyl or isopropyl;
R⁵ is hydrogen;
R⁷ is hydrogen;
A¹ is —N—;
A² is —CH;
A³ is —N—.

Another embodiment of present invention is (ix) a compound of formula I or a pharmaceutically acceptable salt thereof, wherein
R¹ is halogen;
R² is hydrogen;
R³ is halopyridinyl, hydroxycycloalkyl or trifluoromethyl-$C_xH_{2x}$—; wherein x is 1-6;
R⁴ is $C_{1-6}$alkyl;
R⁵ is hydrogen;
R⁷ is hydrogen;
A¹ is —N—;
A² is —NO;
A³ is —N—.

Another embodiment of present invention is (x) a compound of formula I or a pharmaceutically acceptable salt thereof, wherein
R¹ is hydrogen or halogen;
R² is hydrogen;
R³ is $C_{1-6}$alkylsulfonyl-$C_xH_{2x}$—, wherein x is 1-6;
R⁴ is $C_{1-6}$alkyl or cycloalkyl;
R⁵ is hydrogen or halogen;
R⁷ is hydrogen;
A¹ is —CH;
A² is —N— or —CH;
A³ is —N—.

Further embodiment of present invention is (xi) a compound of formula I or a pharmaceutically acceptable salt thereof, wherein
R¹ is hydrogen or chloro;
R² is hydrogen;
R³ is methylsulfonylethyl or methylsulfonylpropyl;
R⁴ is methyl, ethyl, isopropyl or cyclopropyl;
R⁵ is hydrogen or fluoro;
R⁷ is hydrogen;
A¹ is —CH;
A² is —N—, or —CH;
A³ is —N—.

Another embodiment of present invention is (xii) a compound of formula I' or a pharmaceutically acceptable salt thereof,

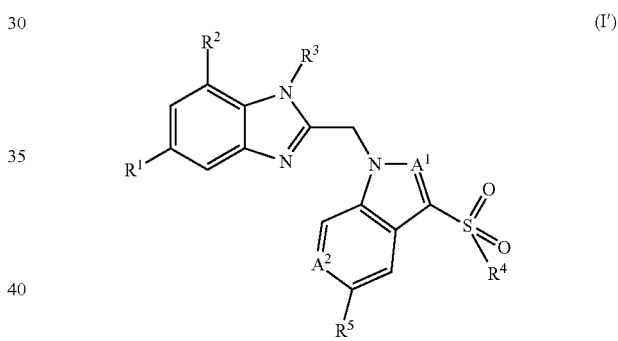

wherein
R¹ is hydrogen or halogen;
R² is hydrogen or halogen;
R³ is azetidinyl; $C_{1-6}$alkoxypyridinyl; $C_{1-6}$alkylsulfonyl-$C_xH_{2x}$—; difluoro$C_{3-7}$cycloalkyl; 1,1-dioxo-tetrahydrothiophenyl; halopyridinyl; hydroxy$C_{3-7}$cycloalkyl; oxetanyl; oxetanyl-$C_xH_{2x}$—; piperidinyl; oxo-piperidinyl; pyrrolidinyl, unsubstituted or once substituted by $C_{1-6}$alkylcarbonyl, hydroxy-$C_xH_{2x}$-carbonyl, amino-$C_xH_{2x}$-carbonyl or trifluoromethyl-$C_xH_{2x}$—; tetrahydrofuranyl; tetrahydropyranyl or trifluoromethyl-$C_xH_{2x}$—; wherein x is 1-6;
R⁴ is $C_{1-6}$alkyl or $C_{3-7}$cycloalkyl;
R⁵ is hydrogen or halogen;
A¹ is —N— or —CH;
A² is —N—, —NO or —CH.

Further embodiment of present invention is (xiii) a compound of formula I' or a pharmaceutically acceptable salt thereof, wherein
R¹ is hydrogen or chloro;
R² is hydrogen or fluoro;
R³ is azetidin-3-yl; methoxypyridinyl; methylsulfonylethyl; methylsulfonylpropyl; difluorocyclopentyl; 1,1-dioxo-tetrahydrothiophenyl; chloropyridinyl; fluoropyridinyl; hydroxycyclohexyl; hydroxycyclopentyl; oxetan-3-yl;

oxetanylmethyl; oxetanylethyl; piperidin-4-yl; 2-oxo-piperidin-4-yl; pyrrolidin-3-yl, unsubstituted or once substituted by methylcarbonyl, hydroxymethylcarbonyl, aminomethylcarbonyl or trifluoromethylmethyl; tetrahydrofuran-3-yl; tetrahydropyran-4-yl; trifluoromethylethyl or trifluoromethylpropyl;

$R^4$ is methyl, ethyl, isopropyl or cyclopropyl;
$R^5$ is hydrogen or fluoro;
$A^1$ is —N— or —CH;
$A^2$ is —N—, —NO or —CH.

Another embodiment of present invention is (xiv) a compound of formula I' or a pharmaceutically acceptable salt thereof, wherein
$R^1$ is halogen;
$R^2$ is hydrogen or halogen;
$R^3$ is azetidinyl; $C_{1-6}$alkoxypyridinyl; $C_{1-6}$alkylsulfonyl-$C_xH_{2x}$—; difluoro$C_{3-7}$cycloalkyl; 1,1-dioxo-tetrahydrothiophenyl; halopyridinyl; hydroxy$C_{3-7}$cycloalkyl; oxetanyl; oxetanyl-$C_xH_{2x}$—; piperidinyl; oxo-piperidinyl; pyrrolidinyl, unsubstituted or once substituted by $C_{1-6}$alkylcarbonyl, hydroxy-$C_xH_{2x}$-carbonyl, amino-$C_xH_{2x}$-carbonyl or trifluoromethyl-$C_xH_{2x}$—; tetrahydrofuranyl; tetrahydropyranyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —N—, —NO or —CH.

Further embodiment of present invention is (xv) a compound of formula I' or a pharmaceutically acceptable salt thereof, wherein
$R^1$ is chloro;
$R^2$ is hydrogen or fluoro;
$R^3$ is azetidin-3-yl; methoxypyridinyl; methylsulfonylethyl; methylsulfonylpropyl; difluorocyclopentyl; 1,1-dioxo-tetrahydrothiophenyl; chloropyridinyl; fluoropyridinyl; hydroxycyclohexyl; hydroxycyclopentyl; oxetan-3-yl; oxetanylmethyl; oxetanylethyl; piperidin-4-yl; 2-oxo-piperidin-4-yl; pyrrolidin-3-yl, unsubstituted or once substituted by methylcarbonyl, hydroxymethylcarbonyl, aminomethylcarbonyl or trifluoromethylmethyl; tetrahydrofuran-3-yl; tetrahydropyran-4-yl; trifluoromethylethyl or trifluoromethylpropyl;
$R^4$ is methyl, ethyl or isopropyl;
$R^5$ is hydrogen;
$A^1$ is —N—;
$A^2$ is —N—, —NO or CH.

Still further embodiment of present invention is (xvi) a compound of formula I' or a pharmaceutically acceptable salt thereof, wherein
$R^1$ is halogen;
$R^2$ is hydrogen or halogen;
$R^3$ is azetidinyl; $C_{1-6}$alkylsulfonyl-$C_xH_{2x}$—; difluoro$C_{3-7}$cycloalkyl; 1,1-dioxo-tetrahydrothiophenyl; halopyridinyl; hydroxy$C_{3-7}$cycloalkyl; oxetanyl; oxetanyl-$C_xH_{2x}$—; oxo-piperidinyl; pyrrolidinyl, unsubstituted or once substituted by $C_{1-6}$alkylcarbonyl, hydroxy-$C_xH_{2x}$-carbonyl, amino-$C_xH_{2x}$-carbonyl or trifluoromethyl-$C_xH_{2x}$—; tetrahydropyranyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —N—.

More further embodiment of present invention is (xvii) a compound of formula I' or a pharmaceutically acceptable salt thereof, wherein
$R^1$ is chloro;
$R^2$ is hydrogen or fluoro;
$R^3$ is azetidin-3-yl; methylsulfonylpropyl; difluorocyclopentyl; 1,1-dioxo-tetrahydrothiophenyl; fluoropyridinyl; hydroxycyclohexyl; oxetan-3-yl; oxetanylethyl; oxetanylmethyl; 2-oxo-piperidin-4-yl; pyrrolidin-3-yl, unsubstituted or once substituted by methylcarbonyl, hydroxymethylcarbonyl, aminomethylcarbonyl or trifluoromethylmethyl; tetrahydropyran-4-yl; trifluoromethylethyl or trifluoromethylpropyl;
$R^4$ is methyl;
$R^5$ is hydrogen;
$A^1$ is —N—;
$A^2$ is —N—.

Another embodiment of present invention is (xviii) a compound of formula I' or a pharmaceutically acceptable salt thereof, wherein
$R^1$ is halogen;
$R^2$ is hydrogen;
$R^3$ is $C_{1-6}$alkoxypyridinyl; $C_{1-6}$alkylsulfonyl-$C_xH_{2x}$—; difluoro$C_{3-7}$cycloalkyl; 1,1-dioxo-tetrahydrothiophenyl; halopyridinyl; oxetanyl; piperidinyl; tetrahydrofuranyl; tetrahydropyranyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —CH.

Further embodiment of present invention is (xix) a compound of formula I' or a pharmaceutically acceptable salt thereof, wherein
$R^1$ is chloro;
$R^2$ is hydrogen;
$R^3$ is methoxypyridinyl; methylsulfonylethyl; methylsulfonylpropyl; difluorocyclopentyl; 1,1-dioxo-tetrahydrothiophenyl; chloropyridinyl; fluoropyridinyl; oxetan-3-yl; piperidin-4-yl; tetrahydrofuran-3-yl; tetrahydropyran-4-yl or trifluoromethylpropyl;
$R^4$ is methyl, ethyl or isopropyl;
$R^5$ is hydrogen;
$A^1$ is —N—;
$A^2$ is —CH.

Another embodiment of present invention is (xx) a compound of formula I' or a pharmaceutically acceptable salt thereof, wherein
$R^1$ is halogen;
$R^2$ is hydrogen;
$R^3$ is halopyridinyl, hydroxy$C_{3-7}$cycloalkyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —NO.

Another embodiment of present invention is (xxi) a compound of formula I' or a pharmaceutically acceptable salt thereof, wherein
$R^1$ is hydrogen or halogen;
$R^2$ is hydrogen;
$R^3$ is $C_{1-6}$alkylsulfonyl-$C_xH_{2x}$—, wherein x is 1-6;
$R^4$ is $C_{1-6}$alkyl or $C_{3-7}$cycloalkyl;
$R^5$ is hydrogen or halogen;
$A^1$ is —CH;
$A^2$ is —N— or —CH.

Further embodiment of present invention is (xxii) a compound of formula I' or a pharmaceutically acceptable salt thereof, wherein
$R^1$ is hydrogen or chloro;
$R^2$ is hydrogen;
$R^3$ is methylsulfonylethyl or methylsulfonylpropyl;
$R^4$ is methyl, ethyl, isopropyl or cyclopropyl;
$R^5$ is hydrogen or fluoro;
$A^1$ is —CH;
$A^2$ is —N— or —CH.

Particular compounds of formula I, including their activity data, NMR data and MS data are summarized in the following Table 1 and 2.

TABLE 1

| Example No. | Structure | Name | CPE Long EC50 (μM) |
|---|---|---|---|
| 1-1 | 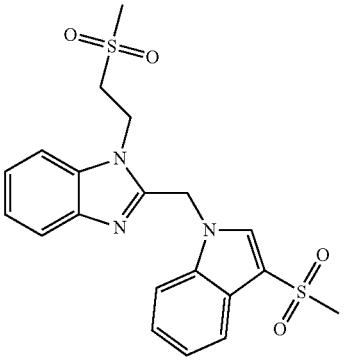 [SMILES: CS(=O)(=O)CCn1c(Cn2cc(S(C)(=O)=O)c3ccccc32)nc2ccccc21] | 1-[2-(Methylsulfonyl)ethyl]-2-{[3-(methylsulfonyl)-1H-indol-1-yl]methyl}-1H-benzimidazole | 2.414 |
| 1-2 | 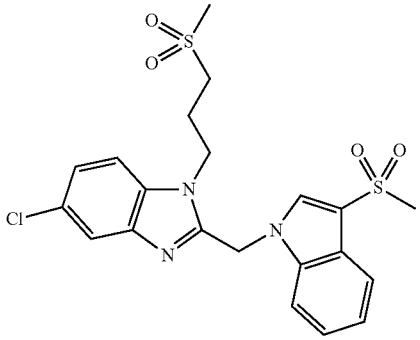 [SMILES: CS(=O)(=O)CCCn1c(Cn2cc(S(C)(=O)=O)c3ccccc32)nc2cc(Cl)ccc21] | 5-Chloro-2-{[3-(methylsulfonyl)-1H-indol-1-yl]methyl}-1-[3-(methylsulfonyl)propyl]-1H-benzimidazole | 0.0625 |
| 1-3 | 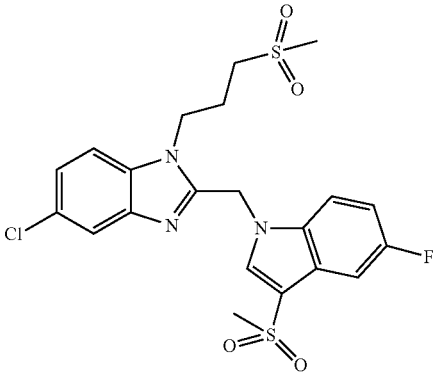 [SMILES: CS(=O)(=O)CCCn1c(Cn2cc(S(C)(=O)=O)c3cc(F)ccc32)nc2cc(Cl)ccc21] | 5-Chloro-2-{[5-fluoro-3-(methylsulfonyl)-1H-indol-1-yl]methyl}-1-[3-(methylsulfonyl)propyl]-1H-benzimidazole | 0.197 |
| 1-4 | 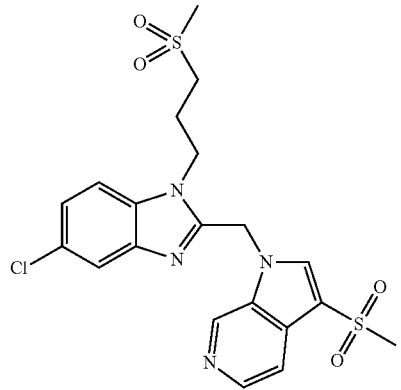 [SMILES: CS(=O)(=O)CCCn1c(Cn2cc(S(C)(=O)=O)c3ccncc32)nc2cc(Cl)ccc21] | 5-Chloro-1-[3-(methylsulfonyl)propyl]-2-{[3-(methylsulfonyl)-1H-pyrrolo[2,3-c]pyridin-1-yl]methyl}-1H-benzimidazole | 0.082 |

TABLE 1-continued

Structure, name and activity data of particular compounds

| Example No. | Structure | Name | CPE Long EC50 (μM) |
|---|---|---|---|
| 1-5 | 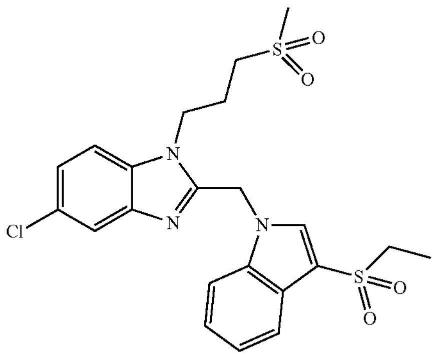 [SMILES: CCS(=O)(=O)c1cn(Cc2nc3cc(Cl)ccc3n2CCCS(C)(=O)=O)c2ccccc12] | 5-Chloro-2-{[3-(ethylsulfonyl)-1H-indol-1-yl]methyl}-1-[3-(methylsulfonyl)propyl]-1H-benzimidazole | 0.065 |
| 1-6 | 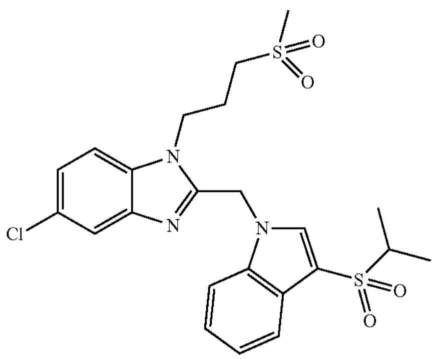 [SMILES: CC(C)S(=O)(=O)c1cn(Cc2nc3cc(Cl)ccc3n2CCCS(C)(=O)=O)c2ccccc12] | 5-Chloro-1-[3-(methylsulfonyl)propyl]-2-{[3-(propan-2-ylsulfonyl)-1H-indol-1-yl]methyl}-1H-benzimidazole | 0.119 |
| 1-7 | 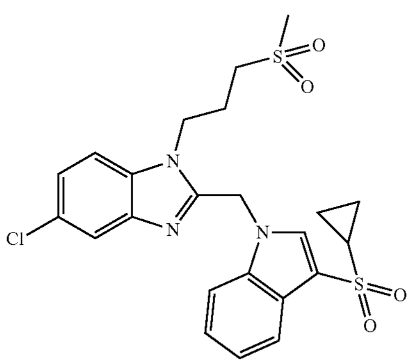 [SMILES: CS(=O)(=O)CCCn1c(Cn2cc(S(=O)(=O)C3CC3)c3ccccc32)nc2cc(Cl)ccc21] | 5-Chloro-2-{[3-(cyclopropylsulfonyl)-1H-indol-1-yl]methyl}-1-[3-(methylsulfonyl)propyl]-1H-benzimidazole | 0.227 |
| 1-8 | 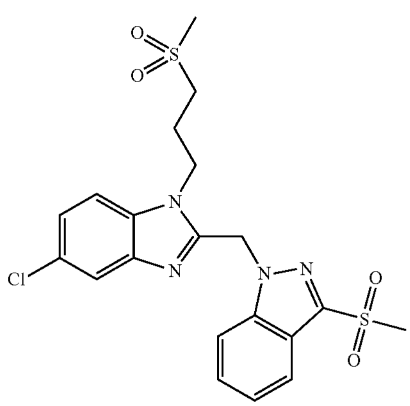 [SMILES: CS(=O)(=O)CCCn1c(Cn2nc(S(C)(=O)=O)c3ccccc32)nc2cc(Cl)ccc21] | 1-({5-Chloro-1-[3-(methylsulfonyl)propyl]-1H-benzimidazol-2-yl}methyl)-3-(methylsulfonyl)-1H-indazole | 0.016 |

TABLE 1-continued

Structure, name and activity data of particular compounds

| Example No. | Structure | Name | CPE Long EC50 (μM) |
|---|---|---|---|
| 1-9 | 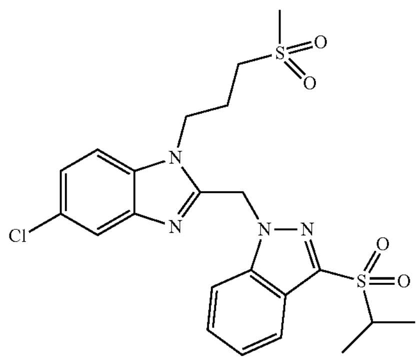 [SMILES: CC(C)S(=O)(=O)c1nn(Cc2nc3cc(Cl)ccc3n2CCCS(C)(=O)=O)c2ccccc12] | 1-({5-Chloro-1-[3-(methylsulfonyl)propyl]-1H-benzimidazol-2-yl}methyl)-3-(propan-2-ylsulfonyl)-1H-indazole | 0.07442 |
| 1-10 | 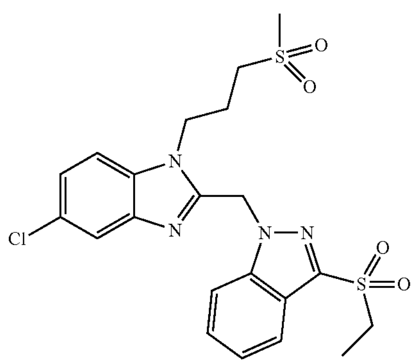 [SMILES: CCS(=O)(=O)c1nn(Cc2nc3cc(Cl)ccc3n2CCCS(C)(=O)=O)c2ccccc12] | 1-({5-Chloro-1-[3-(methylsulfonyl)propyl]-1H-benzimidazol-2-yl}methyl)-3-(ethylsulfonyl)-1H-indazole | 0.03776 |
| 1-11 | 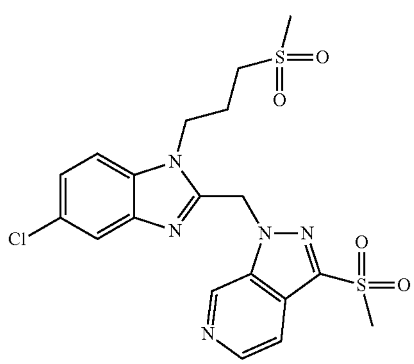 [SMILES: CS(=O)(=O)CCCn1c(Cn2nc(S(C)(=O)=O)c3ccncc32)nc2cc(Cl)ccc21] | 1-({5-Chloro-1-[3-(methylsulfonyl)propyl]-1H-benzimidazol-2-yl}methyl)-3-(methylsulfonyl)-1H-pyrazolo[3,4-c]pyridine | 0.0046 |
| 1-12 | 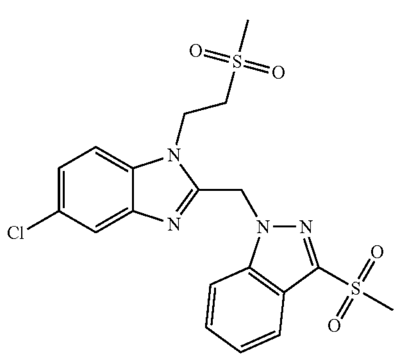 [SMILES: CS(=O)(=O)CCn1c(Cn2nc(S(C)(=O)=O)c3ccccc32)nc2cc(Cl)ccc21] | 1-({5-Chloro-1-[2-(methylsulfonyl)ethyl]-1H-benzimidazol-2-yl}methyl)-3-(methylsulfonyl)-1H-indazole | 0.02616 |

TABLE 1-continued

Structure, name and activity data of particular compounds

| Example No. | Structure | Name | CPE Long EC50 (μM) |
|---|---|---|---|
| 1-13 | 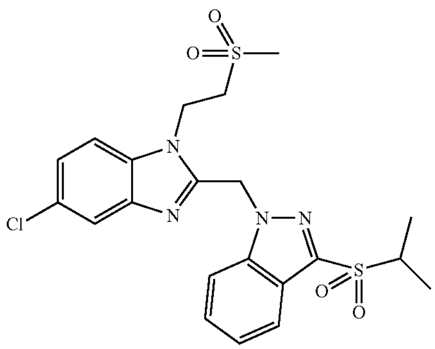 [SMILES: CC(C)S(=O)(=O)c1nn(Cc2nc3cc(Cl)ccc3n2CCS(C)(=O)=O)c2ccccc12] | 1-({5-Chloro-1-[2-(methylsulfonyl)ethyl]-1H-benzimidazol-2-yl}methyl)-3-(propan-2-ylsulfonyl)-1H-indazole | 0.31216 |
| 2-1 | 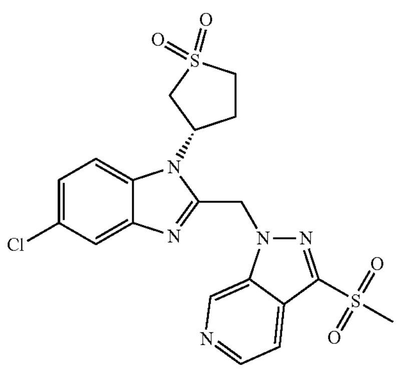 [SMILES: CS(=O)(=O)c1nn(Cc2nc3cc(Cl)ccc3n2[C@H]2CCS(=O)(=O)C2)c2cnccc12] | 1-({5-Chloro-1-[(3R)-1,1-dioxidotetrahydrothiophen-3-yl]-1H-benzimidazol-2-yl}methyl)-3-(methylsulfonyl)-1H-pyrazolo[3,4-c]pyridine | 0.00899 |
| 2-2 | 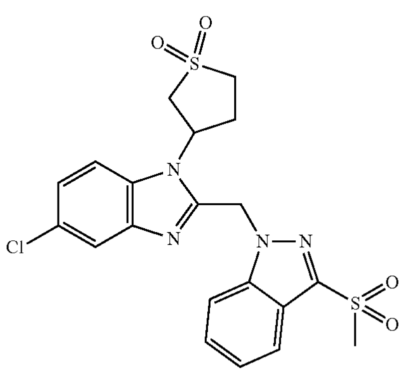 [SMILES: CS(=O)(=O)c1nn(Cc2nc3cc(Cl)ccc3n2C2CCS(=O)(=O)C2)c2ccccc12] | 1-{[5-Chloro-1-(1,1-dioxidotetrahydrothiophen-3-yl)-1H-benzimidazol-2-yl]methyl}-3-(methylsulfonyl)-1H-indazole | 0.00786 |
| 2-3 | 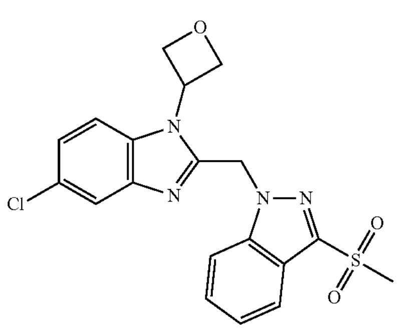 [SMILES: CS(=O)(=O)c1nn(Cc2nc3cc(Cl)ccc3n2C2COC2)c2ccccc12] | 1-{[5-Chloro-1-(oxetan-3-yl)-1H-benzimidazol-2-yl]methyl}-3-(methylsulfonyl)-1H-indazole | 0.0218 |

TABLE 1-continued

Structure, name and activity data of particular compounds

| Example No. | Structure | Name | CPE Long EC50 (μM) |
|---|---|---|---|
| 2-4 | 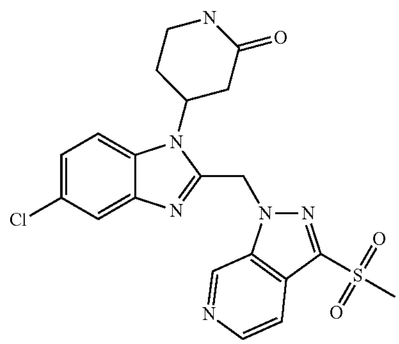 [SMILES: CS(=O)(=O)c1nn(Cc2nc3cc(Cl)ccc3n2C2CCNC(=O)C2)c2cnccc12] | 4-(5-Chloro-2-{[3-(methylsulfonyl)-1H-pyrazolo[3,4-c]pyridin-1-yl]methyl}-1H-benzimidazol-1-yl)piperidin-2-one | 0.00735 |
| 2-5 | 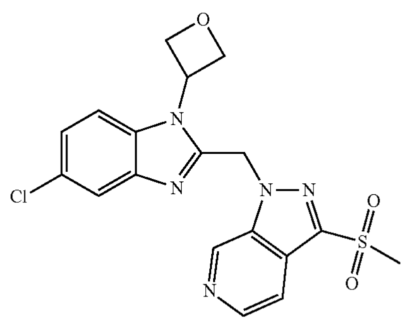 [SMILES: CS(=O)(=O)c1nn(Cc2nc3cc(Cl)ccc3n2C2COC2)c2cnccc12] | 1-{[5-Chloro-1-(oxetan-3-yl)-1H-benzimidazol-2-yl]methyl}-3-(methylsulfonyl)-1H-pyrazolo[3,4-c]pyridine | 0.02238 |
| 2-6 | 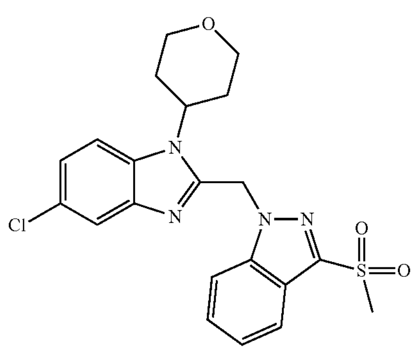 [SMILES: CS(=O)(=O)c1nn(Cc2nc3cc(Cl)ccc3n2C2CCOCC2)c2ccccc12] | 1-{[5-Chloro-1-(tetrahydro-2H-pyran-4-yl)-1H-benzimidazol-2-yl]methyl}-3-(methylsulfonyl)-1H-indazole | 0.02181 |
| 2-7 | 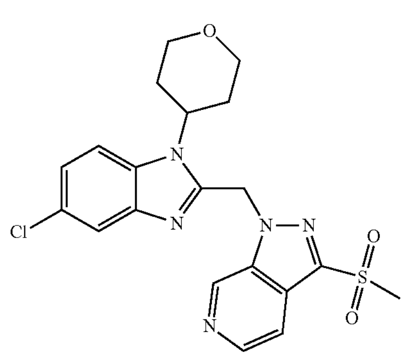 [SMILES: CS(=O)(=O)c1nn(Cc2nc3cc(Cl)ccc3n2C2CCOCC2)c2cnccc12] | 1-{[5-Chloro-1-(tetrahydro-2H-pyran-4-yl)-1H-benzimidazol-2-yl]methyl}-3-(methylsulfonyl)-1H-pyrazolo[3,4-c]pyridine | 0.00772 |

TABLE 1-continued

Structure, name and activity data of particular compounds

| Example No. | Structure | Name | CPE Long EC50 (μM) |
|---|---|---|---|
| 2-8 | 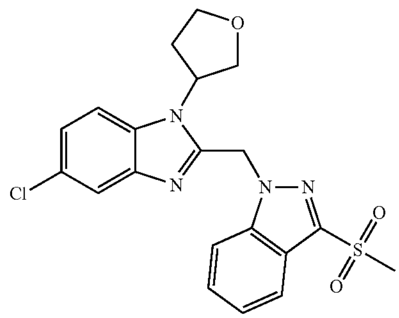 [SMILES: CS(=O)(=O)c1nn(Cc2nc3cc(Cl)ccc3n2C2CCOC2)c2ccccc12] | 1-{[5-Chloro-1-(tetrahydrofuran-3-yl)-1H-benzimidazol-2-yl]methyl}-3-(methylsulfonyl)-1H-indazole | 0.0361 |
| 2-9 | 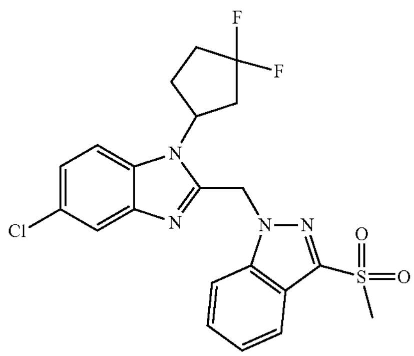 [SMILES: CS(=O)(=O)c1nn(Cc2nc3cc(Cl)ccc3n2C2CCC(F)(F)C2)c2ccccc12] | 1-{[5-Chloro-1-(3,3-difluorocyclopentyl)-1H-benzimidazol-2-yl]methyl}-3-(methylsulfonyl)-1H-indazole | 0.00697 |
| 2-10 | 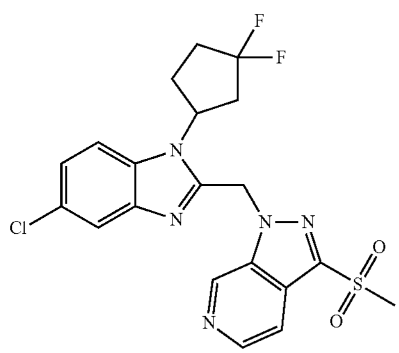 [SMILES: CS(=O)(=O)c1nn(Cc2nc3cc(Cl)ccc3n2C2CCC(F)(F)C2)c2cnccc12] | 1-{[5-Chloro-1-(3,3-difluorocyclopentyl)-1H-benzimidazol-2-yl]methyl}-3-(methylsulfonyl)-1H-pyrazolo[3,4-c]pyridine | 0.01433 |
| 2-11 | 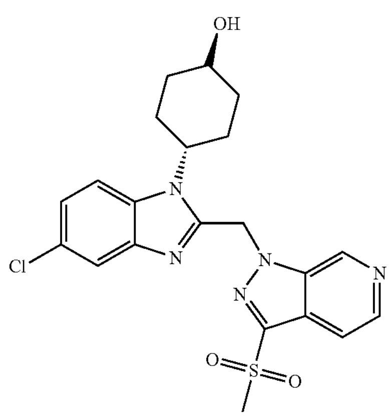 | 4-(5-Chloro-2-{[3-(methylsulfonyl)-1H-pyrazolo[3,4-c]pyridin-1-yl]methyl}-1H-benzimidazol-1-yl)cyclohexanol | 0.0082 |

TABLE 1-continued

Structure, name and activity data of particular compounds

| Example No. | Structure | Name | CPE Long EC50 (μM) |
|---|---|---|---|
| 2-12 | 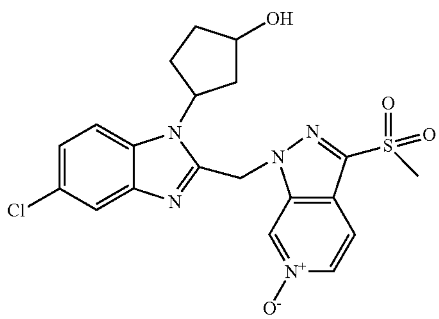 [SMILES: CS(=O)(=O)c1nn(Cc2nc3cc(Cl)ccc3n2C2CCC(O)C2)c2c[n+]([O-])ccc12] | 3-(5-Chloro-2-{[3-(methylsulfonyl)-6-oxido-1H-pyrazolo[3,4-c]pyridin-1-yl]methyl}-1H-benzimidazol-1-yl)cyclopentanol | 0.76896 |
| 2-13 | 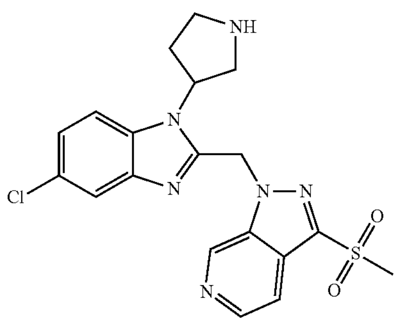 [SMILES: CS(=O)(=O)c1nn(Cc2nc3cc(Cl)ccc3n2C2CCNC2)c2cnccc12] | 1-{[5-Chloro-1-(pyrrolidin-3-yl)-1H-benzimidazol-2-yl]methyl}-3-(methylsulfonyl)-1H-pyrazolo[3,4-c]pyridine | 0.04423 |
| 2-14 | 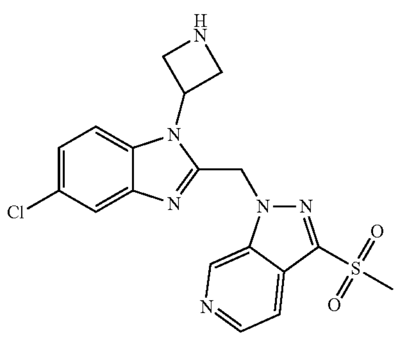 [SMILES: CS(=O)(=O)c1nn(Cc2nc3cc(Cl)ccc3n2C2CNC2)c2cnccc12] | 1-{[1-(Azetidin-3-yl)-5-chloro-1H-benzimidazol-2-yl]methyl}-3-(methylsulfonyl)-1H-pyrazolo[3,4-c]pyridine | 0.70808 |
| 2-15 | 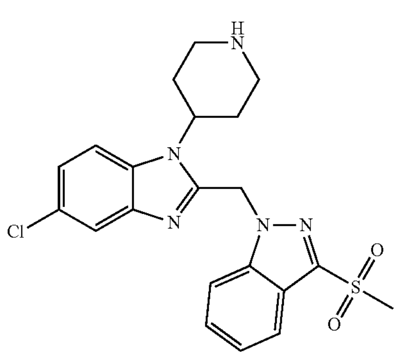 [SMILES: CS(=O)(=O)c1nn(Cc2nc3cc(Cl)ccc3n2C2CCNCC2)c2ccccc12] | 1-{[5-Chloro-1-(piperidin-4-yl)-1H-benzimidazol-2-yl]methyl}-3-(methylsulfonyl)-1H-indazole | 0.59081 |

TABLE 1-continued

Structure, name and activity data of particular compounds

| Example No. | Structure | Name | CPE Long EC50 (μM) |
|---|---|---|---|
| 2-16 | 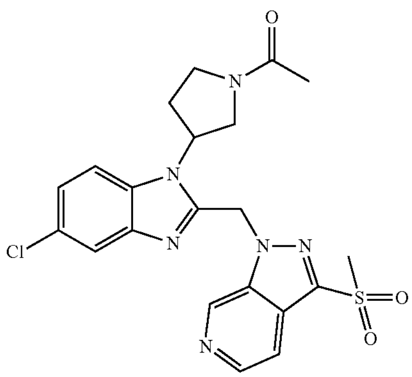 [SMILES: CC(=O)N1CCC(n2c(Cn3nc(S(C)(=O)=O)c4ccncc43)nc3cc(Cl)ccc32)C1] | 1-[3-(5-Chloro-2-{[3-(methylsulfonyl)-1H-pyrazolo[3,4-c]pyridin-1-yl]methyl}-1H-benzimidazol-1-yl)pyrrolidin-1-yl]ethanone | 0.01635 |
| 2-17 | 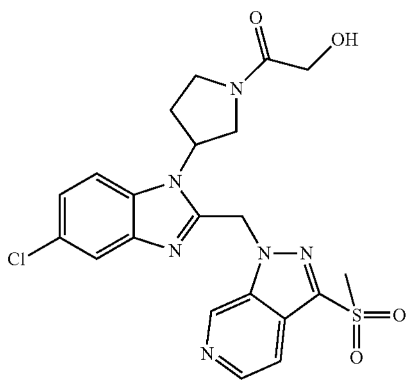 [SMILES: CS(=O)(=O)c1nn(Cc2nc3cc(Cl)ccc3n2C2CCN(C(=O)CO)C2)c2cnccc12] | 1-[3-(5-Chloro-2-{[3-(methylsulfonyl)-1H-pyrazolo[3,4-c]pyridin-1-yl]methyl}-1H-benzimidazol-1-yl)pyrrolidin-1-yl]-2-hydroxyethanone | 0.01093 |
| 2-18 | 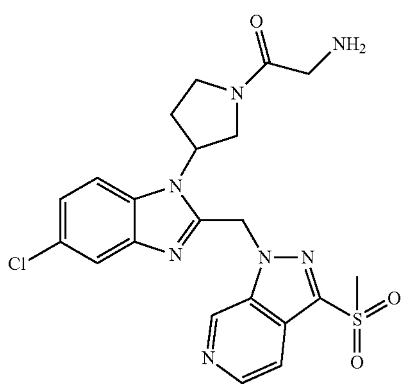 [SMILES: CS(=O)(=O)c1nn(Cc2nc3cc(Cl)ccc3n2C2CCN(C(=O)CN)C2)c2cnccc12] | 2-Amino-1-[3-(5-chloro-2-{[3-(methylsulfonyl)-1H-pyrazolo[3,4-c]pyridin-1-yl]methyl}-1H-benzimidazol-1-yl)pyrrolidin-1-yl]ethanone | 0.03602 |
| 2-19 | 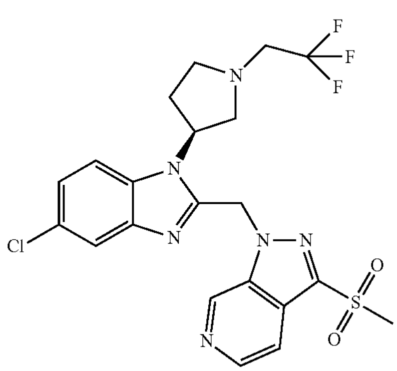 [SMILES: CS(=O)(=O)c1nn(Cc2nc3cc(Cl)ccc3n2[C@H]2CCN(CC(F)(F)F)C2)c2cnccc12] | 1-({5-Chloro-1-[(3S)-1-(2,2,2-trifluoroethyl)pyrrolidin-3-yl]-1H-benzimidazol-2-yl}methyl)-3-(methylsulfonyl)-1H-pyrazolo[3,4-c]pyridine | 1.174 |

TABLE 1-continued

Structure, name and activity data of particular compounds

| Example No. | Structure | Name | CPE Long EC50 (μM) |
|---|---|---|---|
| 2-20 | 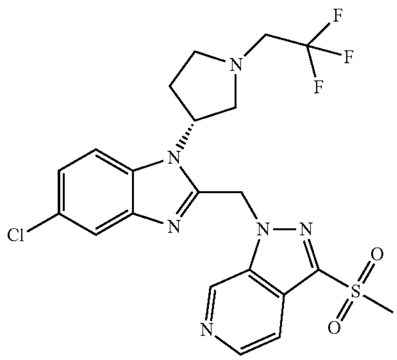 [SMILES: CS(=O)(=O)c1nn(Cc2nc3cc(Cl)ccc3n2[C@@H]2CCN(CC(F)(F)F)C2)c2cnccc12] | 1-({5-Chloro-1-[(3R)-1-(2,2,2-trifluoroethyl)pyrrolidin-3-yl]-1H-benzimidazol-2-yl}methyl)-3-(methylsulfonyl)-1H-pyrazolo[3,4-c]pyridine | 0.188 |
| 2-21 | 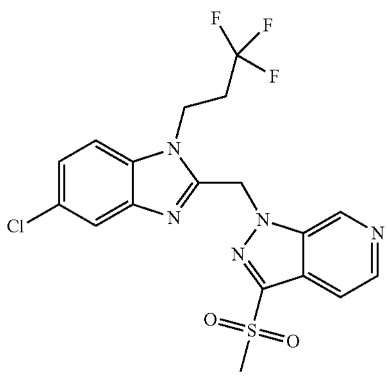 [SMILES: CS(=O)(=O)c1nn(Cc2nc3cc(Cl)ccc3n2CCC(F)(F)F)c2cnccc12] | 1-{[5-Chloro-1-(3,3,3-trifluoropropyl)-1H-benzimidazol-2-yl]methyl}-3-(methylsulfonyl)-1H-pyrazolo[3,4-c]pyridine | 0.01908 |
| 2-22 | 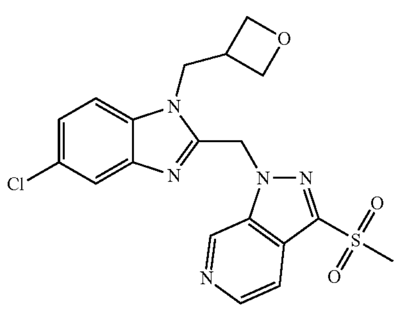 [SMILES: CS(=O)(=O)c1nn(Cc2nc3cc(Cl)ccc3n2CC2COC2)c2cnccc12] | 1-{[5-Chloro-1-(oxetan-3-ylmethyl)-1H-benzimidazol-2-yl]methyl}-3-(methylsulfonyl)-1H-pyrazolo[3,4-c]pyridine | 0.006 |
| 2-23 | 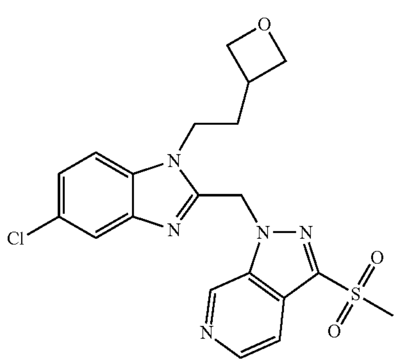 [SMILES: CS(=O)(=O)c1nn(Cc2nc3cc(Cl)ccc3n2CCC2COC2)c2cnccc12] | 1-({5-Chloro-1-[2-(oxetan-3-yl)ethyl]-1H-benzimidazol-2-yl}methyl)-3-(methylsulfonyl)-pyrazolo[3,4-c]pyridine | 0.006 |

TABLE 1-continued

Structure, name and activity data of particular compounds

| Example No. | Structure | Name | CPE Long EC50 (μM) |
|---|---|---|---|
| 2-24 | 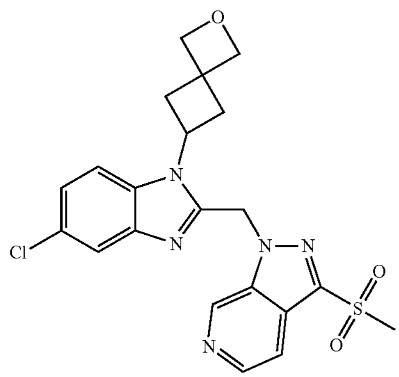 [SMILES: CS(=O)(=O)c1nn(Cc2nc3cc(Cl)ccc3n2C2CC3(COC3)C2)c2cnccc12] | 1-{[5-Chloro-1-(2-oxaspiro[3.3]hept-6-yl)-1H-benzimidazol-2-yl]methyl}-3-(methylsulfonyl)-1H-pyrazolo[3,4-c]pyridine | 0.00866 |
| 2-25 | 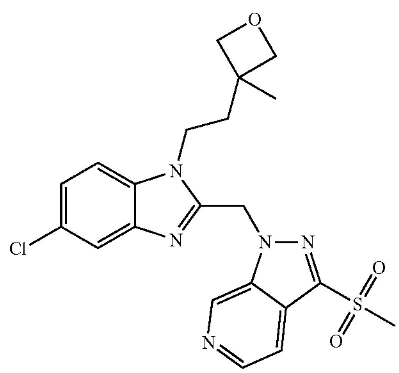 [SMILES: CC1(CCn2c(Cn3nc(S(C)(=O)=O)c4ccncc43)nc3cc(Cl)ccc32)COC1] | 1-({5-Chloro-1-[2-(3-methyloxetan-3-yl)ethyl]-1H-benzimidazol-2-yl}methyl)-3-(methylsulfonyl)-1H-pyrazolo[3,4-c]pyridine | 0.00679 |
| 2-26 | 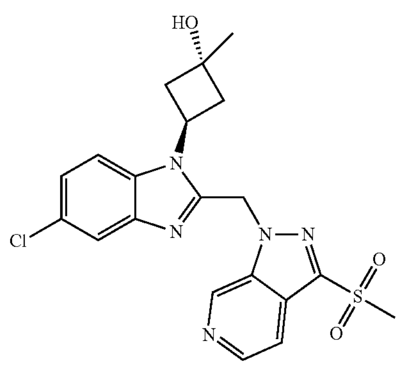 [SMILES: CS(=O)(=O)c1nn(Cc2nc3cc(Cl)ccc3n2[C@H]2C[C@](C)(O)C2)c2cnccc12] | trans-3-(5-Chloro-2-{[3-(methylsulfonyl)-1H-pyrazolo[3,4-c]pyridin-1-yl]methyl}-1H-benzimidazol-1-yl)-1-methylcyclobutanol | 0.007 |
| 2-27 | 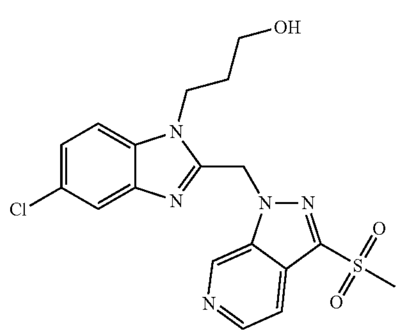 [SMILES: CS(=O)(=O)c1nn(Cc2nc3cc(Cl)ccc3n2CCCO)c2cnccc12] | 3-(5-Chloro-2-{[3-(methylsulfonyl)-1H-pyrazolo[3,4-c]pyridin-1-yl]methyl}-1H-benzimidazol-1-yl)propan-1-ol | 0.00753 |

TABLE 1-continued

Structure, name and activity data of particular compounds

| Example No. | Structure | Name | CPE Long EC50 (μM) |
|---|---|---|---|
| 2-28 | 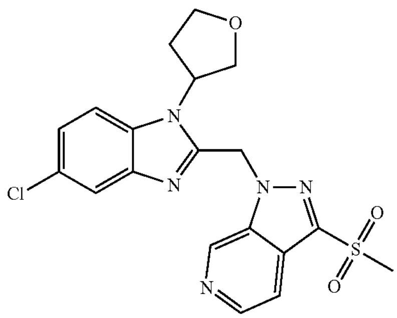 [SMILES: CS(=O)(=O)c1nn(Cc2nc3cc(Cl)ccc3n2C2CCOC2)c2cnccc12] | 1-{[5-Chloro-1-(tetrahydrofuran-3-yl)-1H-benzimidazol-2-yl]methyl}-3-(methylsulfonyl)-1H-pyrazolo[3,4-c]pyridine | 0.00757 |
| 2-29 | 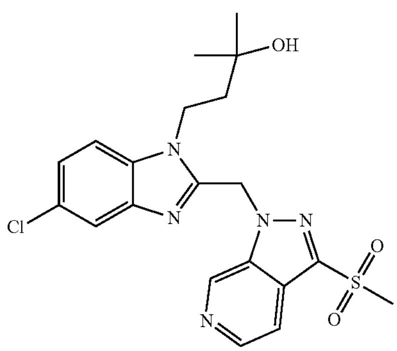 [SMILES: CC(C)(O)CCn1c(Cn2nc(S(C)(=O)=O)c3ccncc32)nc2cc(Cl)ccc21] | 4-(5-Chloro-2-{[3-(methylsulfonyl)-1H-pyrazolo[3,4-c]pyridin-1-yl]methyl}-1H-benzimidazol-1-yl)-2-methylbutan-2-ol | 0.00804 |
| 2-30 | 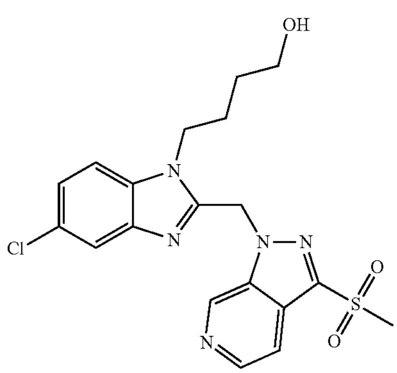 [SMILES: CS(=O)(=O)c1nn(Cc2nc3cc(Cl)ccc3n2CCCCO)c2cnccc12] | 4-(5-Chloro-2-{[3-(methylsulfonyl)-1H-pyrazolo[3,4-c]pyridin-1-yl]methyl}-1H-benzimidazol-1-yl)butan-1-ol | 0.00481 |
| 2-31 | 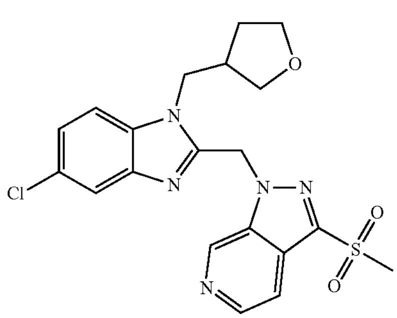 [SMILES: CS(=O)(=O)c1nn(Cc2nc3cc(Cl)ccc3n2CC2CCOC2)c2cnccc12] | 1-{[5-Chloro-1-(tetrahydrofuran-3-ylmethyl)-1H-benzimidazol-2-yl]methyl}-3-(methylsulfonyl)-1H-pyrazolo[3,4-c]pyridine | 0.00434 |

TABLE 1-continued

Structure, name and activity data of particular compounds

| Example No. | Structure | Name | CPE Long EC50 (μM) |
|---|---|---|---|
| 2-32 | 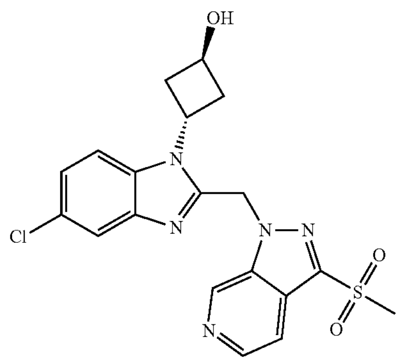 [SMILES: CS(=O)(=O)c1nn(Cc2nc3cc(Cl)ccc3n2[C@H]2C[C@H](O)C2)c2cnccc12] | trans-3-(5-Chloro-2-{[3-(methylsulfonyl)-1H-pyrazolo[3,4-c]pyridin-1-yl]methyl}-1H-benzimidazol-1-yl)cyclobutanol | 0.00332 |
| 2-33 | 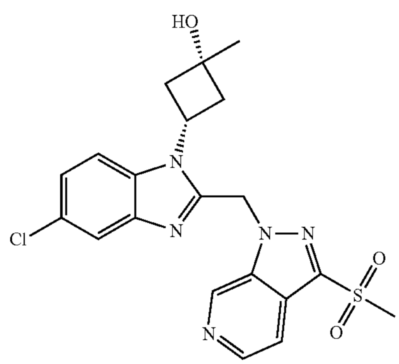 [SMILES: CS(=O)(=O)c1nn(Cc2nc3cc(Cl)ccc3n2[C@H]2C[C@@](C)(O)C2)c2cnccc12] | cis-3-(5-Chloro-2-{[3-(methylsulfonyl)-1H-pyrazolo[3,4-c]pyridin-1-yl]methyl}-1H-benzimidazol-1-yl)-1-methylcyclobutanol | 0.00985 |
| 2-34 | 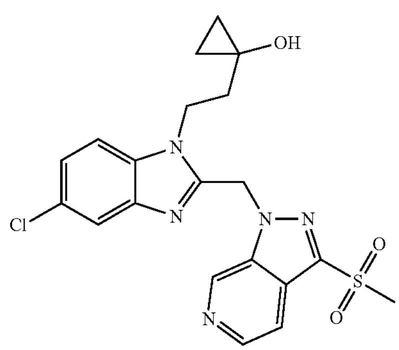 [SMILES: CS(=O)(=O)c1nn(Cc2nc3cc(Cl)ccc3n2CCC2(O)CC2)c2cnccc12] | 1-[2-(5-Chloro-2-{[3-(methylsulfonyl)-1H-pyrazolo[3,4-c]pyridin-1-yl]methyl}-1H-benzimidazol-1-yl)ethyl]cyclopropanol | 0.0087 |
| 2-35 | 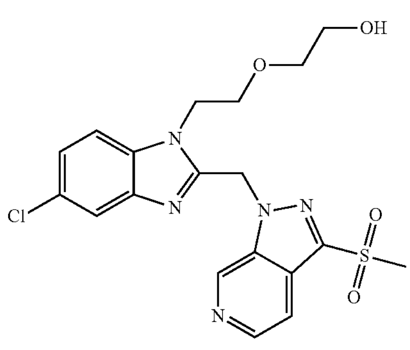 [SMILES: CS(=O)(=O)c1nn(Cc2nc3cc(Cl)ccc3n2CCOCCO)c2cnccc12] | 2-[2-(5-chloro-2-{[3-(methylsulfonyl)-1H-pyrazolo[3,4-c]pyridin-1-yl]methyl}-1H-benzimidazol-1-yl)ethoxy]ethanol | 0.015 |

TABLE 1-continued

Structure, name and activity data of particular compounds

| Example No. | Structure | Name | CPE Long EC50 (μM) |
|---|---|---|---|
| 2-36 | 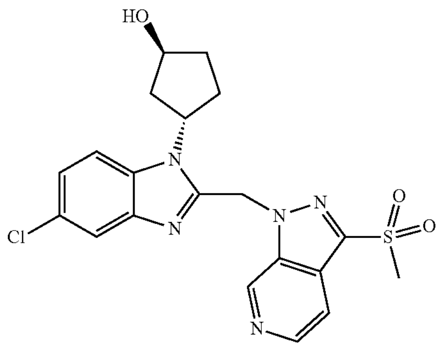 [SMILES: CS(=O)(=O)c1nn(Cc2nc3cc(Cl)ccc3n2[C@H]2CC[C@H](O)C2)c2cnccc12] | trans-3-(5-chloro-2-{[3-(methylsulfonyl)-1H-pyrazolo[3,4-c]pyridin-1-yl]methyl}-1H-benzimidazol-1-yl)cyclopentanol | 0.002 |
| 2-37 | 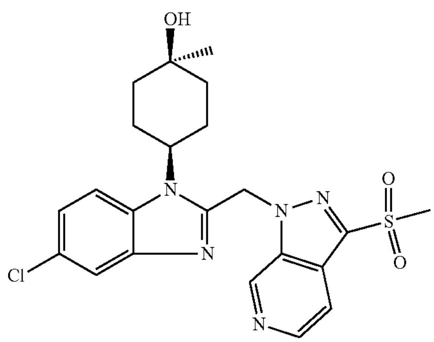 [SMILES: CS(=O)(=O)c1nn(Cc2nc3cc(Cl)ccc3n2[C@H]2CC[C@@](C)(O)CC2)c2cnccc12] | cis-4-(5-chloro-2-{[3-(methylsulfonyl)-1H-pyrazolo[3,4-c]pyridin-1-yl]methyl}-1H-benzimidazol-1-yl)-1-methylcyclohexanol | 0.006 |
| 2-38 | 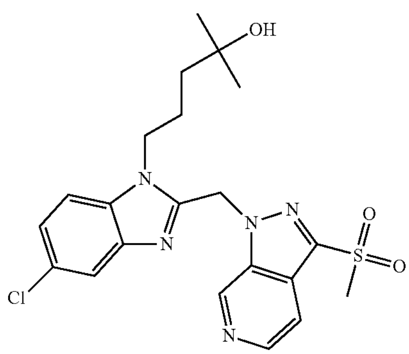 [SMILES: CC(C)(O)CCCn1c(Cn2nc(S(C)(=O)=O)c3ccncc32)nc2cc(Cl)ccc21] | 5-(5-chloro-2-{[3-(methylsulfonyl)-1H-pyrazolo[3,4-c]pyridin-1-yl]methyl}-1H-benzimidazol-1-yl)-2-methylpentan-2-ol | 0.008 |
| 2-39 | 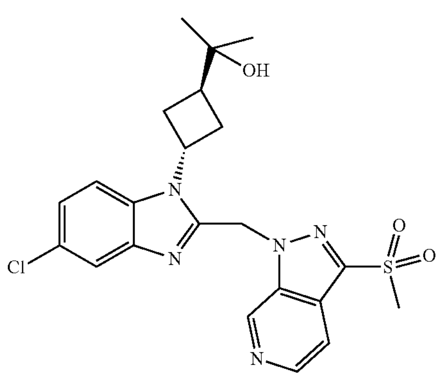 [SMILES: CC(C)(O)[C@H]1C[C@H](n2c(Cn3nc(S(C)(=O)=O)c4ccncc43)nc3cc(Cl)ccc32)C1] | 2-[trans-3-(5-chloro-2-{[3-(methylsulfonyl)-1H-pyrazolo[3,4-c]pyridin-1-yl]methyl}-1H-benzimidazol-1-yl)cyclobutyl]propan-2-ol | 0.002 |

TABLE 1-continued

Structure, name and activity data of particular compounds

| Example No. | Structure | Name | CPE Long EC50 (μM) |
|---|---|---|---|
| 2-40 | 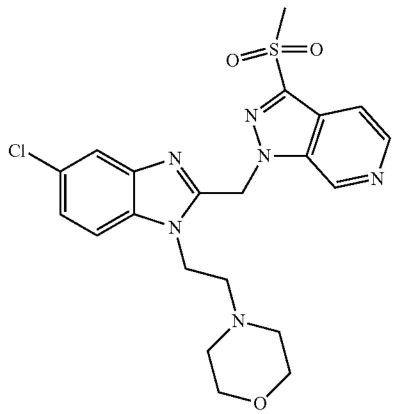 [SMILES: CS(=O)(=O)c1nn(Cc2nc3cc(Cl)ccc3n2CCN2CCOCC2)c2cnccc12] | 1-({5-chloro-1-[2-(morpholin-4-yl)ethyl]-1H-benzimidazol-2-yl}methyl)-3-(methylsulfonyl)-1H-pyrazolo[3,4-c]pyridine | 0.013 |
| 2-41 | 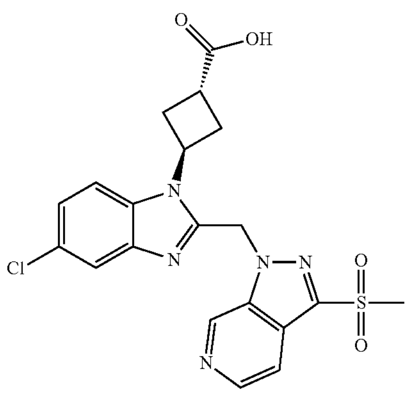 [SMILES: CS(=O)(=O)c1nn(Cc2nc3cc(Cl)ccc3n2[C@H]2C[C@H](C(=O)O)C2)c2cnccc12] | trans-3-(5-chloro-2-{[3-(methylsulfonyl)-1H-pyrazolo[3,4-c]pyridin-1-yl]methyl}-1H-benzimidazol-1-yl)cyclobutanecarboxylic acid | 0.007 |
| 2-42 | 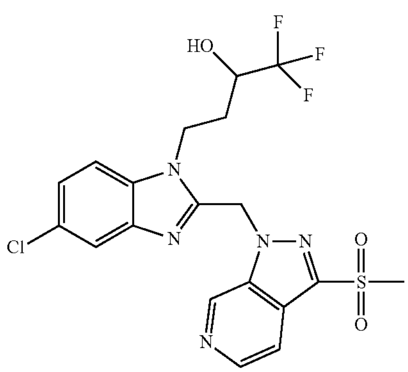 [SMILES: CS(=O)(=O)c1nn(Cc2nc3cc(Cl)ccc3n2CCC(O)C(F)(F)F)c2cnccc12] | 4-(5-chloro-2-{[3-(methylsulfonyl)-1H-pyrazolo[3,4-c]pyridin-1-yl]methyl}-1H-benzimidazol-1-yl)-1,1,1-trifluorobutan-2-ol | 0.0016 |
| 2-43 | 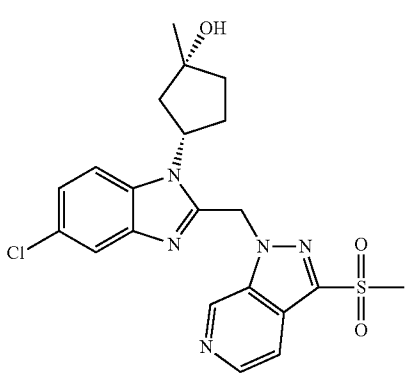 [SMILES: C[C@@]1(O)CC[C@H](n2c(Cn3nc(S(C)(=O)=O)c4ccncc43)nc3cc(Cl)ccc32)C1] | cis-3-(5-chloro-2-{[3-(methylsulfonyl)-1H-pyrazolo[3,4-c]pyridin-1-yl]methyl}-1H-benzimidazol-1-yl)-1-methylcyclopentanol | 0.0179 |

TABLE 1-continued

Structure, name and activity data of particular compounds

| Example No. | Structure | Name | CPE Long EC50 (μM) |
|---|---|---|---|
| 2-44 | 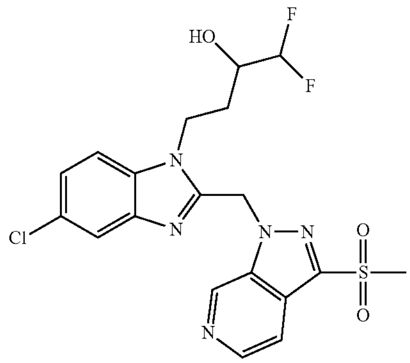 [SMILES: CS(=O)(=O)c1nn(Cc2nc3cc(Cl)ccc3n2CCC(O)C(F)F)c2cnccc12] | 4-(5-chloro-2-{[3-(methylsulfonyl)-1H-pyrazolo[3,4-c]pyridin-1-yl]methyl}-1H-benzimidazol-1-yl)-1,1-difluorobutan-2-ol | 0.0033 |
| 2-45 | 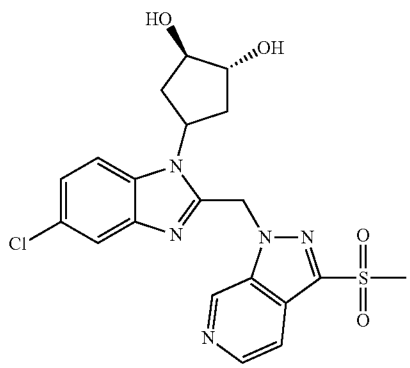 [SMILES: CS(=O)(=O)c1nn(Cc2nc3cc(Cl)ccc3n2C2C[C@@H](O)[C@H](O)C2)c2cnccc12] | trans-4-(5-chloro-2-{[3-(methylsulfonyl)-1H-pyrazolo[3,4-c]pyridin-1-yl]methyl}-1H-benzimidazol-1-yl)cyclopentane-1,2-diol | 0.0061 |
| 2-46 | 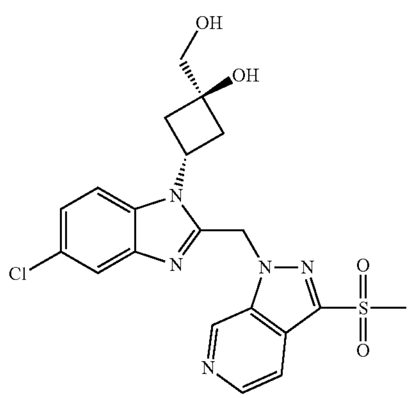 [SMILES: CS(=O)(=O)c1nn(Cc2nc3cc(Cl)ccc3n2[C@H]2C[C@@](O)(CO)C2)c2cnccc12] | trans-3-(5-chloro-2-{[3-(methylsulfonyl)-1H-pyrazolo[3,4-c]pyridin-1-yl]methyl}-1H-benzimidazol-1-yl)-1-(hydroxymethyl)cyclobutanol | 0.0072 |
| 3-1 | 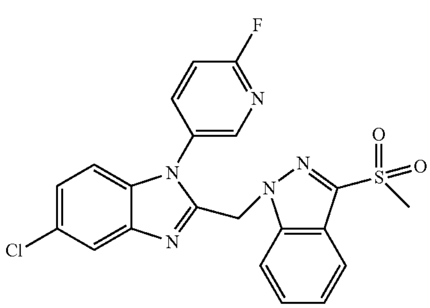 [SMILES: CS(=O)(=O)c1nn(Cc2nc3cc(Cl)ccc3n2-c2ccc(F)nc2)c2ccccc12] | 1-{[5-Chloro-1-(6-fluoropyridin-3-yl)-1H-benzimidazol-2-yl]methyl}-3-(methylsulfonyl)-1H-indazole | 0.00986 |

TABLE 1-continued

Structure, name and activity data of particular compounds

| Example No. | Structure | Name | CPE Long EC50 (μM) |
|---|---|---|---|
| 3-2 | 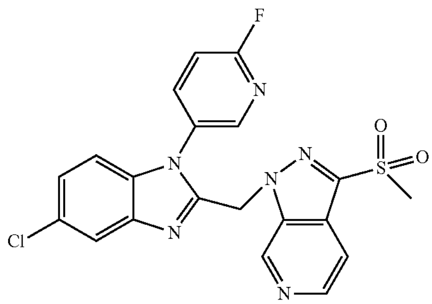 [SMILES: CS(=O)(=O)c1nn(Cc2nc3cc(Cl)ccc3n2-c2ccc(F)nc2)c2cnccc12] | 1-{[5-Chloro-1-(6-fluoropyridin-3-yl)-1H-benzimidazol-2-yl]methyl}-3-(methylsulfonyl)-1H-pyrazolo[3,4-c]pyridine | 0.01868 |
| 3-3 | 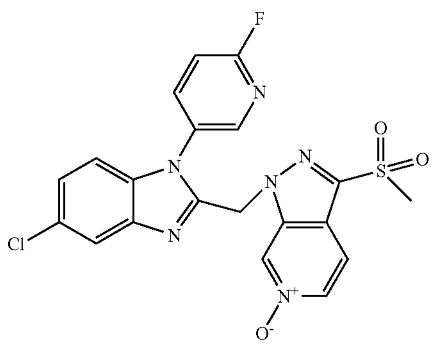 [SMILES: CS(=O)(=O)c1nn(Cc2nc3cc(Cl)ccc3n2-c2ccc(F)nc2)c2c[n+]([O-])ccc12] | 1-{[5-Chloro-1-(6-fluoropyridin-3-yl)-1H-benzimidazol-2-yl]methyl}-3-(methylsulfonyl)-1H-pyrazolo[3,4-c]pyridine 6-oxide | 1.53842 |
| 3-4 | 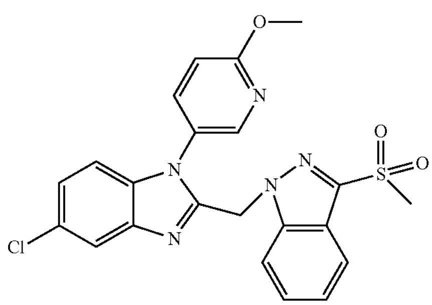 [SMILES: COc1ccc(-n2c(Cn3nc(S(C)(=O)=O)c4ccccc43)nc3cc(Cl)ccc32)cn1] | 1-{[5-Chloro-1-(6-methoxypyridin-3-yl)-1H-benzimidazol-2-yl]methyl}-3-(methylsulfonyl)-1H-indazole | 0.03349 |
| 3-5 | 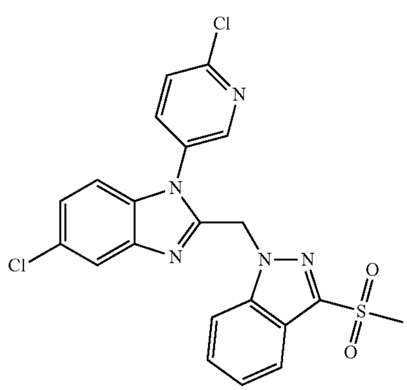 [SMILES: CS(=O)(=O)c1nn(Cc2nc3cc(Cl)ccc3n2-c2ccc(Cl)nc2)c2ccccc12] | 1-{[5-Chloro-1-(6-chloropyridin-3-yl)-1H-benzimidazol-2-yl]methyl}-3-(methylsulfonyl)-1H-indazole | 0.01809 |

TABLE 1-continued

Structure, name and activity data of particular compounds

| Example No. | Structure | Name | CPE Long EC50 (μM) |
|---|---|---|---|
| 4-1 | 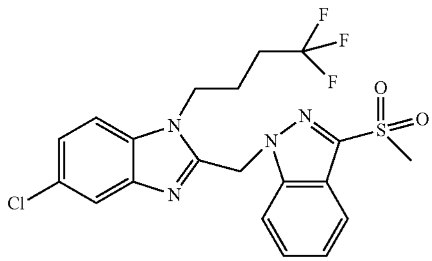 [SMILES: CS(=O)(=O)c1nn(Cc2nc3cc(Cl)ccc3n2CCCC(F)(F)F)c2ccccc12] | 1-{[5-Chloro-1-(4,4,4-trifluorobutyl)-1H-benzimidazol-2-yl]methyl}-3-(methylsulfonyl)-1H-indazole | 0.0146 |
| 4-2 | 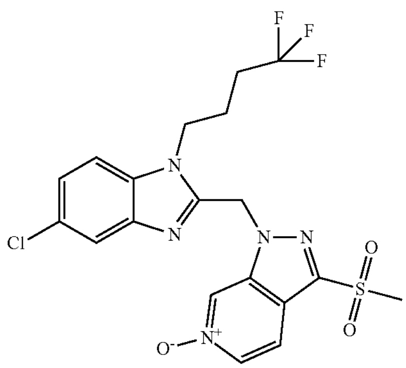 [SMILES: CS(=O)(=O)c1nn(Cc2nc3cc(Cl)ccc3n2CCCC(F)(F)F)c2c[n+]([O-])ccc12] | 1-{[5-Chloro-1-(4,4,4-trifluorobutyl)-1H-benzimidazol-2-yl]methyl}-3-(methylsulfonyl)-1H-pyrazolo[3,4-c]pyridine 6-oxide | 0.01595 |
| 4-3 | 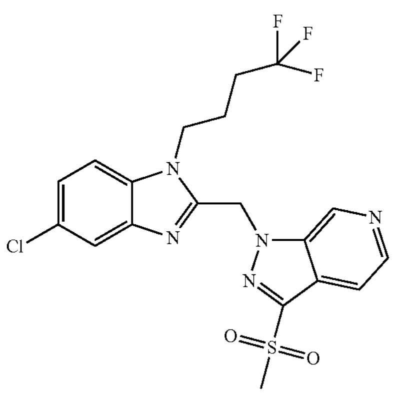 [SMILES: CS(=O)(=O)c1nn(Cc2nc3cc(Cl)ccc3n2CCCC(F)(F)F)c2cnccc12] | 1-{[5-Chloro-1-(4,4,4-trifluorobutyl)-1H-benzimidazol-2-yl]methyl}-3-(methylsulfonyl)-1H-pyrazolo[3,4-c]pyridine | 0.005 |
| 5-1 | 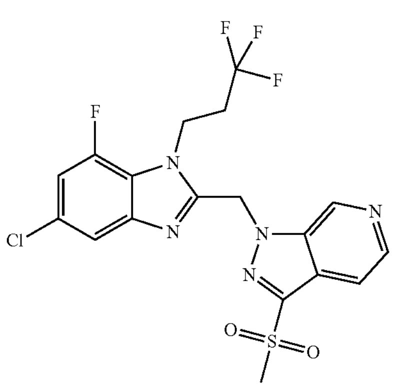 [SMILES: CS(=O)(=O)c1nn(Cc2nc3cc(Cl)cc(F)c3n2CCC(F)(F)F)c2cnccc12] | 1-{[5-Chloro-7-fluoro-1-(3,3,3-trifluoropropyl)-1H-benzimidazol-2-yl]methyl}-3-(methylsulfonyl)-1H-pyrazolo[3,4-c]pyridine | 0.017 |

TABLE 1-continued

Structure, name and activity data of particular compounds

| Example No. | Structure | Name | CPE Long EC50 (μM) |
|---|---|---|---|
| 5-2 | 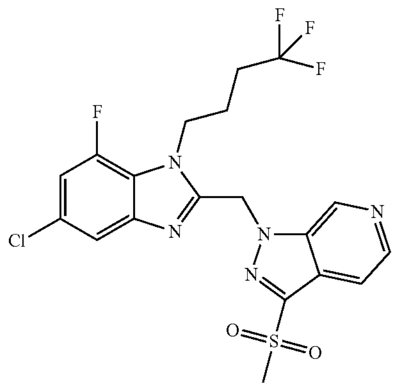 [SMILES: CS(=O)(=O)c1nn(Cc2nc3cc(Cl)cc(F)c3n2CCCC(F)(F)F)c2cnccc12] | 1-{[5-Chloro-7-fluoro-1-(4,4,4-trifluorobutyl)-1H-benzimidazol-2-yl]methyl}-3-(methylsulfonyl)-1H-pyrazolo[3,4-c]pyridine | 0.007 |
| 6-1 | 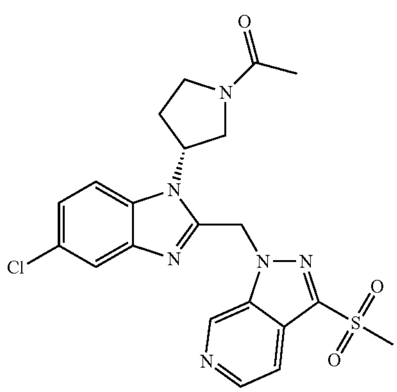 [SMILES: CC(=O)N1CC[C@@H](n2c(Cn3nc(S(C)(=O)=O)c4ccncc43)nc3cc(Cl)ccc32)C1] | 1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]ethanone | 0.007 |
| 6-2 | 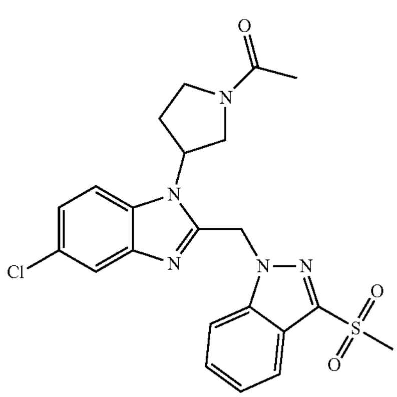 [SMILES: CC(=O)N1CCC(n2c(Cn3nc(S(C)(=O)=O)c4ccccc43)nc3cc(Cl)ccc32)C1] | 1-[3-(5-Chloro-2-{[3-(methylsulfonyl)-1H-indazol-1-yl]methyl}-1H-benzimidazol-1-yl)pyrrolidin-1-yl]ethanone | 0.00875 |

TABLE 1-continued

Structure, name and activity data of particular compounds

| Example No. | Structure | Name | CPE Long EC50 (μM) |
|---|---|---|---|
| 6-3 | Chiral | 1-[(3R)-3-(5-Chloro-2-{[3-(methylsulfonyl)-1H-indazol-1-yl]methyl}-1H-benzimidazol-1-yl)pyrrolidin-1-yl]propan-1-one | 0.00607 |
| 6-4 | Chiral | 1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]-2-methylpropan-1-one | 0.004 |
| 6-5 | Chiral | 1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]-2-hydroxy-2-methylpropan-1-one | 0.01298 |

TABLE 1-continued

Structure, name and activity data of particular compounds

| Example No. | Structure | Name | CPE Long EC50 (μM) |
|---|---|---|---|
| 6-6 | 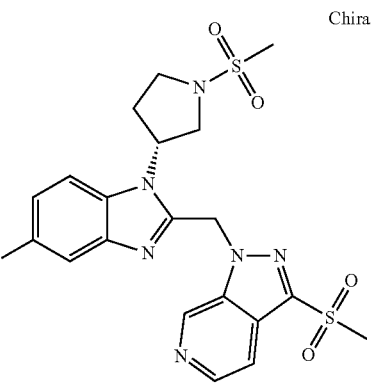 Chiral | 1-({5-Chloro-1-[(3R)-1-(methylsulfonyl)pyrrolidin-3-yl]-1H-benzimidazol-2-yl}methyl)-3-(methylsulfonyl)-1H-pyrazolo[3,4-c]pyridine | 0.003 |
| 6-7 | 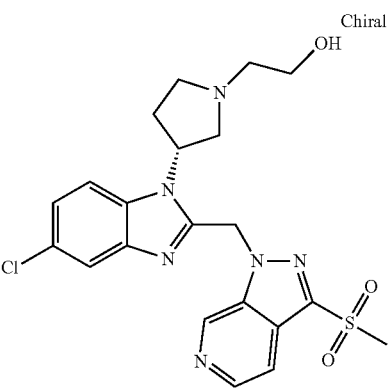 [SMILES: CS(=O)(=O)c1nn(Cc2nc3cc(Cl)ccc3n2[C@@H]2CCN(CCO)C2)c2cnccc12] Chiral | 2-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]ethanol | 0.00368 |
| 7 | 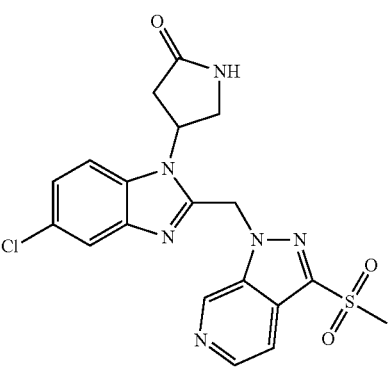 [SMILES: CS(=O)(=O)c1nn(Cc2nc3cc(Cl)ccc3n2C2CNC(=O)C2)c2cnccc12] | 4-(5-Chloro-2-{[3-(methylsulfonyl)-1H-pyrazolo[3,4-c]pyridin-1-yl]methyl}-1H-benzimidazol-1-yl)pyrrolidin-2-one | 0.00843 |

TABLE 1-continued

Structure, name and activity data of particular compounds

| Example No. | Structure | Name | CPE Long EC50 (μM) |
|---|---|---|---|
| 8 | 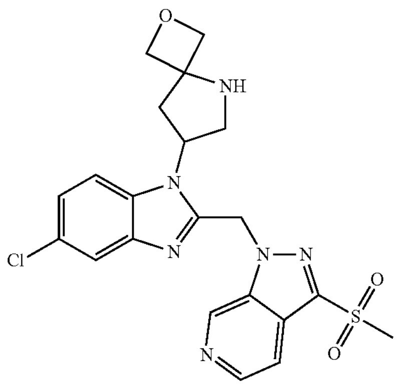 [SMILES: CS(=O)(=O)c1nn(Cc2nc3cc(Cl)ccc3n2C2CNC3(COC3)C2)c2cnccc12] | 1-{[5-Chloro-1-(2-oxa-5-azaspiro[3.4]oct-7-yl)-1H-benzimidazol-2-yl]methyl}-3-(methanesulfonyl)-1H-pyrazolo[3,4-c]pyridine | 0.01939 |
| 9-1 | 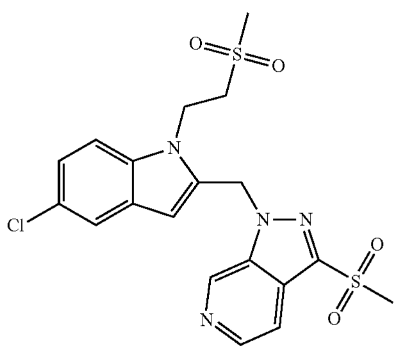 [SMILES: CS(=O)(=O)CCn1c(Cn2nc(S(C)(=O)=O)c3ccncc32)cc2cc(Cl)ccc21] | 1-({5-Chloro-1-[2-(methylsulfonyl)ethyl]-1H-indol-2-yl}methyl)-3-(methylsulfonyl)-1H-pyrazolo[3,4-c]pyridine | 0.00371 |
| 9-2 | 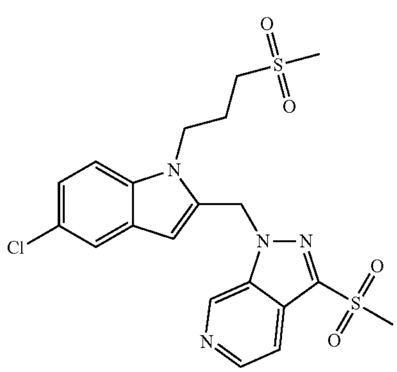 [SMILES: CS(=O)(=O)CCCn1c(Cn2nc(S(C)(=O)=O)c3ccncc32)cc2cc(Cl)ccc21] | 1-({5-Chloro-1-[3-(methylsulfonyl)propyl]-1H-indol-2-yl}methyl)-3-(methylsulfonyl)-1H-pyrazolo[3,4-c]pyridine | 0.00812 |
| 9-3 | 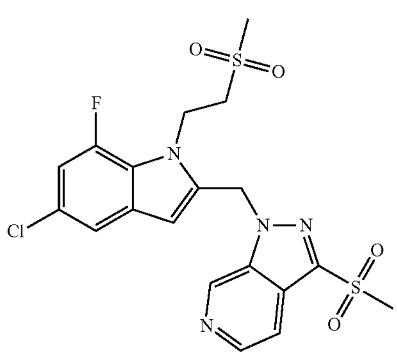 [SMILES: CS(=O)(=O)CCn1c(Cn2nc(S(C)(=O)=O)c3ccncc32)cc2cc(Cl)cc(F)c21] | 1-({5-Chloro-7-fluoro-1-[2-(methylsulfonyl)ethyl]-1H-indol-2-yl}methyl)-3-(methylsulfonyl)-1H-pyrazolo[3,4-c]pyridine | 0.00721 |

TABLE 1-continued

Structure, name and activity data of particular compounds

| Example No. | Structure | Name | CPE Long EC50 (μM) |
|---|---|---|---|
| 10-1 | 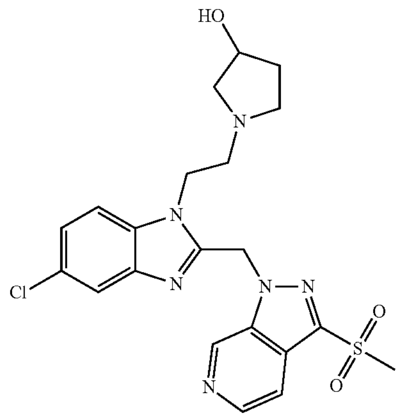 [SMILES: CS(=O)(=O)c1nn(Cc2nc3cc(Cl)ccc3n2CCN2CCC(O)C2)c2cnccc12] | 1-[2-(5-chloro-2-{[3-(methylsulfonyl)-1H-pyrazolo[3,4-c]pyridin-1-yl]methyl}-1H-benzimidazol-1-yl)ethyl]pyrrolidin-3-ol | 0.006 |
| 10-2 | 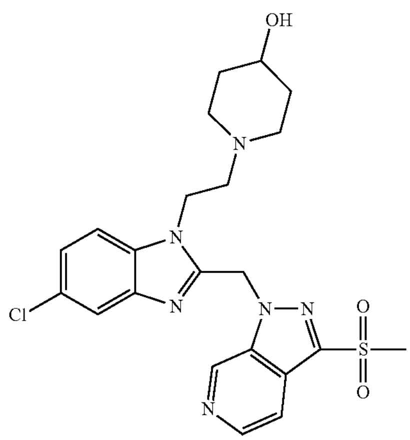 [SMILES: CS(=O)(=O)c1nn(Cc2nc3cc(Cl)ccc3n2CCN2CCC(O)CC2)c2cnccc12] | 1-[2-(5-chloro-2-{[3-(methylsulfonyl)-1H-pyrazolo[3,4-c]pyridin-1-yl]methyl}-1H-benzimidazol-1-yl)ethyl]piperidin-4-ol | 0.0035 |
| 11 | 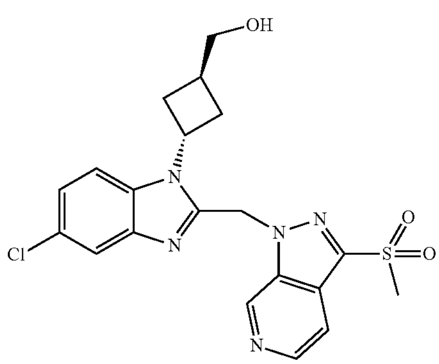 [SMILES: CS(=O)(=O)c1nn(Cc2nc3cc(Cl)ccc3n2[C@H]2C[C@H](CO)C2)c2cnccc12] | [trans-3-(5-chloro-2-{[3-(methylsulfonyl)-1H-pyrazolo[3,4-c]pyridin-1-yl]methyl}-1H-benzimidazol-1-yl)cyclobutyl]methanol | 0.003 |

TABLE 1-continued

Structure, name and activity data of particular compounds

| Example No. | Structure | Name | CPE Long EC50 (μM) |
|---|---|---|---|
| 12 | Chiral | 1-({5-chloro-1-[(3R)-1,1-dioxidotetrahydrothiophen-3-yl]-7-fluoro-1H-benzimidazol-2-yl}methyl)-3-(methylsulfonyl)-1H-pyrazolo[3,4-c]pyridine | 0.002 |
| 13 | 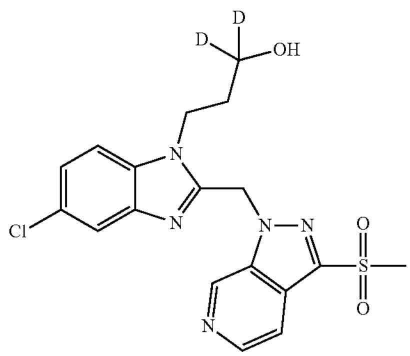 [SMILES: [2H]C([2H])(O)CCn1c(Cn2nc(S(C)(=O)=O)c3ccncc32)nc2cc(Cl)ccc21] | 3-(5-chloro-2-{[3-(methylsulfonyl)-1H-pyrazolo[3,4-c]pyridin-1-yl]methyl}-1H-benzimidazol-1-yl)(1,1-$^2$H$_2$)propan-1-ol | 0.003 |
| 14 | 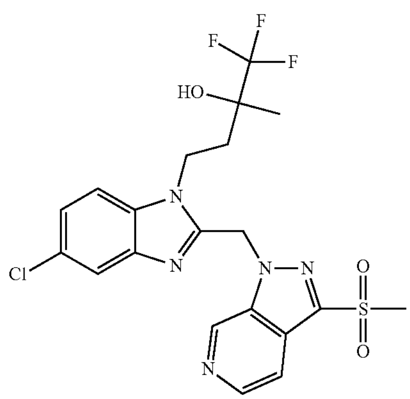 [SMILES: CC(O)(CCn1c(Cn2nc(S(C)(=O)=O)c3ccncc32)nc2cc(Cl)ccc21)C(F)(F)F] | 4-(5-chloro-2-{[3-(methylsulfonyl)-1H-pyrazolo[3,4-c]pyridin-1-yl]methyl}-1H-benzimidazol-1-yl)-1,1,1-trifluoro-2-methylbutan-2-ol | 0.0028 |
| 15-1 | Chiral | 1-{(1R)-1-[5-chloro-1-(3,3,3-trifluoropropyl)-1H-benzimidazol-2-yl]ethyl}-3-(methylsulfonyl)-1H-pyrazolo[3,4-c]pyridine | 0.227 |

TABLE 1-continued

Structure, name and activity data of particular compounds

| Example No. | Structure | Name | CPE Long EC50 (μM) |
|---|---|---|---|
| 15-2 | Chiral structure | 1-{(1S-1-[5-chloro-1-(3,3,3-trifluoropropyl)-1H-benzimidazol-2-yl]ethyl}-3-(methylsulfonyl)-1H-pyrazolo[3,4-c]pyridine | 0.068 |

TABLE 2

NMR and MS data of particular compounds

| Example No. | $^1$H NMR data | MW |
|---|---|---|
| 1-1 | $^1$H NMR (400 MHz, DMSO-d$_6$) δ ppm 8.21 (s, 1H), 7.84-7.86 (m, 1H), 7.50-7.67 (m, 3H), 7.17-7.32 (m, 4H), 6.00 (s, 2H), 4.80 (t, J = 5.6 Hz, 2H), 3.69 (t, J = 5.6 Hz, 2H), 3.25 (s, 3H), 3.09 (s, 3H) | MS obsd. (ESI$^+$) [(M + H)$^+$]: 432.1 |
| 1-2 | $^1$H NMR (400 MHz, DMSO-d6) δ ppm 8.29 (s, 1H), 7.80-7.86 (m, 1H), 7.65-7.73 (m, 3H), 7.26-7.34 (m, 3H), 5.92 (s, 2H), 4.86 (t, J = 7.6 Hz, 2H), 3,73 (br, 3H), 3.19 (t, J = 8.0 Hz, 2H), 2.96 (s, 3H), 2.08 (t, J = 7.6 Hz, 2H) | MS obsd. (ESI$^+$) [(M + H)$^+$]: 480.1 |
| 1-3 | $^1$H NMR (400 MHz, CD$_3$OD) δ ppm 8.22 (s, 1H), 7.69 (d, J = 9.0 Hz, 1H), 7.63-7.56 (m, 3H), 7.41-7.39 (m, 1H), 7.14-7.13 (m, 1H), 5.98 (s, 2H), 4.57 (t, J = 7.5 Hz, 2H), 3.24 (s, 3H), 3.20 (t, J = 7.5 Hz, 2H), 2.97 (s, 3H), 2.17 (t, J = 7.5 Hz, 2H) | MS obsd. (ESI$^+$) [(M + H)$^+$] 498.1 |
| 1-4 | $^1$H NMR (400 MHz, DMSO-d6) δ ppm: 8.47 (s, 2H), 8.28 (d, 1H), 7.75 (d, 1H), 7.64 (s, 1H), 7.40 (d, 1H), 7.32 (d, 1H), 5.96 (s, 2H), 4.57 (t, 2H), 3.29 (s, 3H), 3.26 (t, 2H), 2.99 (s, 3H), 2.23 (m, 2H) | MS obsd. (ESI$^+$) [(M + H)$^+$] 481.1 |
| 1-5 | $^1$H NMR (400 MHz, CDCl$_3$) δ ppm 8.14 (s, 1H), 7.77-7.24 (m, 7H), 5.93 (s, 2H) 4.50-4.49 (m, 2H), 3.25-3.06 (m, 4H), 2.89 (s, 3H), 2.06-2.04 (m, 2H), 1.33-1.28 (m, 3H) | MS obsd. (ESI$^+$) [(M + H)$^+$] 495.1 |
| 1-6 | $^1$H NMR (400 MHz, CDCl$_3$) δ ppm 8.10 (s, 1H), 7.89-7.29 (m, 7H), 5.91 (s, 2H) 4.47-4.44 (m, 2H), 3.35 (s 1H), 3.05-3.02 (m, 2H), 2.87 (s, 3H), 1.95 (m, 2H), 1.36-1.17 (m, 6H) | MS obsd. (ESI$^+$) [(M + H)$^+$] 509.1 |
| 1-7 | $^1$H NMR (400 MHz, CDCl$_3$) δ ppm 8.01 (s, 1H), 7.88 (d, J = 8.0 Hz, 1H), 7.72 (s, 1H) 7.63 (d, J = 8.5 Hz, 1H), 7.41-7.32 (m, 4H), 5.81 (s, 2H), 4.32 (t, J = 7.5 Hz, 2H), 2.82-2.79 (m, 5H), 2.67 (m, 1H), 1.78 (m, 2H), 1.37-1.36 (m, 2H), 1.07-1.05 (m, 2H) | MS obsd. (ESI$^+$) [(M + H)$^+$] 507.1 |
| 1-8 | $^1$H NMR (400 MHz, DMSO-d6) δ ppm 8.02 (d, J = 2.4 Hz, 1H), 7.95 (d, J = 6.2 Hz, 1H), 7.21 (d, J = 2.2 Hz, 1H), 7.66 (d, J = 6.6 Hz, 1H), 7.61 (t, 1H), 6.25 (s, 2H), 4.53 (t, 2H), 3.37 (s, 3H), 3.21 (t, 2H), 2.98 (s, 3H), 2.10 (m, 2H) | MS obsd. (ESI$^+$) [(M + H)$^+$] 481.1 |
| 1-9 | $^1$H NMR (400 MHz, DMSO-d6) δ ppm 8.01 (d, J = 8.0 Hz, 1 H), 7.97 (d, J = 8.0 Hz, 1 H), 7.71 (d, J = 8.5 Hz, 1 H), 7.62 (s, 1 H), 7.61 (d, J = 9.0 Hz, 1 H), 7.43 (t, J = 9.0 Hz, 1 H), 7.33 (m, 1 H), 6.29 (s, 2 H), 4.52 (t, J = 7.5 Hz, 2 H), 3.50 (m, 1 H), 3.24 (t, J = 8.0 Hz, 2 H), 2.30 (s, 3 H), 2.16 (m, 2 H), 1.22 (d, J = 6.5 Hz, 6 H) | MS obsd. (ESI$^+$) [(M + H)$^+$] 509.1 |
| 1-10 | $^1$H NMR (400 MHz, MeOD + CDCl$_3$) δ ppm 8.09 (d, J = 8.0 Hz, 1 H), 7.92 (d, J = 8.0 Hz, 1 H), 7.67 (s, 1 H), 7.65~7.56 (m, 2 H), 7.42 (d, J = 8.0 Hz, 1 H), 7.34 (m, 1 H), 6.13 (s, 2 H), 4.60 (t, J = 8.0 Hz, 2 H), 3.41~3.39 (m, 2 H), 3.22 (t, J = 8.0 Hz, 2 H), 2.96 (s, 3 H), 2.05 (m, 2 H), 1.32 (d, J = 7.5 Hz, 3 H) | MS obsd. (ESI$^+$) [(M + H)$^+$] 495.1 |
| 1-11 | $^1$H NMR (DMSO-d6) δ ppm 9.33 (s, 1H), 8.38 (d, J = 6.4 Hz, 1H), 7.62 (d, J = 2.4 Hz, 1H), 7.65 (m, 2H), 7.33 (d, J = 6.4 Hz , 1H), 6.24 (s, 2H), 4.53 (t, 2H), 3.23 (t, 2H,), 2.99 (s, 3H), 2.16 (t, 3H) | MS obsd. (ESI$^+$) [(M + H)$^+$] 482.1 |
| 1-12 | $^1$HNMR (400 MHz, CDCl$_3$) δ ppm 8.12 (s, 1H), 7.94 (d, J = 9 Hz, 1H), 7.63 (m, 3H), 7.44 (m, 1H), 7.37 (d, J = 2 Hz, 1H), 6.23 (s, 2H), 4.99 (t, 2H), 3.80 (t, 2H), 3.35 (t, 3H), 3.06 (s, 3H) | MS obsd. (ESI$^+$) [(M + H)$^+$] 466.1 |

TABLE 2-continued

NMR and MS data of particular compounds

| Example No. | ¹H NMR data | MW |
|---|---|---|
| 1-13 | ¹H NMR (400 MHz, CDCl₃) δ ppm 8.07 (s, 1H), 7.95 (d, J = 9 Hz, 2H), 7.63 (m, 3H), 7.44 (m, 1H), 7.38 (d, J = 2 Hz, 1H), 6.24 (s, 2H), 5.00 (t, 3H), 3.85 (t, 2H), 3.33 (m, 1H), 3.07 (s, 3H), 1.33 (m, 6H) | MS obsd. (ESI⁺) [(M + H)⁺] 495.1 |
| 2-1 | ¹H NMR (CD₃OD) δ ppm 9.55 (s, 1H), 8.52 (s, 1H), 8.11 (s, 1H), 7.86 (d, 1H, J = 6.8 Hz), 7.66 (s, 1H), 7.38 (d, J = 6.8 Hz, 1H), 6.39 (s, 2H), 6.01 (q, J = 6.0 Hz, 1H), 3.87 (q, J = 8.2 Hz, 1H), 3.66 (q, J = 4.2 Hz, 1H), 3.55 (q, J = 6.4 Hz, 1H), 3.36 (m, 4H), 2.90 (m, 1H), 2.73 (q, J = 6.4 Hz, 1H) | MS obsd. (ESI⁺) [(M + H)⁺] 480.1 |
| 2-2 | ¹H NMR (DMSO-d6) δ ppm 8.02-7.98 (dd, J = 10 Hz, 2H), 7.76 (d, J = 6.8 Hz, 1H), 7.73 (d, J = 1.6 Hz, 1H), 7.62 (t, J = 6.0 Hz, 1H), 7.43 (t, 1H, J = 6.0 Hz), 7.36 (dd, J₁ = 1.6 Hz, J₂ = 6.4 Hz, 1H), 6.32 (s, 2H), 5.86 (m, J = 10.8 Hz, 1H), 3.83 ( dd, J = 8 Hz, 1H), 3.61 (m, 2H), 3.38 (s, 3H), 3.28 (m, 1H), 2.68 (m, 2H) | MS obsd. (ESI⁺) [(M + H)⁺] 479.1 |
| 2-3 | ¹H NMR (400 MHz, DMSO-d₆) δ ppm 8.08 (d, J = 8.84 Hz, 1 H), 8.01 (d, J = 8.34 Hz, 1 h), 7.93 (d, J = 8.59 Hz, 1 H), 7.72 (d, J = 2.02 Hz 1 H), 7.55-7.66 (m, 1 H), 7.41 (dd, J = 8.72, 2.15 Hz, 2 H), 6.23 (s, 2 H), 5.95-6.10 (m, 1 H), 5.09-5.20 (m, 2 H), 4.98-5.08 (m, 2 H), 3.36 (s, 3 H) | MS obsd. (ESI⁺) [(M + H)⁺] 417.1 |
| 2-4 | ¹H NMR (400 MHz, CD₃OD) δ ppm 9.46 (s, 1H), 8.49 (dd, J = 5.5 Hz, 1H), 7.95 (m, 1H), 7.91 (m, 1H), 7.82 (s, 1H), 7.68 (s, 1H), 7.24 (dd, J = 2 Hz, 1H), 6.49 (m, 2H), 5.15 (m, 1H), 3.59 (s, 3H), 2.93-3.00 (m, 1H), 2.55-2.67 (m, 3H), 1.98 (d, J = 5.6 Hz, 1H), 1.23 (s, 1H) | MS obsd. (ESI⁺) [(M + H)⁺] 459.1 |
| 2-5 | ¹H NMR (400 MHz, CD₃OD) δ ppm 9.40 (s, 1 H), 8.49 (d, J = 5.77 Hz, 1H), 8.07 (dd, J = 5.77, 1.25 Hz, 1 H), 7.66 (d, J = 8.78 Hz, 1 H), 7.56 (d, J = 1.76 Hz, 1 H), 7.29-7.38 (m, 1 H), 6.27-6.37 (m, 2 H), 4.77 (dd, J = 7.78, 6.53 Hz, 2 H), 4.56 (t, J = 6.27 Hz, 2 H), 3.35 (s, 3 H) | MS obsd. (ESI⁺) [(M + H)⁺] 418.0 |
| 2-6 | ¹H NMR (400 MHz, MeOH-d₄) δ ppm 8.72-8.90 (m, 2 H), 8.56 (d, J = 8.84 Hz, 1 H), 8.52 (d, J = 2.02 Hz, 1 H), 8.43 (ddd, J = 8.46, 7.07, 1.14 Hz, 1 H), 8.24 (ddd, J = 8.08, 7.07, 0.76 Hz, 1 H), 8.07 (dd, J = 8.84, 2.02 Hz, 1 H), 7.15 (s, 2 H), 5.74 (s, 1 H), 4.82 (dd, J = 11.37, 4.04 Hz, 2 H), 4.27 (t, J = 11.12 Hz, 2 H), 4.17 (s, 3 H), 3.15 (dd, J = 12.25, 4.42 Hz, 2 H), 2.47 (dd, J = 12.13, 2.78 Hz, 2 H) | MS obsd. (ESI⁺) [(M + H)⁺] 445.1 |
| 2-7 | ¹H NMR (400 MHz, DMSO-d₆) δ ppm: 9.43-9.55 (m, 1 H), 8.44-8.60 (m, 1 H), 7.89-8.04 (m, 1 H), 7.73-7.85 (m, 1 H), 7.63-7.73 (m, 1 H), 7.21-7.35 (m, 1 H), 6.51 (s, 2 H), 4.86-5.01 (m, 1 H), 3.98-4.16 (m, 2 H), 3.46-3.61 (m, 2 H), 3.40 (s, 2 H), 3.18 (m, 3 H), 2.28-2.42 (m, 2 H) | MS obsd. (ESI⁺) [(M + H)⁺] 446.1 |
| 2-8 | ¹H NMR (400 MHz, CD₃OD) δ ppm 8.04-8.18 (m, 1 H), 7.86-7.95 (m, 1 H), 7.76-7.84 (m, 1 H), 7.56-7.70 (m, 2 H), 7.38-7.50 (m, 1 H), 7.26-7.37 (m, 1 H), 6.09-6.30 (m, 2 H), 5.64-5.79 (m, 2 H), 4.32-4.42 (m, 1 H), 4.13-4.21 (m, 1 H), 3.97-4.06 (m, 1 H), 3.70-3.83 (m, 1 H), 3.32 (s, 3 H) | MS obsd. (ESI⁺) [(M + H)⁺] 431.0 |
| 2-9 | ¹H NMR (400 MHz, CD₃OD) δ ppm 8.58 (s, 2 H), 8.06-8.13 (m, 1 H), 7.88-7.96 (m, 1 H), 7.67-7.73 (m, 1 H), 7.57-7.66 (m, 2 H), 7.39-7.49 (m, 1 H), 7.27-7.39 (m, 1 H), 6.13-6.27 (m, 2 H), 5.60-5.74 (m, 1 H), 3.32 (s, 3 H), 2.64-2.84 (m, 2 H), 2.41-2.54 (m, 2 H) | MS obsd. (ESI⁺) [(M + H)⁺] 465.1 |
| 2-10 | ¹H NMR (400 MHz, CDCl₃) δ ppm 9.35-9.45 (m, 1 H), 8.56 (d, J = 5.81 Hz, 1 H), 8.01 (d, J = 5.81 Hz, 1 H), 7.81 (d, J = 1.52 Hz, 1 H), 7.42 (d, J = 8.84 Hz, 1 H), 7.32 (d, J = 2.02 Hz, 1 H), 7.30 (d, J = 1.77 Hz, 1 H), 6.13 (s, 2 H), 5.40-5.61 (m, 1 H), 3.31 (s, 3 H). | MS obsd. (ESI⁺) [(M + H)⁺] 466.1 |
| 2-11 | ¹H NMR (CD₃OD) δ ppm 9.58 (s, 1H), 8.54 (s, 1H), 8.21 (d, 1H), 7.80 (d, J = 6.8 Hz, 1H), 7.63 (d, J = 1.6 Hz, 1H), 7.32 (dd, J₁ = 7.2 Hz, J₂ = 1.6 Hz, 1H), 6.44 (s, 2H), 4.81 (m, 1H), 3.37 (s, 3H), 2.40 (q, 2H), 2.15 (d, 1H), 1.90 (d, 2H), 1.60 (q, 2H) | MS obsd. (ESI⁺) [(M + H)⁺] 460 |
| 2-12 | ¹H NMR (400 MHz, DMSO-d₆) δ ppm 9.17 (dd, J = 1.52, 0.76 Hz, 1 H), 8.09-8.15 (m, 2 H), 7.90 (dd, J = 7.07, 0.76 Hz, 1 H), 7.69 (d, J = 2.02 Hz, 1 H), 7.29 (dd, J = 8.84, 2.02 Hz, 1 H), 6.24-6.28 (m, 2 H), 5.04-5.15 (m, 1 H), 4.27-4.35 (m, 1 H), 3.42 (s, 3 H), 2.39-2.48 (m, 1 H), 2.27-2.38 (m, 1 H), 1.93-2.05 (m, 2 H), 1.85 (d, J = 7.33 Hz, 1 H), 1.70-1.79 (m, 1 H) | MS obsd. (ESI⁺) [(M + H)⁺] 462.1 |
| 2-13 | ¹H NMR (400 Mhz, CD₃OD) δ ppm 9.45 (s, 1H), 8.50 (d, 1H, J = 4.8 Hz), 8.07 (d, 1H, J = 4.8 Hz), 7.73 (d, 1H, J = 7.2 Hz), 7.66 (s, 1H), 7.35 (d, 1H, J = 7.2 Hz), 6.37 (s, 2H), 5.65 (m, 1H, J = 7.2 Hz), 3.62 (q, 1H), 3.54-3.49 (m, 1H), 3.44-3.40 (m, 1H), 3.34 (s, 3H), 3.27 (m, 1H), 2.45-2.40 (m, 2H) | MS obsd. (ESI⁺) [(M + H)⁺] 431.1 |
| 2-14 | ¹H NMR (400 MHz, DMSO-d₆) δ ppm 8.48-8.61 (m, 1 H), 8.20 (s, 2 H), 7.86 (s, 1 H), 7.06-7.25 (m, 2 H), 5.19 (s, 2H), 3.65-4.24 (m, 5 H), 3.15-3.26 (m, 3 H) | MS obsd. (ESI⁺) [(M + H)⁺] 417.1 |

TABLE 2-continued

NMR and MS data of particular compounds

| Example No. | ¹H NMR data | MW |
|---|---|---|
| 2-15 | ¹H NMR (400 MHz, DMSO-d₆) δ ppm 7.92-8.07 (m, 2 H), 7.75-7.88 (m, 1 H), 7.70 (d, J = 2.02 Hz, 1 H), 7.61 (ddd, J = 8.53, 7.14, 1.01 Hz, 1 H), 7.43 (ddd, J = 8.15, 7.01, 0.76 Hz, 1 H), 7.26 (d, J = 8.59 Hz, 1 H), 6.31 (s, 2 H), 4.59-4.73 (m, 1 H), 3.34 (br. s., 5H), 2.88-3.16 (m, 2 H), 1.97-2.26 (m, 2 H), 1.52 (d, J = 9.60 Hz, 2 H) | MS obsd. (ESI⁺) [(M + H)⁺] 444 |
| 2-16 | ¹H NMR (CDCl3): δ ppm 9.38 (d, J = 4.2 Hz, 1H), 8.48 (t, J = 4.4 Hz, 1H), 7.90 (d, J = 4.4 Hz, 1H), 7.70 (s, 1H), 7.23-7.17 (m, 1H), 7.26 (t, J = 6.0 Hz, 1H), 6.13-6.02 (m, 2H), 5.69-5.50 (qq, J = 7.2 Hz, 1H), 3.95-3.88 (m, 2H), 3.82-3.71 (m, 1H), 3.64-3.49 (m, 1H), 3.21 (s, 3H), 2.46-2.30 (m, 1H), 2.09-2.02 (m, 5H) | MS obsd. (ESI⁺) [(M + H)⁺] 473 |
| 2-17 | ¹H NMR (acetone-d6): δ ppm 9.50 (d, J = 6.8 Hz, 1H), 8.49 (t, J = 4.0 Hz, 1H), 7.95 (d, J = 4.0 Hz, 1H), 7.78 (d, J = 7.2 Hz, 1H), 7.66 (d, J = 7.2 Hz, 1H), 7.26 (t, J = 6.0 Hz, 1H), 6.47 (s, 2H), 5.97-5.84 (qq, J = 6.8 Hz, 1H), 4.23-4.01 (m, 4H), 3.67-3.57 (m, 1H), 3.36 (s, 3H), 2.86 (s, 2H), 2.77-2.68 (m, 1H), 2.57-2.47 (m, 1H) | MS obsd. (ESI⁺) [(M + H)⁺] 489 |
| 2-18 | ¹H NMR (acetone-d6): δ ppm 9.36 ( d, 1H), 8.34 (t, 1H), 7.80 (d, J = 4.8 Hz, 1H), 7.69-7.49 (d, 1H), 7.10 (m, 1H), 6.33 (s, 2H), 5.85-5.71 (m, J = 6.8 Hz, 1H), 4.16-3.98 (m, 1H), 3.97-3.82 (m, 2H), 3.65-3.39 (m, 1H), 3.21 (s, 3H), 2.62-2.35 (m, 2H) | MS obsd. (ESI⁺) [(M + H)⁺] 488 |
| 2-19 | ¹H NMR (400 MHz, CD₃OD): δ ppm 9.44 ( s, 1H), 8.42 (s, 1H), 8.14 (d, J = 6.8 Hz, 1H), 8.08 (d, J = 4.4 Hz, 1H), 7.50 (s, 1H), 7.19 (dd, J₁ = 1.6 Hz, J₂ = 6.8 Hz, 1H), 6.32 (s, 2H), 5.52 (q, 1H), 3.55-3.26 (m, 3H), 3.23 (s, 3H), 3.18-3.12 (m, 1H), 2.95-2.91 (m, 1H), 2.61-2.57 (m, 1H), 2.38 (m, 1H), 2.10 (m, 1H) | MS obsd. (ESI⁺) [(M + H)⁺] 513 |
| 2-20 | ¹H NMR (400 MHz, CD₃OD): δ ppm 9.58 ( s, 1H), 8.54 (s, 1H), 8.26 (d, J = 6.8 Hz, 1H), 8.23 (d, J = 4.4 Hz, 1H), 7.61 (s, 1H), 7.32 (dd, J₁ = 1.6 Hz, J₂ = 6.8 Hz, 1H), 6.46 (s, 2H), 5.64 (q, 1H), 3.47-3.38 (m, 3H), 3.35 (s, 3H), 3.31-3.24 (m, 1H), 3.08-3.04 (m, 1H), 2.71 (m, 1H), 2.54-2.48 (m, 1H), 2.27-2.22 (m,1H) | MS obsd. (ESI⁺) [(M + H)⁺] 513 |
| 2-21 | ¹H NMR (400 MHz, CD₃OD): δ ppm 9.60 ( s, 1H), 8.63 (s, 1H), 8.18 (s, 1H), 7.62 (s, 1H), 7.60 (s, 1H), 7.39 (d, 1H), 6.35 (s, 2H), 4.80 (t, 2H, J = 6 Hz), 3.35 (s, 3H), 2.94-2.89 (m, 2H) | MS obsd. (ESI⁺) [(M + H)⁺] 458 |
| 2-22 | ¹H NMR (400 MHz, CD₃OD) δ ppm 9.40 (s, 1 H), 8.49 (d, J = 5.77 Hz, 2 H), 8.05-8.11 (m, 1 H), 7.66 (d, J = 8.78 Hz, 1 H), 7.56 (d, J = 2.01 Hz, 1 H), 7.30-7.37 (m, 1 H), 4.83 (s, 2 H), 4.77 (dd, J = 7.78, 6.27 Hz, 2 H), 4.56 (t, J = 6.27 Hz, 2 H), 3.56-3.69 (m, 1 H), 3.33 (dt, J = 3.26, 1.63 Hz, 3 H), 2.05 (s, 2 H) | MS obsd. (ESI⁺) [(M + H)⁺] 431 |
| 2-23 | ¹H NMR (400 MHz, CDCl3) δ ppm 9.45 (s, 1 H), 8.54 (d, J = 5.60 Hz, 1 H), 7.99 (d, J = 5.60 Hz, 1 H), 7.78 (d, J = 2.01 Hz, 1 H), 7.30-7.37 (m, 1 H), 6.06 (s, 2H), 4.77 (dd, J = 7.20, 6.40 Hz, 2 H), 4.56 (t, J = 6.20 Hz, 2 H), 4.23 (t, J = 7.98 Hz, 2H ), 3.00-3.08 (m, 1 H), 1.99-2.05 (m, 2 H) | MS obsd. (ESI⁺) [(M + H)⁺] 446 |
| 2-24 | ¹H NMR (400 MHz, CDCl₃) δ ppm 9.32 (s, 1 H), 8.53-8.51 (d J = 5.6 Hz, 1 H), 7.98-7.97 (d, J = 5.6 Hz, 1 H), 7.75 (d, J = 1.6 Hz, 1 H), 7.31-7.24 (m, 3 H), 6.05 (s, 2 H), 5.14-5.09 (m, 1 H), 4.92 (s, 2 H), 4.79 (s, 2 H), 3.29 (s, 3 H), 3.01-2.96 (m, 2 H), 2.84-2.79 (m, 2 H) | MS obsd. (ESI⁺) [(M + H)⁺] 458.1 |
| 2-25 | ¹H NMR (400 MHz, CDCl₃) δ ppm 9.45 (s, 1 H), 8.54 (d, J = 6.0 Hz, 1 H), 7.99 (d, J = 6.0 Hz, 1 H), 7.80 (s, 1 H), 7.33-7.31 (m, 1 H), 7.27-7.24 (m, 1 H), 6.10 (s, 2 H), 4.53-4.49 (m, 4 H), 4.35-4.31 (m, 2 H), 3.31 (s, 3 H), 1.94-1.90 (m, 2 H), 1.44 (s, 3 H) | MS obsd. (ESI⁺) [(M + H)⁺] 460.1 |
| 2-26 | ¹H NMR (400 MHz, CD₃OD) δ ppm 8.48 (d, J = 5.77 Hz, 1 H), 8.09 (dd, J = 5.77, 1.00 Hz, 1 H), 7.68 (d, J = 8.78 Hz, 1 H), 7.60 (s, 1 H), 7.34 (dd, J = 8.78, 2.01 Hz, 1 H), 6.31 (s, 2 H), 5.53-5.41 (m, 1 H), 3.38 (s, 3 H), 3.00-2.88 (m, 2 H), 2.65 (ddd, J = 9.85, 8.22, 3.01 Hz, 2 H), 1.56 (s, 3 H) | MS obsd. (ESI⁺) [(M + H)⁺] 446.1 |
| 2-27 | ¹H NMR (400 MHz, CD₃OD) δ ppm 9.24 (s, 1 H), 8.38 (d, 1 H), 7.98 (dd, 1 H), 7.48-7.45 (m, 2 H), 7.23 (dd, 1 H), 6.26 (s, 2 H), 4.46 (t, 2 H), 3.48 (t, 2 H), 3.24 (s, 3 H), 1.93-1.86 (m, 1 H) | MS obsd. (ESI⁺) [(M + H)⁺] 420.1 |
| 2-28 | ¹H NMR (400 MHz, CD₃Cl) δ ppm 9.39 (s, 1 H), 8.54-8.53 (d, J = 5.6 Hz, 1 H), 7.99-7.97 (d, J = 5.6 Hz, 1 H), 7.76-7.70 (d, J = 1.6 Hz, 1 H), 7.67-7.65 (d, J = 8.8 Hz, 1 H), 7.25-7.24 (d, J = 2.0 Hz, 1 H), 6.12 (s, 2 H), 5.58-5.56 (m, 1 H), 4.36-4.32 (t, J = 6.4 Hz, 1 H), 4.15-4.12 (dd, J₁ = 2.4 Hz, J₂ = 10.8 Hz, 1 H), 3.99-3.97 (m, 1 H), 3.80-3.73 (m, 1 H), 3.28 (s, 3 H), 2.36-2.28 (m, 1 H), 2.04-1.94 (m, 1 H) | MS obsd. (ESI⁺) [(M + H)⁺] 432.1 |
| 2-29 | ¹H NMR (400 MHz, CD₃OD) δ ppm 9.39 (s, 1 H), 8.50-8.49 (m, 1 H), 8.10-8.08 (m, 1 H), 7.61-7.57 (m, 2 H), 7.36-7.33 (m, 1 H), 6.34 (s, 2 H), 4.58-4.54 (m, 2 H), 3.36-3.32 (m, 3 H), 1.89-1.85 (m, 2 H), 1.29-1.22 (m, 6 H) | MS obsd. (ESI⁺) [(M + H)⁺] 448.11 |
| 2-30 | ¹H NMR (400 MHz, CD₃OD) δ ppm 9.39 (s, 1 H), 8.50-8.49 (m, 1 H), 8.11-8.09 (m, 1 H), 7.62-7.60 (m, 2 H), 7.36-7.35 (m, 1 H), 6.33 (s, 2 H), 4.50-4.46 (m, 2 H), 3.60-3.57 (m, 2 H), 3.36-3.35 (m, 3 H), 1.81 (m, 2 H), 1.59 (m, 2 H) | MS obsd. (ESI⁺) [(M + H)⁺] 434.1 |

TABLE 2-continued

NMR and MS data of particular compounds

| Example No. | ¹H NMR data | MW |
|---|---|---|
| 2-31 | ¹H NMR (400 MHz, CDCl₃) δ ppm 9.43 (s, 1 H), 8.54-8.52 (br, J = 5.6 Hz, 1 H), 8.00-7.98 (br, J = 5.6 Hz, 1 H), 7.75 (s, 1 H), 7.32-7.30 (brs, J = 8.4 Hz, 1 H), 6.13-6.04 (m, 2 H), 4.23-4.18 (m, 2 H), 4.05-4.04 (brs, J = 6 Hz, 1 H), 3.79-3.77 (m, 1 H), 3.54-3.44 (m, 2 H), 3.29 (s, 3 H), 2.67 (s, 1 H), 2.11-2.01 (m, 1 H), 1.71-1.66 (m, 1 H). | MS obsd. (ESI⁺) [(M + H)⁺] 446.3 |
| 2-32 | ¹H NMR (400 MHz, DMSO-d₆) δ ppm 9.36 (s, 1 H), 8.49 (d, J = 5.8 Hz, 1 H), 7.95 (d, J = 5.5 Hz, 1 H), 7.79 (d, J = 8.8 Hz, 1 H), 7.64 (d, J = 1.8 Hz, 1 H), 7.28 (dd, J = 1.9, 8.9 Hz, 1 H), 6.36 (s, 2 H), 5.51 (quin, J = 8.5 Hz, 1 H), 4.55 (t, J = 6.8 Hz, 1 H), 3.39 (s, 3 H), 3.05-2.91 (m, 2 H), 2.47-2.32 (m, 2 H). | MS obsd. (ESI⁺) [(M + H)⁺] 432.1 |
| 2-33 | ¹H NMR (400 MHz, DMSO-d₆) δ ppm 9.38 (s, 1 H), 8.49 (d, J = 5.8 Hz, 1 H), 8.11-7.87 (m, 2 H), 7.64 (d, J = 1.8 Hz, 1 H), 7.30 (dd, J = 2.0, 8.8 Hz, 1 H), 6.39 (s, 2 H), 4.89 (s, 1 H), 3.39 (s, 3 H), 2.86-2.74 (m, 2 H), 2.60-2.54 (m, 2 H), 1.38 (s, 3 H). | MS obsd. (ESI⁺) [(M + H)⁺] 446.1 |
| 2-34 | ¹H NMR (400 MHz, CD₃OD) δ ppm 9.25 (s, 1 H), 8.38 (d, 1 H), 7.97 (d, 1 H), 7.48-7.45 (m, 2 H), 7.21 (dd, 1 H), 6.32 (s, 2 H), 4.57 (t, 2 H), 3.24 (s, 3 H), 1.91 (t, 2 H), 0.49 (t, 2 H), 0.00 (t, 2 H). | MS obsd. (ESI⁺) [(M + H)⁺] 446.1 |
| 2-35 | ¹H NMR (400 MHz, CDCl₃) δ ppm 9.32 (s, 1 H), 8.50-8.48 (d, 1 H), 8.11-8.09 (d, 1 H), 7.63-7.61 (d, 1 H), 7.54 (s, 1 H), 7.34-7.31 (d, 1 H), 6.43 (s, 2 H), 4.70-4.68 (t, 2 H), 3.88-3.85 (t, 2 H), 3.65-3.63 (t, 2 H), 3.52-3.50 (t, 2 H), 3.37 (s, 3 H) | MS obsd. (ESI⁺) [(M + H)⁺] 450.1 |
| 2-36 | ¹H NMR (DMSO-d₆) δ ppm 9.42 (d, J = 1.2 Hz, 1 H), 8.50 (d, J = 5.7 Hz, 1 H), 7.96 (dd, J = 1.2, 5.7 Hz, 1 H), 7.70 (d, J = 2.0 Hz, 1 H), 7.56 (d, J = 8.8 Hz, 1 H), 7.25 (dd, J = 2.0, 8.8 Hz, 1 H), 6.46 (s, 2 H), 5.40-5.34 (m, 1 H), 4.82 (d, J = 3.0 Hz, 1 H), 4.45-4.40 (m, 1 H), 3.41 (s, 3 H), 2.29-2.08 (m, 3 H), 2.05-2.00 (m, 1 H), 1.99-1.93 (m, 1 H), 1.70-1.59 (m, 1 H). | MS obsd. (ESI⁺) [(M + H)⁺] 446.1 |
| 2-37 | ¹H NMR (400 MHz, CDCl₃) δ ppm 9.41 (s, 1 H), 8.57-8.51 (m, 1 H), 8.02-7.96 (m, 2 H), 7.80 (d, J = 1.8 Hz, 1 H), 7.43-7.36 (m, 1 H), 7.27-7.24 (m, 1 H), 6.13 (s, 2 H), 4.77-4.67 (m, 1 H), 3.31 (s, 3 H), 2.35-2.18 (m, 2 H), 1.96-1.74 (m, 4 H), 1.59-1.51 (m, 2 H), 1.49-1.46 (m, 3 H) | MS obsd. (ESI⁺) [(M + H)⁺] 474.1 |
| 2-38 | ¹H NMR (400 MHz, CDCl₃) δ ppm 9.38 (br. s., 1 H), 8.46 (br. s., 1 H), 8.01-7.86 (m, 1 H), 7.77-7.64 (m, 1 H), 7.30-7.19 (m, 2 H), 6.09 (br. s., 2 H), 4.26 (t, J = 7.4 Hz, 2 H), 3.39-3.20 (m, 3 H), 1.73-1.50 (m, 2 H), 1.46-1.31 (m, 2 H), 1.11 (br. s., 6 H) | MS obsd. (ESI⁺) [(M + H)⁺] 462.1 |
| 2-39 | ¹H NMR (DMSO-d₆) δ ppm 9.37 (d, J = 1.1 Hz, 1 H), 8.50 (d, J = 5.7 Hz, 1 H), 7.96 (dd, J = 1.1, 5.7 Hz, 1 H), 7.85 (d, J = 8.4 Hz, 1 H), 7.69 (d, J = 2.0 Hz, 1 H), 7.30 (dd, J = 2.0, 8.4 Hz, 1H), 6.37 (s, 2 H), 5.24-5.20 (m, 1 H), 4.46 (s, 1 H), 3.44 (s, 3 H), 2.76-2.68 (m, 2 H), 2.57-2.50 (m, 2 H), 1.14 (s, 6 H). | MS obsd. (ESI⁺) [(M + H)⁺] 474.1 |
| 2-40 | ¹H NMR (400 MHz, CD₃OD) δ ppm 9.22 (s, 1 H), 8.37 (d, 1 H), 7.97 (dd, 1 H), 7.49-7.46 (m, 2 H), 7.22 (dd, 1 H), 6.28 (s, 2 H), 4.44 (t, 2 H), 3.57 (t, 4 H), 3.24 (s, 3 H), 2.61 (t, 2 H), 2.41 (t, 4 H) | MS obsd. (ESI⁺) [(M + H)⁺] 475.1 |
| 2-41 | ¹H NMR (DMSO-d₆) δ ppm 9.63 (s, 1 H), 8.56 (d, J = 5.8 Hz, 1 H), 8.17-8.02 (m, 1 H), 7.99-7.92 (m, 1 H), 7.66 (d, J = 1.5 Hz, 1 H), 7.54-7.16 (m, 2H), 6.50 (s, 2 H), 5.44 (quin, J = 8.7 Hz, 1 H), 3.46 (s, 3 H), 3.34 (d, J = 10.3 Hz, 1 H), 3.13 - 3.05 (m, 2 H), 2.76 (t, J = 9.9 Hz, 2 H) | MS obsd. (ESI⁺) [(M + H)⁺] 460.1 |
| 2-42 | ¹H NMR (DMSO-d₆) δ ppm 9.43 (s, 1 H), 8.51-8.50 (d, 1 H), 7.97-7.95 (d, 1 H), 7.70-7.65 (m, 2 H), 7.34-7.32 (d, 1 H), 6.54-6.52 (m, 1 H), 6.41 (s, 2 H), 4.57-4.53 (s, 2 H), 4.09-4.07 (s, 1 H), 3.40 (s, 3 H), 2.04 (s, 2 H) | MS obsd. (ESI⁺) [(M + H)⁺] 488.1 |
| 2-43 | ¹H NMR (DMSO-d₆) δ ppm 9.44 (d, J = 1.1 Hz, 1 H), 8.51 (d, J = 5.7 Hz, 1 H), 8.16 (d, J = 8.4 Hz, 1 H), 7.96 (dd, J = 1.1, 5.7 Hz, 1 H), 7.68 (d, J = 2.0 Hz, 1 H), 7.28 (dd, J = 2.0, 8.4 Hz, 1 H), 6.46 (s, 2 H), 5.28-5.24 (m, 1 H), 4.91 (s, 1 H), 3.41 (s, 3 H), 2.42-2.30 (m, 1 H), 2.20-2.12 (m, 2 H), 1.98-1.86 (m, 2 H), 1.84-1.78 (m, 1 H), 1.33 (s, 3 H) | MS obsd. (ESI⁺) [(M + H)⁺] 460.1 |
| 2-44 | ¹H NMR (400 MHz, CD₃OD) δ ppm 9.27 (s, 1 H), 8.38 (d, 1 H), 7.98 (d, 1 H), 7.51 (s, 1 H), 7.48 (d, 1 H), 7.23 (d, 1 H), 6.24 (s, 2 H), 5.73-5.44 (td, 1 H), 4.53 (t, 2 H), 3.60-3.57 (m, 1 H), 3.21 (s, 3 H), 2.00-1.77 (m, 2 H) | MS obsd. (ESI⁺) [(M + H)⁺] 470.1 |
| 2-45 | ¹H NMR (DMSO-d₆) δ ppm 9.41 (s, 1 H), 8.50 (d, J = 5.7 Hz, 1 H), 8.14 (d, J = 8.8 Hz, 1 H), 7.95 (d, J = 5.7 Hz, 1 H), 7.69 (d, J = 1.2 Hz, 1 H), 7.28 (dd, J = 1.2, 8.8 Hz, 1 H), 6.45 (s, 2 H), 5.39-5.30 (m, 2 H), 4.99 (d, J = 2.4 Hz , 1 H), 4.05-4.02 (m, 2 H), 3.43 (s, 3 H), 2.53-2.30 (m, 2 H), 1.87-1.84 (m, 2 H) | MS obsd. (ESI⁺) [(M + H)⁺] 462.1 |
| 2-46 | ¹H NMR (DMSO-d₆) δ ppm 9.40 (d, J = 1.0 Hz, 1 H), 8.50 (d, J = 5.8 Hz, 1 H), 8.09 (d, J = 8.8 Hz, 1 H), 7.96 (dd, J = 1.3, 5.8 Hz, 1H), 7.66 (d, J = 2.0 Hz, 1 H), 7.26 (dd, J = 2.0, 8.8 Hz, 1 H), 6.44 (s, 1 H), 5.43 (quin, J = 8.8 Hz, 1 H), 5.35 (t, J = 5.4 Hz, 1 H), 5.16 (s, 1 H), 4.10 (q, J = 5.3 Hz, 1 H), 3.43 (s, 3 H), 3.17 (d, J = 5.0 Hz, 2 H), 3.05 (d, J = 2.8 Hz, 2 H), 2.22 (dt, J = 2.9, 9.0 Hz, 2 H) | MS obsd. (ESI⁺) [(M + H)⁺] 462.1 |

TABLE 2-continued

NMR and MS data of particular compounds

| Example No. | ¹H NMR data | MW |
|---|---|---|
| 3-1 | ¹H NMR (400 MHz, CDCl3) δ ppm 8.09 (dt, J = 8.34, 1.01 Hz, 1 H), 8.04 (dd, J = 2.78, 0.51 Hz, 1 H), 7.87 (d, J = 1.52 Hz, 1 H), 7.62-7.68 (m, 1 H), 7.45-7.54 (m, 2 H), 7.38 (ddd, J = 8.15, 7.01, 0.76 Hz, 1 H), 7.31 (d, J = 2.02 Hz, 1 H), 7.04-7.11 (m, 1 H), 6.94 (d, J = 8.34 Hz, 1 H), 5.91 (s, 2 H), 3.22 (s, 3 H) | MS obsd. (ESI+) [(M + H)+] 471 |
| 3-2 | ¹H NMR (400 MHz, CDCl3) δ ppm 9.31 (s, 1 H), 8.58 (d, J = 6.4 Hz, 1 H), 8.15 (d, J = 2.4 Hz, 1 H), 7.98 (dd, J = 1.2, 3.6 Hz, 1 H), 7.86 (s, 1H), 7.63 (m, 1H), 7.32 (dd, 1H, J = 1.6, 6.6 Hz), 7.17 (m, 1 H), 6.98 (d, 1H, J = 6.6 Hz), 5.98 (s, 2H), 3.24 (s, 3 H) | MS obsd. (ESI+) [(M + H)+] 457 |
| 3-3 | ¹H NMR (400 MHz, DMSO-d6) δ ppm 9.00-9.07 (m, 1 H), 8.52-8.55 (m, 1 H), 8.23-8.31 (m, 1 H), 8.10 (dd, J = 7.07, 1.52 Hz, 1 H), 7.80-7.87 (m, 2 H), 7.45 (dd, J = 8.84, 2.78 Hz, 1 H), 7.30-7.37 (m, 1 H), 7.21-7.28 (m, 1 H), 6.09 (s, 2 H), 3.40 (s, 3 H) | MS obsd. (ESI+) [(M + H)+] 473.1 |
| 3-4 | ¹H NMR (400 MHz, CDCl3) δ ppm 8.08 (dd, J = 8.34, 2.02 Hz, 1 H), 7.82-7.88 (m, 2 H), 7.60 (dt, J = 8.59, 0.76 Hz, 1 H), 7.43-7.51 (m, 1 H), 7.32-7.40 (m, 1 H), 7.23-7.30 (m, 1 H), 7.19 (dd, J = 8.84, 2.78 Hz, 1 H), 6.90-6.97 (m, 1 H), 6.80 (dd, J = 8.72, 0.63 Hz, 1 H), 5.91 (s, 2 H), 4.00 (s, 3 H), 3.20 (s, 3 H) | MS obsd. (ESI+) [(M + H)+] 468 |
| 3-5 | ¹H NMR (400 MHz, DMSO-d6) δ ppm 8.59-8.63 (m, 1 H), 8.01 (dd, J = 8.53, 2.76 Hz, 1 H), 7.94 (d, J = 8.28 Hz, 1 H), 7.82-7.87 (m, 1 H), 7.75 (d, J = 8.53 Hz, 1 H), 7.62 (dd, J = 8.41, 0.63 Hz, 1 H), 7.51-7.58 (m, 1 H), 7.40 (dd, J = 8.16, 0.88 Hz, 1 H), 7.29-7.34 (m, 1 H), 7.22-7.27 (m, 1 H), 6.16 (s, 2 H), 3.30-3.34 (m, 3 H) | MS obsd. (ESI+) [(M + H)+] 472 |
| 4-1 | ¹H NMR (400 MHz, CDCl3) δ ppm 8.13 (d, J = 8.34 Hz, 1 H), 7.87 (d, J = 8.59 Hz, 1 H), 7.81 (d, J = 1.77 Hz, 1 H), 7.53 (td, J = 7.77, 0.88 Hz, 1 H), 7.39 (t, J = 7.71 Hz, 1 H), 7.22-7.34 (m, 2 H), 6.01 (s, 2 H), 4.37 (d, J = 16.17 Hz, 2 H), 3.29 (s, 3 H), 2.07-2.25 (m, 2 H), 1.62-1.74 (m, 2 H) | MS obsd. (ESI+) [(M + H)+] 471 |
| 4-2 | ¹H NMR (400 MHz, CD3OD) δ ppm 9.25 (s, 1 H), 8.22 (dd, J = 5.20, 0.76, 1 H), 8.10 (d, J = 5.20 Hz, 1 H), 7.60 (m, 2 H), 7.35 (dd, J = 7.20, 1.60 Hz, 1 H), 6.20 (s, 2 H), 4.53 (m, 2 H), 3.32 (s, 3H), 2.37 (m, 2 H), 2.06 (m, 2 H) | MS obsd. (ESI+) [(M + H)+] 488 |
| 4-3 | ¹H NMR (400 MHz, CDCl3) δ ppm 9.46 (s, 1H), 8.55 (d, J = 4.4 Hz, 1H), 8.00 (d, J = 4.4 Hz, 1H) 7.80 (s, 1H), 7.34 (d, J = 7.2, 1H Hz), 6.08 (s, 2H), 4.38 (t, J = 6 Hz, 2H), 3.30 (s, 3H), 2.23-2.18 (m, 2H), 1.80 (q, J = 6 Hz, 2H) | MS obsd. (ESI+) [(M + H)+] 472.1 |
| 5-1 | ¹H NMR (400 MHz, CD3OD) δ ppm 9.41 (s, 1H), 8.50 (d, J = 4.8 Hz, 1H), 8.10 (d, J = 4.8 Hz, 1H), 7.44 (s, 1H), 7.23 (d, J = 9.6 Hz, 1H), 6.34 (s, 2H), 4.85 (m, 2H), 3.35 (s, 3H), 2.96-2.91 (m, 2H) | MS obsd. (ESI+) [(M + H)+] 476.1 |
| 5-2 | ¹H NMR (400 MHz, CD3OD) δ ppm 9.68 (s, 1H), 8.59 (d, J = 6.0 Hz, 1H), 8.35 (t, J = 3.0 Hz, 1H), 7.44 (s, 1H), 7.22 (dd, J₁ = 2.0 Hz, J₂ = 9.6 Hz, 1H), 6.41 (s, 2H), 4.64 (t, J = 8.0 Hz, 2H), 3.38 (s, 3H), 2.40 (m, 2H), 2.10 (m, 2H) | MS obsd. (ESI+) [(M + H)+] 490 |
| 6-1 | ¹H NMR (400 MHz, CD3OD) δ ppm 9.48 (d, J = 15.6 Hz, 1 H), 8.49 (t, J = 2.4 Hz, 1 H), 8.07 (d, J = 4.4 Hz, 1 H), 7.69-7.56 (m, 2 H), 7.33 (t, J = 7.2 Hz, 1 H), 6.38 (s, 2 H), 5.83-5.70 (m, 1 H), 4.19-4.04 (m, 1 H), 4.02-3.92 (m, 2 H), 3.77-3.54 (m, 1 H), 3.34 (s, 3 H), 2.74-2.68 (m, 1 H), 2.48-2.45 (m, 1 H), 2.18-2.13 (d, 3 H) | MS obsd. (ESI+) [(M + H)+] 473.1 |
| 6-2 | ¹H NMR (400 MHz, CD3OD) δ ppm 8.08 (d, J = 6.8 Hz, 1 H), 7.97-7.91 (dd, J = 6.8 Hz, 1 H), 7.67-7.55 (m, 3 H), 7.45-7.41 (m, 1 H), 7.34-7.30 (m, 1 H), 6.26-6.17 (m, 2 H), 5.84-5.72 (m, 1 H), 4.12-3.99 (t, J = 8 Hz, 1 H), 3.72-3.54 (m, 1 H), 3.30 (s, 3 H), 2.67-2.60 (m, 1 H), 2.37-2.31 (m, 1 H), 2.16-2.11 (s, 3 H) | MS obsd. (ESI+) [(M + H)+] 472.1 |
| 6-3 | ¹H NMR (400 MHz, CD3OD) δ ppm 8.05 (s, 1 H), 7.94-7.88 (d, J = 6.8 Hz, 1 H), 7.67-7.54 (m, 3 H), 7.41-7.37 (m, 1 H), 7.32-7.28 (m, 1 H), 6.28-6.19 (m, 2 H), 5.85-5.71 (m, 1 H), 4.12-3.90 (m, 3 H), 3.68-3.54 (m, 1 H), 3.29-3.28 (s, 3 H), 2.66-2.59 (m, 1 H), 2.49-2.34 (m, 3 H), 1.18-1.11 (m, 3 H) | MS obsd. (ESI+) [(M + H)+] 486.1 |
| 6-4 | ¹H NMR (400 MHz, CD3OD) δ ppm 9.44 (s, 1 H), 8.43 (t, J = 3.6 Hz, 1 H), 7.62-7.46 (m, 2 H), 7.27-7.21 (m, 1 H), 6.38 (s, 2 H), 5.80-5.67 (m, 1 H), 4.27-4.14 (m, 3 H), 3.79-3.52 (m, 1H), 2.92-2.75 (m, 1 H), 2.70-2.64 (m, 1 H), 2.48-2.43 (m, H), 3.31 (s, 3 H), 1.19-1.10 (m, 6 H) | MS obsd. (ESI+) [(M + H)+] 501.1 |
| 6-5 | ¹HNMR (400 MHZ, CD3OD) δ ppm 9.45 (s, 1 H), 8.50 (d, J = 5.6 Hz, 1 H), 7.96 (dd, J₁ = 1.6 Hz, J₂ = 5.6 Hz, 1 H), 7.70 (d, J = 1.6 Hz, 1 H), 7.64-7.49 (m, 1 H), 7.28 (dd, J₁ = 2.0 Hz, J₂ = 8.8 Hz, 1 H), 6.49 (s, 2 H), 5.50-5.22 (m, 2 H), 4.37-3.77 (m, 3 H), 3.40 (s, 3 H), 2.43-2.27 (m, 1 H), 1.39 (d, 6 H) | MS obsd. (ESI+) [(M + H)+] 517.1 |
| 6-6 | ¹H NMR (400 MHz, CD3OD) δ ppm 9.46 (s, 1 H), 8.51 (d, J = 5.6 Hz, 1 H), 7.97-7.95 (dd, J₁ = 1.2 Hz, J₂ = 5.6 Hz, 1 H), 7.75-7.70 (m, 2 H), 7.33-7.31 (dd, J₁ = 2 Hz, J₂ = 8.8 Hz, 1 H), 6.49 (s, 2 H), 5.58 (q, J = 8.4 Hz, 1 H), 3.84 (q, J = 8.4 Hz, 1 H), 3.71-3.65 (m, 1 H), 3.62-3.58 (m, 1 H), 3.51 (s, 3 H), 3.42-3.36 (m, 1 H), 3.07 (s, 3 H), 2.47 (m, 1 H) | MS obsd. (ESI+) [(M + H)+] 509.0 |

TABLE 2-continued

NMR and MS data of particular compounds

| Example No. | $^1$H NMR data | MW |
|---|---|---|
| 6-7 | $^1$H NMR (400 MHz, CD$_3$OD) δ ppm 9.40 (s, 1H), 8.48 (d, J = 2.0 Hz, 1 H), 8.24 (d, J = 8.8 Hz, 1 H), 8.07 (dd, J$_1$ = 1.6 Hz, J$_2$ = 6.8 Hz, 1 H), 7.61 (d, J = 2.0 Hz, 1 H), 7.29 (dd, J$_1$ = 2.0 Hz, J$_2$ = 8.8 Hz, 1 H), 6.40 (m, 2 H), 5.54 (q, J = 3.2 Hz, 1 H), 3.74 (t, J = 5.6 Hz, 2 H), 3.34 (s, 3 H), 2.87-2.76 (m, 2 H), 2.70 (m, 1 H), 2.54-2.50 (m, 1 H), 2.40 (m, 1 H), 2.19 (m, 1 H) | MS obsd. (ESI$^+$) [(M + H)$^+$] 475.1 |
| 7 | $^1$H NMR(400 MHz, CD$_3$OD) δ ppm 9.35 (s, 1 H), 8.39 (m, 1 H), 7.97-7.95 (m, 1 H), 7.76-7.55 (m, 1 H), 7.40-7.38 (m, 1 H), 7.26-7.23 (m, 1 H), 6.25 (s, 2 H), 5.92-5.84 (m, 1 H), 4.02-3.40 (m, 1 H), 3.65-3.61 (m, 1 H), 3.22-3.16 (m, 3 H), 3.02-2.95 (m, 1 H), 2.71-2.65 (m, 1 H) | MS obsd. (ESI$^+$) [(M + H)$^+$] 445.1 |
| 8 | $^1$H NMR (400 MHz, CDCl$_3$) δ ppm 9.40 (s, 1 H), 8.56 (d, J = 5.77 Hz, 1 H), 8.00 (d, J = 5.27 Hz, 1 H), 7.83-7.71 (m, 2 H), 7.25 (dd, J = 8.78, 1.76 Hz, 1 H), 6.14 (s, 2 H), 5.52-5.40 (m, 1 H), 4.83 (dd, J = 10.92, 6.65 Hz, 2 H), 4.76 (d, J = 6.78 Hz, 1 H), 4.63 (d, J = 6.27 Hz, 1 H), 3.49-3.40 (m, 1 H), 3.34 (d, J = 4.27 Hz, 1 H), 3.30 (s, 3 H), 2.49 (dd, J = 13.43, 9.16 Hz, 1 H), 2.32-2.20 (m, 2 H). | MS obsd. (ESI$^+$) [(M + H)$^+$] 473.1 |
| 9-1 | $^1$H NMR (400 MHz, CDCl$_3$ + CD$_3$OD) δ ppm 9.74 (s, 1 H), 8.58-8.57 (d, J = 6.4 Hz, 1 H), 8.43-8.41 (d, J = 6.4 Hz, 1 H), 7.57 (s, 1 H), 7.50-7.48 (d, J = 8.8 Hz, 1 H), 7.26-7.24 (d, J = 8.8 Hz, 1 H), 6.69 (s, 1 H), 6.35 (s, 2 H), 4.86-4.83 (t, 2 H), 3.68-3.65 (t, 2 H), 3.43 (s, 3 H), 3.35 (s, 3 H) | MS obsd. (ESI$^+$) [(M + H)$^+$] 467.1 |
| 9-2 | $^1$H NMR (400 MHz, CDCl$_3$ + CD$_3$OD) δ ppm 9.75 (s, 1 H), 8.59-8.57 (d, J = 6.4 Hz, 1 H), 8.47-8.45 (d, J = 6.4 Hz, 1 H), 7.63 (s, 1 H), 7.45-7.43 (d, J = 8.4 Hz, 1 H), 7.27-7.25 (d, J = 9.2 Hz, 1 H), 6.86 (s, 1 H), 6.30 (s, 2 H), 4.54-4.50 (t, 2 H), 3.47 (s, 3 H), 3.24-3.20 (t, 2 H), 3.01 (s, 3 H), 2.11-2.01 (t, 2 H) | MS obsd. (ESI$^+$) [(M + H)$^+$] 481.1 |
| 9-3 | $^1$H NMR (DMSO-d$_6$): δ ppm 9.52 (s, 1 H), 8.50 (d, J = 5.6 Hz, 1 H), 7.96 (dd, J = 1.2, 5.6 Hz, 1 H), 7.45 (d, J = 1.6 Hz, 1 H), 7.17 (dd, J = 2.0 Hz, 12.4 Hz, 1 H), 6.53 (d, J = 2.0 Hz, 1 H), 6.33 (s, 2 H), 4.82 (t, J = 7.2 Hz, 2 H), 3.70 (t, J = 7.2 Hz, 2 H), 3.44 (s, 3 H), 3.06 (s, 3 H) | MS obsd. (ESI$^+$) [(M + H)$^+$] 485.1 |
| 10-1 | $^1$H NMR (400 MHz, CD$_3$OD) δ ppm 9.23 (s, 1 H), 8.36 (d, 1 H), 7.98-7.96 (d, 1 H), 7.49-7.45 (m, 2 H), 7.23-7.21 (t, 1 H), 6.30-6.28 (t, 2 H), 4.47-4.44 (t, 2 H), 4.24 (s, 1 H), 3.25-3.20 (s, 3 H), 2.84-2.76 (m, 3 H), 2.45-2.43 (m, 2 H), 2.63-2.59 (m, 1 H), 1.18-1.14 (m, 2 H). | MS obsd. (ESI$^+$) [(M + H)$^+$] 475.1 |
| 10-2 | $^1$H NMR (400 MHz, CD$_3$OD) δ ppm 9.60-9.55 (m, 1 H), 8.53 (d, J = 5.5 Hz, 1 H), 8.12-8.07 (m, 1 H), 7.69-7.67 (m, 2 H), 7.44-7.40 (m, 1 H), 6.40-6.26 (m, 2 H), 5.43-5.31 (m, 1 H), 5.03-4.96 (m, 3 H), 3.71-3.57 (m, 2 H), 3.36 (s, 3 H), 2.29-2.11 (m, 3 H), 2.11-1.99 (m, 1 H), 1.68-1.58 (m, 1 H), 1.35 (m, 4 H) | MS obsd. (ESI$^+$) [(M + H)$^+$] 489.1 |
| 11 | $^1$H NMR (DMSO-d$_6$) δ ppm 9.39 (d, J = 1.0 Hz, 1 H), 8.50 (d, J = 5.7 Hz, 1 H), 7.94 (dd, J = 1.0, 5.7 Hz, 1 H), 7.88 (d, J = 8.8 Hz, 1 H), 7.68 (d, J = 2.0 Hz, 1 H), 7.30 (dd, J = 2.0, 8.7 Hz, 1 H), 6.40 (s, 2 H), 5.34-5.30 (m, 1 H), 4.80 (brs, 1 H), 3.61 (d, J = 8.0 Hz, 2 H), 3.42 (s, 3 H), 2.89-2.85 (m, 2 H), 2.62-2.5 (m, 1 H), 2.36-2.32 (m, 2 H). | MS obsd. (ESI$^+$) [(M + H)$^+$] 446.1 |
| 12 | $^1$H NMR (DMSO-d$_6$) δ ppm 9.47 (d, J = 1.3 Hz, 1 H), 8.52 (d, J = 5.8 Hz, 1 H), 7.97 (dd, J = 1.3, 5.8 Hz, 1 H), 7.62 (d, J = 1.8 Hz, 1 H), 7.43 (dd, J = 1.8, 11.5 Hz, 1 H), 6.62-6.51 (m, 2 H), 5.83-5.69 (m, 1 H), 3.98-3.86 (m, 1 H), 3.67-3.57 (m, 1 H), 3.54-3.44 (m, 1 H), 3.43 (s, 3 H), 3.39-3.33 (m, 1 H), 2.85-2.74 (m, 1 H), 2.66-2.54 (m, 1 H) | MS obsd. (ESI$^+$) [(M + H)$^+$] 498.0 |
| 13 | $^1$H NMR (DMSO-d$_6$) δ ppm 9.41 (s, 1 H), 8.51-8.50 (d, J = 6 Hz, 1 H), 7.97-7.96 (dd, J$_1$ = 6 Hz, J$_2$ = 1.2 Hz, 1 H), 7.67-7.64 (m, 2 H), 7.31-7.29 (dd, J$_1$ = 8.4 Hz, J$_2$ = 2 Hz, 1 H), 6.41 (s, 2 H), 4.76 (s, 1 H), 4.48-4.44 (t, J = 6.8 Hz, 2 H), 3.42 (s, 3 H), 1.87-1.84 (t, J = 6.8 Hz, 2 H) | MS obsd. (ESI$^+$) [(M + H)$^+$] 422.1 |
| 14 | $^1$H NMR (400 MHz, CD$_3$OD) δ ppm 9.27 (s, 1 H), 8.38 (d, 1 H), 7.98 (d, 1 H), 7.50 (s, 1 H), 7.48 (d, 1 H), 7.25 (d, 1 H), 6.23 (s, 2 H), 4.59-4.44 (m, 2 H), 3.26 (s, 3 H), 2.06-1.86 (m, 2 H), 1.35 (s, 3 H) | MS obsd. (ESI$^+$) [(M + H)$^+$] 502.1 |
| 15-1 | $^1$H NMR (400 MHz, CD$_3$OD) δ ppm 9.42-9.24 (m, 1 H), 8.54-8.38 (m, 1 H), 8.08 (d, J = 5.5 Hz, 1 H), 7.76 (d, J = 1.8 Hz, 1 H), 7.54 (d, J = 8.8 Hz, 1H), 7.37 (dd, J = 1.9, 8.7 Hz, 1 H), 6.79 (d, J = 7.0 Hz, 1 H), 4.65-4.37 (m, 2 H), 3.35 (s, 3 H), 2.83-2.61 (m, 1 H), 2.26 (d, J = 6.8 Hz, 4 H) | MS obsd. (ESI$^+$) [(M + H)$^+$] 472.1 |
| 15-2 | $^1$H NMR (400 MHz, CD$_3$OD) δ ppm 9.63-9.45 (m, 1 H), 8.61-8.46 (m, 1 H), 8.33-8.16 (m, 1 H), 7.78-7.72 (m, 1 H), 7.57 (d, J = 8.5 Hz, 1 H), 7.45-7.31 (m, 1 H), 6.84 (d, J = 7.0 Hz, 1 H) 4.68-4.47 (m, 2 H), 3.41-3.35 (m, 3 H), 2.88-2.34 (m, 2 H), 2.29 (d, J = 7.0 Hz, 3 H) | MS obsd. (ESI$^+$) [(M + H)$^+$] 472.1 |

More particular compounds of formula I include the following:

1-{[5-chloro-1-(pyrrolidin-3-yl)-1H-benzimidazol-2-yl]methyl}-3-(methylsulfonyl)-1H-pyrazolo[3,4-c]pyridine;
1-{[5-chloro-1-(3,3,3-trifluoropropyl)-1H-benzimidazol-2-yl]methyl}-3-(methylsulfonyl)-1H-pyrazolo[3,4-c]pyridine;
1-{[5-chloro-1-(oxetan-3-ylmethyl)-1H-benzimidazol-2-yl]methyl}-3-(methylsulfonyl)-1H-pyrazolo[3,4-c]pyridine;
1-({5-chloro-1-[2-(oxetan-3-yl)ethyl]-1H-benzimidazol-2-yl}methyl)-3-(methylsulfonyl)-1H-pyrazolo[3,4-c]pyridine;
1-{[5-chloro-1-(4,4,4-trifluorobutyl)-1H-benzimidazol-2-yl]methyl}-3-(methylsulfonyl)-1H-pyrazolo[3,4-c]pyridine;
1-{[5-chloro-7-fluoro-1-(3,3,3-trifluoropropyl)-1H-benzimidazol-2-ylmethyl]-3-(methylsulfonyl)-1H-pyrazolo[3,4-c]pyridine;
1-[5-Chloro-1-(3-methanesulfonyl-propyl)-1H-benzoimidazol-2-ylmethyl]-3-methanesulfonyl-1H-pyrazolo[3,4-c]pyridine;
1-[5-Chloro-1-((R)-1,1-dioxo-tetrahydro-1$\lambda^6$-thiophen-3-yl)-1H-benzoimidazol-2-ylmethyl]-3-methanesulfonyl-1H-pyrazolo[3,4-c]pyridine;
1-[5-Chloro-1-(1,1-dioxo-tetrahydro-1$\lambda^6$-thiophen-3-yl)-1H-benzoimidazol-2-ylmethyl]-3-methanesulfonyl-1H-indazole;
4-[5-Chloro-2-(3-methanesulfonyl-pyrazolo[3,4-c]pyridin-1-ylmethyl)-benzoimidazol-1-yl]-piperidin-2-one;
1-[5-Chloro-1-(tetrahydro-pyran-4-yl)-1H-benzoimidazol-2-ylmethyl]-3-methanesulfonyl-1H-pyrazolo[3,4-c]pyridine;
1-[5-Chloro-1-(3,3-difluoro-cyclopentyl)-1H-benzoimidazol-2-ylmethyl]-3-methanesulfonyl-1H-indazole;
4-[5-Chloro-2-(3-methanesulfonyl-pyrazolo[3,4-c]pyridin-1-ylmethyl)-benzoimidazol-1-yl]-cyclohexanol;
1-{[5-Chloro-1-(2-oxaspiro[3.3]hept-6-yl)-1H-benzimidazol-2-yl]methyl}-3-(methylsulfonyl)-1H-pyrazolo[3,4-c]pyridine;
1-({5-Chloro-1-[2-(3-methyloxetan-3-yl)ethyl]-1H-benzimidazol-2-yl}methyl)-3-(methylsulfonyl)-1H-pyrazolo[3,4-c]pyridine;
trans-3-(5-Chloro-2-{[3-(methylsulfonyl)-1H-pyrazolo[3,4-c]pyridin-1-yl]methyl}-1H-benzimidazol-1-yl)-1-methylcyclobutanol;
3-(5-Chloro-2-{[3-(methylsulfonyl)-1H-pyrazolo[3,4-c]pyridin-1-yl]methyl}-1H-benzimidazol-1-yl)propan-1-ol;
1-{[5-Chloro-1-(tetrahydrofuran-3-yl)-1H-benzimidazol-2-yl]methyl}-3-(methylsulfonyl)-1H-pyrazolo[3,4-c]pyridine;
4-(5-Chloro-2-{[3-(methylsulfonyl)-1H-pyrazolo[3,4-c]pyridin-1-yl]methyl}-1H-benzimidazol-1-yl)-2-methylbutan-2-ol;
4-(5-Chloro-2-{[3-(methylsulfonyl)-1H-pyrazolo[3,4-c]pyridin-1-yl]methyl}-1H-benzimidazol-1-yl)butan-1-ol;
1-{[5-Chloro-1-(tetrahydrofuran-3-ylmethyl)-1H-benzimidazol-2-yl]methyl}-3-(methylsulfonyl)-1H-pyrazolo[3,4-c]pyridine;
trans-3-(5-Chloro-2-{[3-(methylsulfonyl)-1H-pyrazolo[3,4-c]pyridin-1-yl]methyl}-1H-benzimidazol-1-yl)cyclobutanol;
cis-3-(5-Chloro-2-{[3-(methylsulfonyl)-1H-pyrazolo[3,4-c]pyridin-1-yl]methyl}-1H-benzimidazol-1-yl)-1-methylcyclobutanol;
1-[2-(5-Chloro-2-{[3-(methylsulfonyl)-1H-pyrazolo[3,4-c]pyridin-1-yl]methyl}-1H-benzimidazol-1-yl)ethyl]cyclopropanol;
trans-3-(5-Chloro-2-{[3-(methylsulfonyl)-1H-pyrazolo[3,4-c]pyridin-1-yl]methyl}-1H-benzimidazol-1-yl)cyclopentanol;
cis-4-(5-Chloro-2-{[3-(methylsulfonyl)-1H-pyrazolo[3,4-c]pyridin-1-yl]methyl}-1H-benzimidazol-1-yl)-1-methylcyclohexanol;
5-(5-Chloro-2-{[3-(methylsulfonyl)-1H-pyrazolo[3,4-c]pyridin-1-yl]methyl}-1H-benzimidazol-1-yl)-2-methylpentan-2-ol;
2-[trans-3-(5-Chloro-2-{[3-(methylsulfonyl)-1H-pyrazolo[3,4-c]pyridin-1-yl]methyl}-1H-benzimidazol-1-yl)cyclobutyl]propan-2-ol;
trans-3-(5-Chloro-2-{[3-(methylsulfonyl)-1H-pyrazolo[3,4-c]pyridin-1-yl]methyl}-1H-benzimidazol-1-yl)cyclobutanecarboxylic acid;
4-(5-Chloro-2-{[3-(methylsulfonyl)-1H-pyrazolo[3,4-c]pyridin-1-yl]methyl}-1H-benzimidazol-1-yl)-1,1,1-trifluorobutan-2-ol;
4-(5-Chloro-2-{[3-(methylsulfonyl)-1H-pyrazolo[3,4-c]pyridin-1-yl]methyl}-1H-benzimidazol-1-yl)-1,1-difluorobutan-2-ol;
1-[5-Chloro-1-(6-fluoro-pyridin-3-yl)-1H-benzoimidazol-2-ylmethyl]-3-methanesulfonyl-1H-indazole;
1-[5-Chloro-7-fluoro-1-(4,4,4-trifluoro-butyl)-1H-benzoimidazol-2-ylmethyl]-3-methanesulfonyl-1H-pyrazolo[3,4-c]pyridine;
1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]ethanone;
1-[3-(5-Chloro-2-{[3-(methylsulfonyl)-1H-indazol-1-yl]methyl}-1H-benzimidazol-1-yl)pyrrolidin-1-yl]ethanone;
1-[(3R)-3-(5-Chloro-2-{[3-(methylsulfonyl)-1H-indazol-1-yl]methyl}-1H-benzimidazol-1-yl)pyrrolidin-1-yl]propan-1-one;
1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]-2-methylpropan-1-one;
1-({5-Chloro-1-[(3R)-1-(methylsulfonyl)pyrrolidin-3-yl]-1H-benzimidazol-2-yl}methyl)-3-(methylsulfonyl)-1H-pyrazolo[3,4-c]pyridine;
2-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]ethanol;
4-(5-Chloro-2-{[3-(methylsulfonyl)-1H-pyrazolo[3,4-c]pyridin-1-yl]methyl}-1H-benzimidazol-1-yl)pyrrolidin-2-one;
1-{[5-Chloro-1-(2-oxa-5-azaspiro[3.4]oct-7-yl)-1H-benzimidazol-2-yl]methyl}-3-(methylsulfonyl)-1H-pyrazolo[3,4-c]pyridine;
1-({5-Chloro-1-[2-(methylsulfonyl)ethyl]-1H-indol-2-yl}methyl)-3-(methylsulfonyl)-1H-pyrazolo[3,4-c]pyridine;
1-({5-Chloro-1-[3-(methylsulfonyl)propyl]-1H-indol-2-yl}methyl)-3-(methylsulfonyl)-1H-pyrazolo[3,4-c]pyridine;
1-({5-Chloro-7-fluoro-1-[2-(methylsulfonyl)ethyl]-1H-indol-2-yl}methyl)-3-(methylsulfonyl)-1H-pyrazolo[3,4-c]pyridine;
1-[2-(5-Chloro-2-{[3-(methylsulfonyl)-1H-pyrazolo[3,4-c]pyridin-1-yl]methyl}-1H-benzimidazol-1-yl)ethyl]pyrrolidin-3-ol;
1-[2-(5-Chloro-2-{[3-(methylsulfonyl)-1H-pyrazolo[3,4-c]pyridin-1-yl]methyl}-1H-benzimidazol-1-yl)ethyl]piperidin-4-ol;

[trans-3-(5-Chloro-2-{[3-(methylsulfonyl)-1H-pyrazolo[3,4-c]pyridin-1-yl]methyl}-1H-benzimidazol-1-yl)cyclobutyl]methanol;

1-({5-Chloro-1-[(3R)-1,1-dioxidotetrahydrothiophen-3-yl]-7-fluoro-1H-benzimidazol-2-yl}methyl)-3-(methylsulfonyl)-1H-pyrazolo[3,4-c]pyridine; and 3-(5-Chloro-2-{[3-(methylsulfonyl)-1H-pyrazolo[3,4-c]pyridin-1-yl]methyl}-1H-benzimidazol-1-yl)(1,1-$^2$H$_2$)propan-1-ol.

Compound with favorable pharmacokinetics is more likely to be efficacious and safe. It is very important for a drug to have a moderate or low clearance and a long half-life, as this often lead to a good oral bioavailability and high exposure in systemic exposure. Reducing the clearance and increasing half-life time of a compound or drug could reduce the daily dose required for efficacy and therefore give a better efficacy and safety profile. From the examples below, it has been found a good SDPK profiling of this invention: good exposure at low dose, longer t ½(more than 1 h), low to moderate clearance and good bioavailability (see Table 3).

The single dose PK in male ICR mouse was performed to assess their pharmacokinetic properties. Two groups of animals were dosed via either bolus intravenous (IV) or oral gavage (PO) of the respective compound. The animals for oral administration were fasted overnight prior to dosing and food was resumed 4 hours postdose. Blood samples (approximately 400 µL) were collected via cardiac puncture after euthanasia by carbon dioxide inhalation at 2 min, 5 min, 15 min, 30 min, 1 h, 2 h, 4 h, 6 h, 8 h, and 24 h postdose for IV group, and at 5 min, 15 min, 30 min, 1 h, 2 h, 4 h, 6 h, 8 h, and 24 h postdose for PO group. Blood samples were placed into tubes containing sodium heparin and centrifuged at 8000 rpm for 6 minutes at 4° C. to separate plasma from the samples.

Following centrifugation, the resulting plasma was transferred to clean tubes for bioanalysis on LC/MS/MS. The pharmacokinetic parameters were calculated using non-compartmental module of WinNonlin® Professional 5.2.

TABLE 3

Selected Pharmacokinetics Parameters of Compounds in Male ICR Mice Following Intravenous and Oral Administration

|  | AUC$_{(0-t)}$ µg/L*hr | t$_{1/2}$ hr | CLz mL/min/kg | F % |
|---|---|---|---|---|
| Example 2-21 | | | | |
| IV (1.65 mg/Kg) | 2590 | 2.82 | 10.6 | NA* |
| PO (8.27 mg/kg) | 4800 | 3.16 | NA* | 37.1 |
| Example 2-22 | | | | |
| IV (1 mg/Kg) | 976 | 1.55 | 16.9 | NA* |
| PO (12.2 mg/kg) | 2430 | 2.45 | NA | 23.8 |
| Example 4-3 | | | | |
| IV (2 mg/kg) | 760 | 1.26 | 43.4 | NA* |
| PO (6 mg/kg) | 1050 | 0.831 | NA* | 46.0 |

In the above Table 3, the abbreviations have the following meanings

AUC$_{(0-t)}$: area under the curve from 0 to t hour;

t$_{1/2}$: elimination half-life;

CLz: clearance;

F: bioavailability;

IV: intravenous;

PO: oral gavage.

NA*: not applicable

Synthesis

The compounds of the present invention can be prepared by any conventional means. Suitable processes for synthesizing these compounds as well as their starting materials are provided in the schemes below and in the examples. All substituents, in particular, R$^1$ to R$^5$, R$^7$, A$^1$, A$^2$ and A$^3$ are as defined above unless otherwise indicated. Furthermore, and unless explicitly otherwise stated, all reactions, reaction conditions, abbreviations and symbols have the meanings well known to a person of ordinary skill in organic chemistry.

General synthetic route for formula Ia (Scheme 1)

Scheme 1

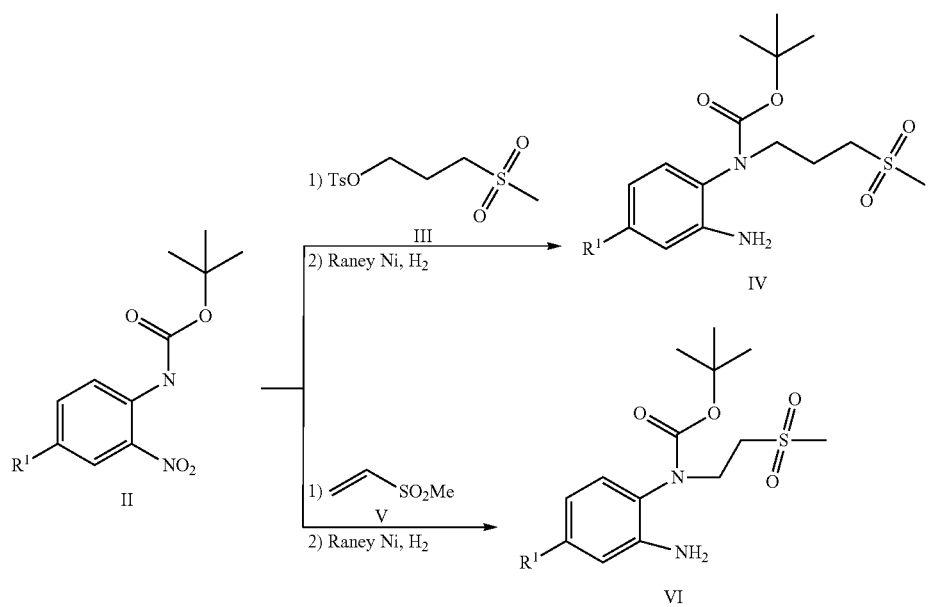

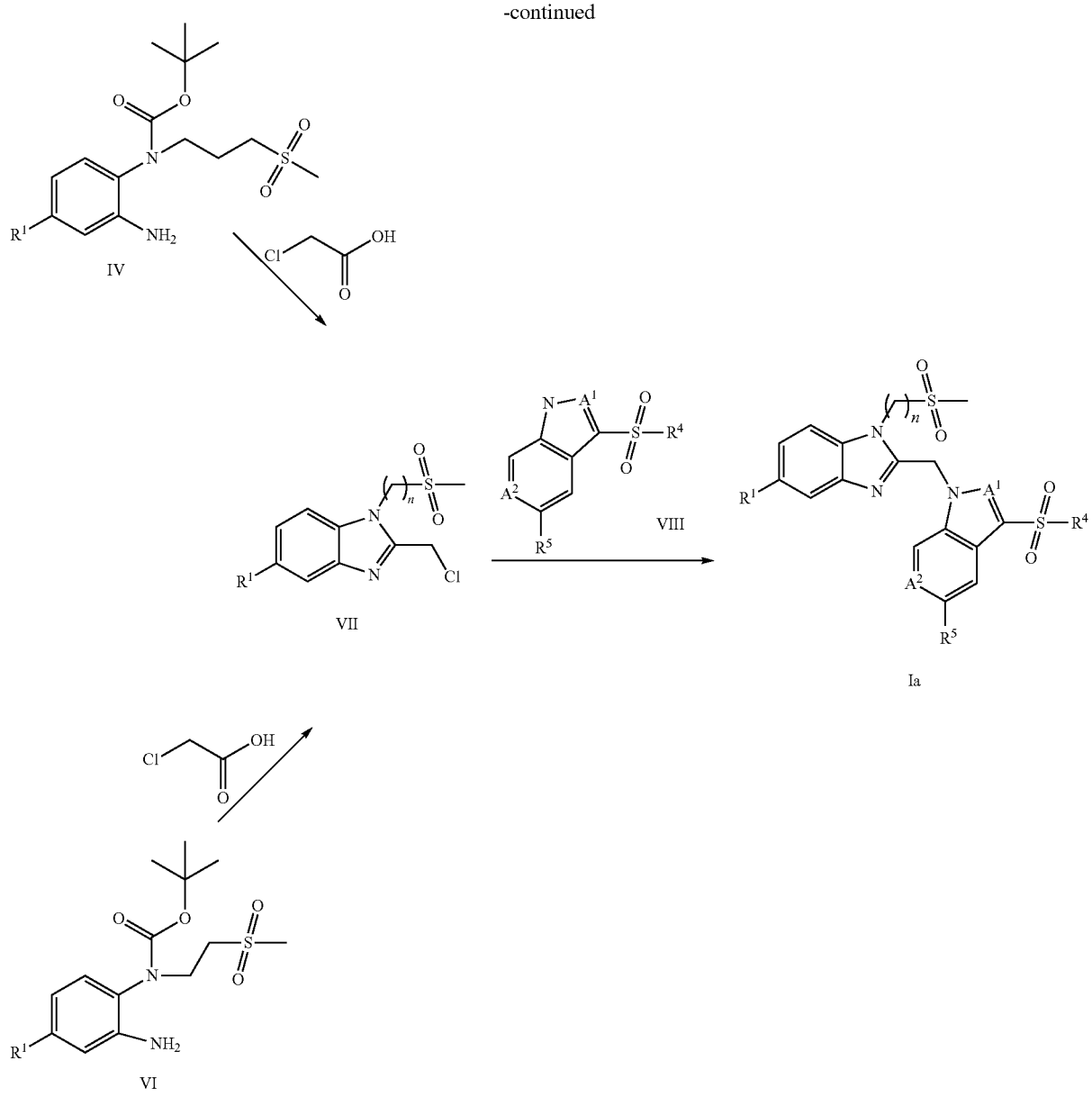

n is 2 or 3.

Compounds of formula Ia can be prepared according to Scheme 1. Alkylation of o-nitro Boc-protected anilines II with methylsulfone sulfonates III in the presence of a base such as K₂CO₃ or Cs₂CO₃, followed by reduction of nitro group affords intermediate IV. Michael addition of o-nitro Boc-protected anilines II with (C₁₋₆alkylsulfonyl)ethenes V affords o-nitro-N-substituted anilines VI accordingly. Treatment of IV or VI with chloroacetic acid in hydrochloric acid produces 2-(chloromethyl)benzimidazoles VII. Coupling of intermediates VII and VIII in the presence of a base such as K₂CO₃ or Cs₂CO₃ gives the compounds of formula Ia.

General synthetic route for formula Ib (Scheme 2)

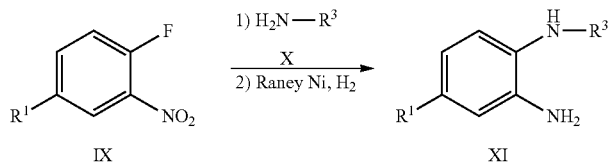

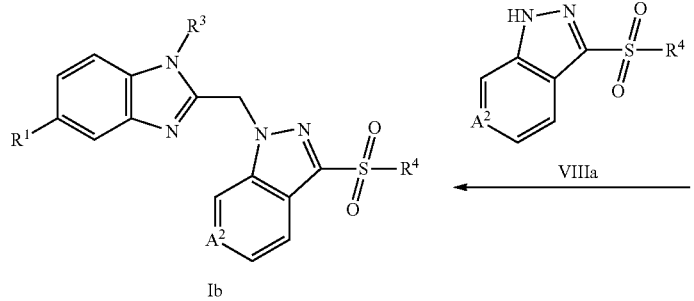
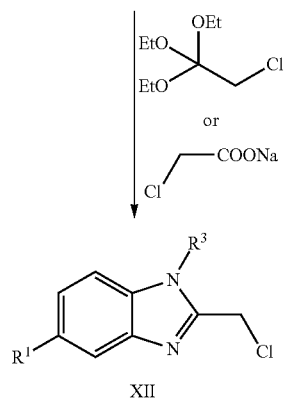

$R^3$ is azetidinyl; hydroxy$C_{3-7}$cycloalkyl, unsubstituted or once substituted by $C_{1-3}$alkyl; oxetanyl; piperidinyl; oxo-piperidinyl; pyrrolidinyl, unsubstituted or substituted by $C_{1-6}$alkylcarbonyl, hydroxy-CxH2x-carbonyl, amino-CxH2x-carbonyl or trifluoromethyl-CxH2x-; tetrahydrofuranyl; tetrahydropyranyl; 1,1-dioxo-tetrahydrothiophenyl, aminooxetanyl-CxH2x—; hydroxyoxetanyl-CxH2x- or trifluoromethyl-CxH2x-.

Compounds of formula Ib can be prepared according to Scheme 2. Coupling of 1-fluoro-2-nitro derivatives IX with amine X, followed by reduction of nitro gives N-substituted anilines XI. Treatment of XI with 2-chloro-1,1,1-triethoxy-ethane under microwave radiation or chloroacetic sodium affords intermediate 2-(chloromethyl)benzimidazoles XII. Benzimindazole XII can be coupled with VIIIa in the presence of a base such as $K_2CO_3$ or $Cs_2CO_3$ to afford compounds of formula Ib.

General synthetic route for formula Ic and Id (Scheme 3)

Scheme 3

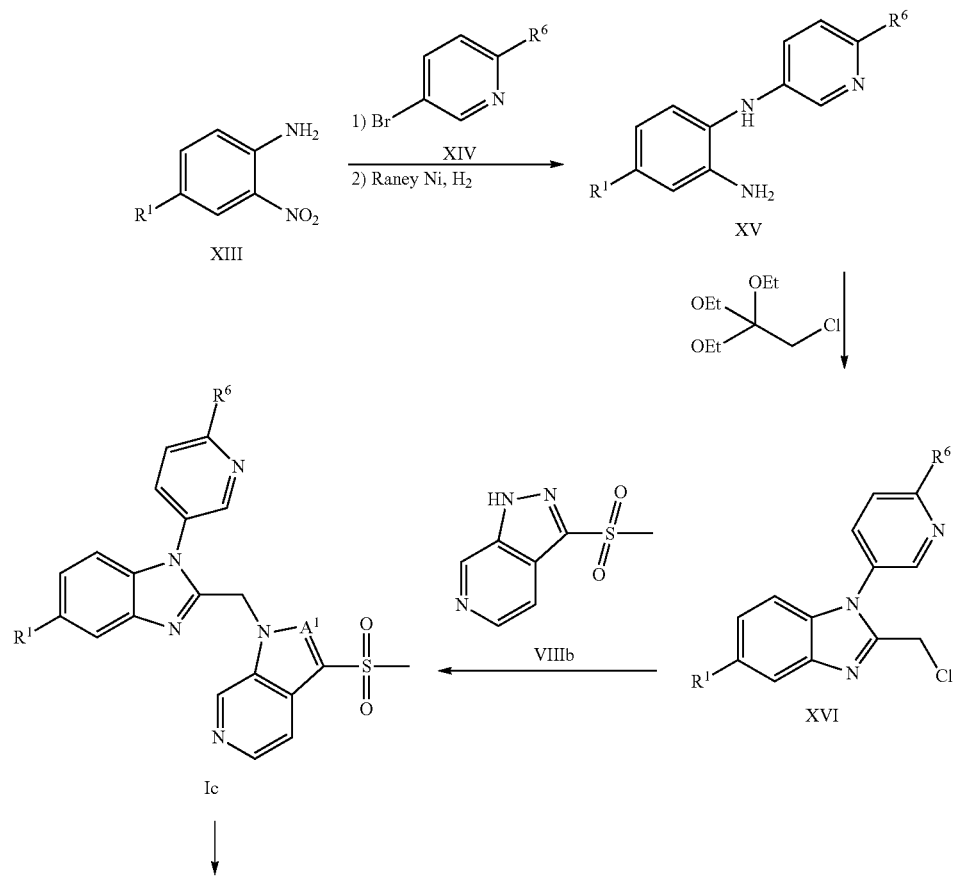

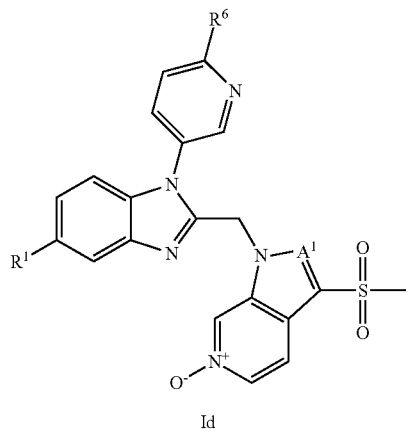

Id

R⁶ is fluoro, chloro or methoxy.

Compounds of formula Ic and Id can be prepared according to Scheme 3. Coupling of o-nitro aniline XIII with aryl bromide XIV in the presence of palladium catalyst, followed by reduction of nitro with hydrogen in the presence of Raney Nickel gives N-substituted anilines XV. Treatment of XV with 2-chloro-1,1,1-triethoxyethane under microwave radiation affords intermediate 2-(chloromethyl)benzimidazoles XVI. Benzimindazole XVI can be coupled with VIIIb in the presence of a base such as $K_2CO_3$ or $Cs_2CO_3$ to afford compounds of formula Ic. Oxidation of Ic with m-CPBA produces N-oxide compounds Id.

General synthetic route for formula Ie (Scheme 4)

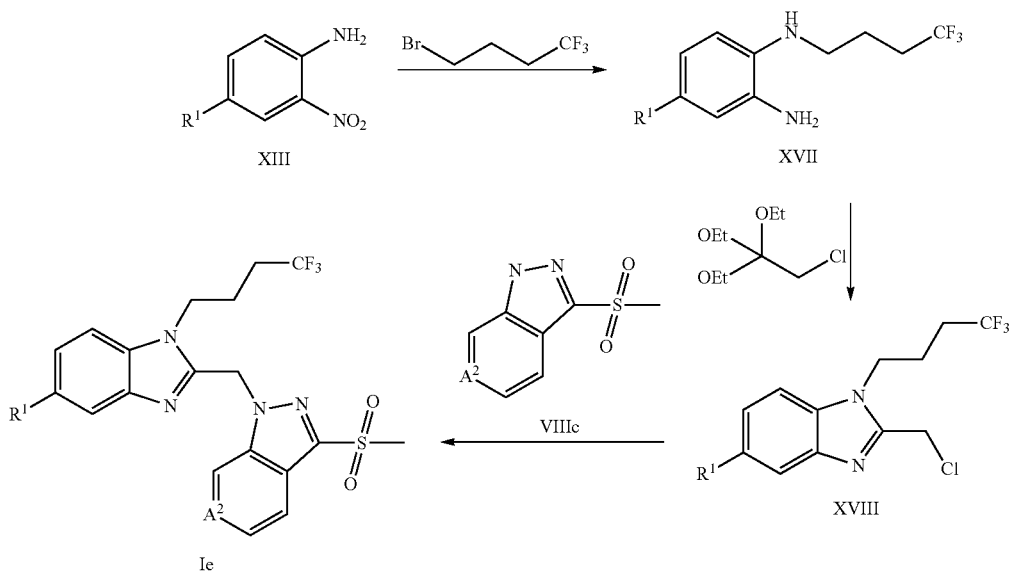

Compounds of formula Ie can be prepared according to Scheme 4. Alkylation of o-nitro anilines XIII with trifluoromethyl $C_{1-6}$alkyl bromide in the presence of a base such as $K_2CO_3$, followed by reduction of nitro group affords intermediate XVII. Treating XVII with 2-chloro-1,1,1-triethoxyethane or chloroacetic acid in hydrochloric acid affords 2-(chloromethyl)benzimidazoles XVIII. Reaction of 2-(chloromethyl)benzimidazoles XVIII with indazole VIIIc in the presence of a base such as $K_2CO_3$ or $Cs_2CO_3$ affords compounds of formula Ie.

General synthetic route for formula If (Scheme 5)

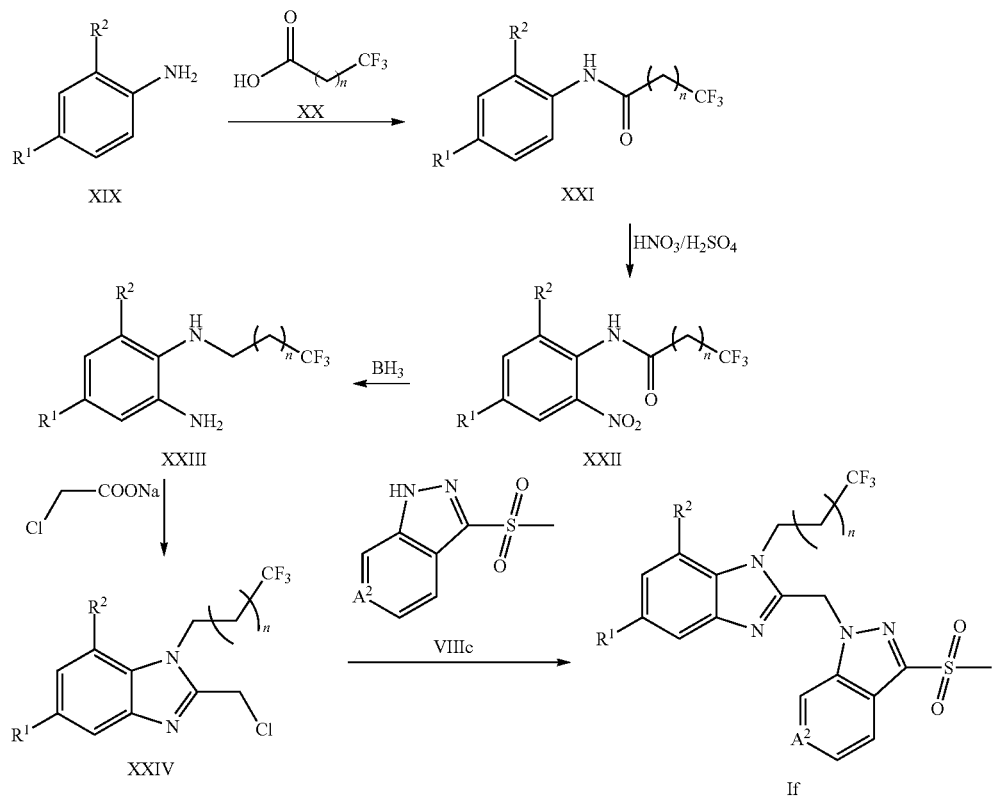

Compounds of formula If can be prepared as shown in Scheme 5. After coupling with trifluoromethyl $C_{1-6}$alkyl acid XX, the amide XXI can be introduced nitro group at ortho-position of amide to give intermediate XXII, which can be further reduced with borane and treated with chloroacetic sodium to afford the 2-(chloromethyl)benzimidazoles XXIV. Coupling of 2-(chloromethyl)benzimidazoles XXIV with indazole VIIIc affords compounds of formula If.

General synthetic route for intermediate VIIIa (Scheme 6)

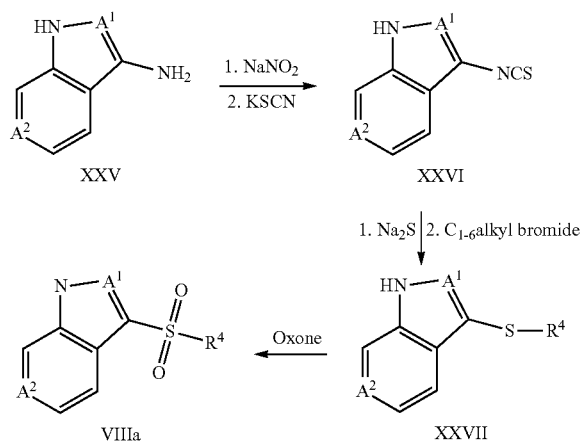

Compound VIIIa can be prepared as shown in Scheme 6.

The nitrosation of hetero aromatic amines XXV with sodium nitrite in acidic condition leads to diazonium salts, which are treated with potassium thiocyanate to afford intermediate XXVI. After reaction with sodium sulfide, and alkylation with $C_{1-6}$alkyl bromide, intermediate $C_{1-6}$alkyl sulfanyl XXVII is generated, which can be further oxidized to afford Compound VIIIa.

General synthetic route for intermediate VIII b/c (Scheme 7)

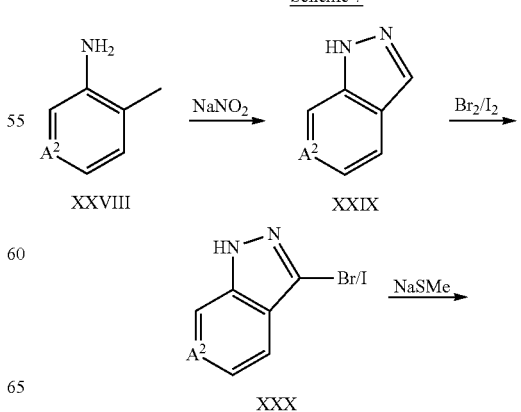

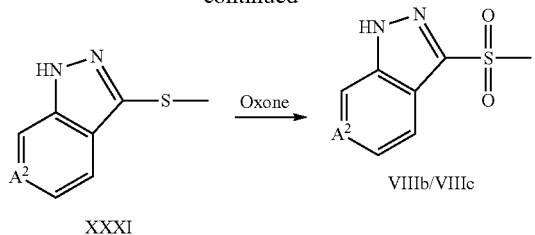

XXXI → VIIIb/VIIIc (Oxone)

Compounds VIIIb and VIIIc can be prepared as shown in Scheme 7.

The nitrosation of hetero aromatic amines XXVIII with sodium nitrite and acid generates diazonium salts, which forms indazole XXIX. Halogenation of indazole XXIX with bromine or iodine, followed by coupling with sodium sulfide affords $C_{1-6}$alkyl sulfanyl intermediate XXXI, which can be further oxidized to give Compounds VIIIb and VIIIc.

General synthetic route for formula Ig (Scheme 8)

Compounds of formula Ig can be prepared as shown in Scheme 8. Reaction of indole XXXII with 1,y-dibromoalkane XXXIII followed by reaction of bromide XXXIV with $NaSCH_3$ and oxidation of sulfide with m-CPBA affords N—$C_{2-6}$alkylsulfonyl-$C_yH_{2y}$-indole XXXV. Reduction of ethyl ester XXXV generates 2-hydroxymethyl indole XXXVIII. XXXVIII also can be generated by coupling of 2-hydroxymethyl indole XXXVI with ($C_{1-6}$alkylsulfonyl)ethene XXXVII. Mitsunobu Reaction of hydroxy XXXVIII with indazole VIIIc in the presence of $PPh_3$ and DIAD affords Compound Ig. Alternatively, Ig can be generated by conversion of hydroxy group to methanesulfonate with MsCl followed by reaction with indazole VIIIc in the presence of a suitable base.

Scheme 8

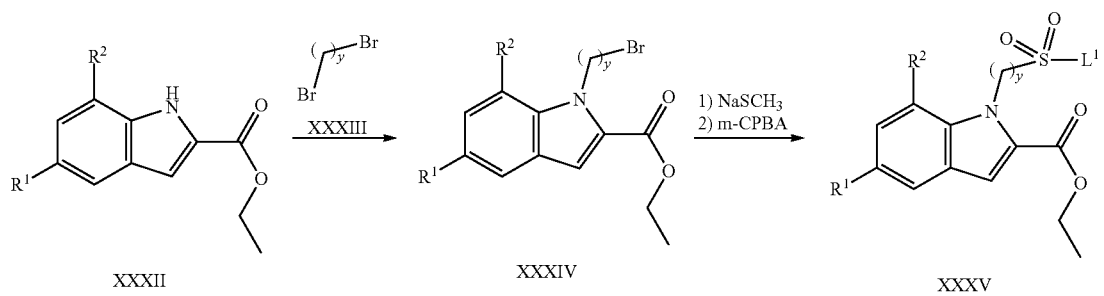

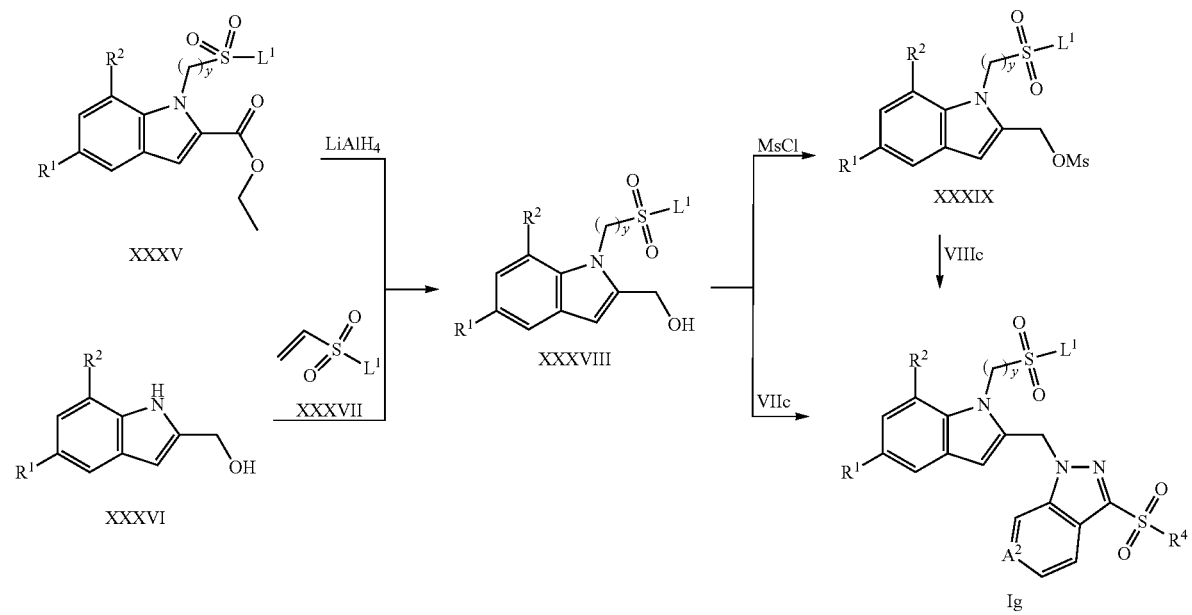

$L^1$ is $C_{1-6}$alkyl.

General synthetic route for formula Ij (Scheme 9)

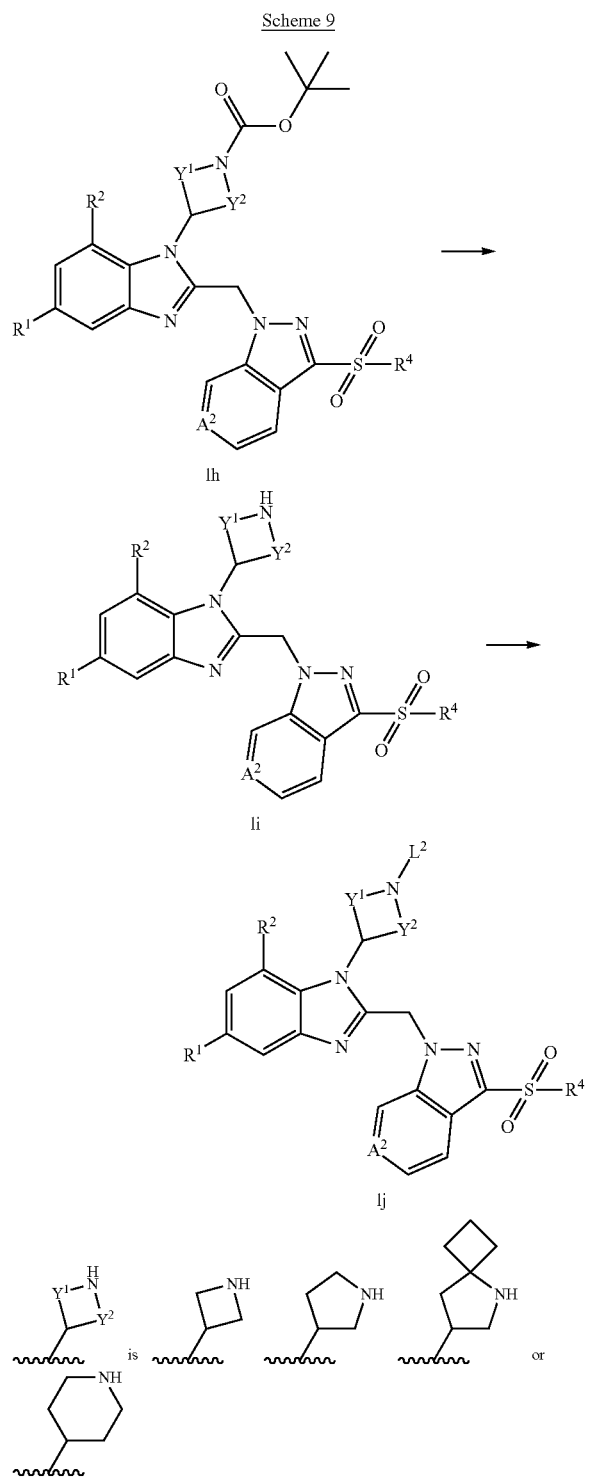

L² is C₁₋₆alkylcarbonyl, C₁₋₆alkylsulfonyl, hydroxyC$_x$H$_{2x}$, hydroxyC$_x$H$_{2x}$carbonyl, CF₃C$_x$H$_{2x}$, or N-Boc aminoC$_x$H$_{2x}$carbonyl Compounds of formula Ii and Ij can be prepared as shown in Scheme 9. tert-Butyl carboxylate Ih can be prepared according to the method described in Scheme 2. Removal of tert-butyl carboxylate of Ih in acid condition generates compound Ii. Reaction of amine Ii with acetic anhydride, substituted acetic acid, C₁₋₆alkylsulfonyl chloride, hydroxyl-C$_x$H$_{2x}$-bromide or trifluoroC₁₋₆alkyl trifluoromethanesulfonate in the presence or absence of a suitable base such as Cs₂CO₃ or DMAP generates Compound Ij.

General synthetic route for formula Im (Scheme 10)

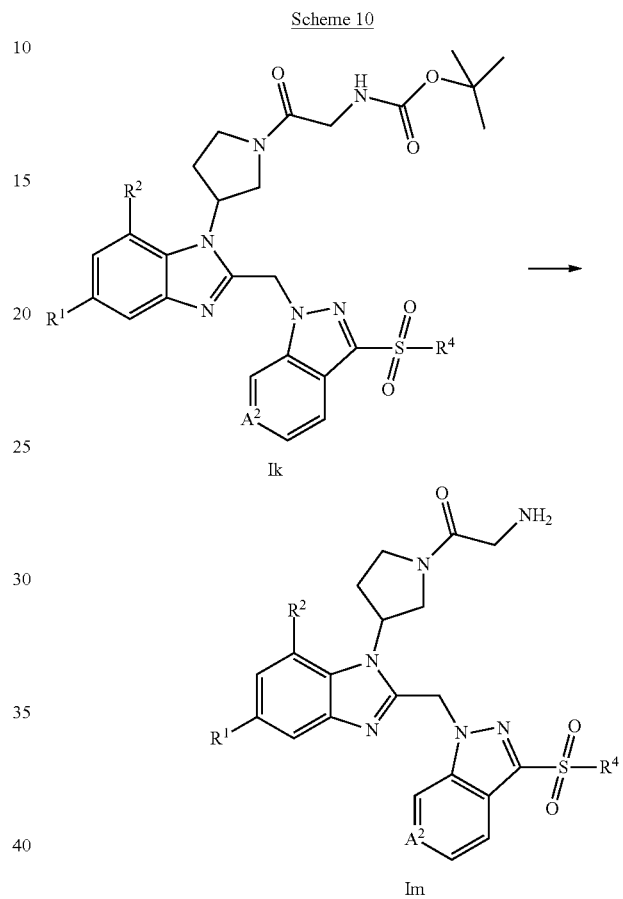

Compounds of formula Im can be prepared as shown in Scheme 10. tert-Butyl carboxylate Ik can be prepared according to the method described in Scheme 9. Removal of tert-butyl carboxylate of Ik in acid condition generates Compound Im.

General synthetic route for formula Io (Scheme 11)

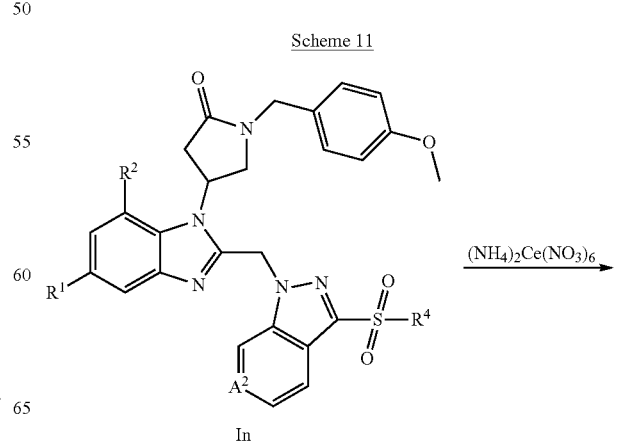

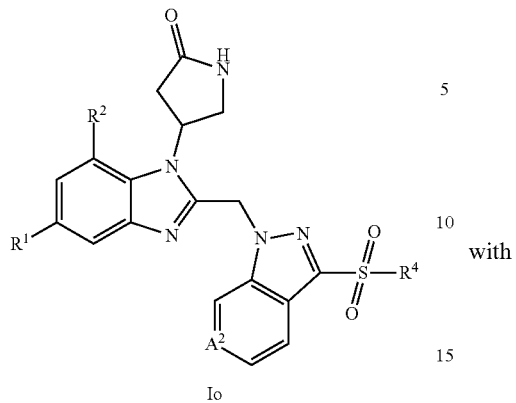

Io

Compounds of formula Io can be prepared as shown in Scheme 11. Compound In can be prepared according to the method described in Scheme 2. Removal of p-methoxy-benzyl group of In by treating In with $(NH_4)_2Ce(NO_3)_6$ generates Compound Io.

General synthetic route for formula Ip (Scheme 12)

Scheme 12

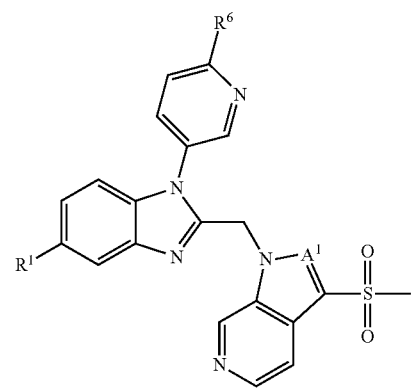

Ip

Compounds of formula Ip can be prepared as shown in Scheme 12. Cyclization of diamine XI with 2-hydroxy-carboxylic acid XL in 6 N HCl affords hydroxy XLI. Mitsunobu reaction of hydroxy XLI with indazole VIM affords Compound Ip.

This invention also relates to a process for the preparation of a compound of formula I comprising the reaction of (a) a compound of formula (A)

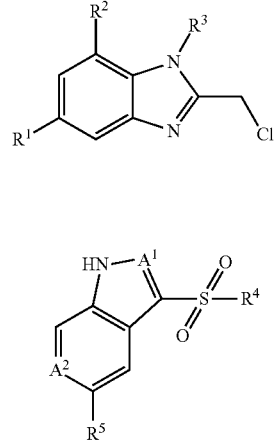

with in the presence of a base;
(b) a compound of formula (B)

(B)

in the presence of m-CPBA;
(c) a compound of formula (C)

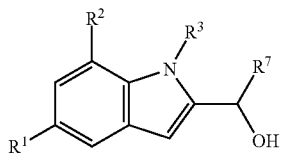

with indazole in the presence of $PPh_3$ and DIAD;
(d) a compound of formula (D)

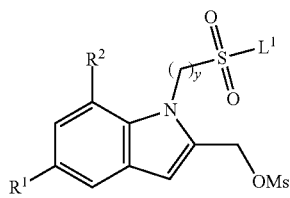

with indazole in the presence of a base;

(e) a compound of formula (E)

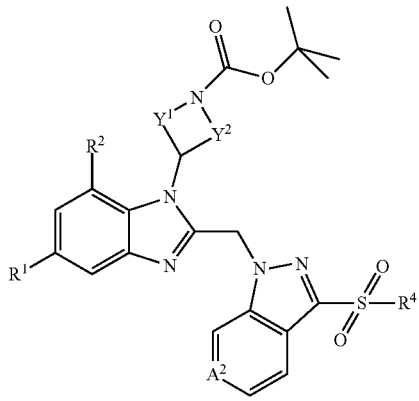

in the presence of an acid;

(f) a compound of formula (F)

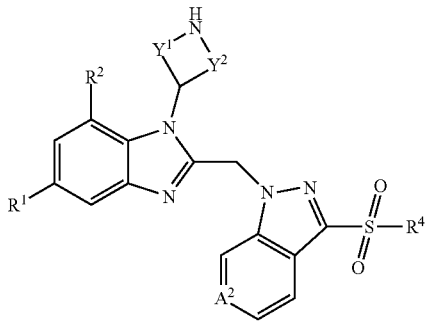

with acetic anhydride, substituted acetic acid, $C_{1-6}$alkylsulfonyl chloride, hydroxyl-$C_xH_{2x}$-bromide or trifluoro$C_{1-6}$alkyl trifluoromethanesulfonate in the presence or absence of a base; (g) a compound of formula (G)

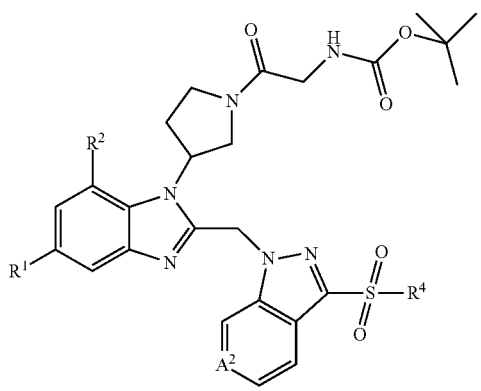

in the presence of an acid;

(h) a compound of formula (H)

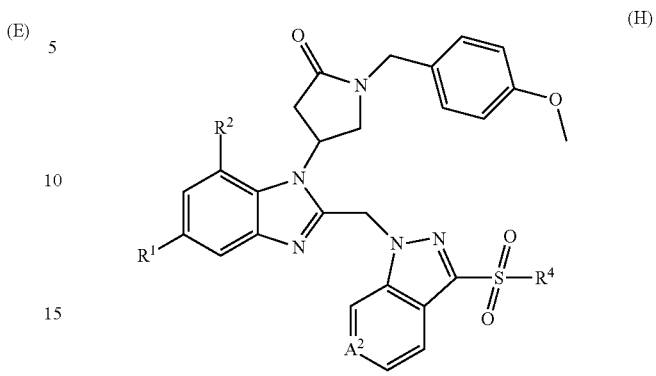

with $(NH_4)_2Ce(NO_3)_6$;
wherein $R^1$ to $R^5$, $R^7$, x, $A^1$ to $A^3$ are defined above unless otherwise indicated; $R^6$ is independently selected from halogen and $C_{1-6}$alkoxy; $L^1$ is $C_{1-6}$alkyl;

In step (a), the base can be for example $K_2CO_3$ or $Cs_2CO_3$.
In step (d), the base can be for example $K_2CO_3$ or $Cs_2CO_3$.
In step (e), the acid can be for example TFA or HCl.
In step (f), the base can be for example TEA, $Cs_2CO_3$ or DMAP.
In step (g), the acid can be for example TFA or HCl.
A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit RSV fusion protein. For example, such amount may be below the amount that is toxic to normal cells, or the mammal as a whole.

In one example, the pharmaceutically effective amount of the compound of the invention administered parenterally per dose will be in the range of about 0.1 to about 50 mg/kg, alternatively about 0.1 to about 20 mg/kg of patient body weight per day, with the typical initial range of compound used being about 0.3 to about 15 mg/kg/day. In another embodiment, oral unit dosage forms, such as tablets and capsules, preferably contain from about 25 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg to about 500 mg of the compound of the invention compounded with about 90 to about 30 mg anhydrous lactose, about 5 to about 40 mg sodium croscarmellose, about 5 to about 30 mg polyvinylpyrrolidone (PVP) K30, and about 1 to about 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg), of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can be utilized to inhibit RSV fusion protein, therefore prevent the virus cell syncytial function. Accordingly, the compounds of the invention are useful for the treatment or prophylaxis of RSV infection.

The use of a compound of formula I for the preparation of medicaments useful in the treatment or prophylaxis diseases that are related to RSV infection is an object of the invention.

The invention relates in particular to the use of a compound of formula I for the preparation of a medicament for the treatment or prophylaxis of RSV infection.

Another embodiment includes a method of treating or preventing RSV infection in a mammal in need of such treatment, wherein the method comprises administering to said mammal a therapeutically effective amount of a compound of Formula I, a stereoisomer, tautomer, prodrug or pharmaceutically acceptable salt thereof.

Combination Therapy

The compounds of the invention can be used in combination with other antiviral ingredients for the treatment or prophylaxis of RSV infection.

EXAMPLES

The invention will be more fully understood by reference to the following examples. They should not, however, be construed as limiting the scope of the invention.

Abbreviations used herein are as follows:

μg: microgram
μL: microliter
μm: micrometer
μM: micromoles per liter
AcOH: acetic acid
aq. aqueous
AUC: area under the curve
Boc$_2$O di-tert-butyl carbonate
CC$_{50}$: half-maximal cytotoxic concentration
CD$_3$OD: deuterated methanol
CDCl$_3$: deuterated chloroform
DCM: dichloromethane
DEAD: diethyl diazenedicarboxylate
DPPA: diphenylphosphoryl azide
DMAP: 4-dimethylaminopyridine
DMF: dimethylformamide
DMSO-d6: deuterated dimethylsulfoxide
EC$_{50}$: the concentration of a compound where 50% of its maximal protection effect against viral induced CPE is observed
Et: ethyl
EA or EtOAc: ethyl acetate
EtOH: ethyl alcohol
g: gram h or hr: hour
HPLC: high performance liquid chromatography
Hz: Hertz
ICR: Imprinting Control Region
J: coupling constants
LC/MS: Liquid chromatography/mass spectrometry
LongStrain: an A subtype RSV strain obtained from ATCC with catalog number VR-26
m: multiple
m-CPBA: 3-chloroperbenzoic acid
Me: methyl
MeOH: methanol
mg: milligram
MHz: megahertz
min: minute
mins: minutes
mL: milliliter
mm: millimeter
mmol: millimole
MS (ESI): mass spectroscopy (electron spray ionization)
NMR: nuclear magnetic resonance
obsd.: observed
oxone: dipotassium peroxymonosulfate
PE: petroleum ether
Ph: phenyl
PK: Pharmacokinetics
Pd/C: palladium on activated carbon
Pd$_2$(dba)$_3$: tris(dibenzylideneacetone)dipalladium(0)
SDPK: Single Dose pharmacokinetics
Prep HPLC: preparative high performance liquid chromatography
q: quartet
RT: room temperature
s: singlet
sat.: saturated
t: triplet
TEA: triethylamine
TFA: trifluoroacetic acid
THF: tetrahydrofuran
TLC: thin layer chromatography
δ: chemical shift
General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):
Acidic condition: A: 0.1% formic acid in H$_2$O; B: 0.1% formic acid in acetonitrile;
Basic condition: A: 0.01% NH$_3$.H$_2$O in H$_2$O; B: acetonitrile;
Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

PREPARATIVE EXAMPLES

Example 1-1

1-[2-(Methylsulfonyl)ethyl]-2-{[3-(methylsulfonyl)-1H-indol-1-yl]methyl}-1H-benzimidazole Step 1: synthesis of 2-chloromethyl-1-(2-methane sulfonyl-ethyl)-1H-benzoimidazole

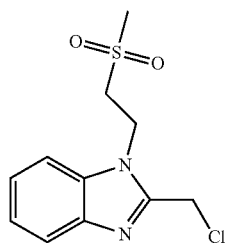 [SMILES: CS(=O)(=O)CCn1c(CCl)nc2ccccc21]

A mixture of (1H-benzo[d]imidazol-2-yl)methanol (1.0 g, 6.75 mmol) and 1-chloro-2-(methylsulfonyl) ethane (1.05 g, 7.42 mmol) in DMF (3 mL) was stirred in the presence of K$_2$CO$_3$ (0.93 g, 6.75 mmol) at RT for overnight. The mixture was poured into water (20 mL) and extracted with DCM (50 mL×3). The combined organic layer was dried over anhydrous Na$_2$SO$_4$ and concentrated under vacuum to give the crude (1-(2-(methylsulfonyl)ethyl)-1H-benzo[d]imidazol-2-yl)methanol which was used for next step directly.

To a solution of crude (1-(2-(methylsulfonyl)ethyl)-1H-benzo[d]imidazol-2-yl)methanol in DCM (30 mL) was added SOCl$_2$ (5 mL). The mixture was heated to reflux and monitored by LCMS. After the reaction completed, the solvents was evaporated. The residue was redissolved in DCM (100 mL) and washed with saturated NaHCO$_3$ (2×30 mL), dried over Na$_2$SO$_4$ and concentrated under vacuum to afford the crude product (600 mg, yield: 33%) as oil. MS obsd. (ESI$^+$) [(M+H)$^+$]: 273.1.

Step 2: synthesis of 3-methanesulfonyl-1H-indole

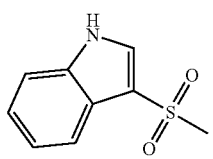

Under N$_2$ atmosphere, to a solution of N-chlorosuccinimide (2.2 g, 16.5 mmol) in DCM (50 mL) was added dimethylsulfide (1 g, 16.5 mmol) at 0° C. After stirring at 0° C. for 15 min, the mixture was cooled to −20° C. Then a solution of indole (1.9 g, 16.5 mmol) in DCM (50 mL) was added slowly. After the completion of addition, the mixture was allowed to warm to RT and stirred for an hour. The solvent was removed under vacuum and the residue was dissolved in xylene (100 mL) and was heated at 150° C. for 30 mins. The mixture was cooled to RT and filtered. To the filtrate was added m-CPBA (7.6 g, 33.0 mmol). The reaction was stirred at RT and monitored by LCMS. After the reaction completed, the organic layer was concentrated and the residue was purified by column on silica gel (EtOAc:Hexane=100:20) to afford 3-(methylsulfonyl)-1H-indole (500 mg, yield: 16%) as off-white solid. MS obsd. (ESI+) [(M+H)+]: 196.0.

Step 3: synthesis of 1-[2-(methylsulfonyl)ethyl]-2-{[3-(methylsulfonyl)-1H-indol-1-yl]methyl}-1H-benzimidazole A mixture of 2-(chloromethyl)-1-(2-(methylsulfonyl)ethyl)-1H-benzo[d]imidazole (200 mg, 0.74 mmol), 3-(methylsulfonyl)-1H-indole (216 mg, 0.89 mmol) and K$_2$CO$_3$ (204 mg, 1.48 mmol) in DMF (3 mL) was stirred overnight at RT. The mixture was filtered, and the filtrate was purified by Prep-HPLC to give the Example 1-1 (80 mg, yield: 25%) as off-white solid.

Example 1-2

5-Chloro-2-{[3-(methylsulfonyl)-1H-indol-1-yl]methyl}-1-[3-(methylsulfonyl)propyl]-1H-benzimidazole Step 1: synthesis of (4-chloro-2-nitro-phenyl)-(3-methanesulfonyl-propyl)-carbamic acid tert-butyl ester

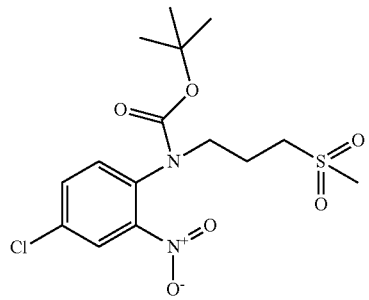 [SMILES: CC(C)(C)OC(=O)N(CCCS(C)(=O)=O)c1ccc(Cl)cc1[N+](=O)[O-]]

(4-Chloro-2-nitro-phenyl)-(3-methanesulfonyl-propyl)-carbamic acid tert-butyl ester was prepared according to Scheme 1. To a solution of tert-butyl 4-chloro-2-nitrophenyl-carbamate (580 mg, 2.1 mmol) in DMF (5 mL) was added NaH (170 mg, 4.3 mmol, 60 wt %). The mixture was stirred for 30 min at RT, then 3-(methylsulfonyl)propyl 4-methylbenzenesulfonate (0.75 g, 2.56 mmol) was added. The solution was heated to 50° C. and stirred for overnight. After cooled to RT, H$_2$O (30 mL) was added and the solution was extracted with DCM (40 mL×3). The organic layer was dried over anhydrous and concentrated. The residue was purified by prep-TLC (DCM) to give tert-butyl 4-chloro-2-nitrophenyl (3-(methylsulfonyl)propyl)carbamate (360 mg, yield: 69%) as pale oil. MS obsd. (ESI+) [(M+H)+]: 393.0.

Step 2: synthesis of (2-amino-4-chloro-phenyl)-(3-methanesulfonyl-propyl)-carbamic acid tert-butyl ester

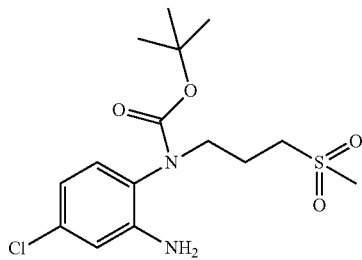 [SMILES: CC(C)(C)OC(=O)N(CCCS(C)(=O)=O)c1ccc(Cl)cc1N]

To a solution of tert-butyl 4-chloro-2-nitrophenyl(3-(methylsulfonyl)propyl)carbamate (360 mg, 1.45 mmol) in MeOH was added 2% Pd/C 30 mg). The reaction was degassed and refilled with H$_2$. The mixture was stirred at RT under H$_2$ atmosphere for 3 hrs. The catalyst was filtered off and the filtrate was concentrated to afford tert-butyl 2-amino-4-chlorophenyl(3-(methylsulfonyl) propyl)carbamate as crude product (330 mg, yield: 100%). MS obsd. (ESI+) [(M+H)+]: 363.1.

Step 3: synthesis of 5-chloro-2-chloromethyl-1-(3-methanesulfonyl-propyl)-1H-benzoimidazole

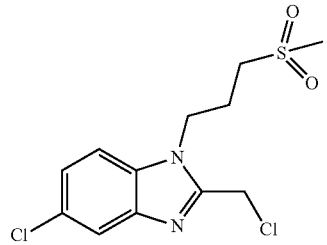 [SMILES: CS(=O)(=O)CCCn1c(CCl)nc2cc(Cl)ccc21]

A mixture of tert-butyl 2-amino-4-chlorophenyl(3-(methylsulfonyl)propyl)carbamate (320 mg, 0.92 mmol) and sodium chloroacetate (130 mg, 1.1 mmol) in 4 N HCl was heated to 100° C. After overnight stirring, the reaction solution was cooled to RT and concentrated. The residue was diluted with DCM (100 mL) and washed with sat. NaHCO$_3$ (50 mL). The organic layer was dried and concentrated under vacuum. The residue was purified by prep-TLC (DCM/EtOAc=3:1) to give 5-chloro-2-(chloromethyl)-1-(3-(methylsulfonyl)propyl)-1H-benzo[d]imidazole (130 mg, yield: 44%) as pale solid. MS obsd. (ESI+) [(M+H)+]: 321.0.

Step 4: synthesis of 5-chloro-2-{[3-(methylsulfonyl)-1H-indol-1-yl]methyl}-1-[3-(methylsulfonyl)propyl)-1H-benzimidazole A mixture of 5-chloro-2-(chloromethyl)-1-(3-(methylsulfonyl)propyl)-1H-benzo[d]imidazole (120 mg, 0.37 mmol) and 3-(methylsulfonyl)-1H-indole (72 mg, 0.37 mmol) in DMF (3 mL) was treated with K$_2$CO$_3$ (104 mg, 0.74 mmol) at RT. The reaction solution was stirred at RT for overnight. The solid was filtered off and the filtrate was purified by prep-HPLC to give 5-chloro-2-{[3-(methylsulfonyl)-1H-indol-1-yl]methyl}-1-[3-(methylsulfonyl)propyl]-1H-benzimidazole (100 mg, yield: 78%) as off-white solid.

Example 1-3

5-Chloro-2-{[5-fluoro-3-(methylsulfonyl)-1H-indol-1-yl]methyl}-1-[3-(methylsulfonyl)propyl]-1H-benzimidazole The title compound was prepared in analogy to Example 1-2 by using 5-fluoro-3-(methylsulfonyl)-1H-indole and 5-chloro-2-(chloromethyl)-1-(3-(methylsulfonyl)propyl)-1H-benzo[d]imidazole instead of 3-(methylsulfonyl)-1H-indole and 5-chloro-2-(chloromethyl)-1-(3-(methylsulfonyl)propyl)-1H-benzo[d]imidazole.

Example 1-4

5-Chloro-1-[3-(methylsulfonyl)propyl]-2-{[3-(methylsulfonyl)-1H-pyrrolo[2,3-c]pyridin-1-yl]methyl}-1H-benzimidazole The title compound was prepared in analogy to Example 1-2 by using 3-(methylsulfonyl)-1H-pyrrolo[2,3-c]pyridine and 5-chloro-2-(chloromethyl)-1-(3-(methylsulfonyl)propyl)-1H-benzo[d]imidazole instead of 3-(methylsulfonyl)-1H-indole and 5-chloro-2-(chloromethyl)-1-(3-(methylsulfonyl)propyl)-1H-benzo[d]imidazole.

Example 1-5

5-Chloro-2-{[3-(ethylsulfonyl)-1H-indol-1-yl]methyl}-1-[3-(methylsulfonyl)propyl]-1H-benzimidazole Step 1: synthesis of 3-isothiocyanato-1H-indole

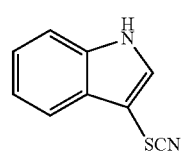

A solution of indole (2.0 g, 17.1 mmol) and ammonium thiocyanate (1.95 g, 25.6 mmol) in methanol (150 mL) was treated with oxone (15.7 g, 25.6 mmol) and allowed to stir at RT for overnight till TLC showed all starting material consumed. The reaction solution was evaporated in vacuum. The residue was purified by chromatography on silica gel (EtOAc:PE=5/95) to afford 2.2 g of 3-isothiocyanato-1H-indole as yellow solid (yield: 73%). MS obsd. (ESI⁺) [(M+H)⁺] 175.1, ¹H NMR: (400 MHz, CDCl₃) δ ppm: 8.67 (brs, 1H), 7.82-7.80 (m, 1H), 7.52 (d, J=3.0 Hz, 1H), 7.44-7.43 (m, 1H), 7.34-7.30 (m, 2H).

Step 2: synthesis of 3-ethylsulfanyl-1H-indole

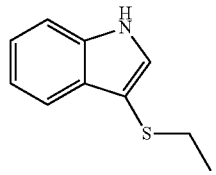

To a solution of compound 3-isothiocyanato-1H-indole (175 mmol, 1.0 mmol) in ethanol (3.0 mL) was added Na₂S (234 mg, 3.0 mmol) in water (0.4 mL). The resultant mixture was stirred for 2 hrs at 50° C., followed by the addition of bromoethane (90 ul, 1.2 mmol) in ethanol (1.0 mL). The reaction solution was allowed to stir at 50° C. overnight. After cooling to RT, the solution was diluted with water and extracted with EtOAc (30 mL×3), the combined organic phase was concentrated in vacuum to afford a residue for next step use without further purification (yield: 50%), MS obsd. (ESI⁺) [(M+H)⁺] 178.1.

Step 3: synthesis of 3-ethanesulfonyl-1H-indole

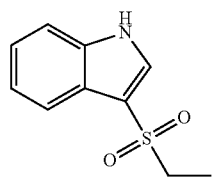

The above residue in dichloromethane (20 mL) was added m-CPBA (350 mg, 2.0 mmol) at RT and the mixture was stirred at RT until all starting materials consumed. The target compound was purified by chromatography on silica gel (EtOAc:PE=5/95) to afford 120 mg product as brown oil (yield: 57%). MS obsd. (ESI⁺) [(M+H)⁺] 210.1.

Step 4: synthesis of 5-chloro-2-{[3-(ethylsulfonyl)-1H-indol-1-yl]methyl}-1-[3-(methylsulfonyl)propyl]-1H-benzimidazole Example 1-5 was prepared in analogy to Example 1-2 by using 3-ethanesulfonyl-1H-indole and 5-chloro-2-(chloromethyl)-1-(3-(methylsulfonyl)propyl)-1H-benzo[d]imidazole instead of 3-(methylsulfonyl)-1H-indole and 5-chloro-2-(chloromethyl)-1-(3-(methylsulfonyl)propyl)-1H-benzo[d]imidazole.

Example 1-6

5-Chloro-1-[3-(methylsulfonyl)propyl]-2-{[3-(propan-2-ylsulfonyl)-1H-indol-1-yl]methyl}-1H-benzimidazole The title compound was prepared in analogy to Example 1-2 by using 5-chloro-2-(chloromethyl)-1-(3-(methylsulfonyl)propyl)-1H-benzo[d]imidazole and 3-(isopropylsulfonyl)-1H-indole instead of 3-(methylsulfonyl)-1H-indole and 5-chloro-2-(chloromethyl)-1-(3-(methylsulfonyl)propyl)-1H-benzo[d]imidazole.

Example 1-7

5-Chloro-2-{[3-(cyclopropylsulfonyl)-1H-indol-1-yl]methyl}-1-[3-(methylsulfonyl)propyl]-1H-benzimidazole The title compound was prepared in analogy to Example 1-2 by using 3-(cyclopropylsulfonyl)-1H-indole (prepared in an analogy to 3-ethanesulfonyl-1H-indole) and 5-chloro-2-(chloromethyl)-1-(3-(methylsulfonyl)propyl)-1H-benzo[d]imidazole instead of 3-(methylsulfonyl)-1H-indole and 5-chloro-2-(chloromethyl)-1-(3-(methylsulfonyl)propyl)-1H-benzo[d]imidazole.

Example 1-8

1-({5-Chloro-1-[3-(methylsulfonyl)propyl]-1H-benzimidazol-2-yl}methyl)-3-(methylsulfonyl)-1H-indazole Step 1: synthesis of 3-methanesulfonyl-1H-indazole

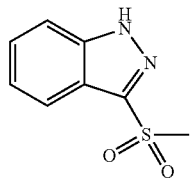

To a solution of 3-chloro-1H-indazole (100 mg, 0.65 mmol) in DMF (2 mL) was added sodium methanethiolate (91 mg, 1.3 mmol). The resultant mixture was heated at 150° C. under microwave radiation for 1 h. After cooled to RT, 10 mL of water was added and extracted with ethyl acetate (3×30 mL). The combined organic phases were dried over anhydrous $Na_2SO_4$ and concentrated to give crude sulfide which was used for next step directly. To a solution of crude sulfide (0.4 g, 2.4 mmol) in DCM (15 mL) was added m-CPBA (0.84 g, 4.8 mmol) at RT. The mixture was stirred for 4 hrs, 20 mL of water was added. The organic phase were washed with brine and dried over anhydrous $Na_2SO_4$, evaporated in vacuum, the residue was purified by chromatography on silica gel to afford product 3-methanesulfonyl-1H-indazole (0.16 g, yield: 34%) as off-white solid, MS obsd. (ESI$^+$) [(M+H)$^+$] 197.1.

Step 2: synthesis of 1-({5-chloro-1-[3-(methylsulfonyl)propyl]-1H-benzimidazol-2-yl}methyl)-3-(methylsulfonyl)-1H-indazole Example 1-8 was prepared in analogy to Example 1-2 by using above 3-(methylsulfonyl)-1H-indazole and 5-chloro-2-(chloromethyl)-1-(3-(methylsulfonyl)propyl)-1H-benzo[d]imidazole instead of 3-(methylsulfonyl)-1H-indol e and 5-chloro-2-(chloromethyl)-1-(3-(methylsulfonyl)propyl)-1H-benzo[d]imidazole.

Example 1-9

1-({5-Chloro-1-[3-(methylsulfonyl)propyl]-1H-benzimidazol-2-yl}methyl)-3-(propan-2-ylsulfonyl)-1H-indazole A mixture of 5-chloro-2-(chloromethyl)-1-(3-(methylsulfonyl)propyl)-1H-benzo[d]imidazole (72 mg, 0.22 mmol), 3-(isopropylsulfonyl)-1H-indazole (50 mg, 0.22 mmol), $K_2CO_3$ (61 mg, 0.44 mmol) and DMF (1.5 mL) was stirred at RT overnight. The resultant mixture was purified by pre-HPLC to give 1-({5-chloro-1-[3-(methylsulfonyl)propyl]-1H-benzimidazol-2-yl}methyl)-3-(propan-2-ylsulfonyl)-1H-indazole as white solid (31.0 mg, yield: 27.2%).

Example 1-10

1-({5-Chloro-1-[3-(methylsulfonyl)propyl]-1H-benzimidazol-2-yl}methyl)-3-(ethylsulfonyl)-1H-indazole The title compound was prepared in analogy to Example 1-2 by using 3-(ethylsulfonyl)-1H-indazole and 5-chloro-2-(chloromethyl)-1-(3-(methylsulfonyl)propyl)-1H-benzo[d]imidazole instead of 3-(methylsulfonyl)-1H-indole and 5-chloro-2-(chloromethyl)-1-(3-(methylsulfonyl)propyl)-1H-benzo[d]imidazole.

Example 1-11

1-({5-Chloro-1-[3-(methylsulfonyl)propyl]-1H-benzimidazol-2-yl}methyl)-3-(methylsulfonyl)-1H-pyrazolo[3,4-c]pyridine The title compound was prepared in analogy to Example 1-9 by using 5-chloro-2-(chloromethyl)-1-(3-(methylsulfonyl)propyl)-1H-benzo[d]imidazole and 3-(methylsulfonyl)-1H-pyrazolo[3,4-c]pyridine instead of 5-chloro-2-(chloromethyl)-1-(3-(methylsulfonyl)propyl)-1H-benzo[d]imidazole and 3-(isopropylsulfonyl)-1H-indazole.

Example 1-12

1-({5-Chloro-1-[2-(methylsulfonyl)ethyl]-1H-benzimidazol-2-yl}methyl)-3-(methylsulfonyl)-1H-indazole Step 1: synthesis of 5-chloro-2-chloromethyl-1-(2-methanesulfonyl-ethyl)-1H-benzoimidazole

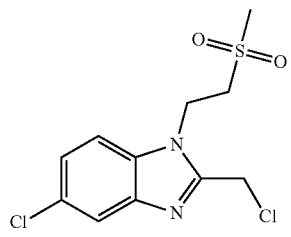 [SMILES: CS(=O)(=O)CCn1c(CCl)nc2cc(Cl)ccc21]

5-Chloro-2-chloromethyl-1-(2-methanesulfonyl-ethyl)-1H-benzoimidazole was prepared in analogy to Example 1-2 by using (4-chloro-2-nitro-phenyl)-carbamic acid tert-butyl ester as starting material instead of 3-(methylsulfonyl)-1H-indole and 5-chloro-2-(chloromethyl)-1-(3-(methylsulfonyl)propyl)-1H-benzo[d]imidazole. MS obsd. (ESI$^+$) [(M+H)$^+$] 308.1.

Step 2: synthesis of 1-({5-chloro-1-[2-(methylsulfonyl)ethyl]-1H-benzimidazol-2-yl}methyl)-3-(methylsulfonyl)-1H-indazole Example 1-12 was prepared in analogy to Example 1-2 by using 5-chloro-2-(chloromethyl)-1-(2-(methylsulfonyl)ethyl)-1H-benzo[d]-imidazole and 3-(methylsulfonyl)-1H-indazole instead of 5-chloro-2-(chloromethyl)-1-(3-(methylsulfonyl)propyl)-1H-benzo[d]imidazole and 3-(methylsulfonyl)-1H-indole.

Example 1-13

1-({5-Chloro-1-[2-(methylsulfonyl)ethyl]-1H-benzimidazol-2-yl}methyl)-3-(propan-2-ylsulfonyl)-1H-indazole

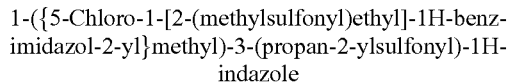

The title compound was prepared in analogy to Example 1-9 by using 5-chloro-2-(chloromethyl)-1-(2-(methylsulfonyl)ethyl)-1H-benzo[d]imidazole and 3-(isopropylsulfonyl)-1H-indazole instead of 5-chloro-2-(chloromethyl)-1-(3-(methylsulfonyl)propyl)-1H-benzo[d]imidazole and 3-(isopropylsulfonyl)-1H-indazole.

Example 2-1

1-({5-Chloro-1-[(3R)-1,1-dioxidotetrahydrothiophen-3-yl]-1H-benzimidazol-2-yl}methyl)-3-(methylsulfonyl)-1H-pyrazolo[3,4-c]pyridine Step 1: synthesis of (4-chloro-2-nitro-phenyl)-((S)-1,1-dioxo-tetrahydro-1λ⁶-thiophen-3-yl)-amine

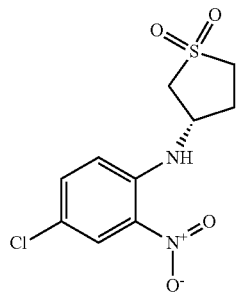 [SMILES: O=[N+]([O-])c1cc(Cl)ccc1N[C@H]1CCS(=O)(=O)C1]

To a mixture of 4-chloro-2-nitro-phenylamine (1.2 g, 6.8 mmol) and (S)-1,1-dioxo-tetrahydro-1λ⁶-thiophen-3-ylamine (0.97 g, 5.7 mmol) and K₂CO₃ (13.6 mmol) in DMF (8 mL) was added Et₃N (13.6 mmol). The mixture was stirred at 100° C. for 2 h. After cooled to RT, the reaction mixture was poured into water, extracted with EtOAc. The organic phase was washed with saturated NH₄Cl, aqueous NaHCO₃ and brine. The organic phase was dried over Na₂SO₄. The nitro compound (1.1 g, yield: 66%) was obtained as yellow solid by flash column (ethyl acetate/petroleum ether=1/1). MS obsd. MS obsd. (ESI⁺) [(M+H)⁺] 291.0.

Step 2: synthesis of 4-chloro-N—((S)-1,1-dioxo-tetrahydro-1λ⁶-thiophen-3-yl)-benzene-1,2-diamine

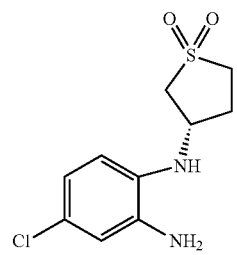 [SMILES: Nc1cc(Cl)ccc1N[C@H]1CCS(=O)(=O)C1]

To a solution of above nitro compound (1.1 g, 3.8 mmol) in MeOH (10 mL), was added N₂H₄ hydrate (2 mL), followed by Raney Ni. The mixture was stirred at room temperature for 1 h. The mixture was filtered and the solvent was evaporated to give the phenylamine (0.65 g, yield: 66%) without further purification. MS obsd. (ESI⁺) [(M+H)⁺] 261.1.

Step 3: synthesis of 5-chloro-2-chloromethyl-1-((S)-1,1-dioxo-tetrahydro-1λ⁶-thiophen-3-yl)-1H-benzoimidazole

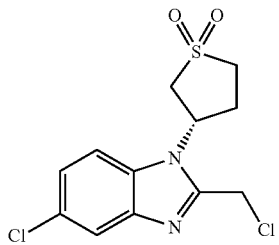 [SMILES: O=S1(=O)CC[C@H](n2c(CCl)nc3cc(Cl)ccc32)C1]

The above phenylamine compound (0.65 g, 2.5 mmol) and sodium 2-chloroacetate (0.87 g, 7.5 mmol) were added to 5N HCl (20 mL). The mixture was stirred at 80° C. overnight. Then the mixture was neutralized to pH=7 and extracted with ethyl acetate (3×50 mL), the organic phase was concentrated in vacuum, the residue was purified by column chromatography to give product 5-chloro-2-chloromethyl-1-((S)-1,1-dioxo-tetrahydro-1λ⁶-thiophen-3-yl)-1H-benzoimidazole (0.58 g, yield: 73%) as pale solid. MS obsd. (ESI⁺) [(M+H)⁺] 319.0.

Step 4: synthesis of 3-methanesulfonyl-1H-pyrazolo[3,4-c]pyridine

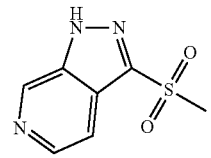

To a solution of 3-iodo-1H-pyrazolo[3,4-c]pyridine 3 (9.5 g, 38.8 mmol) in DMSO (20 mL) was added aq. MeSNa (wt. 20%, 40 mL, 116 mmol), followed by CuI (270 mg, 1.94 mmol). The mixture was degassed and refilled with nitrogen. The reaction was heated at 150° C. overnight. After cooled to RT, the volatiles were removed and the residue was purified by column (PE/EtOAc=2/1 to 1/1) to give 3-(methylthio)-1H-pyrazolo[3,4-c]pyridine (3.2 g, yield: 50%) as a yellow solid. MS obsd. (ESI⁺) [(M+H)⁺] 166.0.

To a solution of 3-(methylthio)-1H-pyrazolo[3,4-c]pyridine (10 g, 60.6 mmol) in DMF (100 mL) was added oxone (37 g, 121.2 mmol.) in portions. The reaction mixture was stirred at RT. After the reaction completed, water (100 mL) was added. The reaction was quenched carefully by addition of Na₂SO₃ and Na₂CO₃. The solid was filtered off and washed with MeOH (300 mL). The filtrate was concentrated under vacuum and the residue was purified by chromatography on silica gel column (DCM/MeOH=20/1) to give 3-(methylsulfonyl)-1H-pyrazolo[3,4-c]pyridine (10.7 g, yield: 90%) as a yellow solid. MS obsd. (ESI⁺) [(M+H)⁺] 198.0.

103

Step 5: synthesis of 1-({5-chloro-1-[(3R)-1,1-dioxi-
dotetrahydrothiophen-3-yl]-1H-benzimidazol-2-
yl}methyl)-3-(methylsulfonyl)-1H-pyrazolo[3,4-c]
pyridine A mixture of compound 5-chloro-2-chloromethyl-1-((S)-1,1-dioxo-tetrahydro-1$\lambda^6$-thiophen-3-yl)-1H-benzoimidazole(115 mg, 0.36 mmol), 3-(methylsulfonyl)-1H-pyrazolo[3,4-c]pyridine (60 mg, 0.36 mmol) and $Cs_2CO_3$ (236 mg, 0.76 mmol) in 4 mL of DMF was stirred at room temperature for 1 h. The mixture was filtered, the filtrate was collected, then to the filtrate was added oxone (300 mg). The mixture was stirred for 4 hrs and purified by prep-HPLC to give the product (60 mg, yield: 34.6%) as an off-white solid.

Example 2-2

1-{[5-Chloro-1-(1,1-dioxidotetrahydrothiophen-3-
yl)-1H-benzimidazol-2-yl]methyl}-3-(methylsulfo-
nyl)-1H-indazole The title compound was prepared in analogy to Example 2-1 by using 5-chloro-2-chloromethyl-1-(1,1-dioxo-tetrahydro-1$\lambda^6$-thiophen-3-yl)-1H-benzoimidazole and 3-Methanesulfonyl-1H-indazole instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-3

1-{[5-Chloro-1-(oxetan-3-yl)-1H-benzimidazol-2-yl]
methyl}-3-(methylsulfonyl)-1H-indazole The title compound was prepared in analogy to Example 2-1 by using 5-chloro-2-chloromethyl-1-oxetan-3-yl-1H-benzoimidazole and 3-methanesulfonyl-1H-indazole instead of 5-chloro-2-chloromethyl-1-((S)-1,1-dioxo-tetrahydro-1$\lambda^6$-thiophen-3-yl)-1H-benzoimidazole and 3-(methylsulfo-nyl)-1H-pyrazolo[3,4-c]pyridine.

Example 2-4

4-(5-Chloro-2-{[3-(methylsulfonyl)-1H-pyrazolo[3,
4-c]pyridin-1-yl]methyl}-1H-benzimidazol-1-yl)
piperidin-2-one The title compound was prepared in analogy to Example 2-1 by using 4-(5-chloro-2-(chloromethyl)-1H-benzo[d]imidazol-1-yl)piperidin-2-one and 3-(methylthio)-1H-pyrazolo[3,4-c]pyridine instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-5

1-{[5-Chloro-1-(oxetan-3-yl)-1H-benzimidazol-2-yl]
methyl}-3-(methylsulfonyl)-1H-pyrazolo[3,4-c]pyri-
dine The title compound was prepared in analogy to Example 2-1 by using 5-chloro-2-chloromethyl-1-oxetan-3-yl-1H-benzoimidazole and 3-methanesulfonyl-1H-pyrazolo[3,4-c]pyridine instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

104

Example 2-6

1-{[5-Chloro-1-(tetrahydro-2H-pyran-4-yl)-1H-ben-
zimidazol-2-yl]methyl}-3-(methylsulfonyl)-1H-inda-
zole The title compound was prepared in analogy to Example 2-1 by using 5-chloro-2-chloromethyl-1-(tetrahydro-pyran-4-yl)-1H-benzoimidazole and 3-methanesulfonyl-1H-indazole instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-7

1-{[5-Chloro-1-(tetrahydro-2H-pyran-4-yl)-1H-ben-
zimidazol-2-yl]methyl}-3-(methylsulfonyl)-1H-pyra-
zolo[3,4-c]pyridine The title compound was prepared in analogy to Example 2-1 by using 5-chloro-2-chloromethyl-1-(tetrahydro-pyran-4-yl)-1H-benzoimidazole and 3-methanesulfonyl-1H-pyrazolo[3,4-c]pyridine instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-8

1-{[5-Chloro-1-(tetrahydrofuran-3-yl)-1H-benzimi-
dazol-2-yl]methyl}-3-(methylsulfonyl)-1H-indazole The title compound was prepared in analogy to Example 2-1 by using 5-chloro-2-chloromethyl-1-(tetrahydro-furan-3-yl)-1H-benzoimidazole and 3-methanesulfonyl-1H-indazole instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-9

1-{[5-Chloro-1-(3,3-difluorocyclopentyl)-1H-benz-
imidazol-2-yl]methyl}-3-(methylsulfonyl)-1H-inda-
zole The title compound was prepared in analogy to Example 2-1 by using 5-chloro-2-chloromethyl-1-(3,3-difluoro-cyclopentyl)-1H-benzoimidazole and 3-methanesulfonyl-1H-indazole instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-10

1-{[5-Chloro-1-(3,3-difluorocyclopentyl)-1H-benz-
imidazol-2-yl]methyl}-3-(methylsulfonyl)-1H-pyra-
zolo[3,4-c]pyridine The title compound was prepared according to the procedures described in Example 2-1 by using 5-chloro-2-chloromethyl-1-(3,3-difluoro-cyclopentyl)-1H-benzoimidazole and 3-methanesulfonyl-1H-pyrazolo[3,4-c]pyridine instead of 5-chloro-2-chloromethyl-1-((S)-1,1-dioxo-tetrahydro-1$\lambda^6$-thiophen-3-yl)-1H-benzoimidazole and 3-(methylsulfo-nyl)-1H-pyrazolo[3,4-c]pyridine.

Example 2-11

4-(5-Chloro-2-{[3-(methylsulfonyl)-1H-pyrazolo[3,4-c]pyridin-1-yl]methyl}-benzoimidazol-1-yl)cyclohexanol The title compound was prepared in analogy to Example 2-1 by using (1R,4R)-4-(5-chloro-2-(chloromethyl)-1H-benzo[d]imidazol-1-yl)cyclohexanol and 3-methanesulfonyl-1H-pyrazolo[3,4-c]pyridine instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-12

3-(5-Chloro-2-{[3-(methylsulfonyl)-6-oxido-1H-pyrazolo[3,4-c]pyridin-1-yl]methyl}-1H-benzimidazol-1-yl)cyclopentanol The title compound was prepared in analogy to Example 2-1 by using 3-(5-chloro-2-chloromethyl-benzoimidazol-1-yl)-cyclopentanol and 3-methanesulfonyl-1H-pyrazolo[3,4-c]pyridine 6-oxide instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine.

Example 2-13

1-{[5-Chloro-1-(pyrrolidin-3-yl)-1H-benzimidazol-2-yl]methyl}-3-(methylsulfonyl)-1H-pyrazolo[3,4-c]pyridine Step 1: synthesis of 3-[5-chloro-2-(3-methanesulfonyl-pyrazolo[3,4-c]pyridin-1-ylmethyl)-benzoimidazol-1-yl]-pyrrolidine-1-carboxylic acid tert-butyl ester

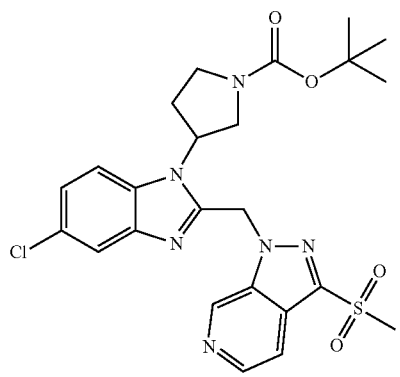 [SMILES: CC(C)(C)OC(=O)N1CCC(n2c(Cn3nc(S(C)(=O)=O)c4ccncc43)nc3cc(Cl)ccc32)C1]

3-[5-Chloro-2-(3-methanesulfonyl-pyrazolo[3,4-c]pyridin-1-ylmethyl)-benzoimidazol-1-yl]-pyrrolidine-1-carboxylic acid tert-butyl ester was prepared in analogy to Example 2-1 by using 3-(5-chloro-2-chloromethyl-benzoimidazol-1-yl)-pyrrolidine-1-carboxylic acid tert-butyl ester and 3-methanesulfonyl-1H-pyrazolo[3,4-c]pyridine instead of 5-chloro-2-chloromethyl-1-((S)-1,1-dioxo-tetrahydro-1$\lambda^6$-thiophen-3-yl)-1H-benzoimidazole and 3-(methylsulfonyl)-1H-pyrazolo[3,4-c]pyridine. MS obsd. (ESI$^+$) [(M+H)$^+$] 531.1.

Step 2: synthesis of 1-{[5-chloro-1-(pyrrolidin-3-yl)-1H-benzimidazol-2-yl]methyl}-3-(methylsulfonyl)-1H-pyrazolo[3,4-c]pyridine To the solution of above crude product (200 mg, 0.376 mmol) in 10 mL of DCM was added TFA (5 mL). The mixture was stirred at room temperature for 1 h. The solvent was removed and purified by prep-HPLC to give Example 2-13 (120 mg, yield: 74%).

Example 2-14

1-{[1-(Azetidin-3-yl)-5-chloro-1H-benzimidazol-2-yl]methyl}-3-(methylsulfonyl)-1H-pyrazolo[3,4-c]pyridine The title compound was prepared in analogy to Example 2-13 by using 3-(5-chloro-2-chloromethyl-benzoimidazol-1-yl)-azetidine-1-carboxylic acid tert-butyl ester and 3-methanesulfonyl-1H-pyrazolo[3,4-c]pyridine instead of 3-(5-chloro-2-chloromethyl-benzoimidazol-1-yl)-pyrrolidine-1-carboxylic acid tert-butyl ester and 3-methanesulfonyl-1H-pyrazolo[3,4-c]pyridine.

Example 2-15

1-{[5-Chloro-1-(piperidin-4-yl)-1H-benzimidazol-2-yl]methyl}-3-(methylsulfonyl)-1H-indazole The title compound was prepared in analogy to Example 2-13 by using 4-(5-chloro-2-chloromethyl-benzoimidazol-1-yl)-piperidine-1-carboxylic acid tert-butyl ester and 3-methanesulfonyl-1H-indazole instead of 3-(5-chloro-2-chloromethyl-benzoimidazol-1-yl)-pyrrolidine-1-carboxylic acid tert-butyl ester and 3-methanesulfonyl-1H-pyrazolo[3,4-c]pyridine.

Example 2-16

1-[3-(5-Chloro-2-{[3-(methylsulfonyl)-1H-pyrazolo[3,4-c]pyridin-1-yl]methyl}-1H-benzimidazol-1-yl)pyrrolidin-1-yl]ethanone To a solution of 1-{[5-chloro-1-(pyrrolidin-3-yl)-1H-benzimidazol-2-yl]methyl}-3-(methylsulfonyl)-1H-pyrazolo[3,4-c]pyridine (30 mg, 0.07 mmol), acetic anhydride (0.1 mL) in 8 mL of DCM was added DMAP (3 mg, 0.025 mmol). The mixture was stirred for 1 h. Then 20 mL of DCM and then 10 mL of water was added. The organic phase was washed with water, NaHCO$_3$ and dried over anhydrous Na$_2$SO$_4$. The solvent was evaporated to give the residue which purified by preparative-HPLC to afford the title compound (15 mg, yield: 50%) as a pale solid.

Example 2-17

1-[3-(5-Chloro-2-{[3-(methylsulfonyl)-1H-pyrazolo[3,4-c]pyridin-1-yl]methyl}-1H-benzimidazol-1-yl)pyrrolidin-1-yl]-2-hydroxyethanone The title compound was prepared in analogy to Example 2-16 by using 1-((5-chloro-1-(pyrrolidin-3-yl)-1H-benzo[d]imidazol-2-yl)methyl)-3-(methylsulfonyl)-1H-pyrazolo[3,4-c]pyridine and 2-hydroxyacetic acid instead of 1-{[5- chloro-1-(pyrrolidin-3-yl)-1H-benzimidazol-2-yl]methyl}-3-(methylsulfonyl)-1H-pyrazolo[3,4-c]pyridine and acetic anhydride.

Example 2-18

2-Amino-1-[3-(5-chloro-2-{[3-(methylsulfonyl)-1H-pyrazolo[3,4-c]pyridin-1-yl]methyl}-1H-benzimidazol-1-yl)pyrrolidin-1-yl]ethanone Step 1: synthesis of (2-{3-[5-chloro-2-(3-methanesulfonyl-pyrazolo[3,4-c]pyridin-1-ylmethyl)-benzoimidazol-1-yl]-pyrrolidin-1-yl}-2-oxo-ethyl)-carbamic acid tert-butyl ester

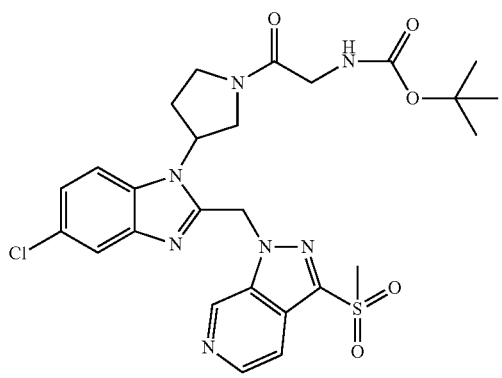 [SMILES: CC(C)(C)OC(=O)NCC(=O)N1CCC(n2c(Cn3nc(S(C)(=O)=O)c4ccncc43)nc3cc(Cl)ccc32)C1]

(2-{3-[5-Chloro-2-(3-methanesulfonyl-pyrazolo[3,4-c]pyridin-1-ylmethyl)-benzoimidazol-1-yl]-pyrrolidin-1-yl}-2-oxo-ethyl)-carbamic acid tert-butyl ester was prepared in analogy to Example 2-16 by using 1-((5-chloro-1-(pyrrolidin-3-yl)-1H-benzo[d]imidazol-2-yl)methyl)-3-(methylsulfonyl)-1H-pyrazolo[3,4-c]pyridine and 2-(tert-butoxycarbonylamino)acetic acid (14 mg) instead of 1-{[5-chloro-1-(pyrrolidin-3-yl)-1H-benzimidazol-2-yl]methyl}-3-(methylsulfonyl)-1H-pyrazolo[3,4-c]pyridine and acetic anhydride, MS obsd. (ESI+) [(M+H)+] 588.

Step 2: synthesis of 2-amino-1-[3-(5-chloro-2-{[3-(methylsulfonyl)-1H-pyrazolo[3,4-c]pyridin-1-yl]methyl}-1H-benzimidazol-1-yl)pyrrolidin-1-yl]ethanone To a solution of tert-butyl 2-(3-(5-chloro-2-((3-(methylsulfonyl)-1H-pyrazolo[3,4-c]pyridin-1-yl)methyl)-1H-benzo[d]imidazol-1-yl)pyrrolidin-1-yl)-2-oxoethylcarbamate(30 mg, 0.05 mmol) in 6 mL of DCM was added 3 mL of TFA. The mixture was stirred overnight. The solvent was removed in vacuum and purified by prep-HPLC to give product 2-amino-1-[3-(5-chloro-2-{[3-(methylsulfonyl)-1H-pyrazolo[3,4-c]pyridin-1-yl]methyl}-1H-benzimidazol-1-yl)pyrrolidin-1-yl]ethanone (10 mg, yield: 42%) as a pale solid.

Example 2-19

1-({5-Chloro-1-[(3S)-1-(2,2,2-trifluoroethyl)pyrrolidin-3-yl]-1H-benzimidazol-2-yl}methyl)-3-(methylsulfonyl)-1H-pyrazolo[3,4-c]pyridine A mixture of (S)-1-((5-chloro-1-(pyrrolidin-3-yl)-1H-benzo[d]imidazol-2-yl)methyl)-3-(methylsulfonyl)-1H-pyrazolo[3,4-c]pyridine (120 mg, 0.28 mmol), 2,2,2-trifluoroethyl trifluoromethanesulfonate (64 mg, 0.28 mmol) and Cs$_2$CO$_3$ (182 mg, 0.56 mmol) in 5 mL of DMF was stirred overnight. The mixture was filtered and purified by prep-HPLC to give 1-({5-chloro-1-[(3S)-(1-(2,2,2-trifluoroethyl)pyrrolidin-3-yl]-1H-benzimidazol-2-yl}methyl)-3-(methylsulfonyl)-1H-pyrazolo[3,4-c]pyridine (30 mg, yield: 21%) as an off-white solid.

Example 2-20

1-({5-Chloro-1-[(3R)-1-(2,2,2-trifluoroethyl)pyrrolidin-3-yl]-1H-benzimidazol-2-yl}methyl)-3-(methylsulfonyl)-1H-pyrazolo[3,4-c]pyridine The title compound was prepared in analogy to Example 2-19 by using (R)-1-((5-chloro-1-(pyrrolidin-3-yl)-1H-benzo[d]imidazol-2-yl)methyl)-3-(methylsulfonyl)-1H-pyrazolo[3,4-c]pyridine and 2,2,2-trifluoroethyl trifluoromethanesulfonate instead of (S)-1-((5-chloro-1-(pyrrolidin-3-yl)-1H-benzo[d]imidazol-2-yl)methyl)-3-(methylsulfonyl)-1H-pyrazolo[3,4-c]pyridine and 2,2,2-trifluoroethyl trifluoromethanesulfonate.

Example 2-21

1-{[5-Chloro-1-(3,3,3-trifluoropropyl)-1H-benzimidazol-2-yl]methyl}-3-(methylsulfonyl)-1H-pyrazolo[3,4-c]pyridine The title compound was prepared in analogy to Example 2-1 by using 5-chloro-2-chloromethyl-1-(3,3,3-trifluoro-propyl)-1H-benzoimidazole (prepared in analogy to Example 2-1) and 3-methanesulfonyl-1H-pyrazolo[3,4-c]pyridine (Example 2-1) instead of 5-chloro-2-chloromethyl-1-((S)-1,1-dioxo-tetrahydro-1λ$^6$-thiophen-3-yl)-1H-benzoimidazole and 3-(methylsulfonyl)-1H-pyrazolo[3,4-c]pyridine.

Example 2-22

1-{[5-Chloro-1-(oxetan-3-ylmethyl)-1H-benzimidazol-2-yl]methyl}-3-(methylsulfonyl)-1H-pyrazolo[3,4-c]pyridine The title compound was prepared in analogy to Example 2-1 by using 5-chloro-2-chloromethyl-1-oxetan-3-yl-1H-benzoimidazole and 3-methanesulfonyl-1H-indazole (Example 2-1) instead of 5-chloro-2-chloromethyl-1-((S)-1,1-dioxo-tetrahydro-1λ$^6$-thiophen-3-yl)-1H-benzoimidazole and 3-(methylsulfonyl)-1H-pyrazolo[3,4-c]pyridine.

Example 2-23

1-({5-Chloro-1-[2-(oxetan-3-yl)ethyl]-1H-benzimidazol-2-yl}methyl)-3-(methylsulfonyl)-1H-pyrazolo[3,4-c]pyridine The title compound was prepared in analogy to Example 2-1 by using 5-chloro-2-chloromethyl-1-oxetan-3-yl-1H-benzoimidazole and 3-methanesulfonyl-1H-indazole (Example 2-1) instead of 5-chloro-2-chloromethyl-1-((S)-1,1-dioxo-tetrahydro-1λ$^6$-thiophen-3-yl)-1H-benzoimidazole and 3-(methylsulfonyl)-1H-pyrazolo[3,4-c]pyridine.

Example 2-24

1-{[5-Chloro-1-(2-oxaspiro[3.3]hept-6-yl)-1H-benzimidazol-2-yl]methyl}-3-(methylsulfonyl)-1H-pyrazolo[3,4-c]pyridine The title compound was prepared in analogy to Example 2-1 by using 2-oxaspiro[3.3]heptan-6-amine and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-25

1-({5-Chloro-1-[2-(3-methyloxetan-3-yl)ethyl]-1H-benzimidazol-2-yl}methyl)-3-(methylsulfonyl)-1H-pyrazolo[3,4-c]pyridine The title compound was prepared in analogy to Example 2-1 by using 2-(3-methyloxetan-3-yl)ethaneamine and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-26 trans-3-(5-Chloro-2-{[3-(methylsulfonyl)-1H-pyrazolo[3,4-c]pyridin-1-yl]methyl}-1H-benzimidazol-1-yl)-1-methylcyclobutanol The title compound was prepared in analogy to Example 2-1 by using trans-3-amino-1-methylcyclobutanol and 3-methanesulfonyl-1H-pyrazolo[3,4-c]pyridine instead of (R)-1,1-dioxo-tetrahydro-1$\lambda^6$-thiophen-3-yl amine and 3-methanesulfonyl-1H-indazole.

Example 2-27

3-(5-Chloro-2-{[3-(methylsulfonyl)-1H-pyrazolo[3,4-c]pyridin-1-yl]methyl}-1H-benzimidazol-1-yl)propan-1-ol The title compound was prepared in analogy to Example 2-1 by using 3-amino-propan-1-ol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-29

1-{[5-Chloro-1-(tetrahydrofuran-3-yl)-1H-benzimidazol-2-yl]methyl}-3-(methylsulfonyl)-1H-pyrazolo[3,4-c]pyridine The title compound was prepared in analogy to Example 2-1 by using tetrahydrofuran-3-amine and 3-methanesulfonyl-1H-pyrazolo[3,4-c]pyridine instead of (R)-1,1-dioxo-tetrahydro-1$\lambda^6$-thiophen-3-yl amine and 3-methanesulfonyl-1H-indazole.

Example 2-29

4-(5-Chloro-2-{[3-(methylsulfonyl)-1H-pyrazolo[3,4-c]pyridin-1-yl]methyl}-1H-benzimidazol-1-yl)-2-methylbutan-2-ol The title compound was prepared in analogy to Example 2-1 by using 4-amino-2-methylbutan-2-ol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-30

4-(5-Chloro-2-{[3-(methylsulfonyl)-1H-pyrazolo[3,4-c]pyridin-1-yl]methyl}-1H-benzimidazol-1-yl)butan-1-ol The title compound was prepared in analogy to Example 2-1 by 4-amino-butan-1-ol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-31

1-{[5-Chloro-1-(tetrahydrofuran-3-ylmethyl)-1H-benzimidazol-2-yl]methyl}-3-(methylsulfonyl)-1H-pyrazolo[3,4-c]pyridine The title compound was prepared in analogy to Example 2-1 by using 1-(tetrahydrofuran-3-yl)methanamine and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-32 trans-3-(5-Chloro-2-{[3-(methylsulfonyl)-1H-pyrazolo[3,4-c]pyridin-1-yl]methyl}-1H-benzimidazol-1-yl)cyclobutanol The title compound was prepared in analogy to Example 2-1 by using trans-3-amino-cyclobutanol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-33 cis-3-(5-Chloro-2-{[3-(methylsulfonyl)-1H-pyrazolo[3,4-c]pyridin-1-yl]methyl}-1H-benzimidazol-1-yl)-1-methylcyclobutanol The title compound was prepared in analogy to Example 2-1 by using cis-3-amino-1-methylcyclobutanol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-34

1-[2-(5-Chloro-2-{[3-(methylsulfonyl)-1H-pyrazolo[3,4-c]pyridin-1-yl]methyl}-1H-benzimidazol-1-yl)ethyl]cyclopropanol The title compound was prepared in analogy to Example 2-1 by using 1-(2-aminoethyl)cyclopropanol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-35

2-[2-(5-Chloro-2-{[3-(methylsulfonyl)-1H-pyrazolo[3,4-c]pyridin-1-yl]methyl}-1H-benzimidazol-1-yl)ethoxy]ethanol The title compound was prepared in analogy to Example 2-1 by using 2-(2-aminoethoxy)ethanol and 3-methanesulfonyl-1H-pyrazolo[3,4-c]pyridine instead of (R)-1,1-dioxo-tetrahydro-1λ⁶-thiophen-3-ylamine and 3-methanesulfonyl-1H-indazole.

Example 2-36 trans-3-(5-Chloro-2-{[3-(methylsulfonyl)-1H-pyrazolo[3,4-c]pyridin-1-yl]methyl}-1H-benzimidazol-1-yl)cyclopentanol Step 1: synthesis of 3-(5-chloro-2-{[3-(methylsulfonyl)-1H-pyrazolo[3,4-c]pyridin-1-yl]methyl}-1H-benzimidazol-1-yl)cyclopentanol 3-(5-Chloro-2-{[3-(methylsulfonyl)-1H-pyrazolo[3,4-c]pyridin-1-yl]methyl}-1H-benzimidazol-1-yl)cyclopentanol was prepared in analogy to Example 2-1 by using 3-hydroxy-cyclopentamine hydrochloride and 3-methanesulfonyl-1H-pyrazolo[3,4-c]pyridine instead of (R)-1,1-dioxo-tetrahydro-1λ⁶-thiophen-3-ylamine and 3-methanesulfonyl-1H-indazole.

Step 2: synthesis of trans-3-(5-Chloro-2-{[3-(methylsulfonyl)-1H-pyrazolo[3,4-c]pyridin-1-yl]methyl}-1H-benzimidazol-1-yl)cyclopentanol The title compound was prepared by separation of 3-(5-chloro-2-{[3-(methylsulfonyl)-1H-pyrazolo[3,4-c]pyridin-1-yl]methyl}-1H-benzimidazol-1-yl)cyclopentanol by preparative-HPLC.

Example 2-37 cis-4-(5-Chloro-2-{[3-(methylsulfonyl)-1H-pyrazolo[3,4-c]pyridin-1-yl]methyl}-1H-benzimidazol-1-yl)-1-methylcyclohexanol Step 1: synthesis of 8-methyl-1,4-dioxaspiro[4.5]decan-8-ol

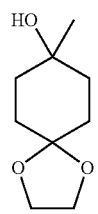

To a cooled solution of 1,4-dioxaspiro[4.5]decan-8-one (7.8 g, 50.0 mmol) in dry THF (75 mL) was added methyllithium solution (1.5 M in ether, 43.3 mL, 65.0 mmol) at −78° C. under argon while keeping inner temperature below −55° C. After addition, the mixture was stirred at −55° C. for additional 4 hours. The reaction was warmed to room temperature and then quenched by saturated NH₄Cl solution. The separated organic layer was concentrated in vacuo and the residue was purified by column chromatography on silica gel (EA:PE=1:9 to 1:3) to afford the product as a white solid (6.8 g, yield: 80%).

Step 2: synthesis of 4-hydroxy-4-methylcyclohexanone

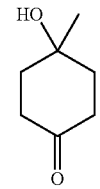

To a solution of 8-methyl-1,4-dioxaspiro[4.5]decan-8-ol (6.1 g, 35.5 mmol) in THF (200 mL) was added 2 N HCl (32 mL). The resulting mixture was stirred at RT overnight, and then was basified to pH 8.0 by saturated K₂CO₃ solution. The separated organic layer was concentrated in vacuo and the residue was purified by column chromatography on silica gel (EA:PE=3:20 to 2:3) to afford the title compound as yellow oil (4.1 g, yield: 86.7%).

Step 3: synthesis of 4-(benzylamino)-1-methylcyclohexanol

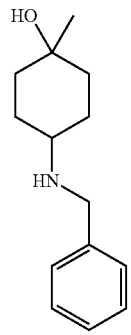

To a mixture of 4-hydroxy-4-methylcyclohexanone (4.1 g, 32.0 mmol) and benzyl amine (6.8 g, 64.0 mmol) in 1,2-dichloroethane (120 mL) was added acetic acid (3.84 g, 64.0 mmol). After the resulting mixture was stirred at RT for 2 hours, the mixture was added NaBH(OAc)₃ (13.6 g, 64.0 mmol). The resulting mixture was then stirred at RT overnight. After the reaction was completed, the mixture was basified to pH 11 by addition of 2 N NaOH. The separated organic layer was concentrated in vacuo and the residue was purified by column chromatography on silica gel (MeOH:DCM=3:100 to 1:10) to afford 4-(benzylamino)-1-methylcyclohexanol as a white solid (5.7 g, yield: 80.0%).

Step 4: synthesis of 4-amino-1-methylcyclohexanol

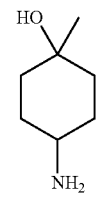

A solution of 4-(benzylamino)-1-methylcyclohexanol (4.9 g, 22.3 mmol) in MeOH (150 mL) was stirred with 7% Pd/C (700 mg) under $H_2$ atmosphere at RT overnight. The resulting mixture was filtered to remove Pd/C and the filtrate was concentrated in vacuo to afford a white solid (2.9 g, quantitative yield) which was used in the next step directly.

Step 5: synthesis of cis-4-[(4-chloro-2-nitrophenyl)amino]-1-methylcyclohexanol

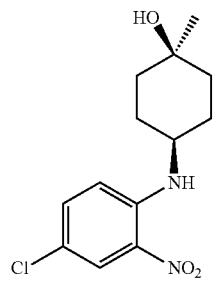 [SMILES: C[C@]1(O)CC[C@@H](Nc2ccc(Cl)cc2[N+](=O)[O-])CC1]

A mixture of 4-amino-1-methylcyclohexanol (2.9 g, 22.3 mmol), 4-chloro-1-fluoro-2-nitro-benzene (3.9 g, 22.3 mmol) and $K_2CO_3$ (9.2 g, 66.9 mmol) in DMF (40 mL) was stirred under argon at RT overnight. The resulting mixture was diluted with EA (200 mL) and then washed by saturated $NH_4Cl$ solution. The resulting organic layer was concentrated in vacuo. The residue was purified by column chromatography on silica gel (EA:PE=1:19 to 1:4) to afford 0.6 g of cis-4-[(4-chloro-2-nitrophenyl)amino]-1-methylcyclohexanol, 1.2 g of trans-4-[(4-chloro-2-nitrophenyl)amino]-1-methylcyclohexanol, and 3.2 g of the mixture of cis-isomer and trans-isomer.

Step 6: synthesis of cis-4-(5-chloro-2-{[3-(methylsulfonyl)-1H-pyrazolo[3,4-c]pyridin-1-yl]methyl}-1H-benzimidazol-1-yl)-1-methylcyclohexanol The title compound was prepared in analogy to Example 2-1 by using cis-4-[(4-chloro-2-nitrophenyl)amino]-1-methylcyclohexanol and 3-methanesulfonyl-1H-pyrazolo[3,4-c]pyridine instead of (4-chloro-2-nitro-phenyl)-((R)-1,1-dioxo-tetrahydro-1$\lambda^6$-thiophen-3-yl)-amine and 3-methanesulfonyl-1H-indazole.

Example 2-38

5-(5-Chloro-2-{[3-(methylsulfonyl)-1H-pyrazolo[3,4-c]pyridin-1-yl]methyl}-1H-benzimidazol-1-yl)-2-methylpentan-2-ol Step 1: synthesis of ethyl 4-(dibenzylamino)butanoate

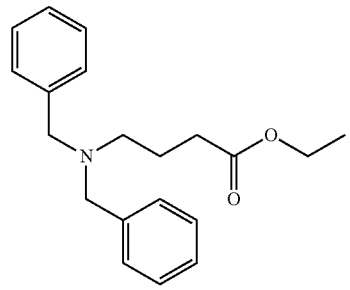 [SMILES: CCOC(=O)CCCN(Cc1ccccc1)Cc1ccccc1]

A mixture of ethyl 4-bromobutyrate (2.0 g, 10.25 mmol), dibenzylamine (2.02 g, 10.25 mmol) and potassium carbonate (2.83 g, 20.5 mmol) in N,N-dimethylformamide (20 mL) was heated with stirring at 100° C. overnight. The resulting mixture was diluted with water (80 mL) and then extracted with ethyl acetate (50 mL×3). The combined organic layers were washed with brine (80 mL×2), and then dried over $Na_2SO_4$ and then concentrated in vacuo. The residue was purified by flash chromatography on silica gel (EtOAc:PE=1:4) to afford ethyl 4-(dibenzylamino)butanoate as a white solid (2.0 g, yield: 64%).

Step 2: synthesis of 5-(dibenzylamino)-2-methylpentan-2-ol

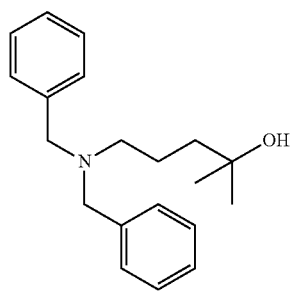 [SMILES: CC(C)(O)CCCN(Cc1ccccc1)Cc1ccccc1]

To a cooled solution of ethyl 4-(dibenzylamino)butanoate (1.5 g, 4.8 mmol) in anhydrous THF (20 mL) was added a solution of methylmagnesiumbromid (4.5 mL, 14.4 mmol) in an ice-water bath. The mixture was stirred at RT overnight, and then the reaction was quenched by addition of saturated aqueous solution of $NH_4Cl$ (5 mL). The resulting mixture was diluted with $H_2O$ (30 mL) and then extracted with EtOAc (50 mL×3). The combined organic layers were dried over $Na_2SO_4$ and concentrated in vacuo to give the crude 5-(dibenzylamino)-2-methylpentan-2-ol (1.7 g, crude), which was directly used in the next step.

Step 3: synthesis of 5-amino-2-methylpentan-2-ol

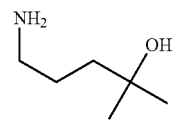

A mixture of 5-(dibenzylamino)-2-methylpentan-2-ol (1.0 g, 3.3 mmol) and $Pd(OH)_2$/C in methanol (20 mL) was stirred at 40° C. under 50 psi of $H_2$ for 3 hours. Then the reaction mixture was filtered and the filtration was concentrated in vacuo to give the crude 5-amino-2-methylpentan-2-ol (0.5 g, crude), which was directly used in the next step.

Step 4: synthesis of 5-(5-chloro-2-{[3-(methylsulfonyl)-1H-pyrazolo[3,4-c]pyridin-1-yl]methyl}-1H-benzimidazol-1-yl)-2-methylpentan-2-ol The title compound was prepared in analogy to Example 2-1 by using 5-amino-2-methylpentan-2-ol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-39

2-[trans-3-(5-chloro-2-{[3-(methylsulfonyl)-1H-pyrazolo[3,4-c]pyridin-1-yl]methyl}-1H-benzimidazol-1-yl)cyclobutyl]propan-2-ol Step 1: synthesis of methyl trans-3-aminocyclobutanecarboxylate hydrochloride

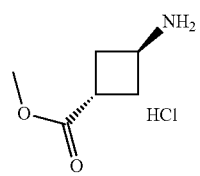

To a solution of trans-3-aminocyclobutanecarboxylic acid (500 mg, 3.3 mmol) in MeOH (20 mL) was added $SOCl_2$ dropwise at 0° C. The resulting mixture was heated at 100° C. for 4 hours and then concentrated in vacuo to afford the crude methyl trans-3-aminocyclobutanecarboxylate hydrochloride which was used in the next step directly.

Step 2: synthesis of methyl trans-3-[(tert-butoxycarbonyl)amino]cyclobutanecarboxylate

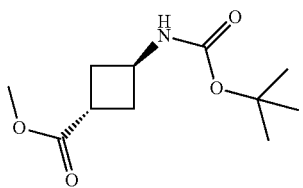 [SMILES: COC(=O)[C@H]1C[C@H](NC(=O)OC(C)(C)C)C1]

A mixture of methyl trans-3-aminocyclobutanecarboxylate hydrochloride (700 mg, 4.22 mmol), di-tert-butyl dicarbonate (1.5 g, 6.9 mmol) and $NEt_3$ (3.0 g, 30 mmol) in DCM (20 mL) was stirred at RT overnight. The resulting mixture was concentrated in vacuo and the residue was purified by silica-gel chromatography to afford methyl trans-3-[(tert-butoxycarbonyl)amino]cyclobutanecarboxylate (480 mg, yield for 2 steps: 63%).

Step 3: synthesis of tert-butyl [trans-3-(2-hydroxypropan-2-yl)cyclobutyl]carbamate

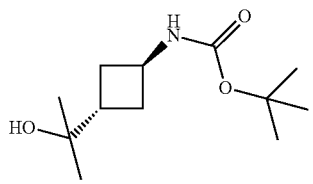 [SMILES: CC(C)(C)OC(=O)N[C@H]1C[C@H](C(C)(C)O)C1]

To a cooled solution of methyl trans-3-[(tert-butoxycarbonyl)amino]cyclobutanecarboxylate (450 mg, 1.97 mmol) in THF (15 mL) was added methylmagnesium bromide (2.7 mL, 3.2 M in THF, 8.8 mmol) dropwise at −78° C. The resulting mixture was slowly warmed up to RT and then quenched with EtOH. The mixture was then concentrated in vacuo and the residue was purified by silica-gel chromatography to afford tert-butyl [trans-3-(2-hydroxypropan-2-yl)cyclobutyl]carbamate as yellow oil (250 mg, yield: 55%).

Step 4: synthesis of 2-(trans-3-aminocyclobutyl)propan-2-ol

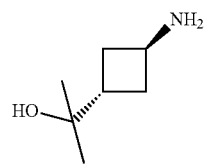

A mixture of tert-butyl [trans-3-(2-hydroxypropan-2-yl)cyclobutyl]carbamate (250 mg, 1.09 mmol) and TFA (10 mL) in DCM (10 mL) was stirred at RT for 2 hours. The resulting mixture was then concentrated in vacuo to afford 2-(trans-3-aminocyclobutyl)propan-2-ol which was used in the next step directly.

Step 5: synthesis of 2-[trans-3-(5-chloro-2-{[3-(methylsulfonyl)-1H-pyrazolo[3,4-c]pyridin-1-yl]methyl}-1H-benzimidazol-1-yl)cyclobutyl]propan-2-ol The title compound was prepared in analogy to Example 2-1 by using 2-(trans-3-aminocyclobutyl)propan-2-ol and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-40

1-({5-Chloro-1-[2-(morpholin-4-yl)ethyl]-1H-benzimidazol-2-yl}methyl)-3-(methylsulfonyl)-1H-pyrazolo[3,4-c]pyridine The title compound was prepared in analogy to Example 2-1 by using 2-(morpholin-4-yl)ethanamine and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-41 trans-3-(5-Chloro-2-{[3-(methylsulfonyl)-1H-pyrazolo[3,4-c]pyridin-1-yl]methyl}-1H-benzimidazol-1-yl)cyclobutanecarboxylic acid The title compound was prepared in analogy to Example 2-1 by using trans-3-aminocyclobutanecarboxylic acid and 3-methanesulfonyl-1H-pyrazolo[3,4-c]pyridine instead of (R)-1,1-dioxo-tetrahydro-1$\lambda^6$-thiophen-3-ylamine and 3-methanesulfonyl-1H-indazole.

Example 2-42

4-(5-Chloro-2-{[3-(methylsulfonyl)-1H-pyrazolo[3,4-c]pyridin-1-yl]methyl}-1H-benzimidazol-1-yl)-1,1,1-trifluorobutan-2-ol Step 1: synthesis of 4,4,4-trifluoro-3-hydroxybutanamide

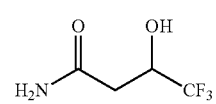

A solution of ethyl 4,4,4-trifluoro-3-hydroxybutanoate (3.0 g, 16.1 mmol) in MeOH (8 mL) was stirred with aqueous ammonium (16 mL) at room temperature overnight. The mixture was concentrated to afford 4,4,4-trifluoro-3-hydroxybutanamide (2.19 g, yield: 87.6%).

Step 2: synthesis of 4-amino-1,1,1-trifluorobutan-2-ol

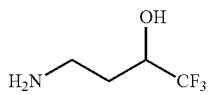

To a cooled solution of 4,4,4-trifluoro-3-hydroxybutanamide (2.84 g, 18.1 mmol) in THF (60 mL) was added LiAlH$_4$ (2.063 g, 54.3 mmol) in batches at 0° C. in an ice-water bath. The reaction mixture was then stirred at room temperature for 4 hours under nitrogen atmosphere. After the reaction was completed, 3.3 mL of water, 3.3 mL of 10% NaOH solution and 9.8 mL of water was added into the solution successively at 0° C. The resulting mixture was then filtered through celite, and the filtrate was concentrated in vacuo to afford 4-amino-1,1,1-trifluorobutan-2-ol (2.06 g, yield: 79.6%).

Step 3: synthesis of 4-(5-chloro-2-{[3-(methylsulfonyl)-1H-pyrazolo[3,4-c]pyridin-1-yl]methyl}-1H-benzimidazol-1-yl)-1,1,1-trifluorobutan-2-ol The title compound was prepared in analogy to Example 2-1 by using 4-amino-1,1,1-trifluorobutan-2-ol and 3-methanesulfonyl-1H-pyrazolo[3,4-c]pyridine instead of (R)-1,1-dioxo-tetrahydro-1λ$^6$-thiophen-3-ylamine and 3-methanesulfonyl-1H-indazole.

Example 2-43 cis-3-(5-chloro-2-{[3-(methylsulfonyl)-1H-pyrazolo[3,4-c]pyridin-1-yl]methyl}-1H-benzimidazol-1-yl)-1-methylcyclopentanol

Step 1: synthesis of tert-butyl(3-hydroxycyclopentyl)carbamate

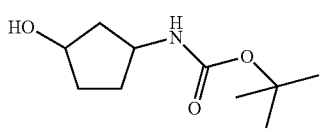

A mixture of 3-aminocyclopentanol (1.0 g, 7.3 mmol), Boc$_2$O (2.0 g, 9.25 mmol) and TEA (3.0 g, 30.0 mmol) in DCM (25 mL) was stirred at RT overnight. The resulting mixture was then concentrated in vacuo. The residue was purified by silica-gel chromatography (EA:PE=1:4 to 1:1) to afford tert-butyl(3-hydroxycyclopentyl)carbamate as a yellow gum.

Step 2: synthesis of tert-butyl(3-oxocyclopentyl)carbamate

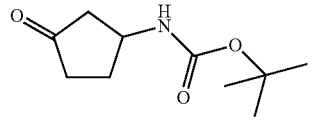

A mixture of tert-butyl(3-hydroxycyclopentyl)carbamate (800 mg, 3.98 mmol) and Dess-martin reagent (3.6 g, 8.15 mmol) in DCM (20 mL) was stirred at RT overnight. And then, the reaction was quenched by addition of sat. aqueous solution of NaHCO$_3$ and sat. aqueous solution of Na$_2$SO$_3$. The resulting mixture was extracted with DCM (20 mL×3). The combined organic layers were dried over Na$_2$SO$_4$, and then concentrated in vacuo. The residue was purified by silica-gel chromatography to afford tert-butyl(3-oxocyclopentyl)carbamate as a white solid (730 mg).

Step 3: synthesis of tert-butyl (cis-3-hydroxy-3-methylcyclopentyl)carbamate

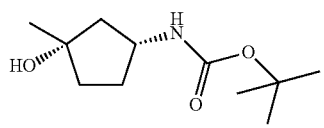

To a cooled solution of tert-butyl(3-oxocyclopentyl)carbamate (424 mg, 2.13 mmol) in dry THF (8 mL) was added methyl lithium (3.0 M, 1.6 mL) dropwise at −78° C. The resulting mixture was slowly warmed up to −20° C. After the reaction was completed as indicated by TLC, the reaction was quenched by addition of aqueous solution of NH$_4$Cl (10 mL). The resulting mixture was extracted with EtOAc (10 mL×4) and the combined organic layers were dried over Na$_2$SO$_4$, and then concentrated in vacuo. The residue was purified by prep-TLC to afford tert-butyl (cis-3-hydroxy-3-methylcyclopentyl)carbamate as colorless oil (290 mg).

Step 4: synthesis of cis-3-amino-1-methylcyclopentanol

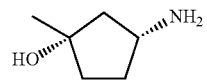

A mixture of tert-butyl (cis-3-hydroxy-3-methylcyclopentyl)carbamate (800 mg crude), TFA (5 mL) and DCM (5 mL) was stirred at RT for 1 hour. The resulting mixture was concentrated in vacuo. The residue was used in the next step directly.

Step 5: synthesis of cis-3-(5-chloro-2-{[3-(methylsulfonyl)-1H-pyrazolo[3,4-c]pyridin-1-yl]methyl}-1H-benzimidazol-1-yl)-1-methylcyclopentanol The title compound was prepared in analogy to Example 2-1 by using cis-3-amino-1-methylcyclopentanol and 3-methanesulfonyl-1H-pyrazolo[3,4-c]pyridine instead of (R)-1,1-dioxo-tetrahydro-1λ$^6$-thiophen-3-yl amine and 3-methanesulfonyl-1H-indazole.

Example 2-44

4-(5-chloro-2-{[3-(methylsulfonyl)-1H-pyrazolo[3,4-c]pyridin-1-yl]methyl}-1H-benzimidazol-1-yl)-1,1-difluorobutan-2-ol Step 1: synthesis of ethyl 4,4-difluoro-3-hydroxybutanoate

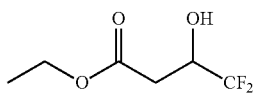

To a cooled solution of ethyl 4,4-difluoro-3-oxobutanoate (5.0 g, 30.1 mmol) in toluene (150 mL) was added NaBH$_4$ (1.26 g, 33.1 mmol) at 0° C. The mixture was then stirred at RT for 4.5 hours. The reaction was quenched with aqueous HCl (10%) carefully. The separated aqueous phase was extracted with EtOAc (20 mL×2). The combined organic phases were dried over Na$_2$SO$_4$, and then filtered and then concentrated in vacuo to give the crude ethyl 4,4-difluoro-3-hydroxybutanoate as colorless oil (3.8 g, yield: 76%).

Step 2: synthesis of 4-amino-1,1-difluorobutan-2-ol

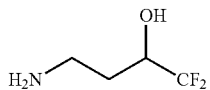

4-Amino-1,1-difluorobutan-2-ol was prepared in analogy to 4-amino-1,1,1-trifluorobutan-2-ol in Example 2-34 by using 4,4-difluoro-3-hydroxybutanoate instead of 4,4,4-trifluoro-3-hydroxybutanoate.

Step 3: synthesis of 4-(5-chloro-2-{[3-(methylsulfonyl)-1H-pyrazolo[3,4-c]pyridin-1-yl]methyl}-1H-benzimidazol-1-yl)-1,1-difluorobutan-2-ol The title compound was prepared in analogy to Example 2-1 by using 4-amino-1,1-difluorobutan-2-ol and 3-methanesulfonyl-1H-pyrazolo[3,4-c]pyridine instead of (R)-1,1-dioxo-tetrahydro-1λ$^6$-thiophen-3-ylamine and 3-methanesulfonyl-1H-indazole.

Example 2-45 trans-4-(5-chloro-2-{[3-(methylsulfonyl)-1H-pyrazolo[3,4-c]pyridin-1-yl]methyl}-1H-benzimidazol-1-yl)cyclopentane-1,2-diol Step 1: synthesis of benzyl cyclopent-3-en-1-ylcarbamate

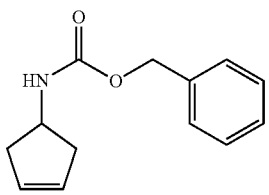 [SMILES: O=C(NC1CC=CC1)OCc1ccccc1]

To a cooled solution of cyclopent-3-ene-1-carboxylic acid (2.0 g, 17.8 mmol) and DPPA (6.05 g, 22.0 mmol) in toluene (50 mL) was added TEA (2.0 g, 22.0 mmol) dropwise at 0° C. The resulting mixture was then warmed and heated at 90° C. for 1 hour. After being added phenylmethanol (4.0 g, 40 mmol), the mixture was heated at 90° C. for additional 4 hours and then concentrated in vacuo. The residue was purified by silica-gel chromatography to afford benzyl cyclopent-3-en-1-ylcarbamate as a white solid (1.9 g).

Step 2: synthesis of benzyl 6-oxabicyclo[3.1.0]hex-3-ylcarbamate

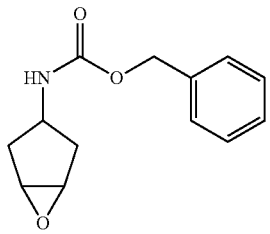 [SMILES: O=C(NC1CC2OC2C1)OCc1ccccc1]

To a solution of benzyl cyclopent-3-en-1-ylcarbamate (920 mg, 4.23 mmol) in DCM (20 mL), was added m-CPBA (2.0 g, 7.6 mmol) in portions at 0° C. The mixture was warmed up to RT and stirred at RT for 2 hours. The reaction was quenched by addition of sat. aqueous solution of K$_2$CO$_3$, and the resulting mixture was extracted with DCM (20 mL×3). The combined organic layers were dried over Na$_2$SO$_4$, and then concentrated in vacuo to afford the crude benzyl 6-oxabicyclo[3.1.0]hex-3-ylcarbamate (1.5 g), which was used in the next step directly.

Step 3: synthesis of benzyl (trans-3,4-dihydroxycyclopentyl)carbamate

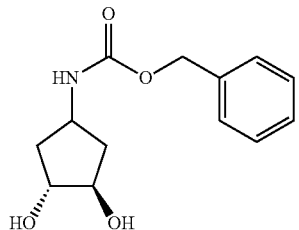 [SMILES: O=C(NC1C[C@@H](O)[C@H](O)C1)OCc1ccccc1]

A mixture of benzyl 6-oxabicyclo[3.1.0]hex-3-ylcarbamate (1.5 g crude) and concentrated H$_2$SO$_4$ (0.5 mL) in THF/water (10 mL/10 mL) was stirred at RT overnight. The mixture was then extracted with DCM (20 mL×3). The combined organic layers were dried over Na$_2$SO$_4$, and then concentrated in vacuo. The residue was purified by silica-gel chromatography to afford benzyl (trans-3,4-dihydroxycyclopentyl)carbamate as colorless gum (470 mg).

Step 4: synthesis of trans-4-aminocyclopentane-1,2-diol

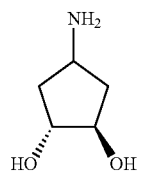

A solution of benzyl (trans-3,4-dihydroxycyclopentyl)carbamate (470 mg, 1.87 mmol) in EtOH (15 mL) was stirred in the presence of 10% Pd/C (100 mg) under hydrogen atmosphere at RT overnight. The mixture was then filtered and the filtration was concentrated in vacuo to afford the crude trans-4-aminocyclopentane-1,2-diol (300 mg), which was used in the next step directly.

Step 5: synthesis of trans-4-(5-chloro-2-{[3-(methylsulfonyl)-1H-pyrazolo[3,4-c]pyridin-1-yl]methyl}-1H-benzimidazol-1-yl)cyclopentane-1,2-diol The title compound was prepared in analogy to Example 2-1 by using trans-4-aminocyclopentane-1,2-diol and 3-methanesulfonyl-1H-pyrazolo[3,4-c]pyridine instead of (R)-1,1-dioxo-tetrahydro-1λ$^6$-thiophen-3-ylamine and 3-methanesulfonyl-1H-indazole.

Example 2-46 trans-3-(5-chloro-2-{[3-(methylsulfonyl)-1H-pyrazolo[3,4-c]pyridin-1-yl]methyl}-1H-benzimidazol-1-yl)-1-(hydroxymethyl)cyclobutanol Step 1: synthesis of tert-butyl(3-methylidenecyclobutyl)carbamate

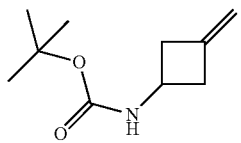

To a three necked flask equipped with additional funnel which was cooled to −78° C. was added a solution of methyl (triphenyl)phosphonium bromide (43 g, 121 mmol) in anhydrous tetrahydrofuran (200 mL) under nitrogen protection. 1 M KHMDS in tetrahydrofuran (105 mL, 105 mmol) was then introduced dropwise over 40 minutes while the internal temperature was kept below −60° C. After addition, the mixture was stirred at −78° C. for 15 minutes. Then a solution of tert-butyl(3-oxocyclobutyl)carbamate (14 g, 81 mmol) in 100 mL of tetrahydrofuran was added slowly while the internal temperature was kept below −60° C. The resulting mixture was then warmed naturally to room temperature and stirred overnight. The resulting reaction mixture was diluted with EtOAc, and then washed with saturated aqueous solution of ammonium chloride and brine, then dried over anhydrous Na$_2$SO$_4$ and then concentrated in vacuo. The residue was purified by flash chromatography (EA:PE=1:10 to 1:2) to afford tert-butyl(3-methylidenecyclobutyl)carbamate (7.5 g).

Step 2: synthesis of tert-butyl [trans-3-hydroxy-3-(hydroxymethyl)cyclobutyl]carbamate

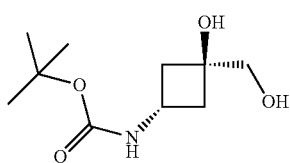

To a cooled mixture of tert-butyl(3-methylidenecyclobutyl)carbamate (7.5 g, 40.93 mmol) and N-methylmorpholine N-oxide (NMO 19.18 g, 163.71 mmol) in acetone/water (200 mL, 3:1) was added potassium osmate(VI) dihydrate (1.43 g, 4.09 mmol) at 0° C. carefully. The resulting mixture was stirred at room temperature for 18 hours and the reaction was quenched by addition of saturated aqueous solution of Na$_2$S$_2$O$_3$ (200 mL). After being stirred for 30 minutes, the mixture was concentrated in vacuo to remove acetone. The residue was extracted with EtOAc (75 mL×2). The combined organic layers were washed with brine, and then dried over anhydrous Na$_2$SO$_4$ and then concentrated in vacuo until the volume of the residue was about 10 mL. The precipitate was filtered to afford 4.0 g of trans-isomer. The filtrate was concentrated in vacuo to afford a mixture of 4.5 g of cis-isomer and trans-isomer (5:1).

Step 3: synthesis of trans-3-amino-1-(hydroxymethyl)cyclobutanol hydrochloride

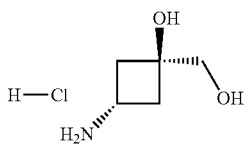

To a cooled suspension of tert-butyl [trans-3-hydroxy-3-(hydroxymethyl)cyclobutyl]carbamate (2.0 g, 9.21 mmol) in dioxane (15 mL) was added a solution of 4 M HCl in dioxane (10 mL) dropwise. After being stirred at room temperature for 18 hours, the mixture was concentrate d in vacuo to afford the crude trans-3-amino-1-(hydroxymethyl)cyclobutanol hydrochloride (1.41 g).

Step 4: synthesis of trans-3-(5-chloro-2-{[3-(methylsulfonyl)-1H-pyrazolo[3,4-c]pyridin-1-yl]methyl}-1H-benzimidazol-1-yl)-1-(hydroxymethyl)cyclobutanol The title compound was prepared in analogy to Example 2-1 by using trans-3-amino-1-(hydroxymethyl)cyclobutanol hydrochloride and 3-methanesulfonyl-1H-pyrazolo[3,4-c]pyridine instead of (R)-1,1-dioxo-tetrahydro-1λ$^6$-thiophen-3-ylamine and 3-methanesulfonyl-1H-indazole.

Example 3-1

1-{[5-Chloro-1-(6-fluoropyridin-3-yl)-1H-benzimidazol-2-yl]methyl}-3-(methylsulfonyl)-1H-indazole Step 1: synthesis of (4-chloro-2-nitro-phenyl)-(6-fluoro-pyridin-3-yl)-amine

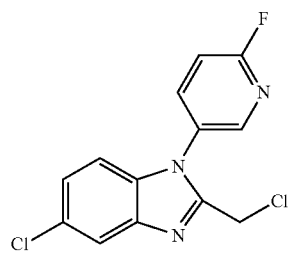 [SMILES: Fc1ccc(-n2c(CCl)nc3cc(Cl)ccc32)cn1]

To the solution of 4-chloro-2-nitro-phenylamine (862 mg, 5.0 mmol), 5-bromo-2-fluoro-pyridine (924 mg, 5.25 mmol) in dioxane (15 mL) was added 2-dicyclohexylphosphino-2',6'-dimethoxybiphenyl (289 mg, 0.5 mmol), Pd$_2$(dba)$_3$ (457.5 mg, 0.5 mmol), followed by cesium carbonate (3.26 g, 10.0 mmol). After degassed and refilled with nitrogen for three times, the reaction mixture in vessel was stirred at 110° C. for overnight till all starting material has been consumed. The reaction mixture was quenched with ice water, the solid was filtered and collected, washed with water, and dried over oven to yield the nitro product about 800 mg as crude solid (yield: 60%). To the solution of (4-chloro-2-nitro-phenyl)-(6-fluoro-pyridin-3-yl)-amine (800 mg, 3.0 mmol) in methanol (10 mL) was added Raney Ni (slurry in water, 100 mg), followed by hydrazine (2 mL), the reaction mixture was stirred at RT for 30 min, till all starting material has gone. The mixture was filtered and the filtrate was combined. After evaporated under reduced pressure, about 600 mg of the residue was obtained as crude product (yield: 90%). The cyclization step is as the same as previous description in Example 2-1. MS obsd. (ESI$^+$) [(M+H)$^+$], 296.

Step 2: synthesis of 1-{[5-chloro-1-(6-fluoropyridin-3-yl)-1H-benzimidazol-2-yl]methyl}-3-(methylsulfonyl)-1H-indazole Example 3-1 was prepared in analogy to Example 2-1 by using 5-chloro-2-chloromethyl-1-(4,4,4-trifluoro-butyl)-1H-benzoimidazole and 3-methanesulfonyl-1H-indazole instead of 5-chloro-2-chloromethyl-1-((S)-1,1-dioxo-tetrahydro-1λ$^6$-thiophen-3-yl)-1H-benzoimidazole and 3-(methylsulfonyl)-1H-pyrazolo[3,4-c]pyridine.

Example 3-2

1-{[5-Chloro-1-(6-fluoropyridin-3-yl)-1H-benzimidazol-2-yl]methyl}-3-(methylsulfonyl)-1H-pyrazolo[3,4-c]pyridine The title compound was prepared in analogy to Example 3-1 by using 5-chloro-2-chloromethyl-1-(4,4,4-trifluoro-butyl)-1H-benzoimidazole and 3-methanesulfonyl 1H-pyrazolo[3,4-c]pyridine instead of 5-chloro-2-chloromethyl-1-(4,4,4-trifluoro-butyl)-1H-benzoimidazole and 3-methanesulfonyl-1H-indazole.

Example 3-3

1-{[5-Chloro-1-(6-fluoropyridin-3-yl)-1H-benzimidazol-2-yl]methyl}-3-(methylsulfonyl)-1H-pyrazolo[3,4-c]pyridine 6-oxide The title compound was prepared in analogy to Example 3-1 by using 5-chloro-2-chloromethyl-1-(4,4,4-trifluoro-butyl)-1H-benzoimidazole and 3-methanesulfonyl- and 3-methanesulfonyl-1H-pyrazolo[3,4-c]pyridine 6-oxide instead of 5-chloro-2-chloromethyl-1-(4,4,4-trifluoro-butyl)-1H-benzoimidazole and 3-methanesulfonyl-1H-indazole.

Example 3-4

1-{[5-Chloro-1-(6-methoxypyridin-3-yl)-1H-benzimidazol-2-yl]methyl}-3-(methylsulfonyl)-1H-indazole The title compound was prepared in analogy to Example 3-1 by using 5-chloro-2-chloromethyl-1-(6-methoxy-pyridin-3-yl)-1H-benzoimidazole and 3-methanesulfonyl-1H-indazole instead of 5-chloro-2-chloromethyl-1-(4,4,4-trifluoro-butyl)-1H-benzoimidazole and 3-methanesulfonyl-1H-indazole.

Example 3-5

1-{[5-Chloro-1-(6-chloropyridin-3-yl)-1H-benzimidazol-2-yl]methyl}-3-(methylsulfonyl)-1H-indazole The title compound was prepared in analogy to Example 3-1 by using 5-chloro-2-chloromethyl-1-(6-chloro-pyridin-3-yl)-1H-benzoimidazole and methanesulfonyl-1H-indazole instead of 5-chloro-2-chloromethyl-1-(4,4,4-trifluoro-butyl)-1H-benzoimidazole and 3-methanesulfonyl-1H-indazole.

Example 4-1

1-{[5-Chloro-1-(4,4,4-trifluorobutyl)-1H-benzimidazol-2-yl]methyl}-3-(methylsulfonyl)-1H-indazole The title compound was prepared in analogy to Example 3-1 by using 5-chloro-2-chloromethyl-1-(4,4,4-trifluoro-butyl)-1H-benzoimidazole (prepared in analogy to Example 2-1), and methanesulfonyl-1H-indazole instead of 5-chloro-2-chloromethyl-1-(4,4,4-trifluoro-butyl)-1H-benzoimidazole and 3-methanesulfonyl-1H-indazole.

Example 4-2

1-{[5-Chloro-1-(4,4,4-trifluorobutyl)-1H-benzimidazol-2-yl]methyl}-3-(methylsulfonyl)-1H-pyrazolo[3,4-c]pyridine 6-oxide The title compound was prepared in analogy to Example 3-1 by using 5-chloro-2-chloromethyl-1-(4,4,4-trifluoro-butyl)-1H-benzoimidazole (prepared in analogy to Example 2-1), and 3-methanesulfonyl-1H-pyrazolo[3,4-c]pyridine 6-oxide instead of 5-chloro-2-chloromethyl-1-(4,4,4-trifluoro-butyl)-1H-benzoimidazole and 3-methanesulfonyl-1H-indazole.

Example 4-3

1-{[5-Chloro-1-(4,4,4-trifluorobutyl)-1H-benzimidazol-2-yl]methyl}-3-(methylsulfonyl)-1H-pyrazolo[3,4-c]pyridine The title compound was prepared in analogy to Example 4-1 by using 5-chloro-2-chloromethyl-1-(4,4,4-trifluoro-butyl)-1H-benzoimidazole and 3-methanesulfonyl-1H-pyrazolo[3,4-c]pyridine instead of 5-chloro-2-chloromethyl-1-(4,4,4-trifluoro-butyl)-1H-benzoimidazole and methanesulfonyl-1H-indazole.

Example 5-1

1-{[5-Chloro-7-fluoro-1-(3,3,3-trifluoropropyl)-1H-benzimidazol-2-yl]methyl}-3-(methylsulfonyl)-1H-pyrazolo[3,4-c]pyridine The title compound was prepared according to the steps in Scheme 5.

Step 1: synthesis of N-(4-chloro-2-fluoro-phenyl)-3,3,3-trifluoro-propionamide

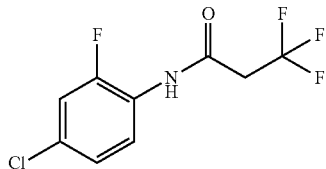 [SMILES: O=C(CC(F)(F)F)Nc1ccc(Cl)cc1F]

4-Chloro-2-fluoroaniline (3 g, 20.7 mmol), 3,3,3-trifluoropropanoic acid (2.6 g, 20.7 mmol) and Et$_3$N (5.8 mL) were dissolved in 50 mL of DCM. To this solution was added HATU (8.6 g, 22.7 mmol) slowly and then stirred overnight. The organic phases was washed with aq. NH$_4$Cl (50 mL), NaHCO$_3$ solution (50 mL) and brine (100 mL). The combined organic phases were evaporated and purified by column chromatography (PE/EA=5/1) to give N-(4-chloro-2-fluorophenyl)-3,3,3-trifluoropropanamide which was pure enough for next step. (4.7 g, yield: 90%) was a yellow solid. MS obsd. (ESI$^+$) [(M+H)$^+$] 256.

Step 2: synthesis of N-(4-chloro-2-fluoro-6-nitrophenyl)-3,3,3-trifluoro-propionamide

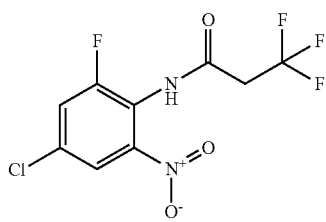 [SMILES: O=C(CC(F)(F)F)Nc1c(F)cc(Cl)cc1[N+](=O)[O-]]

A solution of N-(4-chloro-2-fluorophenyl)-3,3,3-trifluoropropanamide (2 g, 7.8 mmol) in 15 mL of concentrated H$_2$SO$_4$ was added 1 mL of concentrated nitric acid and stirred at room temperature overnight. The reaction was monitored by LC-MS. The reaction mixture was poured into 20 mL of ice-water. The mixture was filtered to give the solid crude N-(4-chloro-2-fluoro-6-nitrophenyl)-3,3,3-trifluoropropanamide (600 mg, yield: 17%) which was further purified by column chromatography (PE/EtOAc=6/1). MS obsd. (ESI$^+$) [(M+H)$^+$] 301.

Step 3: synthesis of 5-chloro-3-fluoro-N-(3,3,3-trifluoro-propyl)-benzene-1,2-diamine

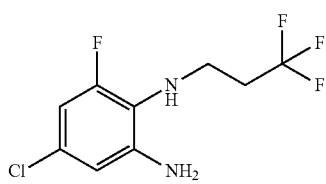

To a solution of N-(4-chloro-2-fluoro-6-nitrophenyl)-3,3,3-trifluoropropanamide (350 mg, 1.1 mmol) in 15 mL of THF was added borane-tetrahydrofuran solution (25 mL, 1 M). The mixture was heated to 70° C. and stirred overnight. The reaction was quenched with MeOH and the solvents were removed by evaporation to give 4-chloro-6-fluoro-N-(3,3,3-trifluoropropyl)benzene-1,2-diamine (300 mg, yield: 82%) as crude oil. MS obsd. (ESI$^+$) [(M+H)$^+$] 257.

Step 4: synthesis of 5-chloro-2-chloromethyl-7-fluoro-1-(3,3,3-trifluoro-propyl)-1H-benzoimidazole

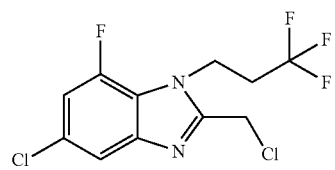 [SMILES: Fc1cc(Cl)cc2nc(CCl)n(CCC(F)(F)F)c12]

5-Chloro-2-chloromethyl-7-fluoro-1-(3,3,3-trifluoro-propyl)-1H-benzoimidazole was prepared according to the procedure described in Example 2-1 by using 4-chloro-6-fluoro-N-(3,3,3-trifluoropropyl)benzene-1,2-diamine and sodium 2-chloroacetate instead of 5-chloro-2-chloromethyl-1-((S)-1,1-dioxo-tetrahydro-1λ$^6$-thiophen-3-yl)-1H-benzoimidazole and 3-(methylsulfonyl)-1H-pyrazolo[3,4-c]pyridine. MS obsd. (ESI$^+$) [(M+H)$^+$] 315.

Step 5: synthesis of 1-{[5-chloro-7-fluoro-1-(3,3,3-trifluoropropyl)-1H-benzimidazol-2-yl]methyl}-3-(methylsulfonyl)-1H-pyrazolo[3,4-c]pyridine Example 5-1 was prepared in analogy to Example 4-1 by using 5-chloro-2-(chloromethyl)-7-fluoro-1-(3,3,3-trifluoropropyl)-1H-benzo[d]imidazole and 3-(methylsulfonyl)-1H-pyrazolo[3,4-c]pyridine instead of 5-chloro-2-chloromethyl-1-(4,4,4-trifluoro-butyl)-1H-benzoimidazole and methanesulfonyl-1H-indazole.

Example 5-2

1-{[5-Chloro-7-fluoro-1-(4,4,4-trifluorobutyl)-1H-benzimidazol-2-yl]methyl}-3-(methylsulfonyl)-1H-pyrazolo[3,4-c]pyridine The title compound was prepared in analogy to Example 5-1 by using 5-chloro-2-(chloromethyl)-7-fluoro-1-(4,4,4-trifluorobutyl)-1H-benzo[d]imidazole and 3-(methylsulfonyl)-1H-pyrazolo[3,4-c]pyridine 5-chloro-2-(chloromethyl)-7-fluoro-1-(3,3,3-trifluoropropyl)-1H-benzo[d]imidazole and 3-(methylsulfonyl)-1H-pyrazolo[3,4-c]pyridine.

Example 6-1

1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]ethanone Step 1: synthesis of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine The title compound was prepared in analogy to Example 2-13 by using tert-butyl (3R)-3-aminopyrrolidine-1-carboxylate and 3-methanesulfonyl-1H-pyrazolo[3,4-c]pyridine.instead of tert-butyl 3-aminopyrrolidine-1-carboxylate and 3-methanesulfonyl-1H-pyrazolo[3,4-c]pyridine.

Step 2: synthesis of 1-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]ethanone To a solution of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine (30 mg), acetic anhydride (0.1 mL) in 8 mL of DCM was added DMAP (3 mg, 0.025 mmol). The mixture was stirred for 1 hour. Then 20 mL of DCM and 10 mL of water was added. The organic phase was washed with water and NaHCO$_3$ and then dried over anhydrous Na$_2$SO$_4$. The solvent was evaporated. The residue was purified by preparative-HPLC to afford the title compound (15 mg) as a pale solid.

Example 6-2

1-[3-(5-Chloro-2-{[3-(methylsulfonyl)-1H-indazol-1-yl]methyl}-1H-benzimidazol-1-yl)pyrrolidin-1-yl]ethanone Step 1: synthesis of 1-({5-chloro-1-[(3R)-(pyrrolidin-3-yl)]-1H-benzo[d]imidazol-2-yl}methyl)-3-(methylsulfonyl)-1H-indazole 1-({5-Chloro-1-[(3R)-(pyrrolidin-3-yl)]-1H-benzo[d]imidazol-2-yl}methyl)-3-(methylsulfonyl)-1H-indazole was prepared in analogy to Example 2-13 by using 3-methanesulfonyl-1H-indazole instead of 3-methanesulfonyl-1H-pyrazolo[3,4-c]pyridine.

Step 2: synthesis of 1-({5-chloro-1-[(3R)-(pyrrolidin-3-yl)]-1H-benzo[d]imidazol-2-yl}methyl)-3-(methylsulfonyl)-1H-indazole 1-({5-Chloro-1-[(3R)-(pyrrolidin-3-yl)]-1H-benzo[d]imidazol-2-yl}methyl)-3-(methylsulfonyl)-1H-indazole was prepared in analogy to Example 2-13 by using tert-butyl (3R)-3-aminopyrrolidine-1-carboxylate and 3-methanesulfonyl-1H-indazole instead of tert-butyl 3-aminopyrrolidine-1-carboxylate and 3-methanesulfonyl-1H-pyrazolo[3,4-c]pyridine.

Step 3: synthesis of 1-[3-(5-chloro-2-{[3-(methylsulfonyl)-1H-indazol-1-yl]methyl}-1H-benzimidazol-1-yl)pyrrolidin-1-yl]ethanone The title compound was prepared in analogy to Example 6-1 by using 1-({5-chloro-1-[(3R)-(pyrrolidin-3-yl)]-1H-benzo[d]imidazol-2-yl}methyl)-3-(methylsulfonyl)-1H-indazole instead of 1-{[5-chloro-1-(pyrrolidin-3-yl)-1H-benzo[d]imidazol-2-yl]methyl}-3-(methylsulfonyl)-1H-pyrazolo[3,4-c]pyridine.

Example 6-3

1-[(3R)-3-(5-Chloro-2-{[3-(methylsulfonyl)-1H-indazol-1-yl]methyl}-1H-benzimidazol-1-yl)pyrrolidin-1-yl]propan-1-one The title compound was prepared in analogy to Example 2-17 by using 1-({5-chloro-1-[(3R)-(pyrrolidin-3-yl)]-1H-benzo[d]imidazol-2-yl}methyl)-3-(methylsulfonyl)-1H-indazole and propionic acid instead of 1-{[5-chloro-1-(pyrrolidin-3-yl)-1H-benzo[d]imidazol-2-yl]methyl}-3-(methylsulfonyl)-1H-pyrazolo[3,4-c]pyridine and acetic anhydride.

Example 6-4

1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]-2-methylpropan-1-one Step 1: synthesis of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine 1-({5-Chloro-1-[(3R)-(pyrrolidin-3-yl)]-1H-benzo[d]imidazol-2-yl}methyl)-3-(methylsulfonyl)-1H-pyrazolo[3,4-c]pyridine was prepared in analogy to Example 2-13 by using tert-butyl (3R)-3-aminopyrrolidine-1-carboxylate instead of tert-butyl 3-aminopyrrolidine-1-carboxylate.

Step 2: synthesis of 1-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]-2-methylpropan-1-one The title compound was prepared in analogy to Example 2-17 by using 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine and 2-methylpropanoic acid instead of 1-{[5-chloro-1-(pyrrolidin-3-yl)-1H-benzo[d]imidazol-2-yl]methyl}-3-(methylsulfonyl)-1H-pyrazolo[3,4-c]pyridine and acetic anhydride.

Example 6-5

1-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]-2-hydroxy-2-methylpropan-1-one Step 1: synthesis of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine 1-({5-Chloro-1-[(3R)-(pyrrolidin-3-yl)]-1H-benzo[d]imidazol-2-yl}methyl)-3-(methylsulfonyl)-1H-pyrazolo[3,4-c]pyridine was prepared in analogy to Example 2-13 by using tert-butyl (3R)-3-aminopyrrolidine-1-carboxylate instead of tert-butyl 3-aminopyrrolidine-1-carboxylate.

Step 2: synthesis of 1-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]-2-hydroxy-2-methylpropan-1-one The title compound was prepared in analogy to Example 2-17 by using 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine and 2-hydroxy-2-methylpropanoic acid instead of 1-{[5-chloro-1-(pyrrolidin-3-yl)-1H-benzo[d]imidazol-2-yl]methyl}-3-(methylsulfonyl)-1H-pyrazolo[3,4-c]pyridine and 2-hydroxyacetic acid.

Example 6-6

1-({5-Chloro-1-[(3R)-1-(methylsulfonyl)pyrrolidin-3-yl]-1H-benzimidazol-2-yl}methyl)-3-(methylsulfonyl)-1H-pyrazolo[3,4-c]pyridine Step 1: synthesis of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine The title compound was prepared in analogy to Example 6-1 by using tert-butyl (3R)-3-aminopyrrolidine-1-carboxylate instead of tert-butyl 3-aminopyrrolidine-1-carboxylate.

Step 2: synthesis of 1-({5-chloro-1-[(3R)-1-(methylsulfonyl)pyrrolidin-3-yl]-1H-benzimidazol-2-yl}methyl)-3-(methylsulfonyl)-1H-pyrazolo[3,4-c]pyridine To a solution of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine (200 mg, 0.46 mmol) and Et₃N (0.2 mL) in 8 mL of DCM was added 80 mg of methanesulfonyl chloride. The mixture was stirred for 2 hours. The mixture was then purified by preparative-HPLC to give the title compound.

Example 6-7

2-[(3R)-3-(5-Chloro-2-{[3-(methylsulfonyl)-1H-pyrazolo[3,4-c]pyridin-1-yl]methyl}-1H-benzimidazol-1-yl)pyrrolidin-1-yl]ethanol Step 1: synthesis of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine 1-({5-Chloro-1-[(3R)-(pyrrolidin-3-yl)]-1H-benzo[d]imidazol-2-yl}methyl)-3-(methylsulfonyl)-1H-pyrazolo[3,4-c]pyridine was prepared in analogy to Example 2-13 by using tert-butyl (3R)-3-aminopyrrolidine-1-carboxylate instead of tert-butyl 3-aminopyrrolidine-1-carboxylate.

Step 2: synthesis of 2-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]ethanol To a solution of 1-({5-chloro-1-[(3R)-(pyrrolidin-3-yl)]-1H-benzo[d]imidazol-2-yl}methyl)-3-(methylsulfonyl)-1H-pyrazolo[3,4-c]pyridine (300 mg, 0.70 mmol) in 5 mL of DMF was added 2-bromoethanol (173 mg, 2.1 mmol) and Cs₂CO₃ (682 mg, 2.1 mmol). The mixture was heated to 70° C. and stirred overnight. The mixture was filtered and then purified by preparative-HPLC to give the title compound.

Example 7

4-(5-Chloro-2-{[3-(methylsulfonyl)-1H-pyrazolo[3,4-c]pyridin-1-yl]methyl}-1H-benzimidazol-1-yl)pyrrolidin-2-one Step 1: synthesis of methyl 1-(4-methoxybenzyl)-5-oxopyrrolidine-3-carboxylate

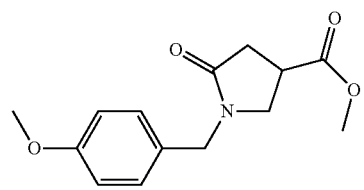 [SMILES: COC(=O)C1CC(=O)N(Cc2ccc(OC)cc2)C1]

A mixture of dimethyl 2-methylidenebutanedioate (47.5 g, 300 mmol) and 1-(4-methoxyphenyl)methanamine (41.2 g, 300 mmol) in 400 mL of MeOH was stirred at room temperature overnight. The resulting reaction mixture was concentrated in vacuo to remove methanol. The residual brown oil was stirred with 40 mL of EtOAc and 40 mL of PE vigorously. The precipitate was collected by filtration and washed with PE (40 mL×2) to afford methyl 1-(4-methoxybenzyl)-5-oxopyrrolidine-3-carboxylate (68.0 g, yield: 86.1%).

Step 2: synthesis of 1-(4-methoxy-benzyl)-5-oxo-pyrrolidine-3-carboxylic acid amide

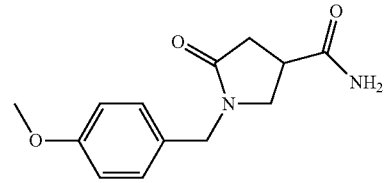 [SMILES: COc1ccc(CN2CC(C(N)=O)CC2=O)cc1]

A mixture of methyl 1-(4-methoxybenzyl)-5-oxopyrrolidine-3-carboxylate (65.8 g, 250 mmol) and aqueous ammonia (1.5 L) was stirred at room temperature overnight. The resulting reaction mixture was filtered. The filter cake was washed with H₂O several times and dried in vacuo to afford 1-(4-methoxy-benzyl)-5-oxo-pyrrolidine-3-carboxylic acid amide as a white solid (60.0 g, yield: 96.5%).

Step 3: synthesis of 4-amino-1-(4-methoxybenzyl)pyrrolidin-2-one

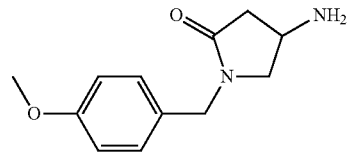 [SMILES: COc1ccc(CN2CC(N)CC2=O)cc1]

To a solution of 1-(4-methoxy-benzyl)-5-oxo-pyrrolidine-3-carboxylic acid amide (50.0 g, 201 mmol) in 560 mL of CH₃CN and 560 mL of H₂O was added bis(acetyloxy)(phenyl)-λ³-iodane (84.0 g, 261 mmol). The color of the mixture turned to light red. After being stirred at room temperature overnight, the reaction mixture was diluted with 1000 mL of H₂O and acidified to pH 2 with concentrated HCl, then extracted with DCM (300 mL×3). The aqueous layer was then basified to pH 10 with 1 N aqueous solution of KOH and then extracted with DCM (400 mL×3). The combined organic layers were dried over Na₂SO₄ and then concentrated in vacuo to afford 4-amino-1-(4-methoxybenzyl)pyrrolidin-2-one as light yellow oil (28.0 g, yield: 63.2%), which solidified after being cooled down to room temperature and was used without further purification.

Step 4: synthesis of 4-[(4-chloro-2-nitrophenyl) amino]-1-(4-methoxybenzyl)pyrrolidin-2-one

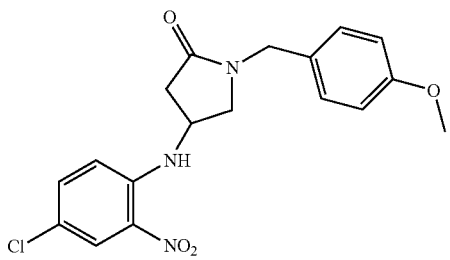 [SMILES: COc1ccc(CN2CC(Nc3ccc(Cl)cc3[N+](=O)[O-])CC2=O)cc1]

A mixture of 4-chloro-1-fluoro-2-nitrobenzene (9.2 g, 52.4 mmol), 4-amino-1-(4-methoxybenzyl)pyrrolidin-2-one (11.5 g, 52.4 mmol) and K$_2$CO$_3$ (14.5 g, 105 mmol) in 300 mL of anhydrous CH$_3$CN was heated with stirring at 50° C. for 16 hours. The reaction mixture was filtered and the filter cake was dissolved with H$_2$O (400 mL), and extracted with EtOAc (200 mL×4). The organic layers and the filtrate was combined and concentrated in vacuo to 50 mL. The precipitate was collected by filtration and washed with 10 mL of PE to afford 4-[(4-chloro-2-nitrophenyl)amino]-1-(4-methoxybenzyl)pyrrolidin-2-one as an orange solid (15.8 g, yield: 80.2%).

Step 5: synthesis of 4-[(2-amino-4-chlorophenyl) amino]-1-(4-methoxybenzyl)pyrrolidin-2-one

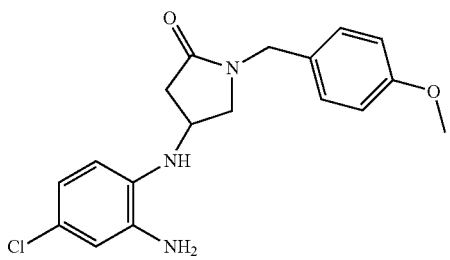

4-[(2-Amino-4-chlorophenyl)amino]-1-(4-methoxybenzyl)pyrrolidin-2-one was prepared in analogy to 4-chloro-N—((S)-1,1-dioxo-tetrahydro-1λ$^6$-thiophen-3-yl)-benzene-1,2-diamine in Example 2-1 by using 4-[(4-chloro-2-nitrophenyl)amino]-1-(4-methoxybenzyl)pyrrolidin-2-one instead of (4-chloro-2-nitro-phenyl)-((S)-1,1-dioxo-tetrahydro-1λ$^6$-thiophen-3-yl)-amine.

Step 6: synthesis of 4-[5-chloro-2-(chloromethyl)-1H-benzimidazol-1-yl]-1-(4-methoxybenzyl)pyrrolidin-2-one

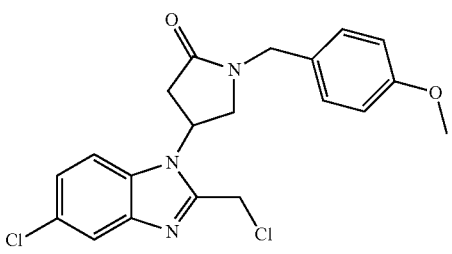 [SMILES: COc1ccc(CN2CC(n3c(CCl)nc4cc(Cl)ccc43)CC2=O)cc1]

A mixture of 4-[(2-amino-4-chlorophenyl)amino]-1-(4-methoxybenzyl)pyrrolidin-2-one (1.35 g, 3.91 mmol) and 2-chloro-1,1,1-triethoxyethane (10 mL) was stirred at 80° C. for 1 hour. The resulting mixture was concentrated in vacuo and the residue was purified by column chromatography (DCM: MeOH=20:1) to afford 4-[5-chloro-2-(chloromethyl)-1H-benzimidazol-1-yl]-1-(4-methoxybenzyl)pyrrolidin-2-one.

Step 7: synthesis of 4-(5-chloro-2-{[3-(methylsulfonyl)-1H-pyrazolo[3,4-c]pyridin-1-yl]methyl}-1H-benzimidazol-1-yl)-1-(4-methoxybenzyl)pyrrolidin-2-one

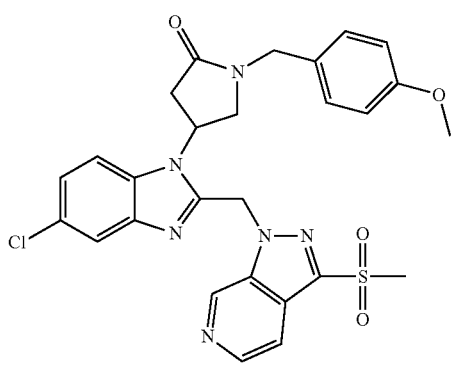 [SMILES: COc1ccc(CN2CC(n3c(Cn4nc(S(C)(=O)=O)c5ccncc54)nc4cc(Cl)ccc43)CC2=O)cc1]

To a solution of 4-[5-chloro-2-(chloromethyl)-1H-benzimidazol-1-yl]-1-(4-methoxybenzyl)pyrrolidin-2-one (294 mg, 1.492 mmol) in 50 mL of DMF was added 3-(methylsulfonyl)-1H-pyrazolo[3,4-c]pyridine (722 mg, 1.791 mmol) and Cs$_2$CO$_3$ (584 mg, 2.985 mmol). The resulting mixture was stirred at RT for 4 hours, then diluted with 40 mL of H$_2$O and EtOAc. The separated aqueous phase was extracted with EtOAc (15 mL×3). The combined organic phases were washed with 30 mL of brine, and then dried over Na$_2$SO$_4$, then filtered and concentrated in vacuo. The residue was purified by column chromatography (DCM: MeOH=20:1) to give 4-(5-chloro-2-{[3-(methylsulfonyl)-1H-pyrazolo[3,4-c]pyridin-1-yl]methyl}-1H-benzimidazol-1-yl)-1-(4-methoxybenzyl)pyrrolidin-2-one as a solid.

Step 8: synthesis of 4-(5-chloro-2-{[3-(methylsulfonyl)-1H-pyrazolo[3,4-c]pyridin-1-yl]methyl}-1H-benzimidazol-1-yl)pyrrolidin-2-one To a solution of 4-(5-chloro-2-{[3-(methylsulfonyl)-1H-pyrazolo[3,4-c]pyridin-1-yl]methyl}-1H-benzimidazol-1-yl)-1-(4-methoxybenzyl)pyrrolidin-2-one (208 mg, 0.37 mmol) in 60 mL of CH$_3$CN and 12 mL of H$_2$O was added (NH$_4$)$_2$Ce(NO$_3$)$_6$ (1.01 g, 1.84 mmol). The resulting mixture was stirred at RT for 6 hours. The solution was diluted with 40 mL of water and 15 mL of EtOAc. The separated aqueous phase was extracted with EtOAc (15 mL×3) and THF (5 mL×3). The combined organic phases were washed with 30 mL of brine, and then dried over Na$_2$SO$_4$, then filtered and concentrated. The residue was purified by column chromatography (DCM: MeOH=20:1) to afford 4-(5-chloro-2-{[3-(methylsulfonyl)-1H-pyrazolo[3,4-c]pyridin-1-yl]methyl}-1H-benzimidazol-1-yl)pyrrolidin-2-one.

Example 8

1'-{[5-Chloro-1-(2-oxa-5-azaspiro[3.4]oct-7-yl)-1H-benzimidazol-2-yl]methyl}-3-methanesulfonyl-1H-pyrazolo[3,4-c]pyridine Step 1: synthesis of ethyl 2-oxa-5-azaspiro[3.4]octane-7-carboxylate

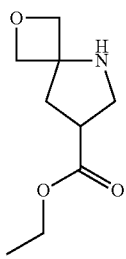

A solution of ethyl 5-benzyl-2-oxa-5-azaspiro[3.4]octane-7-carboxylate (550 mg, 2.00 mmol) in 30 mL of EtOH was stirred with 10% Pd(OH)$_2$/C(105 mg) in the presence of TFA (20 μL) at room temperature overnight. The resulting mixture was concentrated in vacuo. The residue was dissolved in 20 mL of DCM and washed with saturated Na$_2$CO$_3$ (20 mL). The organic layer was dried over Na$_2$SO$_4$ and then concentrated in vacuo to afford ethyl 2-oxa-5-azaspiro[3.4]octane-7-carboxylate (390 mg, yield: 100%) as viscous oil.

Step 2: synthesis of 5-tert-butyl 7-ethyl 2-oxa-5-azaspiro[3.4]octane-5,7-dicarboxylate

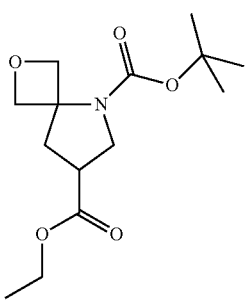 [SMILES: CCOC(=O)C1CN(C(=O)OC(C)(C)C)C2(COC2)C1]

A mixture of ethyl 2-oxa-5-azaspiro[3.4]octane-7-carboxylate (333 mg, 1.80 mmol), Boc$_2$O (972 mg, 4.50 mmol) and NEt$_3$ (0.30 mL, 2.16 mmol) in 10 mL of DCM was stirred at room temperature for 3 hours. The resulting mixture was concentrated in vacuo. The residue was purified by flash column (eluting with 0-5% MeOH in DCM) to afford 5-tert-butyl 7-ethyl 2-oxa-5-azaspiro[3.4]octane-5,7-dicarboxylate (514 mg, yield: 100%) as light viscous oil.

Step 3: synthesis of 5-(tert-butoxycarbonyl)-2-oxa-5-azaspiro[3.4]octane-7-carboxylic acid

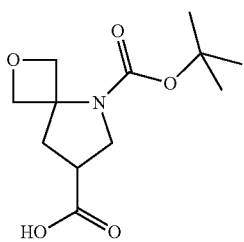 [SMILES: CC(C)(C)OC(=O)N1CC(C(=O)O)CC12COC2]

A mixture of 5-tert-butyl 7-ethyl 2-oxa-5-azaspiro[3.4]octane-5,7-dicarboxylate (514 mg, 1.80 mmol) and lithium hydroxide monohydrate (378 mg, 9.0 mmol) in 1 mL of H$_2$O and 10 mL of MeOH was stirred at room temperature overnight. The resulting mixture was concentrated in vacuo. The residue was stirred with saturated aqueous solution of 2-hydroxypropane-1,2,3-tricarboxylic acid (15 mL) and then extracted with DCM (15 mL×2). The combined organic layers were dried over Na$_2$SO$_4$ and then concentrated in vacuo to afford 5-(tert-butoxycarbonyl)-2-oxa-5-azaspiro[3.4]octane-7-carboxylic acid (444 mg, yield: 95.9%) as a white solid.

Step 4: synthesis of tert-butyl 7-{[(benzyloxy)carbonyl]amino}-2-oxa-5-azaspiro[3.4]octane-5-carboxylate

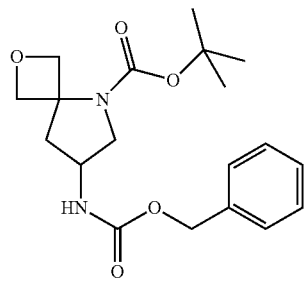 [SMILES: CC(C)(C)OC(=O)N1CC(NC(=O)OCc2ccccc2)CC12COC2]

To a solution of 5-(tert-butoxycarbonyl)-2-oxa-5-azaspiro[3.4]octane-7-carboxylic acid (444 mg, 1.72 mmol) in 5 mL of anhydrous toluene was added diphenyl phosphorazidate (407 μL, 1.89 mmol) and NEt$_3$ (275 μL, 1.89 mmol). The mixture was heated at 80° C. for 3 hours. Then to the mixture was added phenylmethanol (0.5 mL). The resulting mixture was then heated at 90° C. overnight. The reaction mixture was concentrated in vacuo. The residue was purified by flash column (eluting with 0-30% EtOAc in PE) to afford tert-butyl 7-{[(benzyloxy)carbonyl]amino}-2-oxa-5-azaspiro[3.4]octane-5-carboxylate (577 mg, yield: 92.6%) as light viscous oil.

Step 5: synthesis of tert-butyl 7-amino-2-oxa-5-azaspiro[3.4]octane-5-carboxylate

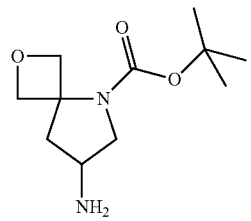 [SMILES: CC(C)(C)OC(=O)N1CC(N)CC12COC2]

A solution of tert-butyl 7-{[(benzyloxy)carbonyl]amino}-2-oxa-5-azaspiro[3.4]octane-5-carboxylate (566 mg, 1.56 mmol) in 20 mL of MeOH was stirred with 10% Pd/C (100 mg) under hydrogen atmosphere at room temperature for 50 minutes. The resulting mixture was filtered and the filtration was concentrated in vacuo to afford tert-butyl 7-amino-2-oxa-5-azaspiro[3.4]octane-5-carboxylate (343 mg, yield: 96.3%) as light viscous oil.

Step 6: synthesis of tert-butyl 7-[(4-chloro-2-nitrophenyl)amino]-2-oxa-5-azaspiro[3.4]octane-5-carboxylate

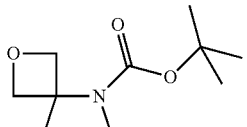

A mixture of 4-chloro-1-fluoro-2-nitrobenzene (264 mg, 1.50 mmol), tert-butyl 7-amino-2-oxa-5-azaspiro[3.4]octane-5-carboxylate (343 mg, 1.50 mmol) and NEt$_3$ (0.44 mL, 3.12 mmol) in 10 mL of tetrahydrofuran was stirred at room temperature overnight and then heated under reflux for 5 hours. The resulting mixture was concentrated in vacuo and the residue was purified by flash column (eluting with 0-5% MeOH in DCM) to afford tert-butyl 7-[(4-chloro-2-nitrophenyl)amino]-2-oxa-5-azaspiro[3.4]octane-5-carboxylate (438 mg, yield: 76.1%) as an orange solid.

Step 7: synthesis of tert-butyl 3-[5-chloro-2-(3-methanesulfonyl-pyrazolo[3,4-c]pyridin-1-ylmethyl)-1H-benzimidazol-1-yl]-2-oxa-5-azaspiro[3.4]octane-5-carboxylate

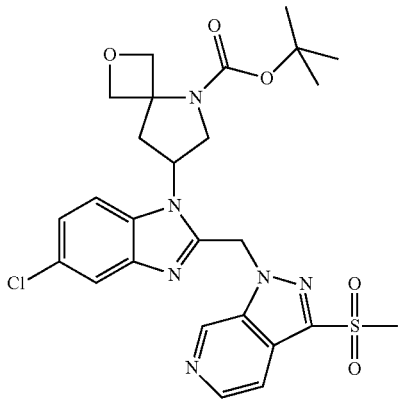 [SMILES: CC(C)(C)OC(=O)N1CC(n2c(Cn3nc(S(C)(=O)=O)c4ccncc43)nc3cc(Cl)ccc32)CC12COC2]

tert-Butyl 3-[5-chloro-2-(3-methanesulfonyl-pyrazolo[3,4-c]pyridin-1-ylmethyl)-1H-benzimidazol-1-yl]-2-oxa-5-azaspiro[3.4]octane-5-carboxylate was prepared in analogy to Example 7 by using tert-butyl 7-[(4-chloro-2-nitrophenyl)amino]-2-oxa-5-azaspiro[3.4]octane-5-carboxylate and 3-methanesulfonyl-1H-indazole instead of 4-[(4-chloro-2-nitrophenyl)amino]-1-(4-methoxybenzyl)pyrrolidin-2-one and 3-(methylsulfonyl)-1H-pyrazolo[3,4-c]pyridine.

Step 8: synthesis of 1'-{[5-chloro-1-(2-oxa-5-azaspiro[3.4]oct-7-yl)-1H-benzimidazol-2-yl]methyl}-3-methanesulfonyl-1H-pyrazolo[3,4-c]pyridine To a cooled solution of tert-butyl 3-[5-chloro-2-(3-methanesulfonyl-pyrazolo[3,4-c]pyridin-1-ylmethyl)-1H-benzimidazol-1-yl]-2-oxa-5-azaspiro[3.4]octane-5-carboxylate (230 mg, 0.401 mmol) in 4.0 mL of DCM was added TFA (1.0 mL) dropwise at 0° C. The resulting mixture was warmed naturally to room temperature and stirred at the temperature for 1.5 hours. The reaction mixture was diluted with 20 mL of DCM and then washed with a saturated Na$_2$CO$_3$ (20 mL). The aqueous layer was extracted with 20 mL of DCM. The combined organic layers were dried over Na$_2$SO$_4$ and then concentrated in vacuo. The residue was purified by preparative HPLC to afford 31.2 mg of the title product as a white solid.

Example 9-1

1-({5-Chloro-1-[2-(methylsulfonyl)ethyl]-1H-indol-2-yl}methyl)-3-(methylsulfonyl)-1H-pyrazolo[3,4-c]pyridine Step 1: synthesis of [5-chloro-1-(2-methanesulfonyl-ethyl)-1H-indol-2-yl]-methanol

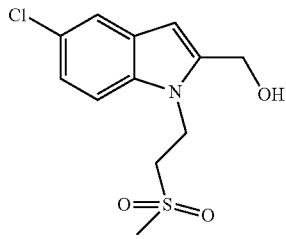 [SMILES: CS(=O)(=O)CCn1c(CO)cc2cc(Cl)ccc21]

To a solution of (5-chloro-1H-indol-2-yl)-methanol (3.6 g, 0.02 mol), Ce$_2$CO$_3$ (13 g, 0.04 mol) in 100 mL of DMF which was cooled to 0° C., was added methanesulfonyl-ethene (2.1 g, 0.02 mol) in portions. The reaction mixture was stirred at a temperature between 30° C. and 50° C. overnight. Ice-water was then added to the mixture, the precipitate was filtered and dried to give [5-chloro-1-(2-methanesulfonyl-ethyl)-1H-indol-2-yl]-methanol (2 g, yield: 34.7%).

Step 2: synthesis of 1-({5-Chloro-1-[2-(methylsulfonyl)ethyl]-1H-indol-2-yl}methyl)-3-(methylsulfonyl)-1H-pyrazolo[3,4-c]pyridine

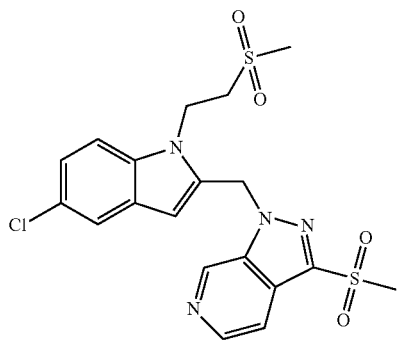 [SMILES: CS(=O)(=O)CCn1c(Cn2nc(S(C)(=O)=O)c3ccncc32)cc2cc(Cl)ccc21]

To a solution of [5-chloro-1-(2-methanesulfonyl-ethyl)-1H-indol-2-yl]-methanol (287 mg, 1.0 mmol), 3-methanesulfonyl-1H-pyrazolo[3,4-c]pyridine (197 mg, 1.0 mmol) and PPh$_3$ (786 mg, 3 mmol) in THF (50 mL) was added DIAD (606 mg, 3 mmol) dropwise in an ice-water bath under N$_2$ protection. The mixture then stirred at RT overnight. The reaction was purified by preparative-HPLC to give the title product (13.5 mg, 2.8%).

Example 9-2

1-({5-Chloro-1-[3-(methylsulfonyl)propyl]-1H-indol-2-yl}methyl)-3-(methylsulfonyl)-1H-pyrazolo[3,4-c]pyridine Step 1: synthesis of ethyl 1-(3-bromopropyl)-5-chloro-1H-indole-2-carboxylate

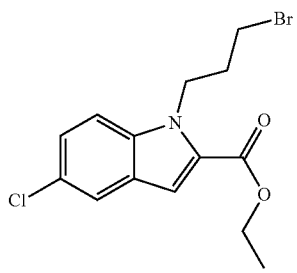 [SMILES: CCOC(=O)c1cc2cc(Cl)ccc2n1CCCBr]

A suspension of ethyl 5-chloro-1H-indole-2-carboxylate (40 g, 0.18 mol), 1,3-dibromo-propane (181 g, 0.90 mol) and potassium carbonate (49.68 g, 0.36 mol) in 500 mL of acetone was heated under reflux for 16 hours. The mixture was concentrated in vacuo to remove the solvent and the residue was diluted with 1000 mL of water, then extracted with ethyl acetate (300 mL×2). The combined organic layers were dried over $Na_2SO_4$ and then concentrated in vacuo. The residue was purified by flash silica gel chromatography (EtOAc:PE=1:10) to afford 38.5 g of ethyl 1-(3-bromopropyl)-5-chloro-1H-indole-2-carboxylate.

Step 2: synthesis of ethyl 5-chloro-1-[3-(methylsulfanyl)propyl]-1H-indole-2-carboxylate

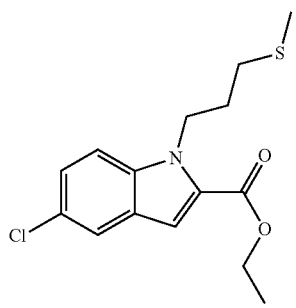 [SMILES: CCOC(=O)c1cc2cc(Cl)ccc2n1CCCSC]

A solution of ethyl 1-(3-bromopropyl)-5-chloro-1H-indole-2-carboxylate (38.5 g, 0.112 mol) and sodium methanethiolate (9.4 g, 0.135 mol) in 500 mL of EtOH was stirred at RT for 16 hours. The mixture was concentrated in vacuo and the residue was diluted with 200 mL of water and then extracted with EtOAc (100 mL×2). The combined organic layers were washed with 100 mL of brine and 100 mL of water, and then dried over $Na_2SO_4$ and concentrated in vacuo to afford 34.1 g of the crude ethyl 5-chloro-1-[3-(methylsulfanyl)propyl]-1H-indole-2-carboxylate, which was used without further purification.

Step 3: synthesis of ethyl 5-chloro-1-[3-(methylsulfonyl)propyl]-1H-indole-2-carboxylate

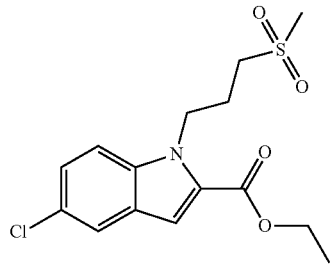 [SMILES: CCOC(=O)c1cc2cc(Cl)ccc2n1CCCS(C)(=O)=O]

To a solution of ethyl 5-chloro-1-[3-(methylsulfanyl)propyl]-1H-indole-2-carboxylate (1.87 g, 0.006 mol) in 50 mL of DCM which was cooled to 0° C., added m-CPBA (4.15 g, 0.024 mol) in portions. The mixture was then stirred at RT for 16 hours. The mixture was washed with saturated $NaHCO_3$ and saturated $Na_2S_2O_3$, then washed with brine. The organic layer was dried over $Na_2SO_4$, and then filtered and concentrated in vacuo. The crude product was purified by flash column (EtOAc:PE=1:10) to afford ethyl 5-chloro-1-[3-(methylsulfonyl)propyl]-1H-indole-2-carboxylate (0.80 g, yield: 38.8%).

Step 4: synthesis of [5-chloro-1-(3-methanesulfonyl-propyl)-1H-indol-2-yl]-methanol

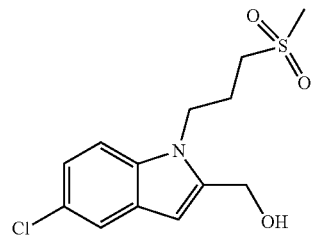 [SMILES: CS(=O)(=O)CCCn1c(CO)cc2cc(Cl)ccc21]

To a suspension of $LiAlH_4$ (0.38 g, 10.0 mmol) in 50 mL of THF was added a solution of ethyl 5-chloro-1-[3-(methylsulfonyl)propyl]-1H-indole-2-carboxylate (1.60 g, 4.6 mmol) dropwise at 0° C. The reaction mixture was warmed naturally to RT and then stirred at RT for 2 hours. The reaction was then quenched with methanol. The resulting mixture was filtered through a celite pad. The filtrate was concentrated in vacuo to afford the crude [5-chloro-1-(3-methanesulfonyl-propyl)-1H-indol-2-yl]-methanol (0.60 g, yield: 43.3%).

Step 5: synthesis of {5-chloro-1-[3-(methylsulfonyl)propyl]-1H-indol-2-yl}methyl methanesulfonate

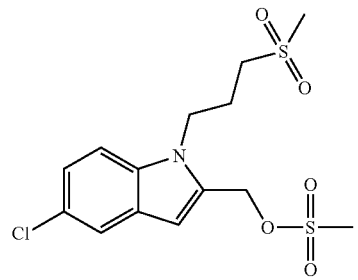 [SMILES: CS(=O)(=O)CCCn1c(COS(C)(=O)=O)cc2cc(Cl)ccc21]

To a solution of [5-chloro-1-(3-methanesulfonyl-propyl)-1H-indol-2-yl]-methanol (0.60 g, 2.0 mmol) and TEA (0.60 g, 6 mmol) in 20 mL of DCM was added MsCl (0.45 g, 4 mmol) in an ice bath. The reaction mixture was stirred at RT for 3 hours. The resulting mixture was diluted with 10 mL of water and then extracted with DCM (10 mL×3). The combined organic layers were dried over Na₂SO₄, and then concentrated in vacuo to afford the crude {5-chloro-1-[3-(methylsulfonyl)propyl]-1H-indol-2-yl}methyl methanesulfonate which was used in the next step without any purification.

Step 6: synthesis of 1-({5-chloro-1-[3-(methylsulfonyl)propyl]-1H-indol-2-yl}methyl)-3-(methylsulfonyl)-1H-pyrazolo[3,4-c]pyridine To a solution of {5-chloro-1-[3-(methylsulfonyl)propyl]-1H-indol-2-yl}methyl methanesulfonate (363 mg, 1.0 mmol), 3-methanesulfonyl-1H-pyrazolo[3,4-c]pyridine (197 mg, 1.0 mmol) and PPh₃ (786 mg, 3.0 mmol) in 50 mL of THF was added DIAD (606 mg, 3.0 mmol) dropwise via an additional funnel in an ice-water bath under N₂ protection. The mixture was then stirred at RT overnight and then concentrated in vacuo. The residue was purified by preparative-HPLC to give the title product (13.592 mg, yield: 19.2%).

Example 9-3

1-({5-Chloro-7-fluoro-1-[2-(methylsulfonyl)ethyl]-1H-indol-2-yl}methyl)-3-(methylsulfonyl)-1H-pyrazolo[3,4-c]pyridine Step 1: synthesis of 4-chloro-2-fluoro-6-iodoaniline

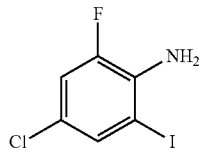

To a solution of 4-chloro-2-fluoroaniline (1.15 g, 7.9 mmol) in 125 mL of ethanol added silver sulphate (1.7 g, 8.3 mmol), then followed by addition of I₂ (2.1 g, 8.3 mmol) in portions. After the addition was completed, the mixture was stirred at RT for 2 hours. The mixture was filtered through celite and the filtration was evaporated to give dark oil which was dissolved in 125 mL of DCM. The solution was washed with 2 M sodium hydroxide (40 mL×2), saturated Na₂S₂O₃ (40 mL×2) and water (40 mL×2). The resulting solution was dried over MgSO₄ and then evaporated to give the crude 4-chloro-2-fluoro-6-iodoaniline as dark oil (2.1 g, yield: 98%).

Step 2: synthesis of 4-chloro-2-fluoro-6-iodo-N-[2-(methylsulfonyl)ethyl]aniline

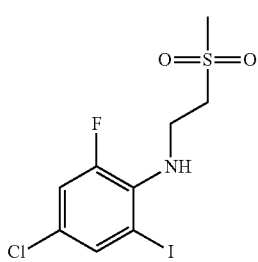 [SMILES: CS(=O)(=O)CCNc1c(F)cc(Cl)cc1I]

A mixture of 4-chloro-2-fluoro-6-iodoaniline (0.5 g, 1.8 mmol), vinylmethylsulfone (0.2 g, 1.8 mmol), Cs₂CO₃ (1.17 g, 3.6 mmol) and DMF (15 mL) was heated with stirring at 50° C. overnight. The resulting mixture was poured into water and then extracted with EA (50 mL×3). The combined organic phases were dried over Na₂SO₄ and then concentrated. The residue was purified by column chromatography (EtOAc:PE=1:40) to give 4-chloro-2-fluoro-6-iodo-N-[2-(methylsulfonyl)ethyl]aniline (0.42 g, yield: 61%).

Step 3: synthesis of {5-chloro-7-fluoro-1-[2-(methylsulfonyl)ethyl]-1H-indol-2-yl}methanol

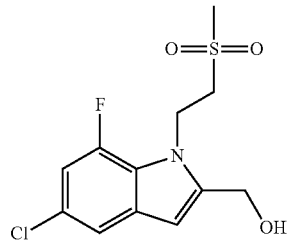 [SMILES: CS(=O)(=O)CCn1c(CO)cc2cc(Cl)cc(F)c21]

A mixture of 4-chloro-2-fluoro-6-iodo-N-(2-(methylsulfonyl)ethyl)aniline (450 mg, 1.2 mmol) and prop-2-yn-1-ol (135 mg, 2.4 mmol) in Et₃N (20 ml) was degassed and refluxed under N₂ atmosphere. PdCl₂(PPh₃)₂ (90 mg, 0.12 mmol) and CuI (45 mg, 0.24 mmol) were added successively to the reaction mixture. After being stirred under reflux overnight, the mixture was concentrated in vacuo and the residue was poured into water and extracted with EtOAc (50 mL×3). The combined organic layers were dried over Na₂SO₄ and then concentrated in vacuo. The residue was purified by preparative-TLC (PE: EtOAc=5:1) to give {5-chloro-7-fluoro-1-[2-(methylsulfonyl)ethyl]-1H-indol-2-yl}methanol as a yellow solid (350 mg, yield: 95%).

Step 4: synthesis of 5-chloro-2-(chloromethyl)-7-fluoro-1-[2-(methylsulfonyl)ethyl]-1H-indole

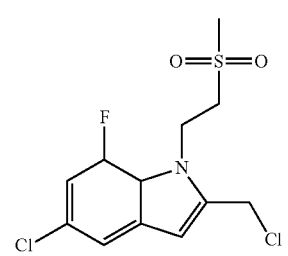 [SMILES: CS(=O)(=O)CCN1C(CCl)=CC2=CC(Cl)=CC(F)C21]

A solution of {5-chloro-7-fluoro-1-[2-(methylsulfonyl)ethyl]-1H-indol-2-yl}methanol (130 mg, 0.43 mmol) in 40 mL of DCM was stirred with SOCl₂ (254 mg, 2.13 mmol) at RT and the reaction was monitored by LC/MS. After all starting materials were consumed, the mixture was concentrated in vacuo to afford the crude 5-chloro-2-(chloromethyl)-7-fluoro-1-[2-(methylsulfonyl)ethyl]-1H-indole, which was used for next step directly.

Step 5: synthesis of 1-({5-chloro-7-fluoro-1-[2-(methylsulfonyl)ethyl]-1H-indol-2-yl}methyl)-3-(methylsulfonyl)-1H-pyrazolo[3,4-c]pyridine A mixture of the crude 5-chloro-2-(chloromethyl)-7-fluoro-1-(2-(methylsulfonyl)ethyl)-1H-indole (0.36 mmol), 3-(methylsulfonyl)-1H-pyrazolo[3,4-c]pyridine (60 mg, 0.30 mmol) and K$_2$CO$_3$ (198 mg, 1.44 mmol) in 3 mL of DMF was stirred overnight and then the precipitate was filtered off. The filtrate was purified by preparative-HPLC to give 1-({5-chloro-7-fluoro-1-[2-(methylsulfonyl)ethyl]-1H-indol-2-yl}methyl)-3-(methylsulfonyl)-1H-pyrazolo[3,4-c]pyridine (16 mg, yield: 11%).

Example 10-1

1-[2-(5-Chloro-2-{[3-(methylsulfonyl)-1H-pyrazolo[3,4-c]pyridin-1-yl]methyl}-1H-benzimidazol-1-yl)ethyl]pyrrolidin-3-ol Step 1: synthesis of 3-(5-chloro-2-{[3-(methylsulfonyl)-1H-pyrazolo[3,4-c]pyridin-1-yl]methyl}-1H-benzimidazol-1-yl)ethan-1-ol

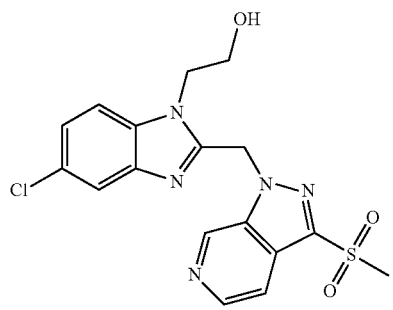 [SMILES: CS(=O)(=O)c1nn(Cc2nc3cc(Cl)ccc3n2CCO)c2cnccc12]

3-(5-Chloro-2-{[3-(methylsulfonyl)-1H-pyrazolo[3,4-c]pyridin-1-yl]methyl}-1H-benzimidazol-1-yl)ethan-1-ol was prepared in analogy to Example 2-1 by using 2-aminoethanol and 3-methanesulfonyl-1H-pyrazolo[3,4-c]pyridine instead of (R)-1,1-dioxo-tetrahydro-1λ$^6$-thiophen-3-yl amine and 3-methane sulfonyl-1H-indazole.

Step 2: synthesis of 1-{[5-chloro-1-(2-chloroethyl)-1H-benzimidazol-2-yl]methyl}-3-(methylsulfonyl)-1H-pyrazolo[3,4-c]pyridine

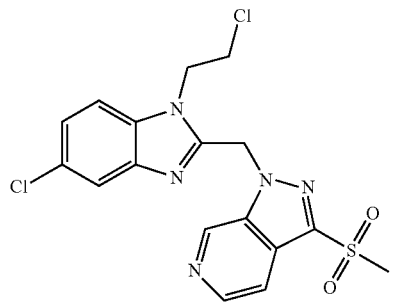 [SMILES: CS(=O)(=O)c1nn(Cc2nc3cc(Cl)ccc3n2CCCl)c2cnccc12]

A mixture of 3-(5-chloro-2-{[3-(methylsulfonyl)-1H-pyrazolo[3,4-c]pyridin-1-yl]methyl}-1H-benzimidazol-1-yl)ethan-1-ol (180 mg, 0.45 mmol) and SOCl$_2$ (8 mL) was stirred at RT for 5 hours. The resulting mixture was concentrated in vacuo and the residue was dissolved in EtOAc (25 mL). The solution was washed with NaHCO$_3$ solution (10 mL×3). The aqueous layers were combined and then extracted with EtOAc (20 mL×2). The combined organic layers were dried, and then filtered and then concentrated in vacuo. The residue was purified by column chromatography (MeOH:DCM=3:20) to afford 1-{[5-chloro-1-(2-chloroethyl)-1H-benzimidazol-2-yl]methyl}-3-(methylsulfonyl)-1H-pyrazolo[3,4-c]pyridine as a solid (135 mg, yield: 74%).

Step 3: synthesis of 1-[2-(5-chloro-2-{[3-(methylsulfonyl)-1H-pyrazolo[3,4-c]pyridin-1-yl]methyl}-1H-benzimidazol-1-yl)ethyl]pyrrolidin-3-ol A solution of 1-{[5-chloro-1-(2-chloroethyl)-1H-benzimidazol-2-yl]methyl}-3-(methylsulfonyl)-1H-pyrazolo[3,4-c]pyridine (110 mg, 0.26 mmol) and 3-pyrrolidinol (1 mL) in CH$_3$CN (2 mL) was heated at 150° C. for 1 hour under microwave irradiation. The resulting mixture was concentrated in vacuo and the residue was purified by column chromatography (MeOH:DCM=3:25) to afford the title product as a grey solid (8 mg, yield: 6%).

Example 10-2

1-[2-(5-chloro-2-{[3-(methylsulfonyl)-1H-pyrazolo[3,4-c]pyridin-1-yl]methyl}-1H-benzimidazol-1-yl)ethyl]piperidin-4-ol The title compound was prepared in analogy to Example 10-1 by using 4-piperidinol instead of 3-pyrrolidinol.

Example 11

[trans-3-(5-Chloro-2-{[3-(methylsulfonyl)-1H-pyrazolo[3,4-c]pyridin-1-yl]methyl}-1H-benzimidazol-1-yl)cyclobutyl]methanol Step 1: synthesis of ethyl trans-3-aminocyclobutanecarboxylate hydrochloride

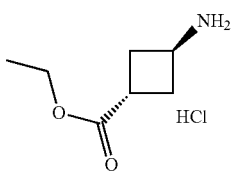

To a solution of trans-3-aminocyclobutanecarboxylic acid hydrochloride (1.0 g, 6.5 mmol) in 20 mL of EtOH was added 10 mL of SOCl$_2$ dropwise at 0° C. The resulting mixture was heated with stirring at 100° C. for 16 hours. And then, the solvent was evaporated to afford the residue which was used in the next step directly.

143

Step 2: synthesis of ethyl trans-3-(5-chloro-2-{[3-(methylsulfonyl)-1H-pyrazolo[3,4-c]pyridin-1-yl]methyl}-1H-benzimidazol-1-yl)cyclobutanecarboxylate

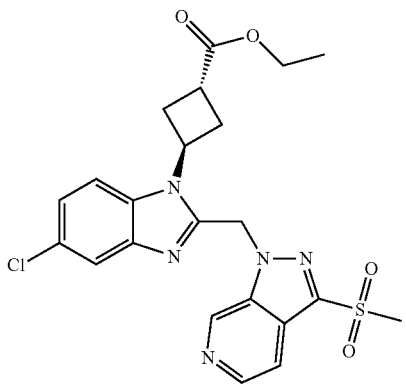 [SMILES: CCOC(=O)[C@H]1C[C@H](n2c(Cn3nc(S(C)(=O)=O)c4ccncc43)nc3cc(Cl)ccc32)C1]

Ethyl trans-3-(5-chloro-2-{[3-(methylsulfonyl)-1H-pyrazolo[3,4-c]pyridin-1-yl]methyl}-1H-benzimidazol-1-yl)cyclobutanecarboxylate was prepared in analogy to Example 2-1 by using ethyl trans-3-aminocyclobutanecarboxylate hydrochloride and 3-(methylsulfonyl)-1H-pyrazolo[3,4-c]pyridine instead of (R)-1,1-dioxo-tetrahydro-1$\lambda^6$-thiophen-3-ylamine and 3-methanesulfonyl-1H-indazole.

Step 3: synthesis of [trans-3-(5-chloro-2-{[3-(methylsulfonyl)-1H-pyrazolo[3,4-c]pyridin-1-yl]methyl}-1H-benzimidazol-1-yl)cyclobutyl]methanol To a solution of ethyl trans-3-(5-chloro-2-{[3-(methylsulfonyl)-1H-pyrazolo[3,4-c]pyridin-1-yl]methyl}-1H-benzimidazol-1-yl)cyclobutanecarboxylate (80 mg, 0.16 mmol) in EtOH was added NaBH$_4$ (80 mg, 2.1 mmol) in portions at RT. The mixture was then heated at 60° C. for 1 hour. The reaction was completed as indicated by LC/MS. The mixture was quenched with 1N HCl to pH7. After the solvent was removed by concentration, the residue was purified by preparative-HPLC to afford 15.1 mg of [trans-3-(5-chloro-2-{[3-(methylsulfonyl)-1H-pyrazolo[3,4-c]pyridin-1-yl]methyl}-1H-benzimidazol-1-yl)cyclobutyl]methanol as a white solid.

Example 12

1-({5-Chloro-1-[(3R)-1,1-dioxidotetrahydrothiophen-3-yl]-7-fluoro-1H-benzimidazol-2-yl}methyl)-3-(methylsulfonyl)-1H-pyrazolo[3,4-c]pyridine Step 1: synthesis of (4-chloro-2-fluoro-6-nitrophenyl)-((R)-1,1-dioxo-tetrahydro-1$\lambda^6$-thiophen-3-yl)-amine

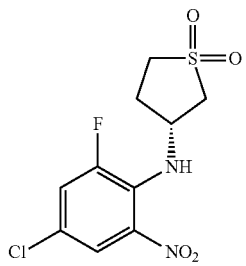 [SMILES: O=[N+]([O-])c1cc(Cl)cc(F)c1N[C@@H]1CCS(=O)(=O)C1]

144

To a solution of (R)-1,1-dioxo-tetrahydro-1$\lambda^6$-thiophen-3-ylamine hydrochloride (9.0 g, 52.43 mmol) in 400 mL of THF was added DIPEA (27.0 g, 210 mmol), followed by addition of a solution of 4-chloro-2-fluoro-6-nitrophenyl trifluoromethanesulfonate (20.36 g, 62.92 mmol). After being stirred at RT for 48 hours, the resulting mixture was diluted with water, and then extracted with EtOAc. The organic layer was washed by brine, and then dried over anhydrous Na$_2$SO$_4$, then filtered and concentrated. The residue was purified by flash chromatography to give 0.9 g of (4-chloro-2-fluoro-6-nitrophenyl)-((R)-1,1-dioxo-tetrahydro-1$\lambda^6$-thiophen-3-yl)-amine.

Step 2: synthesis of 1-({5-chloro-1-[(3R)-1,1-dioxidotetrahydrothiophen-3-yl]-7-fluoro-1H-benzimidazol-2-yl}methyl)-3-(methylsulfonyl)-1H-pyrazolo[3,4-c]pyridine The title compound was prepared in analogy to Example 2-1 by using (4-chloro-2-fluoro-6-nitrophenyl)-((R)-1,1-dioxo-tetrahydro-1$\lambda^6$-thiophen-3-yl)-amine and 3-(methylsulfonyl)-1H-pyrazolo[3,4-c]pyridine instead of (4-chloro-2-nitro-phenyl)-((R)-1,1-dioxo-tetrahydro-1$\lambda^6$-thiophen-3-yl)-amine and 3-methanesulfonyl-1H-indazole.

Example 13

3-(5-Chloro-2-{[3-(methylsulfonyl)-1H-pyrazolo[3,4-c]pyridin-1-yl]methyl}-1H-benzimidazol-1-yl)(1,1-$^2$H$_2$)propan-1-ol Step 1: synthesis of ethyl 3-[(4-chloro-2-nitrophenyl)amino]propanoate

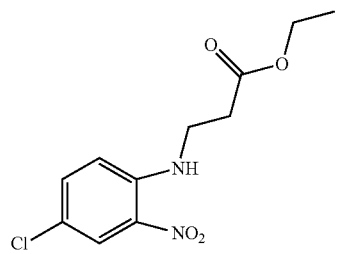 [SMILES: CCOC(=O)CCNc1ccc(Cl)cc1[N+](=O)[O-]]

A mixture of 4-chloro-1-fluoro-2-nitrobenzene (10.0 g, 57.0 mmol), ethyl 3-aminopropanoate hydrochloride (8.75 g, 57.0 mmol) and N-ethyl-N-isopropylpropan-2-amine (36.0 g, 0.285 mol) in tetrahydrofuran (150 mL) was stirred at room temperature for 16 hours. The reaction mixture was then diluted with water and then extracted with EtOAc (200 mL×3). The combined organic layers were washed with water (200 mL×3), and then dried over Na$_2$SO$_4$, then filtered and concentrated in vacuo. The residue was purified by flash chromatography (EtOAc:PE=1:2) to afford ethyl 3-[(4-chloro-2-nitrophenyl)amino]propanoate (10.0 g, yield: 64.5%).

145

Step 2: synthesis of ethyl 3-[(2-amino-4-chlorophenyl)amino]propanoate

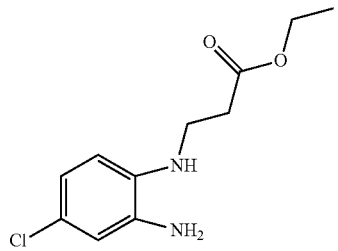 [SMILES: CCOC(=O)CCNc1ccc(Cl)cc1N]

A solution of ethyl 3-[(4-chloro-2-nitrophenyl)amino]propanoate (1.0 g, 3.67 mmol) in methanol (50 mL) was stirred with Raney nickel (0.30 g) under hydrogen atmosphere overnight. The resulting mixture was filtered and the filtrate was concentrated in vacuo to afford the crude ethyl 3-[(2-amino-4-chlorophenyl)amino]propanoate (0.80 g, yield: 89.9%).

Step 3: synthesis of 3-[(2-amino-4-chlorophenyl)amino](1,1-$^2$H$_2$)propan-1-ol

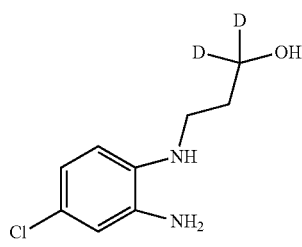 [SMILES: [2H]C([2H])(O)CCNc1ccc(Cl)cc1N]

To a cooled solution of ethyl 3-[(2-amino-4-chlorophenyl)amino]propanoate (700 mg, 2.88 mmol) in tetrahydrofuran (50 mL) was added lithium aluminum deuteride (15.6 mg, 0.41 mmol) at 0° C. The reaction mixture was stirred at room temperature overnight. The reaction mixture was then cooled to 0° C., and then was quenched by addition of water (5 mL) dropwise followed by addition of ethyl acetate (50 mL). The mixture was then stirred for 1 hour and then filtered. The filtrate was dried over Na$_2$SO$_4$, and then filtered and concentrated in vacuo. The residue was purified by flash chromatography (EA:PE=1:1) to afford 3-[(2-amino-4-chlorophenyl)amino](1,1-$^2$H$_2$)propan-1-ol (300 mg, yield: 51.4%).

Step 4: synthesis of 3-(5-chloro-2-{[3-(methylsulfonyl)-1H-pyrazolo[3,4-c]pyridin-1-yl]methyl}-1H-benzimidazol-1-yl)(1,1-$^2$H$_2$)propan-1-ol The title compound was prepared in analogy to Example 2-1 by using 3-[(2-amino-4-chlorophenyl)amino](1,1-$^2$H$_2$)propan-1-ol and 3-(methylsulfonyl)-1H-pyrazolo[3,4-c]pyridine instead of 4-chloro-N—((R)-1,1-dioxo-tetrahydro-1λ$^6$-thiophen-3-yl)-benzene-1,2-diamine and 3-methanesulfonyl-1H-indazole.

146

Example 14

4-(5-Chloro-2-{[3-(methylsulfonyl)-1H-pyrazolo[3,4-c]pyridin-1-yl]methyl}-1H-benzimidazol-1-yl)-1,1,1-trifluoro-2-methylbutan-2-ol Step 1: synthesis of N-(2-amino-4-chlorophenyl)-4,4,4-trifluoro-3-hydroxy-3-methylbutanamide

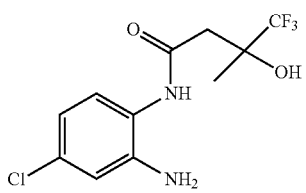 [SMILES: CC(O)(CC(=O)Nc1ccc(Cl)cc1N)C(F)(F)F]

A mixture of 4-chlorobenzene-1,2-diamine (1.32 g, 9.3 mmol), 4,4,4-trifluoro-3-hydroxy-3-methylbutanoic acid (1.6 g, 9.3 mmol), HATU (4.24 g, 11.2 mmol), DIPEA (3.1 mL, 18.6 mmol) and DMF (25 mL) was stirred at room temperature overnight. The mixture was diluted with water (150 mL), and then extracted with EtOAc (50 mL×3). The combined organic phases were washed with brine (50 mL), and then dried over Na2SO4, then filtered and concentrated. The residue was purified with flash column (30% EtOAc in PE to EtOAc) to give N-(2-amino-4-chlorophenyl)-4,4,4-trifluoro-3-hydroxy-3-methylbutanamide as brown oil (2.1 g, 76%).

Step 2: synthesis of 4-[(2-amino-4-chlorophenyl)amino]-1,1,1-trifluoro-2-methylbutan-2-ol

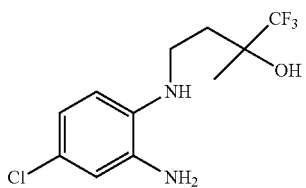 [SMILES: CC(O)(CCNc1ccc(Cl)cc1N)C(F)(F)F]

To a solution of N-(2-amino-4-chlorophenyl)-4,4,4-trifluoro-3-hydroxy-3-methylbutanamide (2.0 g, 6.75 mmol) in THF (30 mL) was added 1.0 M BH$_3$-THF in THF (10 mL). The mixture was stirred at 50° C. overnight. The reaction was quenched by addition of 1 N HCl (15 mL) and the mixture was stirred at room temperature for 1 hour and then washed with EtOAc (30 mL). The resulting aqueous phase was basified to pH 9 with sat. aqueous solution of NaHCO$_3$ and then extracted with EtOAc (30 mL×3). The combined organic phases were washed with brine and then concentrated in vacuo. The residue was purified with flash column (EA:PE=0:1 to 1:1) to afford 4-[(2-amino-4-chlorophenyl)amino]-1,1,1-trifluoro-2-methylbutan-2-ol (0.55 g, yield: 28.8%).

Step 3: synthesis of 4-(5-chloro-2-{[3-(methylsulfonyl)-1H-pyrazolo[3,4-c]pyridin-1-yl]methyl}-1H-benzimidazol-1-yl)-1,1,1-trifluoro-2-methylbutan-2-ol The title compound was prepared in analogy to Example 2-1 by using 4-[(2-amino-4-chlorophenyl)amino]-1,1,1-trifluoro-2-methylbutan-2-ol and 3-(methylsulfonyl)-1H-pyrazolo[3,4-c]pyridine instead of 4-chloro-N—((R)-1,1-dioxo-tetrahydro-1λ$^6$-thiophen-3-yl)-benzene-1,2-diamine and 3-methanesulfonyl-1H-indazole.

Example 15-1

1-{(1R)-1-[5-Chloro-1-(3,3,3-trifluoropropyl)-1H-benzimidazol-2-yl]ethyl}-3-(methylsulfonyl)-1H-pyrazolo[3,4-c]pyridine Step 1: synthesis of 4-chloro-N¹-(3,3,3-trifluoropropyl)benzene-1,2-diamine

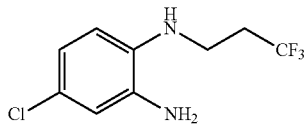

4-Chloro-N¹-(3,3,3-trifluoropropyl)benzene-1,2-diamine was prepared in analogy to 4-chloro-N—((R)-1,1-dioxo-tetrahydro-1$\lambda^6$-thiophen-3-yl)-benzene-1,2-diamine in Example 2-1 by using 3,3,3-trifluoropropan-1-amine instead of (R)-1,1-dioxo-tetrahydro-1$\lambda^6$-thiophen-3-ylamine.

Step 2: synthesis of (1S)-1-[5-chloro-1-(3,3,3-trifluoropropyl)-1H-benzimidazol-2-yl]ethanol

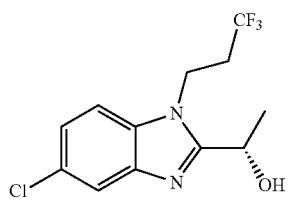 [SMILES: C[C@H](O)c1nc2cc(Cl)ccc2n1CCC(F)(F)F]

A mixture of 4-chloro-N¹-(3,3,3-trifluoropropyl)benzene-1,2-diamine (478 mg, 2.0 mmol) and L-lactic acid (180 mg, 2.0 mmol) in 6 N aqueous HCl (4 mL) was heated with stirring at 100° C. in a sealed tube for 18 hours. After the reaction was complete, the mixture was poured into aqueous ammonia (10 mL) and then extracted by EtOAc (25 mL×3). The organic layers were combined and then concentrated in vacuo. The residue was purified by flash column chromatography to afford (1S)-1-[5-chloro-1-(3,3,3-trifluoropropyl)-1H-benzimidazol-2-yl]ethanol as yellow oil (320 mg, yield 63.0%).

Step 3: synthesis of 1-{(1R)-1-[5-Chloro-1-(3,3,3-trifluoropropyl)-1H-benzimidazol-2-yl]ethyl}-3-(methylsulfonyl)-1H-pyrazolo[3,4-c]pyridine To a mixture of (1S)-1-[5-chloro-1-(3,3,3-trifluoropropyl)-1H-benzimidazol-2-yl]ethanol (145 mg, 0.50 mmol) and 3-methanesulfonyl-1H-pyrazolo[3,4-c]pyridine (140 mg, 0.70 mmol) in DCM (15 mL) was added PPh₃ (262 mg, 1.0 mmol) and DEAD (170 mg, 1.0 mmol). The mixture was then stirred at room temperature overnight. After the reaction was complete, the mixture was washed by 2 N aqueous solution of NaOH and the organic layer was concentrated in vacuo. The residue was purified by preparative HPLC to afford 1-{(1R)-1-[5-Chloro-1-(3,3,3-trifluoropropyl)-1H-benzimidazol-2-yl]ethyl}-3-(methylsulfonyl)-1H-pyrazolo[3,4-c]pyridine (56.6 mg).

Example 15-2

1-{(1S)-1-[5-Chloro-1-(3,3,3-trifluoropropyl)-1H-benzimidazol-2-yl]ethyl}-3-(methylsulfonyl)-1H-pyrazolo[3,4-c]pyridine The title compound was prepared in analogy to Example 15-1 by using 3-(methylsulfonyl)-1H-pyrazolo[3,4-c]pyridine instead of 3-(methylsulfonyl)-1H-pyrazolo[3,4-c]pyridine.

BIOLOGICAL EXAMPLES

Example 16

Viral Cytopathic Effect (CPE) Assay

To measure anti-RSV activity of compounds, 96-well plates are seeded with 6×10³ cells per well in Dulbecco's modified Eagle's medium (DMEM) containing 10% fetal bovine serum (FBS). Cells are infected the next day with sufficient RSV Long strain (ATCC) to produce an approximately 80-90% cytopathic effect after 6 days, in the presence of serial half-log diluted compound in a total volume of 200 µL per well. The viability of cells is assessed after 6 days using Cell Counting kit-8 (Dojindo Molecular Technologies). The absorbance at 450 nm and referenced at 630 nm is measured to determine 50% effective concentration ($EC_{50}$).

The compounds of the present invention were tested for their anti-RSV activity, and the activation as described herein. The Examples were tested in the above assay and found to have $EC_{50}$ of about 0.0001 µM to about 10 µM. Particular compound of formula (I) were found to have $EC_{50}$ of about 0.0001 µM to about 1 µM. Further particular compound of formula (I) were found to have $EC_{50}$ of about 0.0001 µM to about 0.1 µM.

Results of CPE assays are given in Table 1.

Example A

A compound of formula I can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |

-continued

| Per capsule | |
|---|---|
| Lactose | 95.0 mg |
| Talc | 4.5 mg |
| Magnesium stearate | 0.5 mg |
| | 220.0 mg |

The invention claimed is:

1. A compound of formula (I)

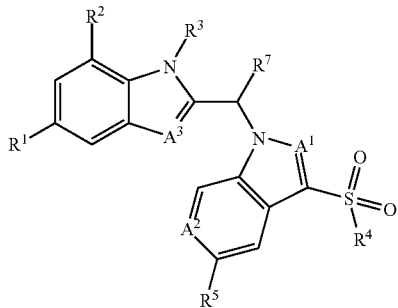

wherein
R$^1$ is hydrogen or halogen;
R$^2$ is hydrogen or halogen;
R$^3$ is azetidinyl; C$_{1-6}$alkoxypyridinyl; C$_{1-6}$alkylsulfonyl-C$_x$H$_{2x}$—; carboxycycloalkyl; difluorocycloalkyl; 1,1-dioxo-tetrahydrothienyl; halopyridinyl; hydroxy-C$_y$H$_{2y}$—; hydroxy-C$_y$H$_{2y}$-cycloalkyl; hydroxy-C$_y$H$_{2y}$—O—C$_y$H$_{2y}$—; hydroxycycloalkyl-C$_z$H$_{2z}$—, unsubstituted or substituted by C$_{1-3}$ alkyl, hydroxy or hydroxy-C$_x$H$_{2x}$—; 4-hydroxypiperidin-1-yl-C$_y$H$_{2y}$—; 3-hydroxy-pyrrolidin-1-yl-C$_y$H$_{2y}$—; morpholinyl-C$_y$H$_{2y}$—; oxetanyl; oxetanyl-C$_x$H$_{2x}$—, unsubstituted or substituted by C$_{1-3}$alkyl; piperidinyl; oxo-piperidinyl; oxo-pyrrolidinyl; pyrrolidinyl, unsubstituted or substituted by C$_{1-6}$alkylcarbonyl, C$_{1-6}$alkylsulfonyl, hydroxy-C$_y$H$_{2y}$—, hydroxy-C$_x$H$_{2x}$-carbonyl, amino-C$_x$H$_{2x}$-carbonyl or trifluoromethyl-C$_x$H$_{2x}$—; tetrahydrofuran-3-yl-C$_z$H$_{2z}$—; tetrahydropyranyl; trifluoromethyl-C$_x$H$_{2x}$—;

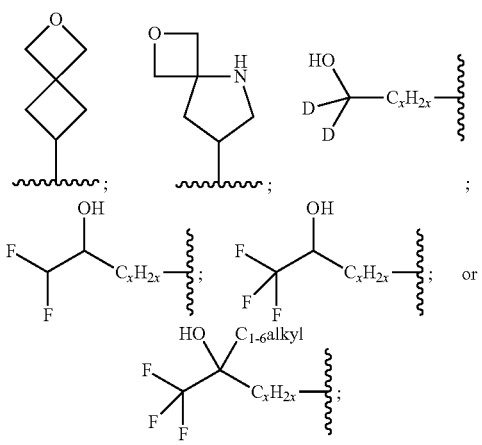

R$^4$ is C$_{1-6}$alkyl or cycloalkyl;
R$^5$ is hydrogen or halogen;
R$^7$ is hydrogen or C$_{1-6}$alkyl;

A$^1$ is —N— or —CH;
A$^2$ is —N—, —NO or —CH;
A$^3$ is —N— or —CH;
x is 1-6;
y is 2-6;
z is 0-6;
or a pharmaceutically acceptable salt thereof.

2. A compound according to claim 1, wherein
R$^1$ is hydrogen or chloro;
R$^2$ is hydrogen or fluoro;
R$^3$ is azetidin-3-yl; methoxypyridinyl; methylsulfonylethyl; methylsulfonylpropyl; carboxycyclobutyl; difluorocyclopentyl; 1,1-dioxo-tetrahydrothienyl; chloropyridinyl; fluoropyridinyl; hydroxypropyl; hydroxybutyl; hydroxyisopropylethyl; hydroxyisopropylpropyl; hydroxymethylcyclobutyl; hydroxyisopropylcyclobutyl; hydroxyethoxyethyl; hydroxycyclobutyl; hydroxycyclohexyl; hydroxycyclopentyl; hydroxycyclopropylethyl; 4-hydroxypiperidin-1-ylethyl; 3-hydroxy-pyrrolidin-1-ylethyl; morpholinylethyl; oxetan-3-yl; oxetan-3-ylmethyl; oxetan-3-ylethyl; piperidin-4-yl; 2-oxo-piperidin-4-yl; 2-oxo-pyrrolidin-4-yl; pyrrolidin-3-yl, unsubstituted or once substituted by methylcarbonyl, ethylcarbonyl, isopropylcarbonyl, methylsulfonyl, hydroxyethyl, hydroxymethylcarbonyl, hydroxyisopropylcarbonyl, aminomethylcarbonyl or trifluoromethylmethyl; tetrahydrofuran-3-yl; tetrahydrofuran-3-ylmethyl; tetrahydropyran-4-yl; trifluoromethylethyl; trifluoromethylpropyl;

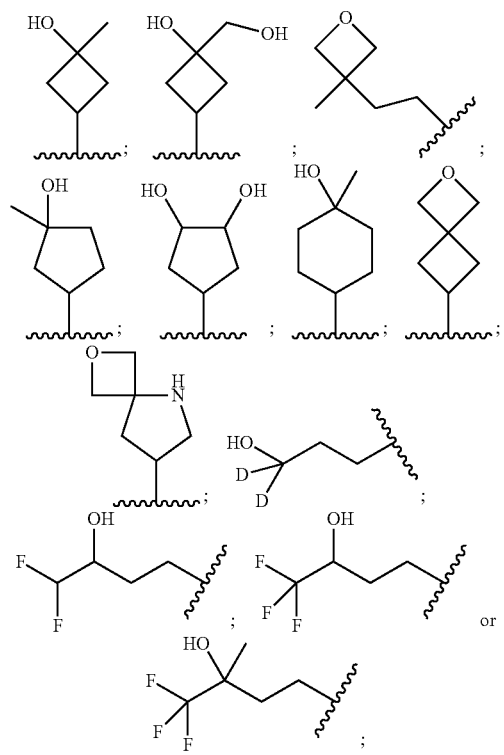

R$^4$ is methyl, ethyl, isopropyl or cyclopropyl;
R$^5$ is hydrogen or fluoro;
R$^7$ is hydrogen or methyl;
A$^1$ is —N— or —CH;
A$^2$ is —N—, —NO or —CH;
A$^3$ is —N— or —CH;
or a pharmaceutically acceptable salt thereof.

3. A compound according to claim 1, or a pharmaceutically acceptable salt thereof, wherein
$R^1$ is halogen;
$R^2$ is hydrogen or halogen;
$R^3$ is azetidinyl; $C_{1-6}$alkoxypyridinyl; $C_{1-6}$alkylsulfonyl-$C_xH_{2x}$—; carboxycycloalkyl; difluorocycloalkyl; 1,1-dioxo-tetrahydrothienyl; halopyridinyl; hydroxy-$C_yH_{2y}$—; hydroxy-$C_xH_{2x}$-cycloalkyl; hydroxy-$C_yH_{2y}$—O—$C_yH_{2y}$—; hydroxycycloalkyl-$C_zH_{2z}$—, unsubstituted or substituted by $C_{1-3}$ alkyl, hydroxy or hydroxy-$C_xH_{2x}$—; 4-hydroxypiperidin-1-yl-$C_yH_{2y}$—; 3-hydroxy-pyrrolidin-1-yl-$C_yH_{2y}$—; morpholinyl-$C_yH_{2y}$—; oxetanyl; oxetanyl-$C_xH_{2x}$—, unsubstituted or substituted by $C_{1-3}$alkyl; piperidinyl; oxo-piperidinyl; oxo-pyrrolidinyl; pyrrolidinyl, unsubstituted or substituted by $C_{1-6}$alkylcarbonyl, $C_{1-6}$alkylsulfonyl, hydroxy-$C_yH_{2y}$—, hydroxy-$C_xH_{2x}$-carbonyl, amino-$C_xH_{2x}$-carbonyl or trifluoromethyl-$C_xH_{2x}$—; tetrahydrofuran-3-yl-$C_zH_{2z}$—; tetrahydropyranyl; trifluoromethyl-$C_xH_{2x}$—;

$R^4$ is $C_{1-6}$alkyl;
$R^5$ is hydrogen;
$R^7$ is hydrogen or $C_{1-6}$alkyl;
$A^1$ is —N—;
$A^2$ is —N—, —NO or —CH;
$A^3$ is —N— or —CH;
x is 1-6;
y is 2-6;
z is 0-6.

4. A compound according to claim 1, or a pharmaceutically acceptable salt thereof, wherein
$R^1$ is chloro;
$R^2$ is hydrogen or fluoro;
$R^3$ is azetidin-3-yl; methoxypyridinyl; methylsulfonylethyl; methylsulfonylpropyl; carboxycyclobutyl; difluorocyclopentyl; 1,1-dioxo-tetrahydrothienyl; chloropyridinyl; fluoropyridinyl; hydroxypropyl; hydroxybutyl; hydroxyisopropylethyl; hydroxyisopropylpropyl; hydroxymethylcyclobutyl; hydroxyisopropylcyclobutyl; hydroxyethoxyethyl; hydroxycyclobutyl; hydroxycyclohexyl; hydroxycyclopentyl; hydroxycyclopropylethyl; 4-hydroxypiperidin-1-ylethyl; 3-hydroxy-pyrrolidin-1-ylethyl; morpholinylethyl; oxetan-3-yl; oxetan-3-ylmethyl; oxetan-3-ylethyl; piperidin-4-yl; 2-oxo-piperidin-4-yl; 2-oxo-pyrrolidin-4-yl; pyrrolidin-3-yl, unsubstituted or once substituted by methylcarbonyl, ethylcarbonyl, isopropylcarbonyl, methylsulfonyl, hydroxyethyl, hydroxymethylcarbonyl, hydroxyisopropylcarbonyl, aminomethylcarbonyl or trifluoromethylmethyl; tetrahydrofuran-3-yl; tetrahydrofuran-3-ylmethyl; tetrahydropyran-4-yl; trifluoromethylethyl; trifluoromethylpropyl;

$R^4$ is methyl, ethyl or isopropyl;
$R^5$ is hydrogen;
$R^7$ is hydrogen or methyl;
$A^1$ is —N—;
$A^2$ is —N—, —NO or —CH;
$A^3$ is —N— or —CH.

5. A compound according to claim 1, or a pharmaceutically acceptable salt thereof, wherein
$R^1$ is halogen;
$R^2$ is hydrogen or halogen;
$R^3$ is azetidinyl; $C_{1-6}$alkylsulfonyl-$C_xH_{2x}$—; carboxycycloalkyl; difluorocycloalkyl; 1,1-dioxo-tetrahydrothienyl; halopyridinyl; hydroxy-$C_yH_{2y}$—; hydroxy-$C_xH_{2x}$-cycloalkyl; hydroxy-$C_yH_{2y}$—O—$C_yH_{2y}$—; hydroxycycloalkyl-$C_zH_{2z}$—, unsubstituted or substituted by $C_{1-3}$alkyl, hydroxy or hydroxy-$C_xH_{2x}$—; 4-hydroxypiperidin-1-yl-$C_yH_{2y}$—; 3-hydroxy-pyrrolidin-1-yl-$C_yH_{2y}$—; morpholinyl-$C_yH_{2y}$—; oxetanyl; oxetanyl-$C_xH_{2x}$—; oxo-piperidinyl; oxo-pyrrolidinyl; pyrrolidinyl, unsubstituted or substituted by $C_{1-6}$alkylcarbonyl, $C_{1-6}$alkylsulfonyl, hydroxy-$C_yH_{2y}$—, hydroxy-$C_xH_{2x}$-carbonyl, amino-$C_xH_{2x}$-carbonyl or trifluoromethyl-$C_xH_{2x}$—; tetrahydrofuran-3-yl-$C_zH_{2z}$—; tetrahydropyranyl; trifluoromethyl-$C_xH_{2x}$—;

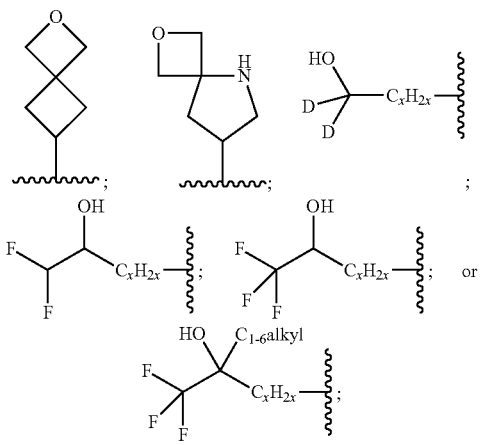

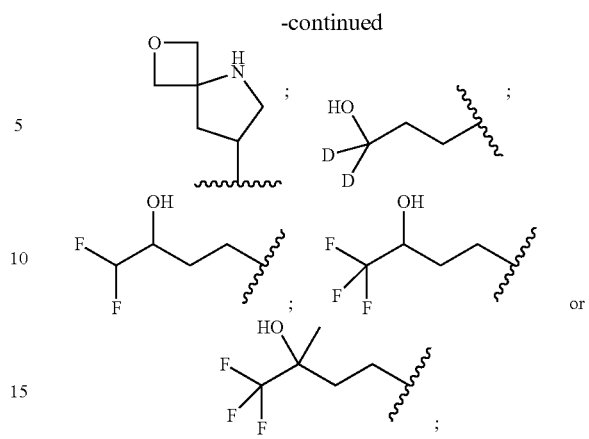

$R^4$ is $C_{1-6}$alkyl;
$R^5$ is hydrogen;
$R^7$ is hydrogen or $C_{1-6}$alkyl;
$A^1$ is —N—;
$A^2$ is —N—;
$A^3$ is —N— or —CH;
x is 1-6;
y is 2-6;
z is 0-6.

6. A compound according to claim 1, or a pharmaceutically acceptable salt thereof, wherein
$R^1$ is chloro;
$R^2$ is hydrogen or fluoro;
$R^3$ is azetidin-3-yl; methylsulfonylethyl; methylsulfonylpropyl; carboxycyclobutyl; difluorocyclopentyl; 1,1-dioxo-tetrahydrothienyl; fluoropyridinyl; hydroxypropyl; hydroxybutyl; hydroxyisopropylethyl; hydroxyisopropylpropyl; hydroxymethylcyclobutyl; hydroxyisopropylcyclobutyl; hydroxyethoxyethyl; hydroxycyclobutyl; hydroxycyclohexyl; hydroxycyclopentyl; hydroxycyclopropylethyl; 4-hydroxypiperidin-1-ylethyl; 3-hydroxy-pyrrolidin-1-ylethyl; morpholinylethyl; oxetan-3-yl; oxetan-3-ylmethyl; oxetan-3-ylethyl; 2-oxo-piperidin-4-yl; 2-oxo-pyrrolidin-4-yl; pyrrolidin-3-yl, unsubstituted or once substituted by methylcarbonyl, isopropylcarbonyl, methylsulfonyl, hydroxyethyl, hydroxymethylcarbonyl, hydroxyisopropylcarbonyl, aminomethylcarbonyl or trifluoromethylmethyl; tetrahydrofuran-3-yl; tetrahydrofuran-3-ylmethyl; tetrahydropyran-4-yl; trifluoromethylethyl; trifluoromethylpropyl;

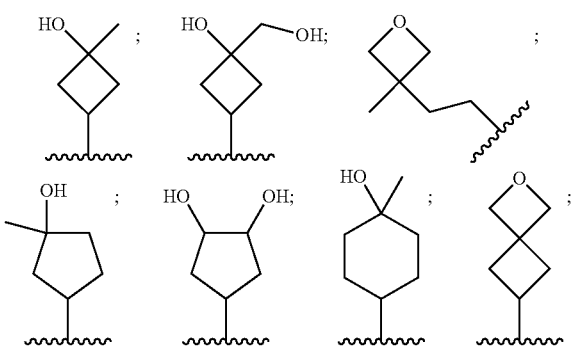

$R^4$ is methyl;
$R^5$ is hydrogen;
$R^7$ is hydrogen or methyl;
$A^1$ is —N—;
$A^2$ is —N—;
$A^3$ is —N— or —CH.

7. A compound according to claim 1, wherein
$R^1$ is halogen;
$R^2$ is hydrogen;
$R^3$ is $C_{1-6}$alkoxypyridinyl; $C_{1-6}$alkylsulfonyl-$C_xH_{2x}$—; difluorocycloalkyl; 1,1-dioxo-tetrahydrothienyl; halopyridinyl; oxetanyl; piperidinyl; $C_{1-6}$alkylcarbonylpyrrolidinyl; tetrahydrofuran-3-yl; tetrahydropyranyl or trifluoromethyl-$C_xH_{2x}$—;
$R^4$ is $C_{1-6}$alkyl;
$R^5$ is hydrogen;
$R^7$ is hydrogen;
$A^1$ is —N—;
$A^2$ is —CH;
$A^3$ is —N—;
x is 1-6.

8. A compound according to claim 1, or a pharmaceutically acceptable salt thereof, wherein
$R^1$ is chloro;
$R^2$ is hydrogen;
$R^3$ is methoxypyridinyl; methylsulfonylethyl; methylsulfonylpropyl; difluorocyclopentyl; 1,1-dioxo-tetrahydrothienyl; chloropyridinyl; fluoropyridinyl; oxetan-3-yl; piperidin-4-yl; 1-methylcarbonylpyrrolidin-3-yl; 1-ethylcarbonylpyrrolidin-3-yl; tetrahydrofuran-3-yl; tetrahydropyran-4-yl or trifluoromethylpropyl;
$R^4$ is methyl, ethyl or isopropyl;
$R^5$ is hydrogen;
$R^7$ is hydrogen;
$A^1$ is —N—;
$A^2$ is —CH;
$A^3$ is —N—.

9. A compound according to claim 1, or a pharmaceutically acceptable salt thereof, wherein
$R^1$ is hydrogen or halogen;
$R^2$ is hydrogen;
$R^3$ is $C_{1-6}$alkylsulfonyl-$C_xH_{2x}$—, wherein x is 1-6;
$R^4$ is $C_{1-6}$alkyl or cycloalkyl;
$R^5$ is hydrogen or halogen;
$R^7$ is hydrogen;
$A^1$ is —CH;
$A^2$ is —N— or —CH;
$A^3$ is —N—.

10. A compound according to claim 1, or a pharmaceutically acceptable salt thereof, wherein
$R^1$ is hydrogen or chloro;
$R^2$ is hydrogen;
$R^3$ is methylsulfonylethyl or methylsulfonylpropyl;
$R^4$ is methyl, ethyl, isopropyl or cyclopropyl;
$R^5$ is hydrogen or fluoro;
$R^7$ is hydrogen;
$A^1$ is —CH;
$A^2$ is —N—, or —CH;
$A^3$ is —N—.

11. A compound according to claim 1 of formula (I')

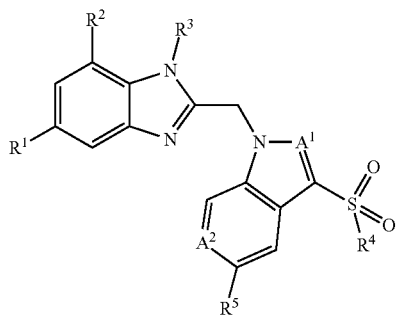

wherein
$R^1$ is hydrogen or halogen;
$R^2$ is hydrogen or halogen;
$R^3$ is azetidinyl; $C_{1-6}$alkoxypyridinyl; $C_{1-6}$alkylsulfonyl-$C_xH_{2x}$—; difluoro$C_{3-7}$cycloalkyl; 1,1-dioxo-tetrahydrothiophenyl; halopyridinyl; hydroxy$C_{3-7}$cycloalkyl; oxetanyl; oxetanyl-$C_xH_{2x}$—; piperidinyl; oxo-piperidinyl; pyrrolidinyl, unsubstituted or once substituted by $C_{1-6}$alkylcarbonyl, hydroxy-$C_xH_{2x}$-carbonyl, amino-$C_xH_{2x}$-carbonyl or trifluoromethyl-$C_xH_{2x}$—; tetrahydrofuranyl; tetrahydropyranyl or trifluoromethyl-$C_xH_{2x}$—; wherein x is 1-6;
$R^4$ is $C_{1-6}$alkyl or $C_{3-7}$cycloalkyl;
$R^5$ is hydrogen or halogen;
$A^1$ is —N— or —CH;
$A^2$ is —N—, —NO or —CH;
or a pharmaceutically acceptable salt thereof.

12. A compound according to claim 11, wherein
$R^1$ is hydrogen or chloro;
$R^2$ is hydrogen or fluoro;
$R^3$ is azetidin-3-yl; methoxypyridinyl; methylsulfonylethyl; methylsulfonylpropyl; difluorocyclopentyl; 1,1-dioxo-tetrahydrothiophenyl; chloropyridinyl; fluoropyridinyl; hydroxycyclohexyl; hydroxycyclopentyl; oxetan-3-yl; oxetanylmethyl; oxetanylethyl; piperidin-4-yl; 2-oxo-piperidin-4-yl; pyrrolidin-3-yl, unsubstituted or once substituted by methylcarbonyl, hydroxymethylcarbonyl, aminomethylcarbonyl or trifluoromethylmethyl; tetrahydrofuran-3-yl; tetrahydropyran-4-yl; trifluoromethylethyl or trifluoromethylpropyl;
$R^4$ is methyl, ethyl, isopropyl or cyclopropyl;
$R^5$ is hydrogen or fluoro;
$A^1$ is —N— or —CH;
$A^2$ is —N—, —NO or —CH;
or a pharmaceutically acceptable salt thereof.

13. A compound according to claim 11, or a pharmaceutically acceptable salt thereof, wherein
$R^1$ is halogen;
$R^2$ is hydrogen or halogen;
$R^3$ is azetidinyl; $C_{1-6}$alkoxypyridinyl; $C_{1-6}$alkylsulfonyl-$C_xH_{2x}$—; difluoro$C_{3-7}$cycloalkyl; 1,1-dioxo-tetrahydrothiophenyl; halopyridinyl; hydroxy$C_{3-7}$cycloalkyl; oxetanyl; oxetanyl-$C_xH_{2x}$—; piperidinyl; oxo-piperidinyl; pyrrolidinyl, unsubstituted or once substituted by $C_{1-6}$alkylcarbonyl, hydroxy-$C_xH_{2x}$-carbonyl, amino-$C_xH_{2x}$-carbonyl or trifluoromethyl-$C_xH_{2x}$—; tetrahydrofuranyl; tetrahydropyranyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —N—, —NO or —CH.

14. A compound according to claim 11, or a pharmaceutically acceptable salt thereof, wherein
$R^1$ is chloro;
$R^2$ is hydrogen or fluoro;
$R^3$ is azetidin-3-yl; methoxypyridinyl; methylsulfonylethyl; methylsulfonylpropyl; difluorocyclopentyl; 1,1-dioxo-tetrahydrothiophenyl; chloropyridinyl; fluoropyridinyl; hydroxycyclohexyl; hydroxycyclopentyl; oxetan-3-yl; oxetanylmethyl; oxetanylethyl; piperidin-4-yl; 2-oxo-piperidin-4-yl; pyrrolidin-3-yl, unsubstituted or once substituted by methylcarbonyl, hydroxymethylcarbonyl, aminomethylcarbonyl or trifluoromethylmethyl; tetrahydrofuran-3-yl; tetrahydropyran-4-yl; trifluoromethylethyl or trifluoromethylpropyl;
$R^4$ is methyl, ethyl or isopropyl;
$R^5$ is hydrogen;
$A^1$ is —N—;
$A^2$ is —N—, —NO or —CH.

15. A compound according to claim 11, or a pharmaceutically acceptable salt thereof, wherein
$R^1$ is halogen;
$R^2$ is hydrogen or halogen;
$R^3$ is azetidinyl; $C_{1-6}$alkylsulfonyl-$C_xH_{2x}$—; difluoro$C_{3-7}$cycloalkyl; 1,1-dioxo-tetrahydrothiophenyl; halopyridinyl; hydroxy$C_{3-7}$cycloalkyl; oxetanyl; oxetanyl-$C_xH_{2x}$—; oxo-piperidinyl; pyrrolidinyl, unsubstituted or once substituted by $C_{1-6}$alkylcarbonyl, hydroxy-$C_xH_{2x}$-carbonyl, amino-$C_xH_{2x}$-carbonyl or trifluoromethyl-$C_xH_{2x}$—; tetrahydropyranyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —N—.

16. A compound according to claim 11, or a pharmaceutically acceptable salt thereof, wherein
$R^1$ is chloro;
$R^2$ is hydrogen or fluoro;
$R^3$ is azetidin-3-yl; methylsulfonylpropyl; difluorocyclopentyl; 1,1-dioxo-tetrahydrothiophenyl; fluoropyridinyl; hydroxycyclohexyl; oxetan-3-yl; oxetanylethyl; oxetanylmethyl; 2-oxo-piperidin-4-yl; pyrrolidin-3-yl, unsubstituted or once substituted by methylcarbonyl, hydroxymethylcarbonyl, aminomethylcarbonyl or trifluoromethylmethyl; tetrahydropyran-4-yl; trifluoromethylethyl or trifluoromethylpropyl;
$R^4$ is methyl;
$R^5$ is hydrogen;
$A^1$ is —N—;
$A^2$ is —N—.

17. A compound according to claim 11, or a pharmaceutically acceptable salt thereof, wherein $R^1$ is halogen;
$R^2$ is hydrogen;
$R^3$ is $C_{1-6}$alkoxypyridinyl; $C_{1-6}$alkylsulfonyl-$C_xH_{2x}$—; difluoro$C_{3-7}$cycloalkyl; 1,1-dioxo-tetrahydrothiophenyl; halopyridinyl; oxetanyl; piperidinyl; tetrahydrofuranyl; tetrahydropyranyl or trifluoromethyl-$C_xH_{2x}$—; wherein x is 1-6;
$R^4$ is $C_{1-6}$alkyl;
$R^5$ is hydrogen;
$A^1$ is —N—;
$A^2$ is —CH.

18. A compound according to claim 11, or a pharmaceutically acceptable salt thereof, wherein $R^1$ is chloro;
$R^2$ is hydrogen;
$R^3$ is methoxypyridinyl; methylsulfonylethyl; methylsulfonylpropyl; difluorocyclopentyl; 1,1-dioxo-tetrahydrothiophenyl; chloropyridinyl; fluoropyridinyl; oxetan-3-yl; piperidin-4-yl; tetrahydrofuran-3-yl; tetrahydropyran-4-yl or trifluoromethylpropyl;
$R^4$ is methyl, ethyl or isopropyl;
$R^5$ is hydrogen;
$A^1$ is —N—;
$A^2$ is —CH.

19. A compound according to claim 11, or a pharmaceutically acceptable salt thereof, wherein
$R^1$ is hydrogen or halogen;
$R^2$ is hydrogen;
$R^3$ is $C_{1-6}$alkylsulfonyl-$C_xH_{2x}$—, wherein x is 1-6;
$R^4$ is $C_{1-6}$alkyl or $C_{3-7}$cycloalkyl;
$R^5$ is hydrogen or halogen;
$A^1$ is —CH;
$A^2$ is —N— or —CH.

20. A compound according to claim 11, or a pharmaceutically acceptable salt thereof, wherein
$R^1$ is hydrogen or chloro;
$R^2$ is hydrogen;
$R^3$ is methylsulfonylethyl or methylsulfonylpropyl;
$R^4$ is methyl, ethyl, isopropyl or cyclopropyl;
$R^5$ is hydrogen or fluoro;
$A^1$ is —CH;
$A^2$ is —N— or —CH.

21. A compound according to claim 1, selected from 1-[2-(methylsulfonyl)ethyl]-2-{[3-(methylsulfonyl)-1H-indol-1-yl]methyl}-1H-benzimidazole; 5-chloro-2-{[3-(methylsulfonyl)-1H-indol-1-yl]methyl}-1-[3-(methylsulfonyl)propyl]-1H-benzimidazole; 5-chloro-2-{[5-fluoro-3-(methylsulfonyl)-1H-indol-1-yl]methyl}-1-[3-(methylsulfonyl)propyl]-1H-benzimidazole; 5-chloro-1-[3-(methylsulfonyl)propyl]-2-{[3-(methylsulfonyl)-1H-pyrrolo[2,3-c]pyridin-1-yl]methyl}-1H-benzimidazole; 5-chloro-2-{[3-(ethylsulfonyl)-1H-indol-1-yl]methyl}-1-[3-(methylsulfonyl)propyl]-1H-benzimidazole; 5-chloro-1-[3-(methylsulfonyl)propyl]-2-{[3-(propan-2-ylsulfonyl)-1H-indol-1-yl]methyl}-1H-benzimidazole; 5-chloro-2-{[3-(cyclopropylsulfonyl)-1H-indol-1-yl]methyl}-1-[3-(methylsulfonyl)propyl]-1H-benzimidazole; 1-({5-chloro-1-[3-(methylsulfonyl)propyl]-1H-benzimidazol-2-yl}methyl)-3-(methylsulfonyl)-1H-indazole; 1-({5-chloro-1-[3-(methylsulfonyl)propyl]-1H-benzimidazol-2-yl}methyl)-3-(propan-2-ylsulfonyl)-1H-indazole; 1-({5-chloro-1-[3-(methylsulfonyl)propyl]-1H-benzimidazol-2-yl}methyl)-3-(ethylsulfonyl)-1H-indazole; 1-({5-chloro-1-[3-(methylsulfonyl)propyl]-1H-benzimidazol-2-yl}methyl)-3-(methylsulfonyl)-1H-pyrazolo[3,4-c]pyridine; 1-({5-chloro-1-[2-(methylsulfonyl)ethyl]-1H-benzimidazol-2-yl}methyl)-3-(methylsulfonyl)-1H-indazole; 1-({5-chloro-1-[2-(methylsulfonyl)ethyl]-1H-benzimidazol-2-yl}methyl)-3-(propan-2-ylsulfonyl)-1H-indazole; 1-({5-chloro-1-[(3R)-1,1-dioxidotetrahydrothiophen-3-yl]-1H-benzimidazol-2-yl}methyl)-3-(methylsulfonyl)-1H-pyrazolo[3,4-c]pyridine; 1-{[5-chloro-1-(1,1-dioxidotetrahydrothiophen-3-yl)-1H-benzimidazol-2-yl]methyl}-3-(methylsulfonyl)-1H-indazole; 1-{[5-chloro-1-(oxetan-3-yl)-1H-benzimidazol-2-yl]methyl}-3-(methylsulfonyl)-1H-indazole; 4-(5-chloro-2-{[3-(methylsulfonyl)-1H-pyrazolo[3,4-c]pyridin-1-yl]methyl}-1H-benzimidazol-1-yl)piperidin-2-one; 1-{[5-chloro-1-(oxetan-3-yl)-1H-benzimidazol-2-yl]methyl}-3-(methylsulfonyl)-1H-pyrazolo[3,4-c]pyridine; 1-{[5-chloro-1-(tetrahydro-2H-pyran-4-yl)-1H-benzimidazol-2-yl]methyl}-3-(methylsulfonyl)-1H-indazole; 1-{[5-chloro-1-(tetrahydro-2H-pyran-4-yl)-1H-benzimidazol-2-yl]methyl}-3-(methylsulfonyl)-1H-pyrazolo[3,4-c]pyridine; 1-{[5-chloro-1-(tetrahydrofuran-3-yl)-1H-benzimidazol-2-yl]methyl}-3-(methylsulfonyl)-1H-indazole; 1-{[5-chloro-1-(3,3-difluorocyclopentyl)-1H-benzimidazol-2-yl]methyl}-3-(methylsulfonyl)-1H-indazole; 1-{[5-chloro-1-(3,3-difluorocyclopentyl)-1H-benzimidazol-2-yl]methyl}-3-(methylsulfonyl)-1H-pyrazolo[3,4-c]pyridine; 4-(5-chloro-2-{[3-(methylsulfonyl)-1H-pyrazolo[3,4-c]pyridin-1-yl]methyl}-1H-benzimidazol-1-yl)cyclohexanol; 3-(5-chloro-2-{[3-(methylsulfonyl)-6-oxido-1H-pyrazolo[3,4-c]pyridin-1-yl]methyl}-1H-benzimidazol-1-yl)cyclopentanol; 1-{[5-chloro-1-(pyrrolidin-3-yl)-1H-benzimidazol-2-yl]methyl}-3-(methylsulfonyl)-1H-pyrazolo[3,4-c]pyridine; 1-{[1-(azetidin-3-yl)-5-chloro-1H-benzimidazol-2-yl]methyl}-3-(methylsulfonyl)-1H-pyrazolo[3,4-c]pyridine; 1-{[5-chloro-1-(piperidin-4-yl)-1H-benzimidazol-2-yl]methyl}-3-(methylsulfonyl)-1H-indazole; 1-[3-(5-chloro-2-{[3-(methylsulfonyl)-1H-pyrazolo[3,4-c]pyridin-1-yl]methyl}-1H-benzimidazol-1-yl)pyrrolidin-1-yl]ethanone; 1-[3-(5-chloro-2-{[3-(methylsulfonyl)-1H-pyrazolo[3,4-c]pyridin-1-yl]methyl}-1H-benzimidazol-1-yl)pyrrolidin-1-yl]-2-hydroxyethanone; 2-amino-1-[3-(5-chloro-2-{[3-(methylsulfonyl)-1H-pyrazolo[3,4-c]pyridin-1-yl]methyl}-1H-benzimidazol-1-yl)pyrrolidin-1-yl]ethanone; 1-({5-chloro-1-[(3S)-1-(2,2,2-trifluoroethyl)pyrrolidin-3-yl]-1H-benzimidazol-2-yl}methyl)-3-(methylsulfonyl)-1H-pyrazolo[3,4-c]pyridine; 1-({5-chloro-1-[(3R)-1-(2,2,2-trifluoroethyl)pyrrolidin-3-yl]-1H-benzimidazol-2-yl}methyl)-3-(methylsulfonyl)-1H-pyrazolo[3,4-c]pyridine; 1-{[5-chloro-1-(3,3,3-trifluoropropyl)-1H-benzimidazol-2-yl]methyl}-3-(methylsulfonyl)-1H-pyrazolo[3,4-c]pyridine; 1-{[5-chloro-1-(oxetan-3-ylmethyl)-1H-benzimidazol-2-yl]methyl}-3-(methylsulfonyl)-1H-pyrazolo[3,4-c]pyridine; 1-({5-chloro-1-[2-(oxetan-3-yl)ethyl]-1H-benzimidazol-2-yl}methyl)-3-(methylsulfonyl)-1H-pyrazolo[3,4-c]pyridine; 1-{[5-chloro-1-(6-fluoropyridin-3-yl)-1H-benzimidazol-2-yl]methyl}-3-(methylsulfonyl)-1H-indazole; 1-{[5-chloro-1-(6-fluoropyridin-3-yl)-1H-benzimidazol-2-yl]methyl}-3-(methylsulfonyl)-1H-pyrazolo[3,4-c]pyridine; 1-{[5-chloro-1-(6-fluoropyridin-3-yl)-1H-benzimidazol-2-yl]methyl}-3-(methylsulfonyl)-1H-pyrazolo[3,4-c]pyridine 6-oxide; 1-{[5-chloro-1-(6-methoxypyridin-3-yl)-1H-benzimidazol-2-yl]methyl}-3-(methylsulfonyl)-1H-indazole; 1-{[5-chloro-1-(6-chloropyridin-3-yl)-1H-benzimidazol-2-yl]methyl}-3-(methylsulfonyl)-1H-indazole; 1-{[5-chloro-1-(4,4,4-trifluorobutyl)-1H-benzimidazol-2-yl]methyl}-3-

(methylsulfonyl)-1H-indazole; 1-{[5-chloro-1-(4,4,4-trifluorobutyl)-1H-benzimidazol-2-yl]methyl}-3-(methylsulfonyl)-1H-pyrazolo[3,4-c]pyridine 6-oxide; 1-{[5-chloro-1-(4,4,4-trifluorobutyl)-1H-benzimidazol-2-yl]methyl}-3-(methylsulfonyl)-1H-pyrazolo[3,4-c]pyridine; 1-{[5-chloro-7-fluoro-1-(3,3,3-trifluoropropyl)-1H-benzimidazol-2-yl]methyl}-3-(methylsulfonyl)-1H-pyrazolo[3,4-c]pyridine; 1-{[5-chloro-7-fluoro-1-(4,4,4-trifluorobutyl)-1H-benzimidazol-2-yl]methyl}-3-(methylsulfonyl)-1H-pyrazolo[3,4-c]pyridine; 1-{[5-chloro-1-(2-oxaspiro[3.3]hept-6-yl)-1H-benzimidazol-2-yl]methyl}-3-(methylsulfonyl)-1H-pyrazolo[3,4-c]pyridine; 1-({5-chloro-1-[2-(3-methyloxetan-3-yl)ethyl]-1H-benzimidazol-2-yl}methyl)-3-(methylsulfonyl)-1H-pyrazolo[3,4-c]pyridine; trans-3-(5-chloro-2-{[3-(methylsulfonyl)-1H-pyrazolo[3,4-c]pyridin-1-yl]methyl}-1H-benzimidazol-1-yl)-1-methylcyclobutanol; 3-(5-chloro-2-{[3-(methylsulfonyl)-1H-pyrazolo[3,4-c]pyridin-1-yl]methyl}-1H-benzimidazol-1-yl)propan-1-ol; 1-{[5-chloro-1-(tetrahydrofuran-3-yl)-1H-benzimidazol-2-yl]methyl}-3-(methylsulfonyl)-1H-pyrazolo[3,4-c]pyridine; 4-(5-chloro-2-{[3-(methylsulfonyl)-1H-pyrazolo[3,4-c]pyridin-1-yl]methyl}-1H-benzimidazol-1-yl)-2-methylbutan-2-ol; 4-(5-chloro-2-{[3-(methylsulfonyl)-1H-pyrazolo[3,4-c]pyridin-1-yl]methyl}-1H-benzimidazol-1-yl)butan-1-ol; 1-{[5-chloro-1-(tetrahydrofuran-3-ylmethyl)-1H-benzimidazol-2-yl]methyl}-3-(methylsulfonyl)-1H-pyrazolo[3,4-c]pyridine; trans-3-(5-chloro-2-{[3-(methylsulfonyl)-1H-pyrazolo[3,4-c]pyridin-1-yl]methyl}-1H-benzimidazol-1-yl)cyclobutanol; cis-3-(5-chloro-2-{[3-(methylsulfonyl)-1H-pyrazolo[3,4-c]pyridin-1-yl]methyl}-1H-benzimidazol-1-yl)-1-methylcyclobutanol; 1-[2-(5-chloro-2-{[3-(methylsulfonyl)-1H-pyrazolo[3,4-c]pyridin-1-yl]methyl}-1H-benzimidazol-1-yl)ethyl]cyclopropanol; 2-[2-(5-chloro-2-{[3-(methylsulfonyl)-1H-pyrazolo[3,4-c]pyridin-1-yl]methyl}-1H-benzimidazol-1-yl)ethoxy]ethanol; trans-3-(5-chloro-2-{[3-(methylsulfonyl)-1H-pyrazolo[3,4-c]pyridin-1-yl]methyl}-1H-benzimidazol-1-yl)cyclopentanol; cis-4-(5-chloro-2-{[3-(methylsulfonyl)-1H-pyrazolo[3,4-c]pyridin-1-yl]methyl}-1H-benzimidazol-1-yl)-1-methylcyclohexanol; 5-(5-chloro-2-{[3-(methylsulfonyl)-1H-pyrazolo[3,4-c]pyridin-1-yl]methyl}-1H-benzimidazol-1-yl)-2-methylpentan-2-ol; 2-[trans-3-(5-chloro-2-{[3-(methylsulfonyl)-1H-pyrazolo[3,4-c]pyridin-1-yl]methyl}-1H-benzimidazol-1-yl)cyclobutyl]propan-2-ol; 1-({5-chloro-1-[2-(morpholin-4-yl)ethyl]-1H-benzimidazol-2-yl}methyl)-3-(methylsulfonyl)-1H-pyrazolo[3,4-c]pyridine; trans-3-(5-chloro-2-{[3-(methylsulfonyl)-1H-pyrazolo[3,4-c]pyridin-1-yl]methyl}-1H-benzimidazol-1-yl)cyclobutane carboxylic acid; 4-(5-chloro-2-{[3-(methylsulfonyl)-1H-pyrazolo[3,4-c]pyridin-1-yl]methyl}-1H-benzimidazol-1-yl)-1,1,1-trifluorobutan-2-ol; cis-3-(5-chloro-2-{[3-(methylsulfonyl)-1H-pyrazolo[3,4-c]pyridin-1-yl]methyl}-1H-benzimidazol-1-yl)-1-methylcyclopentanol; 4-(5-chloro-2-{[3-(methylsulfonyl)-1H-pyrazolo[3,4-c]pyridin-1-yl]methyl}-1H-benzimidazol-1-yl)-1,1-difluorobutane-2-ol; trans-4-(5-chloro-2-{[3-(methylsulfonyl)-1H-pyrazolo[3,4-c]pyridin-1-yl]methyl}-1H-benzimidazol-1-yl)cyclopentane-1,2-diol; trans-3-(5-chloro-2-{[3-(methylsulfonyl)-1H-pyrazolo[3,4-c]pyridin-1-yl]methyl}-1H-benzimidazol-1-yl)-1-(hydroxymethyl)cyclobutanol; 1-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]ethanone; 1-[3-(5-chloro-2-{[3-(methylsulfonyl)-1H-indazol-1-yl]methyl}-1H-benzimidazol-1-yl)pyrrolidin-1-yl]ethanone; 1-[(3R)-3-(5-chloro-2-{[3-(methylsulfonyl)-1H-indazol-1-yl]methyl}-1H-benzimidazol-1-yl)pyrrolidin-1-yl]propan-1-one; 1-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]-2-methylpropan-1-one; 1-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]-2-hydroxy-2-methylpropan-1-one; 1-({5-chloro-1-[(3R)-1-(methylsulfonyl)pyrrolidin-3-yl]-1H-benzimidazol-2-yl}methyl)-3-(methylsulfonyl)-1H-pyrazolo[3,4-c]pyridine; 2-[(3R)-3-(5-chloro-2-{[3-(methylsulfonyl)-1H-pyrazolo[3,4-c]pyridin-1-yl]methyl}-1H-benzimidazol-1-yl)pyrrolidin-1-yl]ethanol; 4-(5-chloro-2-{[3-(methylsulfonyl)-1H-pyrazolo[3,4-c]pyridin-1-yl]methyl}-1H-benzimidazol-1-yl)pyrrolidin-2-one; 1-{[5-chloro-1-(2-oxa-5-azaspiro[3.4]oct-7-yl)-1H-benzimidazol-2-yl]methyl}-3-(methylsulfonyl)-1H-pyrazolo[3,4-c]pyridine; 1-({5-chloro-1-[2-(methylsulfonyl)ethyl]-1H-indol-2-yl}methyl)-3-(methylsulfonyl)-1H-pyrazolo[3,4-c]pyridine; 1-({5-chloro-1-[3-(methylsulfonyl)propyl]-1H-indol-2-yl}methyl)-3-(methylsulfonyl)-1H-pyrazolo[3,4-c]pyridine; 1-({5-chloro-7-fluoro-1-[2-(methylsulfonyl)ethyl]-1H-indol-2-yl}methyl)-3-(methylsulfonyl)-1H-pyrazolo[3,4-c]pyridine; 1-[2-(5-chloro-2-{[3-(methylsulfonyl)-1H-pyrazolo[3,4-c]pyridin-1-yl]methyl}-1H-benzimidazol-1-yl)ethyl]pyrrolidin-3-ol; 1-[2-(5-chloro-2-{[3-(methylsulfonyl)-1H-pyrazolo[3,4-c]pyridin-1-yl]methyl}-1H-benzimidazol-1-yl)ethyl]piperidin-4-ol; [trans-3-(5-chloro-2-{[3-(methylsulfonyl)-1H-pyrazolo[3,4-c]pyridin-1-yl]methyl}-1H-benzimidazol-1-yl)cyclobutyl]methanol; 1-({5-chloro-1-[(3R)-1,1-dioxidotetrahydrothiophen-3-yl]-7-fluoro-1H-benzimidazol-2-yl}methyl)-3-(methylsulfonyl)-1H-pyrazolo[3,4-c]pyridine; 3-(5-chloro-2-{[3-(methylsulfonyl)-1H-pyrazolo[3,4-c]pyridin-1-yl]methyl}-1H-benzimidazol-1-yl)(1,1-$^2$H$_2$)propan-1-ol; 4-(5-chloro-2-{[3-(methylsulfonyl)-1H-pyrazolo[3,4-c]pyridin-1-yl]methyl}-1H-benzimidazol-1-yl)-1,1,1-trifluoro-2-methylbutan-2-ol; 1-{(1R)-1-[5-chloro-1-(3,3,3-trifluoropropyl)-1H-benzimidazol-2-yl]ethyl}-3-(methylsulfonyl)-1H-pyrazolo[3,4-c]pyridine; and 1-{(1S)-1-[5-chloro-1-(3,3,3-trifluoropropyl)-1H-benzimidazol-2-yl]ethyl}-3-(methylsulfonyl)-1H-pyrazolo[3,4-c]pyridine.

22. A process for the preparation of a compound according to claim 1, comprising the reaction of (a) a compound of formula (A)

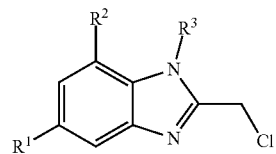

(A)

with

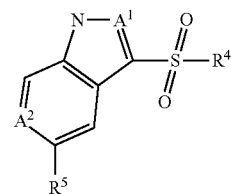

in the presence of a base;

(b) a compound of formula (B)

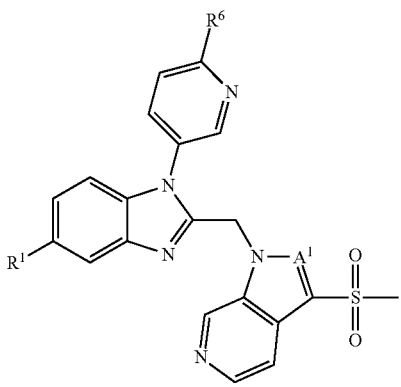
(B)

in the presence of m-CPBA;
(c) a compound of formula (C)

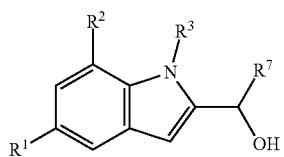
(C)

with indazole in the presence of PPh₃ and DIAD;
(d) a compound of formula (D)

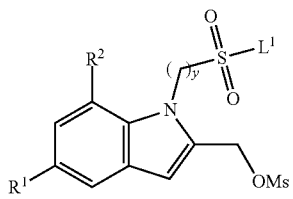
(D)

with indazole in the presence of a base;
(e) a compound of formula (E)

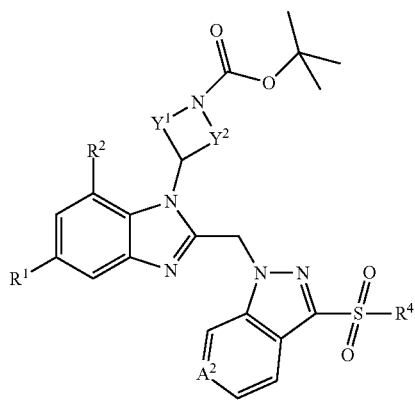
(E)

in the presence of an acid;

(f) a compound of formula (F)

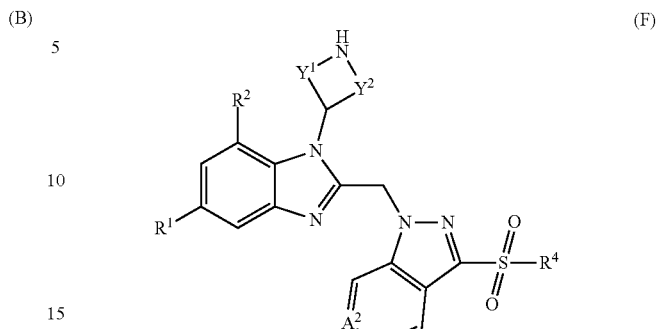
(F)

with acetic anhydride, substituted acetic acid, $C_{1-6}$alkyl-sulfonyl chloride, hydroxyl-$C_xH_{2x}$-bromide or trifluoro$C_{1-6}$alkyl trifluoromethanesulfonate in the presence or absence of a base;

(g) a compound of formula (G)

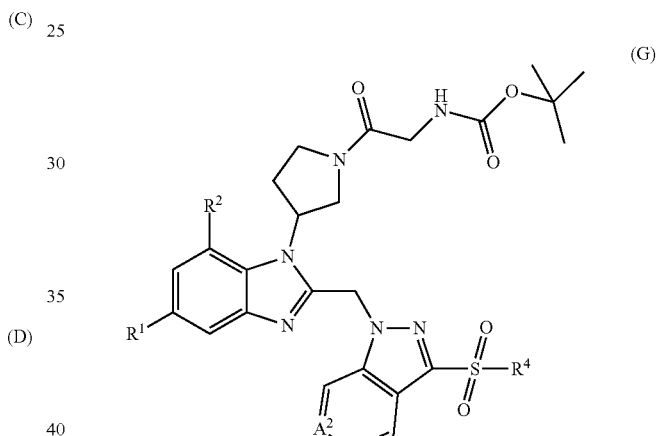
(G)

in the presence of an acid;
(h) a compound of formula (H)

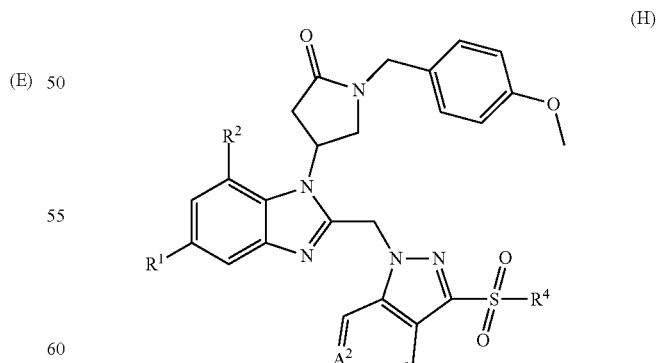
(H)

with $(NH_4)_2Ce(NO_3)_6$;
wherein $R^1$ to $R^5$, $R^7$, x, $A^1$ to $A^3$ are defined as in any one of claims 1 to 19; $R^6$ is independently selected from halogen and $C_{1-6}$alkoxy; $L^1$ is $C_{1-6}$alkyl;

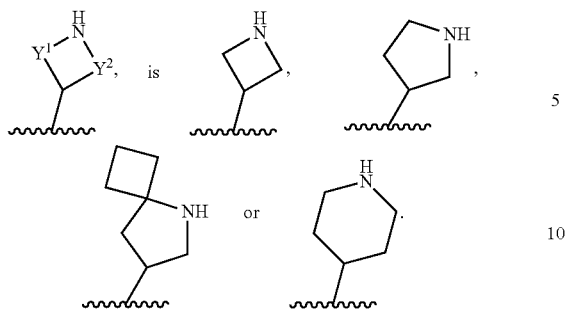

23. A pharmaceutical composition comprising a compound in accordance with claim 1 and a therapeutically inert carrier.

24. A compound of formula (I) manufactured according to the process of claim 22.

25. A method for the treatment or prophylaxis of respiratory syncytial virus infection, which method comprises administering an effective amount of a compound as defined in claim 1 to a patient in need thereof.

\* \* \* \* \*